US008404837B2

(12) United States Patent
Adams et al.

(10) Patent No.: US 8,404,837 B2
(45) Date of Patent: *Mar. 26, 2013

(54) QUINOLINE DERIVATIVES AS P13 KINASE INHIBITORS

(75) Inventors: Nicholas D. Adams, Collegeville, PA (US); Joelle Lorraine Burgess, Collegeville, PA (US); Michael Gerard Darcy, Collegeville, PA (US); Carla A. Donatelli, Collegeville, PA (US); Steven David Knight, Collegeville, PA (US); Kenneth Allen Newlander, Collegeville, PA (US); Lance Ridgers, Collegeville, PA (US); Martha A. Sarpong, Collegeville, PA (US); Stanley J. Schmidt, Collegeville, PA (US)

(73) Assignee: GlaxoSmithKline LLC, Philadelph, PA (US)

( * ) Notice: Subject to any disclaimer, the term of this patent is extended or adjusted under 35 U.S.C. 154(b) by 520 days.

This patent is subject to a terminal disclaimer.

(21) Appl. No.: 12/600,745

(22) PCT Filed: May 16, 2008

(86) PCT No.: PCT/US2008/063819
§ 371 (c)(1),
(2), (4) Date: Nov. 18, 2009

(87) PCT Pub. No.: WO2008/144463
PCT Pub. Date: Nov. 27, 2008

(65) Prior Publication Data
US 2010/0152112 A1 Jun. 17, 2010

Related U.S. Application Data

(60) Provisional application No. 60/938,761, filed on May 18, 2007.

(51) Int. Cl.
C07D 401/14 (2006.01)
C07D 413/14 (2006.01)
C07D 498/04 (2006.01)

(52) U.S. Cl. ............... 544/105; 544/128; 546/167

(58) Field of Classification Search ................ None
See application file for complete search history.

(56) References Cited

U.S. PATENT DOCUMENTS

| 5,925,656 | A | 7/1999 | Kallam et al. | 514/369 |
|---|---|---|---|---|
| 5,965,589 | A | 10/1999 | Sohda et al. | 514/369 |
| 6,452,014 | B1 | 9/2002 | Akama et al. | 546/260 |
| 6,949,537 | B2 | 9/2005 | Garlich et al. | 514/183 |
| 7,153,875 | B2 | 12/2006 | Pfahl et al. | 514/342 |
| 7,348,348 | B2 | 3/2008 | Kuo et al. | 514/369 |
| 7,667,043 | B2 * | 2/2010 | Getty et al. | 546/285 |
| 8,138,347 | B2 | 3/2012 | Knight et al. | 546/167 |
| 2002/0120144 | A1 | 8/2002 | Akama et al. | 546/114 |
| 2002/0143182 | A1 | 10/2002 | Pfahl et al. | 546/14 |
| 2003/0003396 | A1 | 1/2003 | Berneth et al. | 430/270.18 |
| 2004/0009527 | A1 | 1/2004 | Dong et al. | 435/7.1 |
| 2004/0092561 | A1 | 5/2004 | Ruckle et al. | 514/369 |
| 2005/0019825 | A9 | 1/2005 | Dong et al. | 435/7.1 |
| 2005/0042213 | A1 | 2/2005 | Gelder et al. | 424/94.64 |
| 2005/0165072 | A1 | 7/2005 | Ayer et al. | 514/369 |
| 2005/0222225 | A1 | 10/2005 | De Luca | 514/369 |
| 2006/0004046 | A1 | 1/2006 | Chen et al. | 514/314 |
| 2006/0106077 | A1 | 5/2006 | Suto et al. | 514/369 |
| 2006/0122176 | A1 | 6/2006 | Rueckle et al. | 514/230.5 |
| 2006/0276520 | A1 | 12/2006 | Singh et al. | 514/369 |
| 2006/0281907 | A1 | 12/2006 | Gold | 536/23.1 |
| 2007/0021447 | A1 | 1/2007 | Rueckle et al. | 514/266.23 |
| 2007/0054903 | A1 | 3/2007 | Kim et al. | 514/230.5 |
| 2007/0215866 | A1 | 9/2007 | Getty et al. | 257/40 |
| 2012/0165321 | A1 | 6/2012 | Adams et al. | 514/223.2 |

FOREIGN PATENT DOCUMENTS

| EP | 801063 A1 | 10/1997 |
|---|---|---|
| EP | 801063 B1 | 1/2003 |
| EP | 1277738 A1 | 1/2003 |
| WO | WO 99/28315 A1 | 6/1999 |
| WO | WO 99/59586 A1 | 11/1999 |
| WO | WO 01/83456 A1 | 11/2001 |
| WO | WO 02/092076 A1 | 11/2002 |
| WO | WO 02/094833 A1 | 11/2002 |
| WO | WO 03/013523 A1 | 2/2003 |
| WO | WO 03/062392 A2 | 7/2003 |
| WO | WO 2004/017950 A2 | 3/2004 |
| WO | WO 2004/045611 A1 | 6/2004 |
| WO | WO 2004/069232 A2 | 8/2004 |
| WO | WO 2004/080463 A1 | 9/2004 |
| WO | WO 2004/087160 A1 | 10/2004 |
| WO | WO 2005/070890 A2 | 8/2005 |
| WO | WO2005/085227 | 9/2005 |
| WO | WO 2005/085227 A1 | 9/2005 |
| WO | WO 2006/117522 A1 | 11/2006 |
| WO | WO 2006/117570 A1 | 11/2006 |
| WO | WO 2006/135649 A2 | 12/2006 |
| WO | WO 2007/022241 A2 | 2/2007 |
| WO | WO 2007/139496 A1 | 12/2007 |

OTHER PUBLICATIONS

Opposition. "Quinoline Derivatives as PI3 Kinase Inhibitors", La Gaceta, (Official Journal Mar. 3, 2010 (3rd publication) Exp. 11.165.
Abid, et al. Arteriosclerosis, Thrombosis, and Vascular Biology, 24: 294-300 (2004).
Drees, et al. Combinational Chemistry and High Throughput Screening, 6(4): 321 (2003).

(Continued)

Primary Examiner — Janet Andres
Assistant Examiner — Timothy R Rozof
(74) Attorney, Agent, or Firm — Duke M. Fitch; Kathryn A. Lutomski; John Lemanowicz

(57) ABSTRACT

Invented is a method of inhibiting the activity/function of PI3 kinases using quinoline derivatives. Also invented is a method of treating one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries by the administration of quinoline derivatives.

9 Claims, No Drawings

OTHER PUBLICATIONS

Foster, et al. *Journal of Cell Science,* 116: 3037-3040 (2003).
Fraser, et al. *Science,* 251(4991): 313-316 (1991).
Froman, et al. *Annual Review of Biochemistry,* 67: 481-507 (1998).
Gerard, et al. *Nature Immunology,* 2(2): 108-115 (2001).
Harari, et al. *Oncogene,* 19: 6102-6114 (2000).
Hirsch, et al. *Science,* 287(5455): 1049-1053 (2000).
Hirsch, et al. *Faseb Journal,* 15(11): 2019-2021 (2001).
Janusz, et al. *Journal of Medicinal Chemistry,* 41(18): 3515-3529 (1998).
Katso, et al. *Annual Review of Cell and Developmental Biology,* 17: 615-675 (2001).
Kauffmann-Zeh, et al. *Nature,* 385: 544-548 (1997).
Laffargue, et al. *Immunity,* 16(3): 441-451 (2002).
Lawlor, et al. *Journal of Cell Science,* 114(16): 2903-2910 (2001).
Leslie, et al. *Chemical Reviews,* 101(8): 2365-2380 (2001).
Lopez-Ilasaca, et al. *Journal of Biological Chemistry,* 273(5): 2505-2508 (1998).
Ma, et al. *Oncogene,* 19: 2739-2744 (2000).
Meier, et al. *Protein Expression and Purification,* 35(2): 218 (2004).
Nicholson, et al. *Cellular Signaling,* 14: 381-395 (2002).
Pages, et al. *Nature,* 369: 327-329 (1994).
Panayotou, et al. *Trends in Cell Biology,* 2: 358-360 (1992).
Parker, et al. *Current Biology,* 5: 577-579 (1995).
Philp, et al. *Cancer Research,* 61: 7426-7429 (2001).
Rudd. *Immunity,* 4: 524-534 (1996).
Samuels, et al. *Science,* 304: 554 (2004).
Sawyer. *Expert Opinion on Investigational Drugs,* 13: 1-19 (2004).
Shayesteh, et al. *Nature Genetics,* 21: 99-102 (1999).
Simpson, et al. *Experimental Cell Research,* 264: 29-41 (2001).
Stein, et al. *Molecular Medicine Today,* 6(9): 347-357 (2000).
Stephens, et al. *Current Opinion in Cell Biology,* 14(2): 203-213 (2002).
Thelen, et al. *Proceedings of the Natural Academy of Sciences,* 91: 4960-4964 (1994).
Toker, et al. *Cellular and Molecular Life Sciences,* 59(5): 761-779 (2002).
Vanhaesebroeck, et al. *Trends in Biochemical Sciences,* 22(7): 267-272 (1997).
Vanhaesebroeck, et al. *Experimental Cell Research,* 253(1): 239-254 (1999).
Vara, et al. *Cancer Treatment Reviews,* 30: 193-204 (2004).
Vivanco, et al. *Nature Reviews Cancer,* 2: 489-501 (2002).
Wymann, et al. *Immunology Today,* 21(6): 260-264 (2000).
Yao, et al. *Science,* 267(5206): 2003-2005 (1995).
PCT Written Opinion and Search Report, PCT/ISA/237, PCT/US08/63819, Aug. 8, 2008.

\* cited by examiner

QUINOLINE DERIVATIVES AS P13 KINASE INHIBITORS

This application is a 371 of International Application No. PCT/US2008/063819, filed 16 May 2008, which claims the benefit of U.S. Provisional Application No. 60/938,761, filed 18 May 2007, which are incorporated herein in their entirety.

FIELD OF THE INVENTION

This invention relates to the use of quinoline derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ, particularly PI3Kα. Suitably, the present invention relates to the use of quinolines derivatives in the treatment of one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, particularly cancer.

BACKGROUND OF THE INVENTION

Cellular membranes represent a large store of second messengers that can be enlisted in a variety of signal transduction pathways. In regards function and regulation of effector enzymes in phospholipids signaling pathways, these enzymes generate second messengers from the membrane phospholipid pools (class I PI3 kinases (e.g. PI3Kalpha) are dual-specificity kinase enzymes, meaning they display both: lipid kinase (phosphorylation of phosphoinositides) as well as protein kinase activity, shown to be capable of phosphorylation of protein as substrate, including auto-phosphorylation as intramolecular regulatory mechanism. These enzymes of phospholipids signaling are activated in response to a variety of extra-cellular signals such as growth factors, mitogens, integrins (cell-cell interactions) hormones, cytokines, viruses and neurotransmitters such as described in Scheme I hereinafter and also by intracellular regulation by other signaling molecules (cross-talk, where the original signal can activate some parallel pathways that in a second step transmit signals to PI3Ks by intra-cellular signaling events), such as small GTPases, kinases or phosphatases for example. Intracellular regulation can also occur as a result of aberrant expression or lack of expression of cellular oncogenes or tumor suppressors. The inositol phospholipid (phosphoinositides) intracellular signaling pathways begin with activation of signaling molecules (extra cellular ligands, stimuli, receptor dimerization, transactivation by heterologous receptor (e.g. receptor tyrosine kinase) and the recruitment and activation of PI3K including the involvement of G-protein linked transmembrane receptor integrated into the plasma membrane.

PI3K converts the membrane phospholipid PI(4,5)P$_2$ into PI(3,4,5)P$_3$ that functions as a second messenger. PI and PI(4)P are also substrates of PI3K and can be phosphorylated and converted into PI3P and PI(3,4)P$_2$, respectively. In addition, these phosphoinositides can be converted into other phosphoinositides by 5'-specific and 3'-specific phosphatases, thus PI3K enzymatic activity results either directly or indirectly in the generation of two 3'-phosphoinositide subtypes that function as $2^{nd}$ messengers in intra-cellular signal transduction pathways (Trends Biochem. Sci. 22(7) p. 267-72 (1997) by Vanhaesebroeck et al.: Chem. Rev. 101(8) p. 2365-80 (2001) by Leslie et al (2001); Annu. Rev. Cell. Dev. Biol. 17p, 615-75 (2001) by Katso et al. and Cell. Mol. Life Sci. 59(5) p. 761-79 (2002) by Toker et al.). Multiple PI3K isoforms categorized by their catalytic subunits, their regulation by corresponding regulatory subunits, expression patterns and signaling-specific functions (p110α, β, δ and γ) perform this enzymatic reaction (Exp. Cell. Res. 25 (1) p. 239-54 (1999) by Vanhaesebroeck and Katso et al., 2001, above).

The closely related isoforms p110α and β are ubiquitously expressed, while δ and γ are more specifically expressed in the haematopoietic cell system, smooth muscle cells, myocytes and endothelial cells (Trends Biochem. Sci. 22(7) p. 267-72 (1997) by Vanhaesebroeck et al.). Their expression might also be regulated in an inducible manner depending on the cellular, tissue type and stimuli as well as disease context. Inducibility of protein expression includes synthesis of protein as well as protein stabilization that is in part regulated by association with regulatory subunits.

To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate (PI(4,5)P$_2$) to produce phosphatidylinositol-3-phosphate (PI3P), phosphatidylinositol-3,4-bisphosphate (PI(3,4)P$_2$, and phosphatidylinositol-3,4,5-trisphosphate (PI(3,4,5)P$_3$, respectively. Class II PI3Ks phosphorylate PI and phosphatidylinositol-4-phosphate. Class III PI3Ks can only phosphorylate PI (Vanhaesebrokeck et al., 1997, above; Vanhaesebroeck et al., 1999, above and Leslie et al, 2001, above)

Scheme I: Conversion of PI(4,5)P2 to PIP3

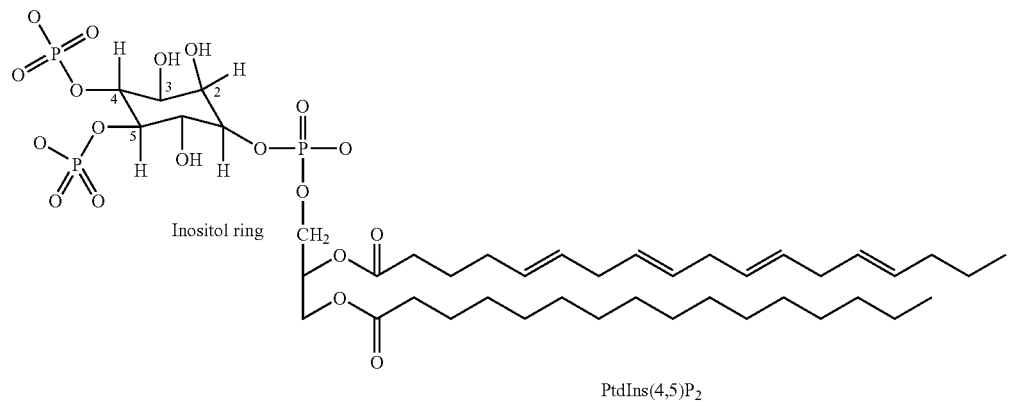

PtdIns(4,5)P$_2$

PI3K

-continued

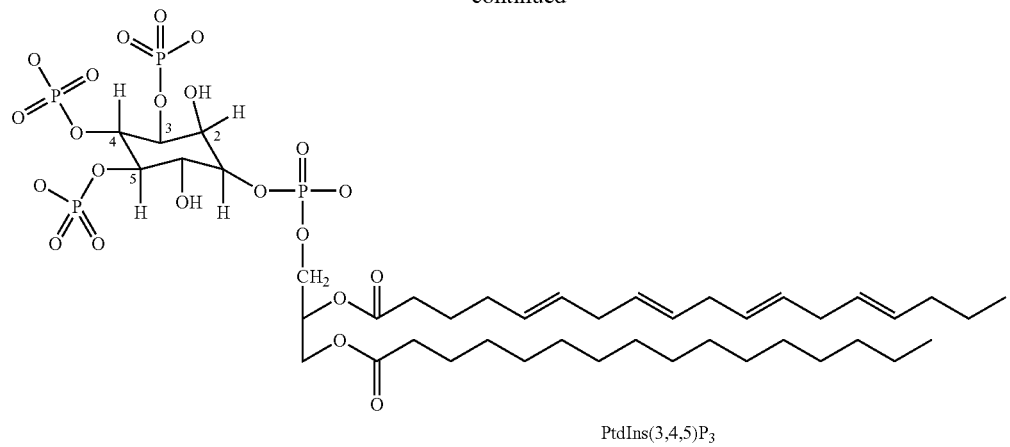

PtdIns(3,4,5)P₃

As illustrated in Scheme A above, phosphoinositide 3-kinases (PI3Ks) phosphorylate the hydroxyl of the third carbon of the inositol ring. The phosphorylation of phosphoinositides that generate PtdIns to 3,4,5-trisphosphate (PtdIns(3,4,5) P3), PtdIns(3,4)P2 and PtdIns(3)P produce second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al., 2001, above and Mol. Med. Today 6(9) p. 347-57 (2000) by Stein). G-protein coupled receptors mediate phosphoinositide 3'OH-kinase activation via small GTPases such as Gβγ and Ras, and consequently PI3K signaling plays a central role in establishing and coordinating cell polarity and dynamic organization of the cytoskeleton—which together provides the driving force of cells to move.

Chemotaxis—the directed movement of cells toward a concentration gradient of chemical attractants, also called chemokines is involved in many important diseases such as inflammation/auto-immunity, neurodegeneration, antiogenesis, invasion/metastasis and wound healing (Immunol. Today 21(6) p. 260-4 (2000) by Wyman et al.; Science 287 (5455) p. 1049-53 (2000) by Hirsch et al.; FASEB J. 15(11) p. 2019-21 (2001) by Hirsch et al. and Nat. Immunol. 2(2) p. 108-15 (2001) by Gerard et al.).

Advances using genetic approaches and pharmacological tools have provided insights into signalling and molecular pathways that mediate chemotaxis in response to chemoattractant activated G-protein coupled receptors. PI3-Kinase, responsible for generating these phosphorylated signalling products, was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol. 2 p. 358-60 (1992)). However, more recent biochemical studies revealed that class I PI3 kinases (e.g. class IB isoform PI3Kγ) are dual-specific kinase enzymes, meaning they display both lipid kinase and protein kinase activity, shown to be capable of phosphorylation of other proteins as substrates, as well as auto-phosphorylation as an intra-molecular regulatory mechanism.

PI3-kinase activation, is therefore believed to be involved in a range of cellular responses including cell growth, differentiation, and apoptosis (Parker et al., Current Biology, 5 p. 577-99 (1995); Yao et al., Science, 267 p. 2003-05 (1995)). PI3-kinase appears to be involved in a number of aspects of leukocyte activation. A p85-associated PI3-kinase activity has been shown to physically associate with the cytoplasmic domain of CD28, which is an important costimulatory molecule for the activation of T-cells in response to antigen (Pages et al., Nature, 369 p. 327-29 (1994); Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science 251 p. 313-16 (1991)). Mutation of CD28 such that it can no longer interact with PI3-kinase leads to a failure to initiate IL2 production, suggesting a critical role for PI3-kinase in T cell activation. PI3Kγ has been identified as a mediator of G beta-gamma-dependent regulation of INK activity, and G beta-gamma are subunits of heterotrimeric G proteins (Lopez-Ilasaca et al., J. Biol. Chem. 273(5) p. 2505-8 (1998)). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

Recently, (Laffargue et al., Immunity 16(3) p. 441-51 (2002)) it has been described that PI3Kγ relays inflammatory signals through various G(i)-coupled receptors and its central to mast cell function, stimuli in context of leukocytes, immunology includes cytokines, chemokines, adenosines, antibodies, integrins, aggregation factors, growth factors, viruses or hormones for example (J. Cell. Sci. 114(Pt 16) p. 2903-10 (2001) by Lawlor et al.; Laffargue et al., 2002, above and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (cf hereinafter), have been widely used as PI3-kinase inhibitors. These compounds are non-specific PI3K inhibitors, as they do not distinguish among the four members of Class I PI3-kinases. For example, the $IC_{50}$ values of wortmannin against each of the various Class I PI3-kinases are in the range of 1-10 nM. Similarly, the $IC_{50}$ values for LY294002 against each of these PI3-kinases is about 15-20 μM (Fruman et al., Ann. Rev. Biochem., 67, p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3,4,5)P$_3$. This synthesis correlates with activation of the respirators burst involved in neutrophil destruction of invading microorganisms. Treatment of neutrophils with wortmannin prevents the fMLP-induced respiratory burst response (Thelen et al., Proc. Natl. Acad. Sci. USA, 91, p. 4960-64 (1994)). Indeed, these experiments with wortmannin, as well as other experimental evidence, shows that PI3K activity in cells of hematopoietic lineage, particularly neutrophils, monocytes, and other types of leukocytes, is involved in many of the non-memory immune response associated with acute and chronic inflammation.

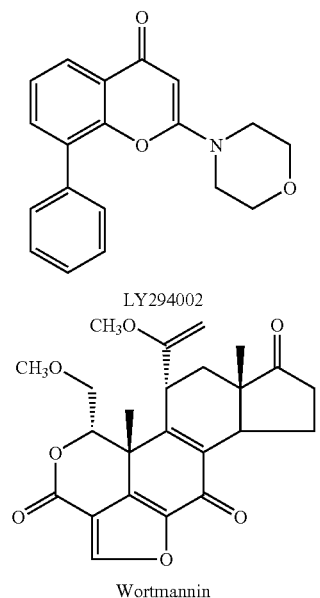

Based on studies using wortmannin, there is evidence that PI3-kinase function is also required for some aspects of leukocyte signaling through G-protein coupled receptors (Thelen et al., 1994, above). Moreover, it has been shown that wortmannin and LY294002 block neutrophil migration and superoxide release. Cyclooxygenase inhibiting benzofuran derivatives are disclosed by John M. Janusz et al., in J. Med. Chem. 1998; Vol. 41, No. 18.

It is now well understood that deregulation of onocogenes and tumour-suppressor genes contributes to the formation of malignant tumours, for example by way of increase cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al., *Annual Rev. Cell Dev. Biol.*, 2001, 17: 615-617 and Foster et al., *J. Cell Science*, 2003, 116: 3037-3040).

Class I PI3K is a heterodimer consisting of a p110 catalytic subunit and a regulatory subunit, and the family is further divided into class Ia and Class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50β, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

There is now considerable evidence indicating that Class Ia PI3K enzymes contribute to tumourigenesis in a wide variety of human cancers, either directly or indirectly (Vivanco and Sawyers, *Nature Reviews Cancer*, 2002, 2, 489-501). For example, the p110α subunit is amplified in some tumours such as those of the ovary (Shayesteh, et al., *Nature Genetics*, 1999, 21: 99-102) and cervix (Ma et al., *Oncogene*, 2000, 19: 2739-2744). More recently, activating mutations within p110α (PIK3CA gene) have been associated with various other tumors such as those of the colon and of the breast and lung (Samuels, et al., *Science*, 2004, 304, 554). Tumor-related mutations in p85α have also been identified in cancers such as those of the ovary and colon (Philp et al., *Cancer Research*, 2001, 61, 7426-7429). In addition to direct effects, it is believed that activation of Class Ia PI3K contributes to tumourigenic events that occur upstream in signaling pathways, for example by way of ligand-dependent or ligand-independent activation of receptor tyrosine kinases, GPCR systems or integrins (Vara et al., *Cancer Treatment Reviews*, 2004, 30, 193-204). Examples of such upstream signaling pathways include over-expression of the receptor tyrosine kinase Erb2 in a variety of tumors leading to activation of PI3K-mediated pathways (Harari et al., *Oncogene*, 2000, 19, 6102-6114) and over-expression of the oncogene Ras (Kauffmann-Zeh et al., *Nature*, 1997, 385, 544-548). In addition, Class Ia PI3Ks may contribute indirectly to tumourigenesis caused by various downstream signaling events. For example, loss of function of the PTEN tumor-suppressor phosphatase that catalyses conversion of PI(3,4,5)P3 back to PI(4,5)P2 is associated with a very broad range of tumors via deregulation of PI3K-mediated production of PI(3,4,5)P3 (Simpson and Parsons, *Exp. Cell Res.*, 2001, 264, 29-41). Furthermore, augmentation of the effects of other PI3K-mediated signaling events is believed to contribute to a variety of cancers, for example by activation of AKT (Nicholson and Andeson, *Cellular Signaling*, 2002, 14, 381-395).

In addition to a role in mediating proliferative and survival signaling in tumor cells, there is also good evidence that class Ia PI3K enzymes also contributes to tumourigenesis via its function in tumor-associated stromal cells. For examples, PI3K signaling is known to play an important role in mediating angiogenic events in endothelial cells in response to pro-angiogenic factors such as VEGF (abid et al., *Arterioscler, Thromb. Vasc. Biol.*, 2004, 24, 294-300). As Class I PI3K enzymes are also involved in motility and migration (Sawyer, Expert Opinion investing. Drugs, 2004, 13, 1-19), PI3K inhibitors are anticipated to provide therapeutic benefit via inhibition of tumor cell invasion and metastasis.

SUMMARY OF THE INVENTION

This invention relates to novel compounds of Formula (I):

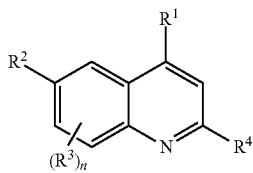
(I)

in which

R² is an optionally substituted ring system selected from a group consisting of: formula (II), (III), (IV), (V), (VI), (VII),(VIII), (IX) and (X):

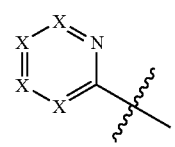
(II)

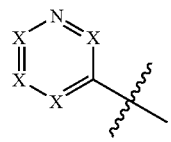
(III)

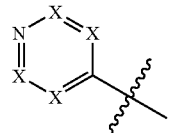
(IV)

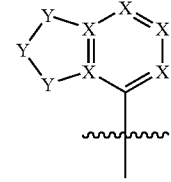
(V)

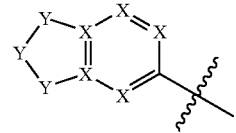
(VI)

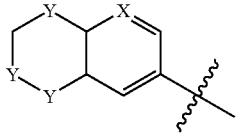
(VII)

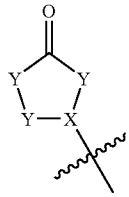
(VIII)

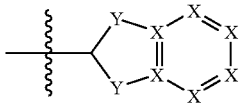
(IX)

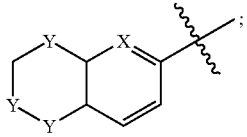
(X)

R¹ is selected from a group consisting of: heterocycloalkyl, substituted heterocycloalkyl, aryl, substituted aryl, heteroaryl and substituted heteroaryl;

each R³ and R⁴ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, nitro, acyloxy, and aryloxy;

n is 1-2;

X is C or N; Y is C, O, N or S;

and/or a pharmaceutically acceptable salt thereof;

provided that in each of formula (V) to (X) at least one X or Y is not carbon;

further provided that R² is not quinoline or substituted quinoline.

R³ can be attached to any one of the four open carbon positions.

Suitably, this invention relates to a compound of formula (I) or a pharmaceutically acceptable salt thereof.

Suitably, this invention relates to a method of treating cancer, which comprises administering to a subject in need thereof an effective amount of a compound of Formula (I).

Suitably, this invention relates to a method of treating one or more disease states selected from: autoimmune disorders, inflammatory diseases, cardiovascular diseases, neurodegenerative diseases, allergy, asthma, pancreatitis, multiorgan failure, kidney diseases, platelet aggregation, sperm motility, transplantation rejection, graft rejection and lung injuries, which comprises administering to a subject in need thereof an effective amount of a compound of Formula (I).

Included in the present invention are methods of co-administering the present PI3 kinase inhibiting compounds with further active ingredients.

DETAILED DESCRIPTION OF THE INVENTION

Present compounds of Formula (I) inhibit one or more PI3 kinases. Suitably, the compounds of formula (I) inhibit PI3Kα. Also, compounds within the scope of this invention inhibit one or more PI3 kinases selected from: PI3Kδ, PI3Kβ and PI3Kγ.

Suitably, this invention relates to novel compounds of Formula (I)(A):

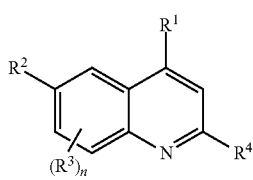

in which
R² is an optionally substituted ring system selected from a group consisting of: formula (II), (III), and (IV) as defined above;
R¹ is selected from a group consisting of: heterocycloalkyl, substituted heterocycloalkyl, aryl, substituted aryl, heteroaryl and substituted heteroaryl;
each R³ and R⁴ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, nitro, acyloxy, and aryloxy;
n is 1-2;
X is C or N; Y is C, O, N or S;
and/or a pharmaceutically acceptable salt thereof;

Suitably, included among the presently invented compounds of formula (I) are those of formula (I)(B),

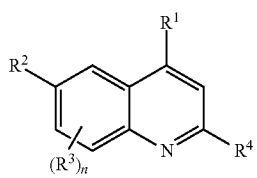

wherein R² is selected from a group consisting of: formula (V),(VI) and (IX) as defined above;
R¹ is selected from a group consisting of: heterocycloalkyl, substituted heterocycloalkyl, aryl, substituted aryl, heteroaryl and substituted heteroaryl;
each R³ and R⁴ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, nitro, acyloxy, and aryloxy;
n is 1-2;
X is C or N; Y is C, O, N or S;
and/or a pharmaceutically acceptable salt thereof;
provided that in each of formula (V), (VI) and (IX) at least one X or Y is not carbon.

Suitably, included among the presently invented compounds of formula (I) are those of formula (I)(C),

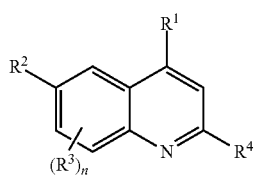

wherein R² is selected from a group consisting of: formula (VII), (VIII) and (X) as defined above;
R¹ is selected from a group consisting of: heterocycloalkyl, substituted heterocycloalkyl, aryl, substituted aryl, heteroaryl and substituted heteroaryl;
each R³ and R⁴ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, nitro, acyloxy, and aryloxy;
n is 1-2;
X is C or N; Y is C, O, N or S;
and/or a pharmaceutically acceptable salt thereof;
provided that in each of formula (VII), (VIII) and (X) at least one X or Y is not carbon.

Suitably, included among the presently invented compounds of formula (I) are those of formula (I)(D):

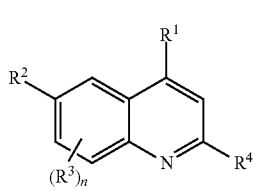

in which
R² is an optionally substituted ring system selected from a group consisting of: formula (II), (III), (IV), (V), (VI), and (VIII):

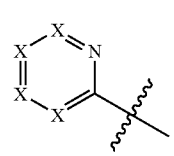

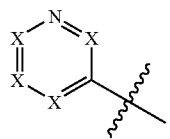

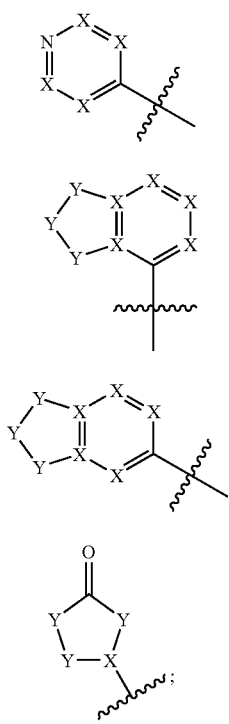

(IV)

(V)

(VI)

(VIII)

R[1] is selected from a group consisting of: heterocycloalkyl, substituted heterocycloalkyl, aryl, substituted aryl, heteroaryl and substituted heteroaryl;

each R[3] and R[4] is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, nitro, acyloxy, and aryloxy;

n is 1-2;

X is C or N; Y is C, O, N or S;

and/or a pharmaceutically acceptable salt thereof;

provided that in each of formula (V), (VI) and (VIII) at least one X or Y is not carbon.

Suitably, among the present invention are compounds of Formula (I)(D),wherein R[1] is heteroaryl or substituted heteroaryl; R[2] is selected from a group consisting of: formula (III) and formula (VI).

Suitably, among the present invention are compounds of Formulas (I), (I)(A), (I)(B), (I)(C) and (I)(D), wherein R[2] is pyridinyl or substituted pyridinyl.

Suitably, among the present invention are compounds of Formulas (I), (I)(A), (I)(B), (I)(C) and (I)(D), wherein R[2] is not pyridinyl or substituted pyridinyl.

Suitably, among the present invention are compounds of Formula (I) wherein R[2] is an optionally substituted ring system selected from the group consisting of Formulas (V)(A), (VI)(A), (VI)(B) and (IX)(A):

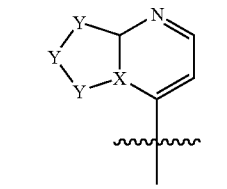

(V)(A)

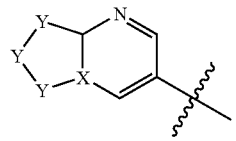

(VI)(A)

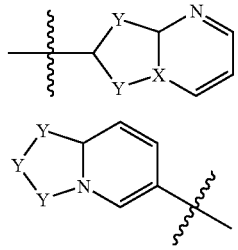

(IX)(A)

(VI)(B)

wherein X is C or N; Y is C, O, N or S;

Suitably, among the present invention are compounds of Formula (I) wherein R[2] is an optionally substituted ring system selected from the group consisting of Formulas (VII)(A), (VIII)(A) and (X)(A):

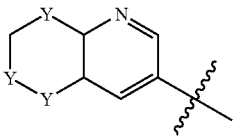

(VII)(A)

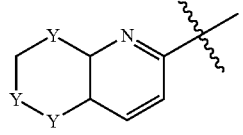

(X)(A)

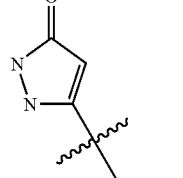

(VIII)(A)

wherein X is C or N; Y is C, O, N or S; provided that at least one Y is not carbon.

Suitably, this invention relates to novel compounds of Formula (I)(G):

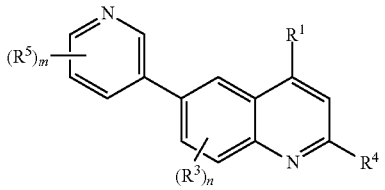

(I)(G)

in which
each $R^1$, $R^3$, $R^4$ and $R^5$ is independently selected from: hydrogen, halogen, acyl, amino, substituted amino, arylamino, acylamino, heterocycloalkylamino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, acyloxy, and aryloxy;

or $R^5$ is $R^6$, wherein $R^6$ is —$SO_2NHR^{80}$ or —$NHSO_2R^{80}$, in which $R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo or —$(CH_2)_pCOOH$, or heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, or —$(CH_2)_pCOOH$, wherein p is 0-2, n is 0-2, m is 0-3;

or a pharmaceutically acceptable salt thereof;

Suitably, this invention relates to novel compounds of Formula (I)(H):

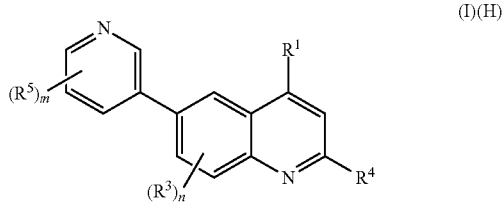

(I)(H)

in which
$R^1$ is selected from a group consisting of: heteroaryl, substituted heteroaryl, heterocycloalkyl, substituted heterocycloalkyl, amino, substituted amino, arylamino, acylamino, heterocycloalkylamino, alkoxy, $C_1$-$C_6$alkyl and substituted $C_1$-$C_6$alkyl;

each $R^3$ and $R^4$ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, cyano, hydroxyl and alkoxy;

each $R^5$ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, cyano, hydroxyl and alkoxy; or $R^5$ is $R^6$, wherein $R^6$ is —$SO_2NHR^{80}$ or —$NHSO_2R^{80}$, in which $R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo or —$(CH_2)_pCOOH$, or heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, or —$(CH_2)_pCOOH$, wherein p is 0-2, n is 0-2, m is 0-2;

or a pharmaceutically acceptable salt thereof;

Suitably, this invention relates to novel compounds of Formula (I)(J):

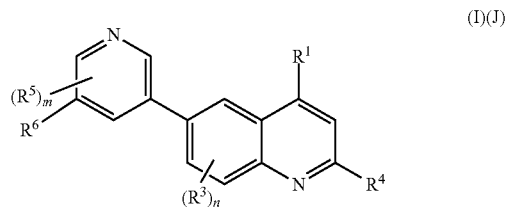

(I)(J)

in which
$R^1$ is selected from a group consisting of: heteroaryl, substituted heteroaryl, heterocycloalkyl, substituted heterocycloalkyl, amino, substituted amino, arylamino, acylamino, heterocycloalkylamino, alkoxy, $C_1$-$C_6$alkyl and substituted $C_1$-$C_6$alkyl;

each $R^3$ and $R^4$ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, cyano, hydroxyl and alkoxy;

each $R^5$ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, cyano, hydroxyl, alkoxy, nitro;

$R^6$ is —$SO_2NHR^{80}$ or —$NHSO_2R^{80}$, in which $R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo or —$(CH_2)_pCOOH$, or heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, or —$(CH_2)_pCOOH$, wherein p is 0-2;

n is 0-2, m is 0-2;

or a pharmaceutically acceptable salt thereof.

Suitably, this invention relates to novel compounds of Formula (I)(K):

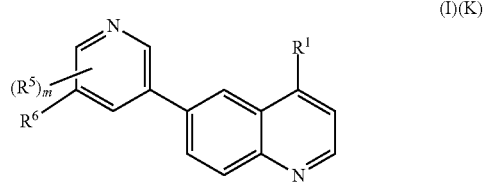

(I)(K)

in which
R¹ is selected from a group consisting of: heteroaryl, substituted heteroaryl, heterocycloalkyl, substituted heterocycloalkyl, amino, substituted amino, arylamino, acylamino, heterocycloalkylamino, alkoxy, $C_1$-$C_6$alkyl and substituted $C_1$-$C_6$alkyl;

each $R^5$ is independently selected from: hydrogen, halogen, acyl, amino, substituted amino, $C_1$-$C_6$alkyl, substituted $C_1$-$C_6$alkyl, cyano, hydroxyl, alkoxy;

n is 0-2, m is 0-1;

$R^6$ is —$SO_2NHR^{80}$ or —$NHSO_2R^{80}$, in which $R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo or —$(CH_2)_pCOOH$, or heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, or —$(CH_2)_pCOOH$, wherein p is 0-2;

or a pharmaceutically acceptable salt thereof.

Suitably, this invention relates to novel compounds of Formula (I)(L):

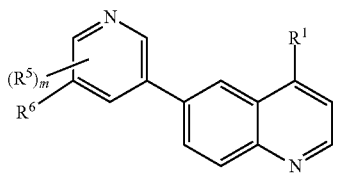

(I)(L)

in which
R¹ is selected from a group consisting of: heteroaryl, substituted heteroaryl, heterocycloalkyl, substituted heterocycloalkyl, amino, substituted amino, arylamino, acylamino, heterocycloalkylamino, alkoxy, $C_1$-$C_6$alkyl and substituted $C_1$-$C_6$alkyl;

each $R^5$ is independently selected from: hydrogen, halogen, acyl, amino, substituted amino, $C_1$-$C_6$alkyl, substituted $C_1$-$C_6$alkyl, cyano, hydroxyl, alkoxy;

$R^6$ is —$SO_2NHR^{80}$ or —$NHSO_2R^{80}$, wherein $R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo or —$(CH_2)_pCOOH$, or heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, or —$(CH_2)_pCOOH$;

p is 0-2, m is 0-1;

or a pharmaceutically acceptable salt thereof

Suitably, this invention relates to novel compounds of Formula (I)(M):

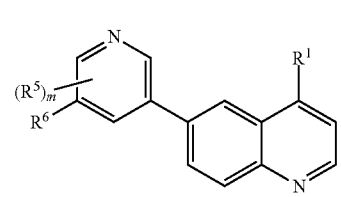

(I)(M)

in which
R¹ is selected from a group consisting of: heteroaryl, substituted heteroaryl, heterocycloalkyl, substituted heterocycloalkyl, amino, substituted amino, arylamino, acylamino, heterocycloalkylamino, alkoxy, $C_1$-$C_6$alkyl and substituted $C_1$-$C_6$alkyl;

each $R^5$ is independently selected from: hydrogen, halogen, acyl, amino, substituted amino, $C_1$-$C_6$alkyl, substituted $C_1$-$C_6$alkyl, cyano, hydroxyl, alkoxy;

$R^6$ is —$NHSO_2R^{80}$, wherein $R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo or —$(CH_2)_pCOOH$, or heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, or —$(CH_2)_pCOOH$; p is 0-2, m is 0-1;

or a pharmaceutically acceptable salt thereof.

Suitably, this invention relates to novel compounds of Formula (I)(N):

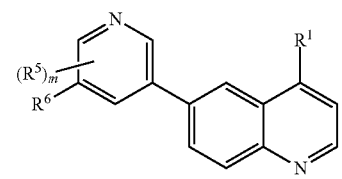

(I)(N)

in which
R¹ is selected from a group consisting of: heteroaryl, substituted heteroaryl, heterocycloalkyl, substituted heterocycloalkyl, amino, substituted amino, arylamino, acylamino, heterocycloalkylamino, alkoxy, $C_1$-$C_6$alkyl and substituted $C_1$-$C_6$alkyl;

each $R^5$ is independently selected from: hydrogen, halogen, acyl, amino, substituted amino, $C_1$-$C_6$alkyl, substituted $C_1$-$C_6$alkyl, cyano, hydroxyl, alkoxy;

$R^6$ is —$SO_2NHR^{80}$, wherein $R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo or —$(CH_2)_pCOOH$, or heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, or —$(CH_2)_p$COOH;

p is 0-2, m is 0-1 or a pharmaceutically acceptable salt thereof.

Suitably, this invention relates to compounds of Formulas (I)M and (I)(N), wherein $R^1$ is selected from the group consisting of: optionally substituted piperazine, optionally substituted pyridazine, optionally substituted morphline, optionally substituted pyrazole, substituted amino and optionally substituted piperidine.

Suitably, this invention relates to compounds of Formulas (I)M and (I)(N), wherein $R^1$ is selected from the group consisting of: optionally substituted piperazine, optionally substituted pyridazine, optionally substituted morphline, optionally substituted pyrazole, substituted amino and optionally substituted piperidine;

$R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl and substituted aryl.

Suitably, this invention relates to compounds of Formulas (I)M and (I)(N), wherein $R^1$ is selected from the group consisting of: optionally substituted piperazine, optionally substituted pyridazine, optionally substituted morphline, optionally substituted pyrazole, substituted amino and optionally substituted piperidine;

$R^{80}$ is selected from a group consisting of: aryl optionally substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo or —$(CH_2)_p$COOH, or heteroaryl optionally substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, or —$(CH_2)_p$COOH; p is 0-2.

Suitably, this invention relates to the compound defined in formula (I), (I)(A), (I)(B), (I)(C), (I)D), (I)(E), (I)(F), (I)(G), (I)(H), (I)(J), (I)(K), (I)(M) or (I)(N).

Suitably, among the present invention are compounds selected from a group consisting of:

5-[4-(4-pyridinyl)-6-quinolinyl]-1H-indazol-3-amine;
4,4'-di-4-pyridinyl-6,6'-biquinoline;
3-(4-morpholinylsulfonyl)-5-[4-(4-pyridinyl)-6-quinolinyl]-2-pyridinamine;
2-amino-N-methyl-5-[4-(4-pyridinyl)-6-quinolinyl]-3-pyridinesulfonamide;
2-amino-N,N-dimethyl-5-[4-(4-pyridinyl)-6-quinolinyl]-3-pyridinesulfonamide;
2-amino-5-[4-(4-pyridinyl)-6-quinolinyl]-3-pyridinesulfonamide;
5-[4-(4-pyridinyl)-6-quinolinyl]-3-(1H-tetrazol-5-yl)-2-pyridinamine;
6-(3-methyl-3H-imidazo[4,5-b]pyridin-6-yl)-4-(4-pyridinyl)quinoline;
6-(1-methyl-1H-imidazo[4,5-b]pyridin-6-yl)-4-(4-pyridinyequinoline;
3-(1-piperidinylsulfonyl)-5-[4-(4-pyridinyl)-6-quinolinyl]-2-pyridinamine;
2-amino-N-ethyl-5-[4-(4-pyridinyl)-6-quinolinyl]-3-pyridinesulfonamide;
2-amino-N-[2-(dimethylamino)ethyl]-N-methyl-5-[4-(4-pyridinyl)-6-quinolinyl]-3-pyridinesulfonamide;
2-amino-N-(3-pyridinylmethyl)-5-[4-(4-pyridinyl)-6-quinolinyl]-3-pyridinesulfonamide;
2-amino-N-3-pyridinyl-5-[4-(4-pyridinyl)-6-quinolinyl]-3-pyridinesulfonamide;
2-amino-N-phenyl-5-[4-(4-pyridinyl)-6-quinolinyl]-3-pyridinesulfonamide;
2-amino-N-(3-hydroxypropyl)-5-[4-(4-pyridinyl)-6-quinolinyl]-3-pyridinesulfonamide;
3-(1-piperazinylsulfonyl)-5-[4-(4-pyridinyl)-6-quinolinyl]-2-pyridinamine;
3-{[4-(methylsulfonyl)-1-piperazinyl]sulfonyl}-5-[4-(4-pyridinyl)-6-quinolinyl]-2-pyridinamine;
2-amino-5-[4-(4-pyridinyl)-6-quinolinyl]-N-[3-(1-pyrrolidinyl)propyl]-3-pyridinesulfonamide;
3-[(3-amino-1H-pyrazol-1-yl)sulfonyl]-5-[4-(4-pyridinyl)-6-quinolinyl]-2-pyridinamine;
3-[(4-methyl-1-piperazinyl)sulfonyl]-5-[4-(4-pyridinyl)-6-quinolinyl]-2-pyridinamine;
2-[4-({2-amino-5-[4-(4-pyridinyl)-6-quinolinyl]-3-pyridinyl}sulfonyl)-1-piperazinyl]ethanol;
2-amino-N-(2,4-difluorophenyl)-5-[4-(4-pyridinyl)-6-quinolinyl]-3-pyridinesulfonamide;
2-amino-N-[3-(2-oxo-1-pyrrolidinyl)propyl]-5-[4-(4-pyridinyl)-6-quinolinyl]-3-pyridinesulfonamide;
2-amino-N-2-pyridinyl-5-[4-(4-pyridinyl)-6-quinolinyl]-3-pyridinesulfonamide;
2-amino-N-4-pyridinyl-5-[4-(4-pyridinyl)-6-quinolinyl]-3-pyridinesulfonamide;
3-{[4-(2-chlorophenyl)-1-piperazinyl]sulfonyl}-5-[4-(4-pyridinyl)-6-quinolinyl]-2-pyridinamine;
2-amino-N-[2-(methyloxy)ethyl]-5-[4-(4-pyridinyl)-6-quinolinyl]-3-pyridinesulfonamide;
N,N-dimethyl-3-(4-morpholinylsulfonyl)-5-[4-(4-pyridinyl)-6-quinolinyl]-2-pyridinamine;
N-methyl-3-(4-morpholinylsulfonyl)-5-[4-(4-pyridinyl)-6-quinolinyl]-2-pyridinamine;
N-ethyl-3-(4-morpholinylsulfonyl)-5-[4-(4-pyridinyl)-6-quinolinyl]-2-pyridinamine;
N,N-diethyl-3-(4-morpholinylsulfonyl)-5-[4-(4-pyridinyl)-6-quinolinyl]-2-pyridinamine;
6-[6-(ethyloxy)-5-(4-morpholinylsulfonyl)-3-pyridinyl]-4-(4-pyridinyl)quinoline;
6-[6-(methyloxy)-5-(4-morpholinylsulfonyl)-3-pyridinyl]-4-(4-pyridinyl)quinoline;
3-methyl-7-[4-(4-pyridinyl)-6-quinolinyl]-2H-1,2,4-benzothiadiazine 1,1-dioxide;
6-[4-(4-pyridinyl)-6-quinolinyl]-3,4-dihydro-1(2H)-isoquinolinone;
4-(4-pyridinyl)-6-(1H-pyrrolo[2,3-b]pyridin-5-yl)quinoline;
6-(1H-indazol-5-yl)-4-(4-pyridinyl)quinoline;
6-[4-(4-pyridinyl)-6-quinolinyl]-1H-indazol-3-amine;
4-(4-pyridinyl)-6-(1H-pyrrolo[2,3-b]pyridin-4-yl)quinoline;
6-(1H-indazol-6-yl)-4-(4-pyridinyl)quinoline;
{3-oxo-6-[4-(4-pyridinyl)-6-quinolinyl]-2,3-dihydro-1H-isoindol-1-yl}acetic acid;
4-(4-pyridinyl)-6-(7H-pyrrolo[2,3-d]pyrimidin-4-yl)quinoline;
6-[4-(4-pyridinyl)-6-quinolinyl]-1,3-dihydro-2H-imidazo[4,5-b]pyridin-2-one;
6-[4-(4-pyridinyl)-6-quinolinyl][1,3]oxazolo[4,5-b]pyridin-2(3H)-one;
6-(1H-pyrazolo[3,4-b]pyridin-5-yl)-4-(4-pyridinyl)quinoline;
4-(4-pyridinyl)-6-(1H-[1,2,3]triazolo[4,5-b]pyridin-6-yl)quinoline;
6-(1H-imidazo[4,5-b]pyridin-6-yl)-4-(4-pyridinyl)quinoline;
6-(1-oxido-3-pyridinyl)-4-(4-pyridinyl)quinoline;
4-(4-pyridinyl)-6-(1H-pyrrolo[3,2-b]pyridin-6-yl)quinoline;

5-[4-(4-pyridinyl)-6-quinolinyl]-1H-pyrazolo[3,4-b]pyridin-3-amine;
6-(3-methyl-1H-pyrazolo[3,4-b]pyrazin-5-yl)-4-(4-pyridinyl)quinoline;
2-methyl-N-{5-[4-(4-pyridinyl)-6-quinolinyl]-1H-pyrazolo[3,4-b]pyridin-3-yl}propanamide;
N-{5-[4-(4-pyridinyl)-6-quinolinyl]-1H-pyrazolo[3,4-b]pyridin-3-yl}acetamide;
N-{5-[4-(4-pyridinyl)-6-quinolinyl]-1H-pyrazolo[3,4-b]pyridin-3-yl}methanesulfonamide;
2-(methyloxy)-N-{5-[4-(4-pyridinyl)-6-quinolinyl]-1H-pyrazolo[3,4-b]pyridin-3-yl}acetamide;
6-pyrazolo[1,5-a]pyrimidin-6-yl-4-(4-pyridinyl)quinoline;
5-[4-(4-pyridinyl)-6-quinolinyl]-1,2-dihydro-3H-pyrazolo[3,4-b]pyridin-3-one;
6-(1-methyl-1H-pyrrolo[3,2-b]pyridin-6-yl)-4-(4-pyridinyl)quinoline;
6-(3-methyl-1H-pyrazolo[3,4-b]pyridin-5-yl)-4-(4-pyridinyl)quinoline;
3-[6-(1H-pyrazolo[3,4-b]pyridin-5-yl)-4-quinolinyl]benzenesulfonamide;
7-[4-(4-pyridinyl)-6-quinolinyl]-2H-pyrido[3,2-b][1,4]oxazin-3(4H)-one;
4-[4-(4-pyridinyl)-6-quinolinyl]-1,3-dihydro-2H-pyrrolo[2,3-b]pyridin-2-one;
2-amino-N,N-dimethyl-5-[2-methyl-4-(4-pyridinyl)-6-quinolinyl]-3-pyridinesulfonamide;
2-amino-5-[8-fluoro-4-(4-pyridinyl)-6-quinolinyl]-N,N-dimethyl-3-pyridinesulfonamide;
2-amino-N,N-dimethyl-5-[8-methyl-4-(4-pyridinyl)-6-quinolinyl]-3-pyridinesulfonamide;
2-amino-5-[7-fluoro-4-(4-pyridinyl)-6-quinolinyl]-N,N-dimethyl-3-pyridinesulfonamide;
5-[5-fluoro-4-(4-pyridinyl)-6-quinolinyl]-3-pyridinesulfonamide;
5-[7-methyl-4-(4-pyridinyl)-6-quinolinyl]-3-pyridinesulfonamide;
5-[5-methyl-4-(4-pyridinyl)-6-quinolinyl]-3-pyridinesulfonamide;
4-(4-pyridinyl)-6-[5-(trifluoromethyl)-3-pyridinyl]quinoline;
(4,6-di-4-pyridinylquinoline;
6-(3-pyridinyl)-4-(4-pyridinyl)quinoline;
6-(2-pyridinyl)-4-(4-pyridinyl)quinoline;
6-(2,1,3-benzoxadiazol-5-yl)-4-(4-pyridinyl)quinoline;
6-(2,1,3-benzothiadiazol-5-yl)-4-(4-pyridinyl)quinoline;
5-[4-(4-pyridinyl)-6-quinolinyl]-1,2-dihydro-3H-pyrazol-3-one;
2-ethyl-6-[4-(4-pyridinyl)-6-quinolinyl]-4(1H)-pyrimidinone;
7-[4-(4-pyridinyl)-6-quinolinyl]-2-quinoxalinol;
2-(4-morpholinyl)-7-[4-(4-pyridinyl)-6-quinolinyl]quinoxaline;
4-(4-morpholinyl)-6-[4-(4-pyridinyl)-6-quinolinyl]quinazoline;
1-phenyl-5-[4-(4-pyridinyl)-6-quinolinyl]-1,2-dihydro-3H-pyrazol-3-one;
1-(3-methylphenyl)-5-[4-(4-pyridinyl)-6-quinolinyl]-1,2-dihydro-3H-pyrazol-3-one;
1-(3-chlorophenyl)-5-[4-(4-pyridinyl)-6-quinolinyl]-1,2-dihydro-3H-pyrazol-3-one;
1-methyl-5-[4-(4-pyridinyl)-6-quinolinyl]-1,2-dihydro-3H-pyrazol-3-one;
N-(2,4-difluorophenyl)-5-[4-(4-pyridinyl)-6-quinolinyl]-3-pyridinesulfonamide;
6-(1H-indol-5-yl)-4-(4-pyridinyl)quinoline;
6-(1H-indol-6-yl)-4-(4-pyridinyl)quinoline;
5-[4-(4-pyridinyl)-6-quinolinyl]-1,3-dihydro-2H-indol-2-one;
6-[4-(4-pyridinyl)-6-quinolinyl]-1,3-dihydro-2H-indol-2-one;
7-[4-(4-pyridinyl)-6-quinolinyl]-4(1H)-quinazolinone;
6-[4-(4-pyridinyl)-6-quinolinyl]-4(1H)-quinazolinone;
6-[4-(4-pyridinyl)-6-quinolinyl]-1,2-benzisothiazol-3(2H)-one 1,1-dioxide;
6-[4-(4-pyridinyl)-6-quinolinyl]-1,8-naphthyridin-2(1H)-one;
6-(1,3-benzoxazol-5-yl)-4-(4-pyridinyl)quinoline;
7-[4-(4-pyridinyl)-6-quinolinyl]-1,4-dihydropyrido[2,3-b]pyrazine-2,3-dione;
3-amino-5-[4-(4-pyridinyl)-6-quinolinyl]-2-pyridinecarboxamide;
5-[4-(4-pyridinyl)-6-quinolinyl]-3-pyridinamine;
4-[4-(4-pyridinyl)-6-quinolinyl]thieno[2,3-c]pyridine-2-carboxamide;
methyl 4-[4-(4-pyridinyl)-6-quinolinyl]-1H-pyrrolo[2,3-c]pyridine-2-carboxylate;
4-[4-(4-pyridinyl)-6-quinolinyl]-1H-pyrrolo[2,3-c]pyridine-2-carboxamide;
6-(1H-benzimidazol-2-yl)-4-(4-pyridinyl)quinoline;
6-(1H-imidazo[4,5-c]pyridin-2-yl)-4-(4-pyridinyequinoline;
6-(1H-imidazo[4,5-b]pyridin-2-yl)-4-(4-pyridinyl)quinoline;
6-(1H-purin-8-yl)-4-(4-pyridinyl)quinoline;
6-imidazo[1,2-a]pyridin-6-yl-4-(4-pyridinyl)quinoline;
6-imidazo[1,2-a]pyrimidin-6-yl-4-(4-pyridinyl)quinoline;
1-{6-[4-(4-pyridinyl)-6-quinolinyl]imidazo[1,2-a]pyridin-3-yl}-1-propanone;
6-(4-pyridazinyl)-4-(4-pyridinyl)quinoline;
1-{6-[4-(4-pyridinyl)-6-quinolinyl]imidazo[1,2-a]pyridin-3-yl}-1-propanol;
4-(1-piperidinyl)-6-(1H-pyrazolo[3,4-b]pyridin-5-yl)quinoline;
4-(4-morpholinyl)-6-(1H-pyrazolo[3,4-b]pyridin-5-yl)quinoline;
4-(4-methyl-1-piperazinyl)-6-(1H-pyrazolo[3,4-b]pyridin-5-yl)quinoline;
4-(4-pyridazinyl)-6-(1H-pyrrolo[2,3-b]pyridin-5-yl)quinoline;
6-(1H-imidazo[4,5-b]pyridin-6-yl)-4-(1-piperidinyl)quinoline;
6-(1H-imidazo[4,5-b]pyridin-6-yl)-4-(4-morpholinyl)quinoline;
2-amino-5-{4-[3-(aminosulfonyl)phenyl]-6-quinolinyl}-N,N-dimethyl-3-pyridinesulfonamide;
2-amino-N,N-dimethyl-5-[4-(2-methyl-4-pyridinyl)-6-quinolinyl]-3-pyridinesulfonamide;
2-amino-5-(4-{3-[(dimethylamino)sulfonyl]phenyl}-6-quinolinyl)-N,N-dimethyl-3-pyridinesulfonamide;
2-amino-N,N-dimethyl-5-[4-(4-pyridazinyl)-6-quinolinyl]-3-pyridinesulfonamide;
2-amino-N,N-dimethyl-5-[4-(1H-pyrazol-4-yl)-6-quinolinyl]-3-pyridinesulfonamide;
2-amino-N,N-dimethyl-5-(4-phenyl-6-quinolinyl)-3-pyridinesulfonamide;
2-amino-N,N-dimethyl-5-[4-(1H-pyrazol-3-yl)-6-quinolinyl]-3-pyridinesulfonamide;
2-amino-5-[4-(2,6-dimethyl-4-pyridinyl)-6-quinolinyl]-N,N-dimethyl-3-pyridinesulfonamide;
2-amino-5-(4-{3-[(aminosulfonyl)methyl]phenyl}-6-quinolinyl)-N,N-dimethyl-3-pyridinesulfonamide;
2-amino-5-[4-(3-cyanophenyl)-6-quinolinyl]-N,N-dimethyl-3-pyridinesulfonamide;

2-amino-5-{4-[5-(aminosulfonyl)-3-pyridinyl]-6-quinolinyl}-N,N-dimethyl-3-pyridinesulfonamide;
5,5'-(4,6-quinolinediyl)di(3-pyridinesulfonamide);
2-amino-N,N-dimethyl-5-[4-(3-{[(1-methylethyl)amino]sulfonyl}phenyl)-6-quinolinyl]-3-pyridinesulfonamide;
2-amino-N,N-dimethyl-5-(4-{3-[(methylamino)sulfonyl]phenyl}-6-quinolinyl)-3-pyridinesulfonamide;
2-amino-N,N-dimethyl-5-{4-[6-(4-methyl-1-piperazinyl)-3-pyridinyl]-6-quinolinyl}-3-pyridinesulfonamide;
5-[4-(3-cyanophenyl)-6-quinolinyl]-3-pyridinesulfonamide;
5-[4-(2-methyl-4-pyridinyl)-6-quinolinyl]-3-pyridinesulfonamide;
5-[4-(4-pyridazinyl)-6-quinolinyl]-3-pyridinesulfonamide;
5-{4-[6-(4-methyl-1-piperazinyl)-3-pyridinyl]-6-quinolinyl}-3-pyridinesulfonamide;
5-[4-(2,6-dimethyl-4-pyridinyl)-6-quinolinyl]-3-pyridinesulfonamide;
5-[4-(1H-pyrazol-4-yl)-6-quinolinyl]-3-pyridinesulfonamide;
5-(4-{3-[(dimethylamino)sulfonyl]phenyl}-6-quinolinyl)-3-pyridinesulfonamide;
5-[4-(1-methyl-1H-pyrazol-4-yl)-6-quinolinyl]-3-pyridinesulfonamide;
5-{4-[2-(4-morpholinylmethyl)phenyl]-6-quinolinyl}-3-pyridinesulfonamide;
5-{4-[2-(4-morpholinylcarbonyl)phenyl]-6-quinolinyl}-3-pyridinesulfonamide;
5-{4-[2-(4-morpholinyl)phenyl]-6-quinolinyl}-3-pyridinesulfonamide;
4'-(4-pyridinyl)-3,4-dihydro-6,6'-biquinolin-2(1H)-one;
6-[4-(4-pyridinyl)-6-quinolinyl]-3,4-dihydro-1,8-naphthyridin-2(1H)-one;
2-amino-5-[4-(4-pyridinyl)-6-quinolinyl]-3-pyridinecarbaldehyde;
{2-amino-5-[4-(4-pyridinyl)-6-quinolinyl]-3-pyridinyl}methyl acetate;
5-[4-(4-pyridinyl)-6-quinolinyl]-2,3-pyridinediamine;
2-amino-5-[4-(4-pyridinyl)-6-quinolinyl]-3-pyridinecarboxamide;
6-[4-(4-pyridinyl)-6-quinolinyl]pyrido[2,3-d]pyrimidin-4(1H)-one;
5-{5-[4-(4-pyridinyl)-6-quinolinyl]-3-pyridinyl}-1,2-dihydro-3H-pyrazol-3-one;
7-[4-(4-pyridinyl)-6-quinolinyl]pyrido[3,2-d]pyrimidin-4(1H)-one;
6-[5-(1H-pyrazol-5-yl)-3-pyridinyl]-4-(4-pyridinyl)quinoline;
N-(2,4-difluorophenyl)-5-[4-(4-pyridinyl)-6-quinolinyl]-3-pyridinecarboxamide;
6-[2-(methyloxy)-4-pyridinyl]-4-(4-pyridinyequinoline;
6-[6-(methyloxy)-3-pyridinyl]-4-(4-pyridinyl)quinoline;
4-[4-(4-pyridinyl)-6-quinolinyl]-2-pyridinol;
6-[2-(methyloxy)-5-pyrimidinyl]-4-(4-pyridinyl)quinoline;
{6-[4-(4-pyridinyl)-6-quinolinyl]-2-pyridinyl}methanol;
6-(2-chloro-4-pyridinyl)-4-(4-pyridinyl)quinoline;
4-(4-pyridinyl)-6-(5-pyrimidinyl)quinoline;
5-[4-(4-pyridinyl)-6-quinolinyl]-2(1H)-pyrimidinone;
6-[2,6-bis(methyloxy)-3-pyridinyl]-4-(4-pyridinyl)quinoline;
6-[6-(4-methyl-1-piperazinyl)-3-pyridinyl]-4-(4-pyridinyl)quinoline;
6-[6-(4-morpholinyl)-3-pyridinyl]-4-(4-pyridinyl)quinoline;
6-(6-chloro-3-pyridinyl)-4-(4-pyridinyl)quinoline;
6-[6-(ethyloxy)-3-pyridinyl]-4-(4-pyridinyl)quinoline;
N,N-dimethyl-3-({5-[4-(4-pyridinyl)-6-quinolinyl]-2-pyridinyl}oxy)-1-propanamine;
5-[4-(4-pyridinyl)-6-quinolinyl]-3-pyridinecarboxamide;
methyl 5-[4-(4-pyridinyl)-6-quinolinyl]-2-pyridinecarboxylate;
N-{5-[4-(4-pyridinyl)-6-quinolinyl]-2-pyridinyl}acetamide;
N-[2-(4-morpholinyl)ethyl]-5-[4-(4-pyridinyl)-6-quinolinyl]-2-pyridinamine;
6-[6-(1-piperazinyl)-3-pyridinyl]-4-(4-pyridinyl)quinoline;
6-[5-(methyloxy)-3-pyridinyl]-4-(4-pyridinyl)quinoline;
6-(6-fluoro-3-pyridinyl)-4-(4-pyridinyl)quinoline;
5-[4-(4-pyridinyl)-6-quinolinyl]-2-pyrimidinecarbonitrile;
6-[2-(methyloxy)-3-pyridinyl]-4-(4-pyridinyl)quinoline;
5-[4-(4-pyridinyl)-6-quinolinyl]-3-pyridinecarbonitrile;
6-[6-(methyloxy)-2-pyridinyl]-4-(4-pyridinyl)quinoline;
6-[5-(4-morpholinylcarbonyl)-3-pyridinyl]-4-(4-pyridinyl)quinoline;
6-[4-(methyloxy)-3-pyridinyl]-4-(4-pyridinyl)quinoline;
6-[5-(4-morpholinylsulfonyl)-3-pyridinyl]-4-(4-pyridinyl)quinoline;
7-[4-(4-pyridinyl)-6-quinolinyl]-2,3-dihydro[1,4]dioxino[2,3-b]pyridine;
5-[4-(4-pyridinyl)-6-quinolinyl]-3-pyridinesulfonamide;
2-(methyloxy)-5-[4-(4-pyridinyl)-6-quinolinyl]-3-pyridinecarbaldehyde;
6-(4-chloro-3-pyridinyl)-4-(4-pyridinyl)quinoline;
4-(4-pyridinyl)-6-[5-(1H-tetrazol-5-yl)-3-pyridinyl]quinoline;
N-methyl-5-[4-(4-pyridinyl)-6-quinolinyl]-3-pyridinesulfonamide;
N,N-dimethyl-5-[4-(4-pyridinyl)-6-quinolinyl]-3-pyridinesulfonamide;
6-[4-methyl-6-(methyloxy)-3-pyridinyl]-4-(4-pyridinyl)quinoline;
N-{4-methyl-5-[4-(4-pyridinyl)-6-quinolinyl]-2-pyridinyl}acetamide;
6-(4-methyl-3-pyridinyl)-4-(4-pyridinyl)quinoline;
6-[5-(1,3,4-oxadiazol-2-yl)-3-pyridinyl]-4-(4-pyridinyl)quinoline;
2-amino-N-(4-pyridinylmethyl)-5-[4-(4-pyridinyl)-6-quinolinyl]-3-pyridinesulfonamide;
2-amino-N,N-diethyl-5-[4-(4-pyridinyl)-6-quinolinyl]-3-pyridinesulfonamide;
5-[4-(4-pyridinyl)-6-quinolinyl]-3-(1-pyrrolidinylsulfonyl)-2-pyridinamine;
2-amino-5-[4-(4-pyridinyl)-6-quinolinyl]-N-[2-(1-pyrrolidinyl)ethyl]-3-pyridinesulfonamide;
6-[6-(methylsulfonyl)-3-pyridinyl]-4-(4-pyridinyl)quinoline;
2-amino-N-(phenylmethyl)-5-[4-(4-pyridinyl)-6-quinolinyl]-3-pyridinesulfonamide;
2-amino-N-(2-hydroxyethyl)-5-[4-(4-pyridinyl)-6-quinolinyl]-3-pyridinesulfonamide;
1-({2-amino-5-[4-(4-pyridinyl)-6-quinolinyl]-3-pyridinyl}sulfonyl)-4-piperidinol;
2-amino-N-(2-aminoethyl)-5-[4-(4-pyridinyl)-6-quinolinyl]-3-pyridinesulfonamide;
6-[5-(methylthio)-3-pyridinyl]-4-(4-pyridinyl)quinoline;
6-[5-(methylsulfonyl)-3-pyridinyl]-4-(4-pyridinyl)quinoline;
2-amino-N-(2-hydroxyethyl)-N-methyl-5-[4-(4-pyridinyl)-6-quinolinyl]-3-pyridinesulfonamide;
2-amino-N-cyclopropyl-5-[4-(4-pyridinyl)-6-quinolinyl]-3-pyridinesulfonamide;
2-amino-N-1,3-benzodioxol-5-yl-5-[4-(4-pyridinyl)-6-quinolinyl]-3-pyridinesulfonamide;
N,N-diethyl-5-[4-(4-pyridinyl)-6-quinolinyl]-3-pyridinesulfonamide;
1-({5-[4-(4-pyridinyl)-6-quinolinyl]-3-pyridinyl}sulfonyl)-4-piperidinol;

4-(4-pyridinyl)-6-[5-(1-pyrrolidinylsulfonyl)-3-pyridinyl]quinoline;
N-(2-hydroxyethyl)-5-[4-(4-pyridinyl)-6-quinolinyl]-3-pyridinesulfonamide;
N-(phenylmethyl)-5-[4-(4-pyridinyl)-6-quinolinyl]-3-pyridinesulfonamide;
5-[4-(4-pyridinyl)-6-quinolinyl]-N-[2-(1-pyrrolidinyl)ethyl]-3-pyridinesulfonamide;
6-{5-[(4-methyl-1-piperazinyl)sulfonyl]-3-pyridinyl}-4-(4-pyridinyl)quinoline;
N-cyclopropyl-5-[4-(4-pyridinyl)-6-quinolinyl]-3-pyridinesulfonamide;
N-[2-(methyloxy)ethyl]-5-[4-(4-pyridinyl)-6-quinolinyl]-3-pyridinesulfonamide;
N-phenyl-5-[4-(4-pyridinyl)-6-quinolinyl]-3-pyridinesulfonamide;
N-1,3-benzodioxol-5-yl-5-[4-(4-pyridinyl)-6-quinolinyl]-3-pyridinesulfonamide;
N-(3-pyridinylmethyl)-5-[4-(4-pyridinyl)-6-quinolinyl]-3-pyridinesulfonamide;
N-2-pyridinyl-5-[4-(4-pyridinyl)-6-quinolinyl]-3-pyridinesulfonamide;
N-(2-chlorophenyl)-5-[4-(4-pyridinyl)-6-quinolinyl]-3-pyridinesulfonamide;
N-cyclohexyl-5-[4-(4-pyridinyl)-6-quinolinyl]-3-pyridinesulfonamide;
N-[2-(methyloxy)phenyl]-5-[4-(4-pyridinyl)-6-quinolinyl]-3-pyridinesulfonamide;
2,4-difluoro-N-{5-[4-(4-pyridinyl)-6-quinolinyl]-3-pyridinyl}benzenesulfonamide;
1-methyl-N-{5-[4-(4-pyridinyl)-6-quinolinyl]-3-pyridinyl}-1H-imidazole-4-sulfonamide;
N-{5-[4-(4-pyridinyl)-6-quinolinyl]-3-pyridinyl}-2-thiophenesulfonamide;
3,5-dimethyl-N-{5-[4-(4-pyridinyl)-6-quinolinyl]-3-pyridinyl}-4-isoxazolesulfonamide;
3,4-bis(methyloxy)-N-{5-[4-(4-pyridinyl)-6-quinolinyl]-3-pyridinyl}benzenesulfonamide;
2-methyl-N-{5-[4-(4-pyridinyl)-6-quinolinyl]-3-pyridinyl}-1-propanesulfonamide;
N-{5-[4-(4-pyridinyl)-6-quinolinyl]-3-pyridinyl}cyclopropanesulfonamide;
N-{5-[4-(4-pyridinyl)-6-quinolinyl]-3-pyridinyl}benzenesulfonamide;
N-{2-chloro-5-[4-(4-pyridinyl)-6-quinolinyl]-3-pyridinyl}benzenesulfonamide; and
1-phenyl-N-{5-[4-(4-pyridinyl)-6-quinolinyl]-3-pyridinyl}methanesulfonamide;
5-{4-[3-chloro-4-(methyloxy)phenyl]-6-quinolinyl}-3-pyridinesulfonamide;
5-{4-[3-(aminosulfonyl)phenyl]-6-quinolinyl}-3-pyridinesulfonamide;
5-{4-[1-(2-hydroxyethyl)-1H-pyrazol-4-yl]-6-quinolinyl}-3-pyridinesulfonamide;
N-(cyclopropylsulfonyl)-N-{5-[4-(4-pyridinyl)-6-quinolinyl]-3-pyridinyl}cyclopropanesulfonamide;
N-(2,4-difluorophenyl)-5-[4-(1-ethyl-1H-pyrazol-4-yl)-6-quinolinyl]-3-pyridinesulfonamide;
N-methyl-N-phenyl-5-[4-(4-pyridinyl)-6-quinolinyl]-3-pyridinesulfonamide;
N-(2,4-difluorophenyl)-5-(4-{1-[2-(dimethylamino)ethyl]-1H-pyrazol-4-yl}-6-quinolinyl)-3-pyridinesulfonamide;
N-(2,4-difluorophenyl)-5-[4-(4-isoquinolinyl)-6-quinolinyl]-3-pyridinesulfonamide;
N-phenyl-N'-{5-[4-(4-pyridinyl)-6-quinolinyl]-3-pyridinyl}urea;
2-{4-[6-(5-{[(2,4-difluorophenyl)amino]sulfonyl}-3-pyridinyl)-4-quinolinyl]-1H-pyrazol-1-yl}acetamide;
N-{5-[4-(1-methyl-1H-pyrazol-4-yl)-6-quinolinyl]-3-pyridinyl}benzenesulfonamide;
4'-(4-pyridinyl)-3,6'-biquinoline;
N-{5-[4-(4-pyridinyl)-6-quinolinyl]-3-pyridinyl}benzamide;
5-[4-(1-benzofuran-2-yl)-6-quinolinyl]-N-(2,4-difluorophenyl)-3-pyridinesulfonamide;
6-[5-(1H-pyrazol-4-yl)-3-pyridinyl]-4-(4-pyridinyl)quinoline;
N,N-diethyl-2-oxo-5-[4-(4-pyridinyl)-6-quinolinyl]-1,2-dihydro-3-pyridinesulfonamide;
4-cyano-N-{5-[4-(4-pyridinyl)-6-quinolinyl]-3-pyridinyl}benzenesulfonamide;
N-methyl-N-phenyl-5-[4-(4-pyridinyl)-6-quinolinyl]-3-pyridinecarboxamide;
N-{5-[4-(4-pyridinyl)-6-quinolinyl]-3-pyridinyl}ethanesulfonamide;
4-(methyloxy)-N-{5-[4-(4-pyridinyl)-6-quinolinyl]-3-pyridinyl}benzenesulfonamide;
4-(1-methylethyl)-N-{5-[4-(4-pyridinyl)-6-quinolinyl]-3-pyridinyl}benzenesulfonamide;
2-chloro-5-[4-(4-pyridinyl)-6-quinolinyl]-3-pyridinamine;
4-fluoro-N-{5-[4-(4-pyridinyl)-6-quinolinyl]-3-pyridinyl}benzenesulfonamide;
N-{5-[4-(1-ethyl-1H-pyrazol-4-yl)-6-quinolinyl]-3-pyridinyl}-2,4-difluorobenzenesulfonamide;
1-methyl-N-{5-[4-(4-pyridinyl)-6-quinolinyl]-3-pyridinyl}-1H-pyrazole-3-sulfonamide;
2-fluoro-N-{5-[4-(4-pyridinyl)-6-quinolinyl]-3-pyridinyl}benzenesulfonamide;
N-{2-amino-5-[4-(4-pyridinyl)-6-quinolinyl]-3-pyridinyl}benzenesulfonamide;
N-{2-methyl-5-[4-(4-pyridinyl)-6-quinolinyl]-3-pyridinyl}benzenesulfonamide;
N-{2-cyano-5-[4-(4-pyridinyl)-6-quinolinyl]-3-pyridinyl}benzenesulfonamide;
2-methyl-5-nitro-N-{5-[4-(4-pyridinyl)-6-quinolinyl]-3-pyridinyl}benzenesulfonamide;
N-{5-[4-(4-pyridinyl)-6-quinolinyl]-3-pyridinyl}-1H-pyrazole-4-sulfonamide;
N-{2-chloro-5-[4-(4-pyridinyl)-6-quinolinyl]-3-pyridinyl}-2-methyl-5-nitrobenzenesulfonamide;
N-{2-chloro-5-[4-(1-ethyl-1H-pyrazol-4-yl)-6-quinolinyl]-3-pyridinyl}benzenesulfonamide;
N-{2-chloro-5-[4-(4-pyridazinyl)-6-quinolinyl]-3-pyridinyl}benzenesulfonamide;
3-nitro-N-{5-[4-(4-pyridinyl)-6-quinolinyl]-2-pyridinyl}benzenesulfonamide;
2-methyl-N-{5-[4-(4-pyridinyl)-6-quinolinyl]-3-pyridinyl}benzenesulfonamide;
2,4-difluoro-N-{5-[4-(4-pyridazinyl)-6-quinolinyl]-3-pyridinyl}benzenesulfonamide;
5-fluoro-2-methyl-N-{5-[4-(4-pyridinyl)-6-quinolinyl]-3-pyridinyl}benzenesulfonamide;
N-{2-chloro-5-[4-(4-pyridinyl)-6-quinolinyl]-3-pyridinyl}-3-nitrobenzenesulfonamide;
N-{2-chloro-5-[4-(2-methyl-4-pyridinyl)-6-quinolinyl]-3-pyridinyl}benzenesulfonamide;
N-{2-chloro-5-[4-(4-pyridinyl)-6-quinolinyl]-3-pyridinyl}-2-methylbenzenesulfonamide;
N-{2-chloro-5-[4-(4-pyridinyl)-6-quinolinyl]-3-pyridinyl}-3-fluorobenzenesulfonamide;
N-{2-chloro-5-[4-(4-pyridinyl)-6-quinolinyl]-3-pyridinyl}-2-thiophenesulfonamide;

N-{2-chloro-5-[4-(4-pyridinyl)-6-quinolinyl]-3-pyridinyl}cyclopropanesulfonamide;
N-{2-chloro-5-[4-(4-pyridinyl)-6-quinolinyl]-3-pyridinyl}-5-fluoro-2-methylbenzenesulfonamide;
N-(2-chloro-5-{4-[3-(methylsulfonyl)phenyl]-6-quinolinyl}-3-pyridinyl)benzenesulfonamide;
N-{2-chloro-5-[4-(4-pyridinyl)-6-quinolinyl]-3-pyridinyl}-3,5-dimethyl-4-isoxazolesulfonamide;
2,4-difluoro-N-(5-{4-[3-(methylsulfonyl)phenyl]-6-quinolinyl}-3-pyridinyl)benzenesulfonamide;
2,4-difluoro-N-{5-[4-(2-methyl-4-pyridinyl)-6-quinolinyl]-3-pyridinyl}benzenesulfonamide;
3-(methyloxy)-N-{5-[4-(4-pyridinyl)-6-quinolinyl]-3-pyridinyl}benzenesulfonamide;
N-[4-(cyanomethyl)phenyl]-5-[4-(4-pyridinyl)-6-quinolinyl]-3-pyridinesulfonamide;
3-fluoro-N-{5-[4-(4-pyridinyl)-6-quinolinyl]-3-pyridinyl}benzenesulfonamide;
N-{2-(methyloxy)-5-[4-(4-pyridinyl)-6-quinolinyl]-3-pyridinyl}benzenesulfonamide;
N-{2-chloro-5-[4-(4-pyridinyl)-6-quinolinyl]-3-pyridinyl}-2,4-difluorobenzenesulfonamide;
3-nitro-N-{5-[4-(4-pyridinyl)-6-quinolinyl]-3-pyridinyl}benzenesulfonamide;
N-{5-[4-(1-benzofuran-2-yl)-6-quinolinyl]-3-pyridinyl}-2,4-difluorobenzenesulfonamide;
3-cyano-N-{5-[4-(4-pyridinyl)-6-quinolinyl]-3-pyridinyl}benzenesulfonamide;
N-{5-[4-(4-pyridinyl)-6-quinolinyl]-3-pyridinyl}-4-(trifluoromethyl)benzenesulfonamide;
N-{2-hydroxy-5-[4-(4-pyridinyl)-6-quinolinyl]-3-pyridinyl}benzenesulfonamide;
N-{5-[4-(4-pyridinyl)-6-quinolinyl]-3-pyridinyl}-3-(trifluoromethyl)benzenesulfonamide;
N-{5-[4-(1-benzofuran-2-yl)-6-quinolinyl]-2-chloro-3-pyridinyl}benzenesulfonamide;
N-methyl-N-{5-[4-(4-pyridinyl)-6-quinolinyl]-3-pyridinyl}benzamide;
2,4-difluoro-N-{5-[4-(4-fluorophenyl)-6-quinolinyl]-3-pyridinyl}benzenesulfonamide;
N-methyl-N-{5-[4-(4-pyridinyl)-6-quinolinyl]-3-pyridinyl}benzenesulfonamide;
2,4-difluoro-N-[5-(4-pyrazolo[1,5-a]pyridin-3-yl-6-quinolinyl)-3-pyridinyl]benzenesulfonamide;
2,4-difluoro-N-{5-[4-(2-fluorophenyl)-6-quinolinyl]-3-pyridinyl}benzenesulfonamide;
2,4-difluoro-N-(5-{4-[4-(trifluoromethyl)phenyl]-6-quinolinyl}-3-pyridinyl)benzenesulfonamide;
2,4-difluoro-N-(5-{4-[4-(methylsulfonyl)phenyl]-6-quinolinyl}-3-pyridinyl)benzenesulfonamide;
methyl 1-methyl-5[({5-[4-(4-pyridinyl)-6-quinolinyl]-3-pyridinyl}amino)sulfonyl]-1H-pyrrole-2-carboxylate;
5-bromo-2-(methyloxy)-N-{5-[4-(4-pyridinyl)-6-quinolinyl]-3-pyridinyl}benzenesulfonamide;
5-(5-isoxazolyl)-N-{5-[4-(4-pyridinyl)-6-quinolinyl]-3-pyridinyl}-2-thiophenesulfonamide;
2,4-difluoro-N-{5-[4-(3-fluorophenyl)-6-quinolinyl]-3-pyridinyl}benzenesulfonamide;
2,4-difluoro-N-(5-{4-[3-(trifluoromethyl)phenyl]-6-quinolinyl}-3-pyridinyl)benzenesulfonamide;
2-chloro-4-cyano-N-{5-[4-(4-pyridinyl)-6-quinolinyl]-3-pyridinyl}benzenesulfonamide;
N-[5-(4-{3-[(dimethylamino)sulfonyl]phenyl}-6-quinolinyl)-3-pyridinyl]-2,4-difluorobenzenesulfonamide;
N-[5-(4-{4-[(dimethylamino)sulfonyl]phenyl}-6-quinolinyl)-3-pyridinyl]-2,4-difluorobenzenesulfonamide;
1,2-dimethyl-N-{5-[4-(4-pyridinyl)-6-quinolinyl]-3-pyridinyl}-1H-imidazole-4-sulfonamide;
3-[6-(5-{[(2,4-difluorophenyl)sulfonyl]amino}-3-pyridinyl)-4-quinolinyl]benzamide;
4-[6-(5-{[(2,4-difluorophenyl)sulfonyl]amino}-3-pyridinyl)-4-quinolinyl]benzamide;
N-{4-[6-(5-{[(2,4-difluorophenyl)sulfonyl]amino}-3-pyridinyl)-4-quinolinyl]phenyl}acetamide;
N-{3-[6-(5-{[(2,4-difluorophenyl)sulfonyl]amino}-3-pyridinyl)-4-quinolinyl]phenyl}acetamide;
6-(4-morpholinyl)-N-{5-[4-(4-pyridinyl)-6-quinolinyl]-3-pyridinyl}-3-pyridinesulfonamide;
2-fluoro-4-methyl-N-{5-[4-(4-pyridinyl)-6-quinolinyl]-3-pyridinyl}benzenesulfonamide;
N-{5-[4-(4-pyridinyl)-6-quinolinyl]-3-pyridinyl}-2-furansulfonamide;
1,3-dimethyl-N-{5-[4-(4-pyridinyl)-6-quinolinyl]-3-pyridinyl}-1H-pyrazole-4-sulfonamide;
N-{5-[4-(4-pyridinyl)-6-quinolinyl]-3-pyridinyl}-2-(trifluoromethyl)benzenesulfonamide;
N-{2-(methyloxy)-5-[4-(4-pyridinyl)-6-quinolinyl]-3-pyridinyl}cyclohexanesulfonamide;
N-[5-(4-cyclopentyl-6-quinolinyl)-2-(methyloxy)-3-pyridinyl]benzenesulfonamide;
2,5-dichloro-N-{5-[4-(4-pyridinyl)-6-quinolinyl]-3-pyridinyl}benzenesulfonamide;
3-cyano-4-fluoro-N-{5-[4-(4-pyridinyl)-6-quinolinyl]-3-pyridinyl}benzenesulfonamide;
N-{5-[4-(4-pyridinyl)-6-quinolinyl]-3-pyridinyl}-1-pyrrolidinesulfonamide;
(5Z)-5-({5-[4-(4-pyridinyl)-6-quinolinyl]-3-pyridinyl}methylidene)-1,3-thiazolidine-2,4-dione;
N-{2-(methyloxy)-5-[4-(4-pyridinyl)-6-quinolinyl]-3-pyridinyl}cyclopropanesulfonamide;
N-{5-[4-(4-pyridinyl)-6-quinolinyl]-3-pyridinyl}-2-pyridinesulfonamide;
1,2-dimethyl-N-{5-[4-(4-pyridinyl)-6-quinolinyl]-3-pyridinyl}-1H-imidazole-5-sulfonamide;
1-methyl-N-{5-[4-(4-pyridinyl)-6-quinolinyl]-3-pyridinyl}-3-(trifluoromethyl)-1H-pyrazole-4-sulfonamide;
1,3,5-trimethyl-N-{5-[4-(4-pyridinyl)-6-quinolinyl]-3-pyridinyl}-1H-pyrazole-4-sulfonamide;
N-{2-(ethyloxy)-5-[4-(4-pyridinyl)-6-quinolinyl]-3-pyridinyl}benzenesulfonamide;
N,N-dimethyl-N'-{5-[4-(4-pyridinyl)-6-quinolinyl]-3-pyridinyl}sulfamide;
N-{2-chloro-5-[4-(4-pyridazinyl)-6-quinolinyl]-3-pyridinyl}-2,4-difluorobenzenesulfonamide;
N-{2-chloro-1-oxido-5-[4-(4-pyridinyl)-6-quinolinyl]-3-pyridinyl}benzenesulfonamide;
N-{6-methyl-5-[4-(4-pyridinyl)-6-quinolinyl]-3-pyridinyl}benzenesulfonamide;
N-{2-(methyloxy)-5-[4-(4-pyridinyl)-6-quinolinyl]-3-pyridinyl}methanesulfonamide;
N-{2-chloro-5-[4-(4-pyridinyl)-6-quinolinyl]-3-pyridinyl}methanesulfonamide;
2,4-difluoro-N-{2-(methyloxy)-5-[4-(4-pyridazinyl)-6-quinolinyl]-3-pyridinyl}benzenesulfonamide;
and/or a pharmaceutically acceptable salt thereof.

This invention also relates to a method of treating cancer, which comprises co-administering to a subject in need thereof an effective amount of a compound of Formula (I), and/or a pharmaceutically acceptable salt thereof; and at least one anti-neoplastic agent such as one selected from the group consisting of: anti-microtubule agents, plantinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

This invention also relates to a method of treating cancer, which comprises co-administering to a subject in need thereof an effective amount of a compound of Formula (I), and/or a pharmaceutically acceptable salt thereof; and at least one signal transduction pathway inhibitor such as one selected from the group consisting of: receptor tyrosine kinase inhibitor, non-receptor tyrosine kinase inhibitor, SH2/SH3 domain blocker, serine/threonine kinase inhibitor, phosphotidyl inositol-3 kinase inhibitor, myo-inositol signaling inhibitor, and Ras oncogene inhibitor.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Compounds of Formula (I) are included in the pharmaceutical compositions of the invention.

DEFINITIONS

By the term "substituted amino" as used herein, is meant —NR3OR40 wherein each R30 and R40 is independently selected from a group including hydrogen, C1-6alkyl, acyl, C3-C7cycloalkyl, wherein at least one of R30 and R40 is not hydrogen.

By the term "acyl" as used herein, unless otherwise defined, is meant —C(O)(alkyl), —C(O)(cycloalkyl), —C(O)(aryl) or —C(O)(heteroaryl), wherein heteroaryl and aryl are optionally substituted.

By the term "aryl" as used herein, unless otherwise defined, is meant aromatic, hydrocarbon, ring system. The ring system may be monocyclic or fused polycyclic (e.g. bicyclic, tricyclic, etc.). In various embodiments, the monocyclic aryl ring is C5-C10, or C5-C7, or C5-C6, where these carbon numbers refer to the number of carbon atoms that form the ring system. A C6 ring system, i.e. a phenyl ring is a suitable aryl group. In various embodiments, the polycyclic ring is a bicyclic awl group, where suitable bicyclic aryl groups are C8-C12, or C9-C10. A naphthyl ring, which has 10 carbon atoms, is a suitable polycyclic awl group.

By the term "heteroaryl" as used herein, unless otherwise defined, is meant an aromatic ring system containing carbon(s) and at least one heteroatom. Heteroaryl may be monocyclic or polycyclic. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene.

By the term "monocyclic heteroaryl" as used herein, unless otherwise defined, is meant a monocyclic heteroaryl ring containing 1-5 carbon atoms and 1-4 hetero atoms.

By the term "alkylcarboxy" as used herein, unless otherwise defined, is meant —$(CH_2)_n COOR_{80}$, wherein R80 is hydrogen or C1-C6alkyl, n is 0-6.

By the term "alkoxy" as used herein is meant —O(alkyl) including —$OCH_3$, —$OCH_2CH_3$ and —$OC(CH_3)_3$ where alkyl is as described herein.

By the term "alkylthio" as used herein is meant —S(alkyl) including —$SCH_3$, —$SCH_2CH_3$ where alkyl is as described herein.

The term "cycloalkyl" as used herein unless otherwise defined, is meant a nonaromatic, unsaturated or saturated, cyclic or polycyclic $C_3$-$C_{12}$.

Examples of cycloalkyl and substituted cycloalkyl substituents as used herein include: cyclohexyl, aminocyclohexyl, cyclobutyl, aminocyclobutyl, 4-hydroxy-cyclohexyl, 2-ethylcyclohexyl, propyl4-methoxycyclohexyl, 4-methoxycyclohexyl, 4-carboxycyclohexyl, cyclopropyl, aminocyclopentyl, and cyclopentyl.

By the term "heterocycloalkyl" as used herein is meant a non-aromatic, unsaturated or saturated, monocyclic or polycyclic, heterocyclic ring containing at least one carbon and at least one heteroatom. Exemplary monocyclic heterocyclic rings include: piperidine, piperazine, pyrrolidine, and morpholine. Exemplary polycyclic heterocyclic rings include quinuclidine.

By the term "substituted" as used herein, unless otherwise defined, is meant that the subject chemical moiety has one to five substituents, suitably from one to three substituents selected from the group consisting of: hydrogen, halogen, C1-C6alkyl, amino, urea, trifluoromethyl, —$(CH_2)_n COOH$, C3-C7cycloalkyl, substituted amino, aryl, heteroaryl, arylalkyl, arylcycloalkyl, heteroarylalkyl, heterocycloalkyl, cyano, hydroxyl, alkoxy, alkylthio, aryloxy, acyloxy, acyl, acylamino, aminoacyl, arylamino, nitro, oxo, —$CO_2R_{50}$, —$SO_2R_{70}$, —$NR_{50}SO_2R_{70}$, $NR_{50}C(O)R_{75}$ and —$CONR_{55}R_{60}$, wherein R50 and R55 are each independently selected from: hydrogen, alkyl, and C3-C7cycloalkyl; R55 and R60 can optionally form a heterocycloalkyl ring; n is 0 to 6; R75 is selected from the group consisting of: C1-C6alkyl, C3-C7cylcoalkyl, substituted C3-7cycloalkyl, aryl, substituted aryl, heteroaryl, substituted heteroaryl, amino, substituted amino, arylamino, C1-C6heterocycloalkyl, alkoxy, aryloxy and substituted C1-C6heterocycloalkyl; each R60 and R70 is independently selected from the group consisting of: C1-C6alkyl, C3-C7cycloalkyl, substituted C1-C6heterocycloalkyl, C1-C6heterocycloalkyl, halogen, amino, substituted amino, arylamino, trifluoromethyl, cyano, hydroxyl, alkoxy, oxo, —$(CH_2)_n COOH$, aryl optionally fused with a five-membered ring or substituted with one to five groups selected from the group consisting of: C1-C6alkyl, C3-C7cycloalkyl, halogen, amino, substituted amino, trifluoromethyl, cyano, hydroxyl, alkoxy, oxo, or —$(CH_2)_n COOH$, or heteroaryl optionally fused with a five-membered ring or substituted with one to five groups selected from the group consisting of: C1-C6alkyl, C3-C7cycloalkyl, halogen, amino, trifluoromethyl, cyano, hydroxyl, alkoxy, oxo, or —$(CH_2)_n COOH$.

By the term "substituted", when referred in the definition of R60, R70, R75, "arylamino", and "aryloxy", is meant that the subject chemical moiety has one to five substituents, suitably from one to three, selected from the group consisting of: hydrogen, C1-C6alkyl, halogen, trifluoromethyl, —(CH$_2$)$_n$COOH, amino, substituted amino, cyano, hydroxyl, alkoxy, alkylthio, aryloxy, acyloxy, acyl, acylamino, and nitro, n is 0-6.

By the term "acyloxy" as used herein is meant —OC(O)alkyl where alkyl is as described herein. Examples of acyloxy substituents as used herein include: —OC(O)CH$_3$, —OC(O)CH(CH$_3$)$_2$ and —OC(O)(CH$_2$)$_3$CH$_3$.

By the term "acylamino" as used herein is meant —N(H)C(O)alkyl, —N(H)C(O)(cycloalkyl) where alkyl is as described herein. Examples of N-acylamino substituents as used herein include: —N(H)C(O)CH$_3$, —N(H)C(O)CH(CH$_3$)$_2$ and —N(H)C(O)(CH$_2$)$_3$CH$_3$.

By the term "aminoacyl" as used herein is meant —C(O)N(alkyl)$_n$, —C(O)N(cycloalkyl)$_n$ where alkyl is as described herein, n is 1-2.

By the term "aryloxy" as used herein is meant —O(aryl), —O(substituted aryl), —O(heteroaryl) or —O(substituted heteroaryl).

By the term "arylamino" as used herein is meant —NR$_{80}$(aryl), —NR$_{80}$(substituted aryl), —NR$_{80}$(heteroaryl) or —NR$_{80}$(substituted heteroaryl), wherein R80 is H, C1-6alkyl or C3-C7cycloalkyl.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein, including alkyl chains defined by the term "—(CH$_2$)$_n$", "—(CH$_2$)$_m$" and the like, is meant a linear or branched, saturated or unsaturated hydrocarbon chain, and unless otherwise defined, the carbon chain will contain from 1 to 12 carbon atoms.

By the term "substituted alkyl" as used herein is meant an alkyl group substituted with one to six substituents selected from the group consisting of: halogen, trifluoromethyl, alkylcarboxy, amino, substituted amino, cyano, hydroxyl, alkoxy, alkylthio, aryloxy, acyloxy, acyl, acylamino, carbamate, urea, sulfonamate, C3-7cycloheteralkyl, C3-7cycloalkyl and nitro.

Examples of alkyl and substituted alkyl substituents as used herein include:
—CH$_3$, —CH$_2$—CH$_3$, —CH$_2$—CH$_2$—CH$_3$, —CH(CH$_3$)$_2$, —CH$_2$—CH$_2$—C(CH$_3$)$_3$, —CH$_2$—CF$_3$, —C≡C—C(CH$_3$)$_3$, —C≡C—CH$_2$—OH, cyclopropylmethyl, —CH$_2$—C(CH$_3$)$_2$—CH$_2$—NH$_2$, —C≡C—C$_6$H$_5$, —C≡C—C(CH$_3$)$_2$—OH, —CH$_2$—CH(OH)—CH(OH)—CH(OH)—CH(OH)—CH$_2$—OH, piperidinylmethyl, methoxyphenylethyl, —C(CH$_3$)$_3$, —(CH$_2$)$_3$—CH$_3$, —CH$_2$—CH(CH$_3$)$_2$, —CH(CH$_3$)—CH$_2$—CH$_3$, —CH═CH$_2$, and —C≡C—CH$_3$.

By the term "treating" and derivatives thereof as used herein, is meant prophylatic and therapeutic therapy. Prophylatic therapy is meant the institution of measures to protect a person from a disease to which he or she has been, or may be, exposed. Also called preventive treatment.

By the term "co-administering" and derivatives thereof as used herein is meant either simultaneous administration or any manner of separate sequential administration of a PI3 kinase inhibiting compound, as described herein, and a further active ingredient or ingredients. The term further active ingredient or ingredients, as used herein, includes any compound or therapeutic agent known to or that demonstrates advantageous properties when administered to a patient in need of treatment. Suitably, if the administration is not simultaneous, the compounds are administered in a close time proximity to each other. Furthermore, it does not matter if the compounds are administered in the same dosage form, e.g. one compound may be administered topically and another compound may be administered orally.

The term "compound" as used herein includes all isomers of the compound. Examples of such isomers include: enantiomers, tautomers, rotamers.

In formula (V) to (X), when a "dot" bond is drawn between two atoms, it is meant that such bond can be either single or double bond. A ring system containing such bonds can be aromatic or non-aromatic.

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by formula I or II above as well as any wholly or partially equilibrated mixtures thereof The present invention also covers the individual isomers of the compounds represented by the formulas above as mixtures with isomers thereof in which one or more chiral centers are inverted. Further, an example of a possible tautomer is an oxo substituent in place of a hydroxy substituent. Also, as stated above, it is understood that all tautomers and mixtures of tautomers are included within the scope of the compounds of Formula I or II.

Compounds of Formula (I) are included in the pharmaceutical compositions of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

It has now been found that compounds of the present invention are inhibitors of the Phosphatoinositides 3-kinases (PI3Ks), particularly PI3Kα. When the phosphatoinositides 3-kinase (PI3K) enzyme is inhibited by a compound of the present invention, PI3K is unable to exert its enzymatic, biological and/or pharmacological effects. The compounds of the present invention are therefore useful in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, particularly cancer.

Compounds according to Formula (I) are suitable for the modulation, notably the inhibition of the activity of phosphatoinositide 3-kinases (PI3K), suitably phosphatoinositides 3-kinase (PI3Kα). Therefore the compounds of the present invention are also useful for the treatment of disorders which are mediated by PI3Ks. Said treatment involves the modulation—notably the inhibition or the down regulation—of the phosphatoinositides 3-kinases.

Suitably, the compounds of the present invention are used for the preparation of a medicament for the treatment of a disorder selected from multiple sclerosis, psoriasis, rheumatoid arthritis, systemic lupus erythematosis, inflammatory bowel disease, lung inflammation, thrombosis or brain infection/inflammation, such as meningitis or encephalitis, Alzheimer's disease, Huntington's disease, CNS trauma, stroke or ischemic conditions, cardiovascular diseases such as atherosclerosis, heart hypertrophy, cardiac myocyte dysfunction, elevated blood pressure or vasoconstriction.

Suitably, the compounds of Formula (I) are useful for the treatment of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

Suitably, the compounds of Formula (I) are useful for the treatment of neurodegenerative diseases including multiple sclerosis, Alzheimer's disease, Huntington's disease, CNS trauma, stroke or ischemic conditions.

Suitably, the compounds of Formula (I) are useful for the treatment of cardiovascular diseases such as atherosclerosis, heart hypertrophy, cardiac myocyte dysfunction, elevated blood pressure or vasoconstriction.

Suitably, the compounds of Formula (I) are useful for the treatment of chronic obstructive pulmonary disease, anaphylactic shock fibrosis, psoriasis, allergic diseases, asthma, stroke, ischemic conditions, ischemia-reperfusion, platelets aggregation/activation, skeletal muscle atrophy/hypertrophy, leukocyte recruitment in cancer tissue, angiogenesis, invasion metastasis, in particular melanoma, Karposi's sarcoma, acute and chronic bacterial and viral infections, sepsis, transplantation rejection, graft rejection, glomerulo sclerosis, glomerulo nephritis, progressive renal fibrosis, endothelial and epithelial injuries in the lung, and lung airway inflammation.

Because the pharmaceutically active compounds of the present invention are active as PI3 kinase inhibitors, particularly the compounds that inhibit PI3Kα, either selectively or in conjunction with one or more of PI3Kδ, PI3Kβ, and/or PI3Kγ, they exhibit therapeutic utility in treating cancer.

Suitably, the invention relates to a method of treating cancer in a mammal, including a human, wherein the cancer is selected from: brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone and thyroid.

Suitably, the invention relates to a method of treating cancer in a mammal, including a human, wherein the cancer is selected from: Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, Acute megakaryocytic leukemia, promyelocytic leukemia and Erythroleukemia.

Suitably, the invention relates to a method of treating cancer in a mammal, including a human, wherein the cancer is selected from: malignant lymphoma, hodgkins lymphoma, non-hodgkins lymphoma, lymphoblastic T cell lymphoma, Burkitt's lymphoma and follicular lymphoma.

Suitably, the invention relates to a method of treating cancer in a mammal, including a human, wherein the cancer is selected from: neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

When a compound of Formula (I) is administered for the treatment of cancer, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (anti-neoplastic agent) for use in combination or co-administered with the presently invented AKT inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann Intern, Med., 111:273,1989) and for the treatment of breast cancer (Holmes et al., J. Nat. Cancer Inst., 83:1797,1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

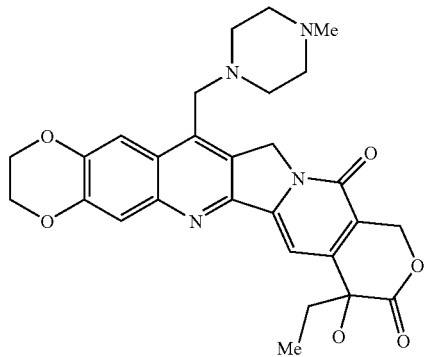

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha, beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., =1-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of formula I and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Because the pharmaceutically active compounds of the present invention are active as PI3 kinase inhibitors, particularly the compounds that modulate/inhibit PI3Kα, it is useful in treating cancer. Because the pharmaceutically active compounds of the present invention are also active against one or more of PI3Kδ, PI3Kβ, and/or PI3Kγ, they exhibit therapeutic utility in treating a disease state selected from: autoimmune disorders, inflammatory diseases, cardiovascular diseases, neurodegenerative diseases, allergy, asthma, pancreatitis, multiorgan failure, kidney diseases, platelet aggregation, sperm motility, transplantation rejection, graft rejection and lung injuries.

When a compound of Formula (I) is administered for the treatment of a disease state selected from: autoimmune disorders, inflammatory diseases, cardiovascular diseases, neurodegenerative diseases, allergy, cancer, asthma, pancreatitis, multiorgan failure, kidney diseases, platelet aggregation, sperm motility, transplantation rejection, graft rejection or lung injuries, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of such autoimmune disorder, cancer, inflammatory diseases, cardiovascular disease, neurodegenerative disease, allergy, asthma, pancreatitis, multiorgan failure, kidney diseases, platelet aggregation, sperm motility, transplantation rejection, graft rejection and/or lung injuries.

Biological Assays

PI3K Alpha Leadseeker SPA Assay

Compounds of the present invention were tested according to the following assays and found as inhibitors of PI3 kinases, particularly PI3Kα. The exemplified compounds were tested and found active against PI3Kα. The $IC_{50}$'s ranged from about 1 nM to 10 μM. The majority of the compounds were under 500 nM; the most active compounds were under 10 nM.

The compound of Example 249 was tested generally according to the assays described herein and in at least one experimental run exhibited a IC50 value: equal to 1.6 nM against PI3Kα.

The compound of Example 252 was tested generally according to the assays described herein and in at least one experimental run exhibited a IC50 value: equal to 0.8 nM against PI3Kα.

The compound of Example 263 was tested generally according to the assays described herein and in at least one experimental run exhibited a IC50 value: equal to 7.9 nM against PI3Kα.

The compound of Example 289 was tested generally according to the assays described herein and in at least one experimental run exhibited a IC50 value: equal to 2.5 nM against PI3Kα.

The compound of Example 154 was tested generally according to the assays described herein and in at least one experimental run exhibited a IC50 value: equal to 316 nM against PI3Kα.

The compound of Example 156 was tested generally according to the assays described herein and in at least one experimental run exhibited a IC50 value: equal to 79 nM against PI3Kα.

The compound of Example 224 was tested generally according to the assays described herein and in at least one experimental run exhibited a IC50 value: equal to 1000 nM against PI3Kα.

Assay Principle

SPA imaging beads are microspheres containing scintillant which emit light in the red region of the visible spectrum. As a result, these beads are ideally suited to use with a CCD imager such as the Viewlux. The Leadseeker beads used in this system are polystyrene beads that have been coupled with polyethyleneimine. When added to the assay mixture, the beads absorb both the substrate (PIP2) and product (PIP3). Adsorbed $P^{33}$-PIP3 will cause an increase in signal, measured as ADUs (analog to digital units). This protocol details the use of the PEI-PS Leadseeker beads for assays using His-p110/p85 PI3K alpha.

Assay Protocol

Solid compounds are typically plated with 0.1 μl of 100% DMSO in all wells (except column 6 and 18) of a 384-well, flat bottom, low volume plate (Greiner 784075). The compounds are serially diluted (3-fold in 100% DMSO) across the plate from column 1 to column 12 and column 13 to column 24 and leave column 6 and 18 containing only DMSO to yield 11 concentrations for each test compound.

The assay buffer contains MOPS (pH 6.5), CHAPS, and DTT. PI3K alpha and PIP2 (L-alpha-D-myo-Phosphatidylinositol 4,5-bisphosphate [PI(4,5)P2]3-O-phospho linked, D(+)-sn-1,2-di-O-octanoylglyceryl, CellSignals #901) are mixed and incubated in the plate with compound for 30 min prior to starting the reaction with the addition of $P^{33}$-ATP and $MgCl_2$ (reagents added using Zoom). Enzyme-free wells (column 18) are typically done to determine the low control. PEI-PS Leadseeker beads in PBS/EDTA/CHAPS are added (by Multidrop) to quench the reaction, and the plates are allowed to incubate for at least one hour (typically overnight) before centrifugation. The signal is determined using a Viewlux detector and is then imported into curve fitting software (Activity Base) for construction of concentration response curves. The percent inhibition of activity is calculated relative to high controls (C1, 0.1 μl DMSO in column 6, rows A-P)) and low controls (C2, 5 μl of 40 uM PIP2 in buffer in column 18, rows A-P) using, $100*(1-(U1-C2)/(C1-C2))$. The concentration of test compound yielding 50% inhibition is determined using the equation, $y=((Vmax*x)/(K+x))+Y2$, where "K" is equal to the IC50. The IC50 values are converted to pIC50 values, i.e., −log IC50 in Molar concentration.

Cellular Assays:
DAY 1
Plate cells before noon
    10K cells/well in clear flat-bottomed 96-well plates (fv. 105 ul)
    Last four wells in last column receive media only
    Place in 37 deg C. incubator overnight
Compound Plate
    Prepare in polypropylene round-bottomed 96-well plates; 8 compounds per
    plate, 11-pt titrations of each (3× serial dilution), DMSO in last column (0.15% f. c. on cells)
    15 ul in first well, 10ul DMSO in the rest; take 5 ul from first well and mix in next, continue across plate (excluding last column); seal with foil lid and place at 4 deg C.
DAY 2
Take out Lysis buffer inhibitors (4 deg C./−20 deg C.) and compound plates (4 deg C.), thaw on bench top; make 1× Tris wash buffer (WB) to fill reservoir on plate washer and top off bench supply (use MiliQ), turn on centrifuge to allow it to cool
Block MSD plates
    Make 20 ml 3% blocking solution/plate (600 mg blocker A in 20 ml WB), add 150 ul/well and incubate at RT for at least 1 hr
Add compound (while blocking)
    Add 300 ul growth media (RPMI w/Q, 10% FBS) per well (682× dil of compound) to each compound plate
    Add 5 ul compound dilution into each well (fv. 110 ul) on duplicate plates
    Place in 37 deg C. incubator for 30 min
Make Lysates
    Prepare MSD Lysis buffer; for 10 ml add 200 ul protease inhibitor solution, and 100 ul each of Phosphatase inhibitors I & II (Keep on ice until ready for use)
    Remove plates post-incubation, aspirate media with plate washer, wash 1× with cold PBS, and add 80 ul MSD Lysis buffer per well; incubate on shaker at 4 deg C. for >30 min
    Spin cold at 2500 rpm for 10 min; leave plates in 4 deg C. centrifuge until ready for use
AKT Duplex Assay
    Wash plates (4× with 200 ul/well WB in plate washer); tap plates on paper towel to blot
    Add 60 ul of lysates/well, incubate on shaker at RT for 1 hr
    During incubation prepare detection Ab (3 ml/plate; 2 ml WB and 1 ml blocking solution w/Ab at 10 nM); repeat wash step as above
    Add 25 ul of Ab/well, incubate on shaker at RT for 1 hr; repeat wash step as above
    Add 150 ul/well 1× Read Buffer (dilute 4× stock in ddH2O, 20 ml/plate), read immediately
Analysis
    Observe all the data points at each compound concentration.
    The data point from highest inhibitor concentration must be equal or greater than 70% of DMSO control.
    IC50 for duplicate runs must be within 2-fold of each other (not flagged in summary template).
    Y min must be greater than zero; if both mins are red flagged (>35) then compound is listed as inactive (IC50=>highest dose). If only one min is red flagged, but still ≦50 then call IC50 as listed.
    Any data points equal or greater than 30% off the curve will not be considered.

Cell Growth/Death Assay:
BT474, HCC1954 and T-47D (human breast) were cultured in RPMI-1640 containing 10% fetal bovine serum at 37° C. in 5% $CO_2$ incubator. Cells were split into T75 flask (Falcon #353136) two to three days prior to assay set up at density which yields approximately 70-80% confluence at time of harvest for assay. Cells were harvested using 0.25% trypsin-EDTA (Sigma #4049). Cell counts were performed on cell suspension using Trypan Blue exclusion staining. Cells were then plated in 384 well black flat bottom polystyrene (Greiner #781086) in 48 µl of culture media per well at 1,000 cells/well. All plates were placed at 5% $CO_2$, 37° C. overnight and test compounds were added the following day. One plate was treated with CellTiter-Glo (Promega #G7573) for a day 0 (t=0) measurement and read as described below. The test compounds were prepared in clear bottom polypropylene 384 well plates (Greiner#781280) with consecutive two fold dilutions. 4 µl of these dilutions were added to 105 µl culture media, after mixing the solution, 2 µl of these dilutions were added into each well of the cell plates. The final concentration of DMSO in all wells was 0.15%. Cells were incubated at 37° C., 5% $CO_2$ for 72 hours. Following 72 hours of incubation with compounds each plate was developed and read. CellTiter-Glo reagent was added to assay plates using a volume equivalent to the cell culture volume in the wells. Plates were shaken for approximately two minutes and incubated at room temperature for approximately 30 minutes and chemiluminescent signal was read on the Analyst GT (Molecular Devices) reader. Results were expressed as a percent of the t=0 and plotted against the compound concentration. Cell growth inhibition was determined for each compound by fitting the dose response with a 4 or 6 parameter curve fit using XLfit software and determining the concentration that inhibited 50% of the cell growth (gIC50) with the Y min as the t=0 and Y max as the DMSO control. Value from wells with no cells was subtracted from all samples for background correction.

ADDITIONAL REFERENCES

The compounds of the present invention can also be tested to determine their inhibitory activity at PI3Kα, PI3Kδ, PI3Kβ and PI3Kγ according to the assays in the following references:
For all PI3K isoforms:
1. Cloning, expression, purification, and characterization of the human Class Ia phosphoinositide 3-kinase isoforms: Meier, T. I.; Cook, J. A.; Thomas, J. E.; Radding, J. A.; Horn, C.; Lingaraj, T.; Smith, M. C. Protein Expr. Purif., 2004, 35(2), 218.
2. Competitive fluorescence polarization assays for the detection of phosphoinositide kinase and phosphatase activity: Drees, B. E.; Weipert, A.; Hudson, H.; Ferguson, C. G.; Chakravarty, L.; Prestwich, G. D. Comb. Chem. High Throughput. Screen., 2003, 6(4), 321.
For PI3Kγ: WO 2005/011686 A1
The pharmaceutically active compounds within the scope of this invention are useful as PI3 Kinase inhibitors in mammals, particularly humans, in need thereof.
The present invention therefore provides a method of treating diseases associated with PI3 kinase inhibition, particularly: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries and other conditions requiring PI3 kinase modulation/inhibition, which comprises administering an effective compound of Formula (I) or a pharmaceutically acceptable salt thereof. The compounds of Formula (I) also provide for a method of treating the above indicated disease states because of their ability to act as PI3 inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a PI3K inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular PI3 kinase inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing PI3 kinase inhibitory activity in mammals, including humans, comprises administering to a subject in need of such activity an effective PI3 kinase modulating/inhibiting amount of a pharmaceutically active compound of the present invention.

The invention also provides for the use of a compound of Formula (I) in the manufacture of a medicament for use as a PI3 kinase inhibitor.

The invention also provides for the use of a compound of Formula (I) in the manufacture of a medicament for use in therapy.

The invention also provides for the use of a compound of Formula (I) in the manufacture of a medicament for use in treating autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

The invention also provides for a pharmaceutical composition for use as a PI3 inhibitor which comprises a compound of Formula (I) or a pharmaceutically acceptable carrier.

The invention also provides for a pharmaceutical composition for use in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, which comprises a compound of Formula (I) or a pharmaceutically acceptable carrier.

In addition, the pharmaceutically active compounds of the present invention can be co-administered with further active ingredients, including compounds known to have utility when used in combination with a PI3 kinase inhibitor.

Without further elaboration, it is believed that one skilled in the art can, using the preceding description, utilize the present invention to its fullest extent. The following examples are, therefore, to be construed as merely illustrative and not a limitation of the scope of the present invention in any way.

EXPERIMENTAL DETAILS

The compounds of the following examples are readily made according to Schemes 1 or by analogous methods.

Scheme 1:

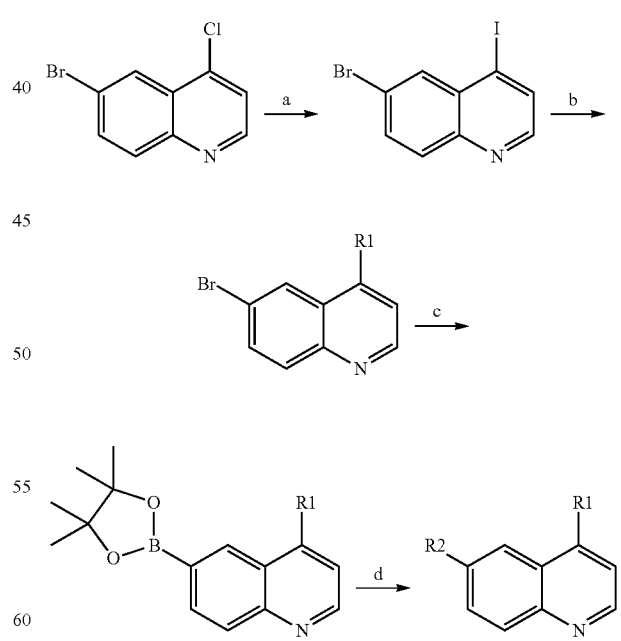

Conditions: a) 2 M HCl in diethylether, THF, rt; then sodium iodide, propionitrile, reflux; b) aryl (R1) bromide, palladium catalyst, 2 M K$_2$CO$_3$, dioxane, heat; c) bis(pinacolato)diboron, potassium acetate, palladium catalyst, dioxane, heat; d) heteroaryl (R2) bromide, palladium catalyst, saturated aqueous NaHCO$_3$, dioxane, heat.

Example 1

5-[4-(4-pyridinyl)-6-quinolinyl]-3-pyridinesulfonamide

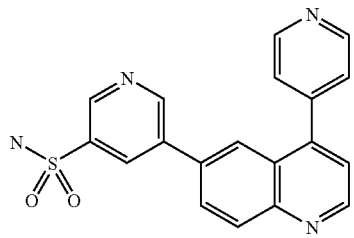 [SMILES: NS(=O)(=O)c1cncc(-c2ccc3nccc(-c4ccncc4)c3c2)c1]

a) 6-bromo-4-iodoquinoline

Following the general procedure of Wolf, Christian et al. (*SynLett* 2003 12, 1801-1804), to a solution of 6-bromo-4-chloroquinoline (30 g, 0.124 mol) in anhydrous THF (500 mL) was added 2 M HCl in diethylether (74 mL, 0.148 mol). A white precipitate formed immediately. After stirring for 30 min, the suspension was concentrated in vacuo and dried under vacuum to provide 6-bromo-4-chloroquinoline hydrochloride as an off-white solid (34.6 g, quantitative yield).

A 3-neck roundbottom flask equipped with a reflux condenser and mechanical stirrer was charged with 6-bromo-4-chloroquinoline hydrochloride (34.6 g, 0.124 mol), anhydrous sodium iodide (92.93 g, 0.62 mol) and propionitrile (1 L). The resulting slurry was stirred vigorously at reflux for 96 hrs. The solution was cooled to room temperature and 500 mL of 10% $K_2CO_3$ solution was added, followed by a 200 mL of a 5% sodium sulfite solution. The reaction mixture was extracted with $CH_2Cl_2$ (600 mL×4). The combined organic extracts were dried ($Na_2SO_4$), filtered and conc. in vacuo to provide the title compound as an off-white solid (41.8 g, >quantitative yield), which was used without further purification. LCMS $[M]^+$=333.8, 334.8, 336.0 and 337.0; $H^1$ NMR (400 MHz, d-DMSO) δ (ppm)=7.98-7.96 (2H, m), 8.14-8.16 (1H, m), 8.23 (1H, d), 8.53 (1H, d).

b) 6-bromo-4-(4-pyridinyl)quinoline

A 1 L sealed tube charged with 6-bromo-4-iodoquinoline (11.58 g, 0.0347 mol), 4-pyridineboronic acid (5.97 g, 0.0486 mol), tetrakis(triphenyphosphine)palladium[0] (2.0 g, 0.00173 mol), 2 M aqueous potassium carbonate (152 mL) and 1,4-dioxane (152 mL) was stirred at 100° C. for 28 hrs. After cooling to rt, the organic layer was separated and the aqueous portion extracted with EtOAc (200 mL×3). The combined organic extracts were dried ($Na_2SO_4$), filtered and partially concentrated in vacuo. The resultant mixture was filtered to give the title compound (9.13 g) as a tan solid. The residual supernatant was concentrated to dryness and purified by silica gel chromatography (100% ethyl acetate to 2% methanol in ethyl acetate) to provide an additional 0.036 g of the title compound as a tan solid (combined 9.166 g, 92% yield).

LCMS $[M]^+$=285.9; 287.8. $H^1$ NMR (400 MHz, d-DMSO) δ (ppm)=7.53-7.71 (3H, m), 7.85 (1H, s), 8.05 (1H, d), 8.17 (1H, d), 8.81 (2H, d), 9.05 (1H, d)

c) 4-(4-pyridinyl)-6-(4,4,5,5-tetramethyl-1,3,2-dioxaborolan-2-yl)quinoline

A mixture of (6-bromo-4-(4-pyridinyl)quinoline (5.0 g, 17.5 mmol), bis(pinacolato)diboron (4.9 g, 19.3 mmole), potassium acetate (5.2 g, 52 6 mmol), and dichloro-[1,1'bis(diphenylphosphino)ferrocene]palladium(II)dichloromethane adduct (430 mg, 0.53 mmol) in dioxane (30 mL) was heated at 130° C. for 4 h and cooled to room temperature. The reaction was cooled and filtered through $Na_2SO_4$ and Celite onto silica. The mixture was purified by silica gel chromatography eluting with EtOAc/ethanol (0-20% methanol gradient) to give the title compound as a semi-pure solid. (2.14 g, 64%) mix of boronic acid and ester used without further purification.

d) 5-[4-(4-pyridinyl)-6-quinolinyl]-3-pyridinesulfonamide

A mixture of 4-(4-pyridinyl)-6-(4,4,5,5-tetramethyl-1,3,2-dioxaborolan-2-yl)quinoline (250 mg, 0.75 mmol), 5-bromopyridine-3-sulfonamide (213 mg, 0.9 mmol), tetrakistriphenylphosphine palladium (0) (95 mg, 0.08 mmol), and saturated aqueous $NaHCO_3$ (2.5 mL), and dioxane (5 mL)) was heated at 120° C. for 1 h and cooled to room temperature. The reaction mixture was filtered through Celite and the solvent was removed under reduced pressure. The crude product was purified by Gilson reverse phase HPLC (8-25% 6 min gradient 0.1% TFA in $H_2O/CH_3CN$) followed by neutralization with saturated aqueous $NaHCO_3$ and extracted into EtOAc. Evaporation provided the title compound as an off white solid. (85 mg, 31%). ESMS $[M+H]^+$=363.1

The following compounds were or can be prepared following the general procedures used to prepare the compound of Example 1:

| Example | Structure | MS(ES) [M + H]⁺ |
|---|---|---|
| 2 | 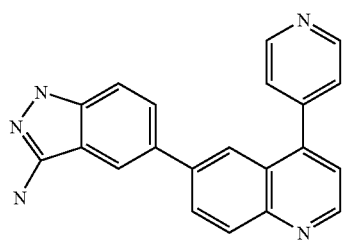 [SMILES: Nc1n[nH]c2ccc(-c3ccc4nccc(-c5ccncc5)c4c3)cc12] | 338 |

-continued

| Example | Structure | MS(ES) [M + H]+ |
|---------|-----------|-----------------|
| 3 | 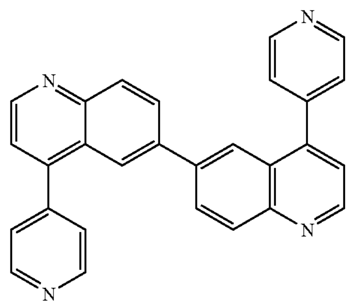 [SMILES: c1cc(-c2ccnc3ccc(-c4ccc5nccc(-c6ccncc6)c5c4)cc23)ccn1] | 411 |
| 4 | 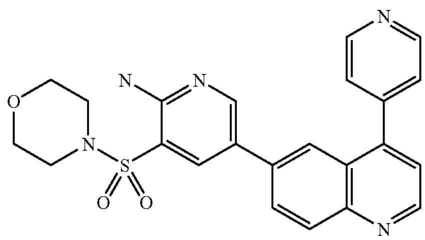 | 448 |
| 5 | 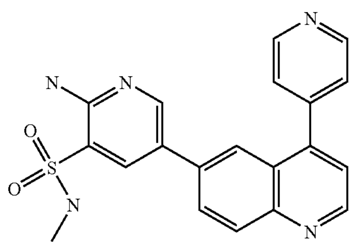 [SMILES: CNS(=O)(=O)c1cc(-c2ccc3nccc(-c4ccncc4)c3c2)cnc1N] | 392 |
| 6 | 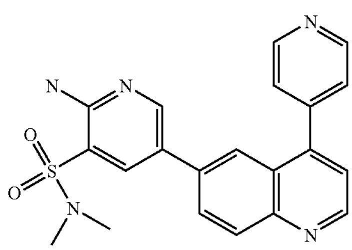 [SMILES: CN(C)S(=O)(=O)c1cc(-c2ccc3nccc(-c4ccncc4)c3c2)cnc1N] | 406 |
| 7 | 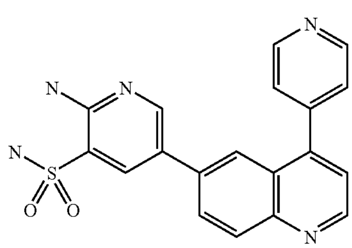 [SMILES: Nc1ncc(-c2ccc3nccc(-c4ccncc4)c3c2)cc1S(N)(=O)=O] | 378 |
| 8 | 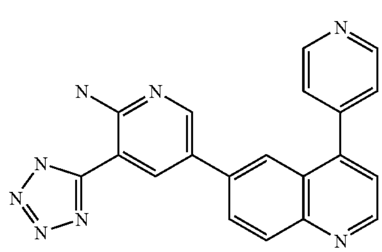 [SMILES: Nc1ncc(-c2ccc3nccc(-c4ccncc4)c3c2)cc1-c1nnn[nH]1] | 367 |

-continued

| Example | Structure | MS(ES) [M + H]+ |
|---|---|---|
| 9 | 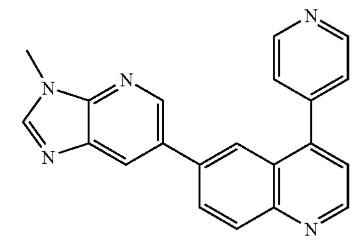 [SMILES: Cn1cnc2cc(-c3ccc4nccc(-c5ccncc5)c4c3)cnc21] | 338 |
| 10 | 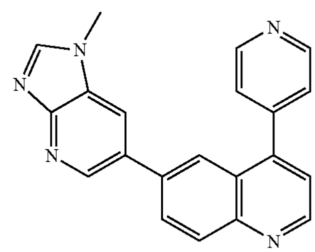 [SMILES: Cn1cnc2ncc(-c3ccc4nccc(-c5ccncc5)c4c3)cc21] | 338 |
| 11 | 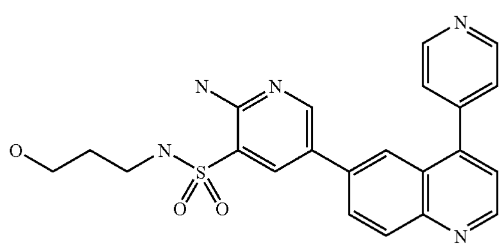 [SMILES: Nc1ncc(-c2ccc3nccc(-c4ccncc4)c3c2)cc1S(=O)(=O)NCCCO] | 436 |
| 12 | 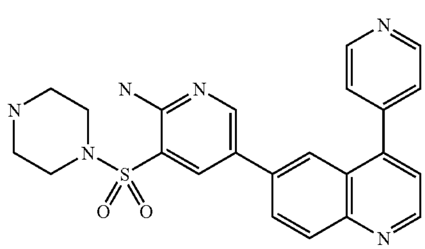 [SMILES: Nc1ncc(-c2ccc3nccc(-c4ccncc4)c3c2)cc1S(=O)(=O)N1CCNCC1] | 447 |
| 13 | 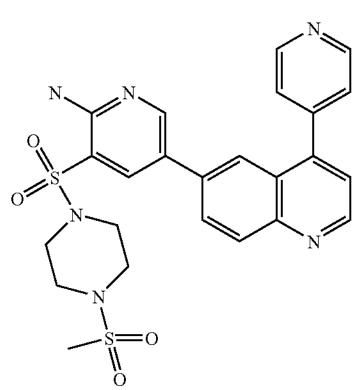 [SMILES: CS(=O)(=O)N1CCN(S(=O)(=O)c2cc(-c3ccc4nccc(-c5ccncc5)c4c3)cnc2N)CC1] | 525 |

-continued

| Example | Structure | MS(ES) [M + H]+ |
|---------|-----------|-----------------|
| 14 | 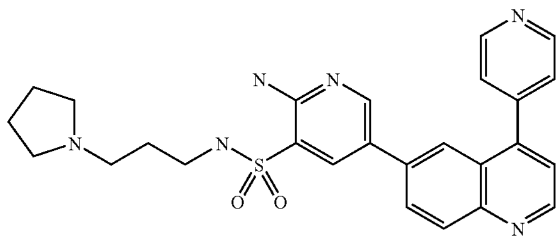 [SMILES: Nc1ncc(-c2ccc3nccc(-c4ccncc4)c3c2)cc1S(=O)(=O)NCCCN1CCCC1] | 489 |
| 15 | 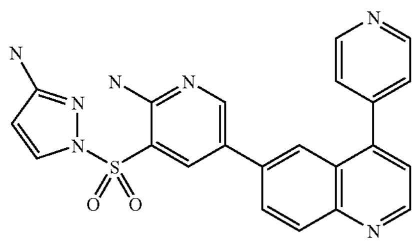 [SMILES: Nc1ccn(S(=O)(=O)c2cc(-c3ccc4nccc(-c5ccncc5)c4c3)cnc2N)n1] | 444 |
| 16 | 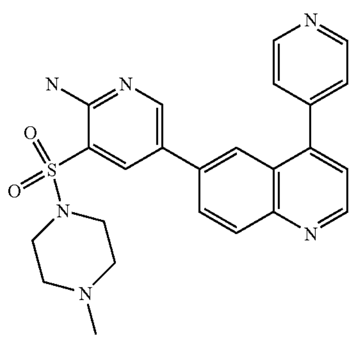 [SMILES: CN1CCN(S(=O)(=O)c2cc(-c3ccc4nccc(-c5ccncc5)c4c3)cnc2N)CC1] | 461 |
| 17 | 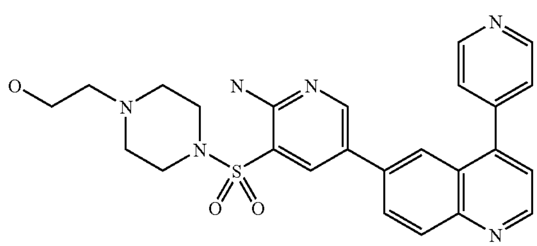 [SMILES: Nc1ncc(-c2ccc3nccc(-c4ccncc4)c3c2)cc1S(=O)(=O)N1CCN(CCO)CC1] | 491 |
| 18 | 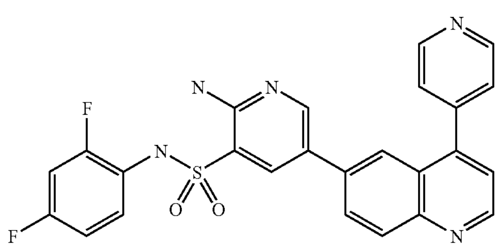 [SMILES: Nc1ncc(-c2ccc3nccc(-c4ccncc4)c3c2)cc1S(=O)(=O)Nc1ccc(F)cc1F] | 490 |
| 19 | 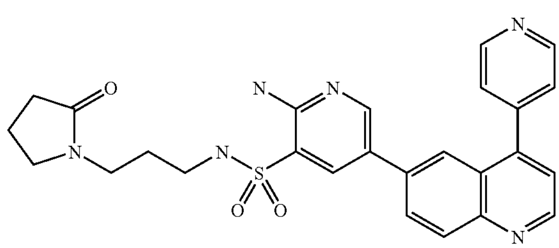 [SMILES: Nc1ncc(-c2ccc3nccc(-c4ccncc4)c3c2)cc1S(=O)(=O)NCCCN1CCCC1=O] | 503 |

-continued

| Example | Structure | MS(ES) [M + H]+ |
|---|---|---|
| 20 | 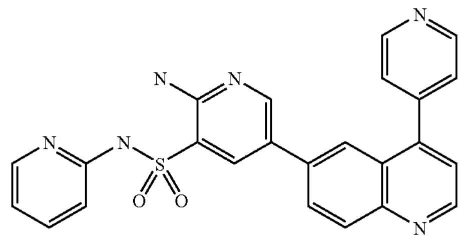 | 454 |
| 21 | 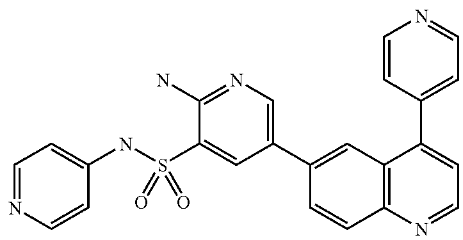 | 454 |
| 22 | 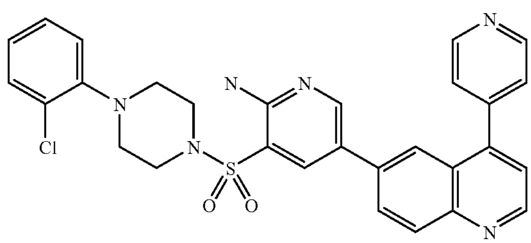 [SMILES: Nc1ncc(-c2ccc3nccc(-c4ccncc4)c3c2)cc1S(=O)(=O)N1CCN(c2ccccc2Cl)CC1] | 557 |
| 23 | 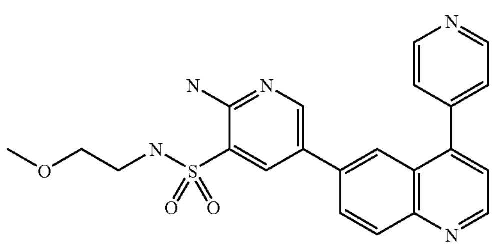 [SMILES: COCCNS(=O)(=O)c1cc(-c2ccc3nccc(-c4ccncc4)c3c2)cnc1N] | 436 |
| 24 | 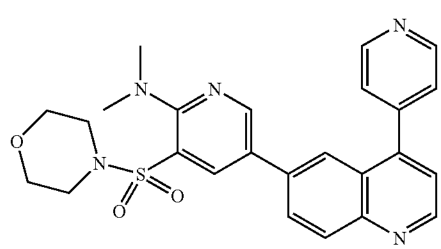 [SMILES: CN(C)c1ncc(-c2ccc3nccc(-c4ccncc4)c3c2)cc1S(=O)(=O)N1CCOCC1] | 476 |
| 25 | 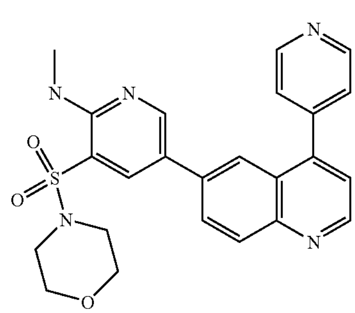 [SMILES: CNc1ncc(-c2ccc3nccc(-c4ccncc4)c3c2)cc1S(=O)(=O)N1CCOCC1] | 462 |

-continued

| Example | Structure | MS(ES) [M + H]+ |
|---|---|---|
| 26 | 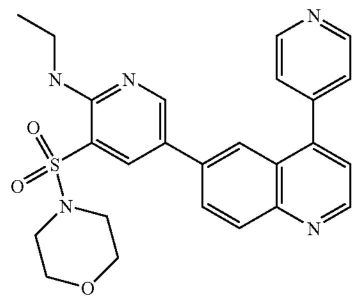 [SMILES: CCNc1ncc(-c2ccc3nccc(-c4ccncc4)c3c2)cc1S(=O)(=O)N1CCOCC1] | 476 |
| 27 | 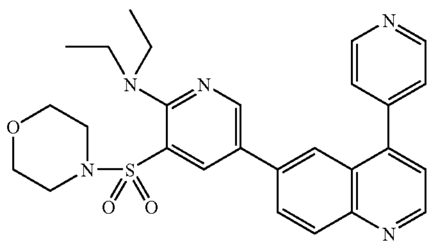 [SMILES: CCN(CC)c1ncc(-c2ccc3nccc(-c4ccncc4)c3c2)cc1S(=O)(=O)N1CCOCC1] | 504 |
| 28 | 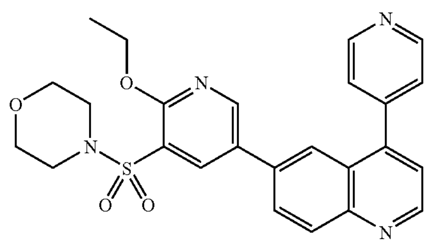 [SMILES: CCOc1ncc(-c2ccc3nccc(-c4ccncc4)c3c2)cc1S(=O)(=O)N1CCOCC1] | 477 |
| 29 | 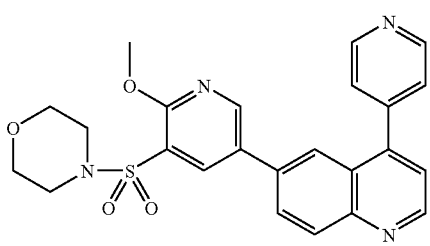 [SMILES: COc1ncc(-c2ccc3nccc(-c4ccncc4)c3c2)cc1S(=O)(=O)N1CCOCC1] | 463 |
| 30 | 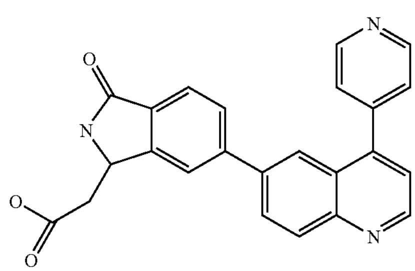 [SMILES: O=C(O)CC1NC(=O)c2ccc(-c3ccc4nccc(-c5ccncc5)c4c3)cc21] | 396 |
| 31 | 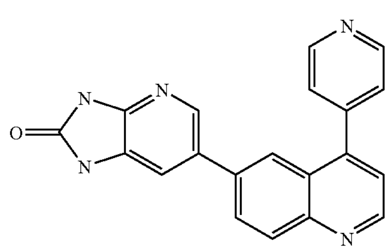 | 340 |

-continued

| Example | Structure | MS(ES) [M + H]+ |
|---------|-----------|-----------------|
| 32 | 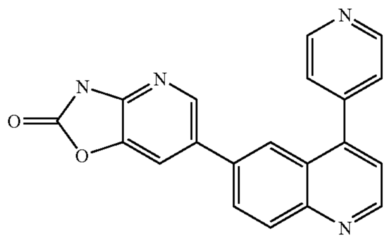 [SMILES: O=c1[nH]c2ncc(-c3ccc4nccc(-c5ccncc5)c4c3)cc2o1] | 341 |
| 33 | 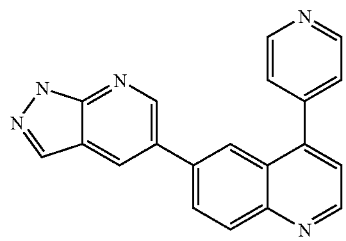 | 324 |
| 34 | 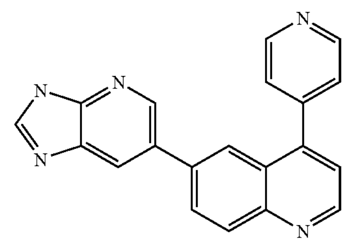 [SMILES: c1cc(-c2ccnc3ccc(-c4cnc5[nH]cnc5c4)cc23)ccn1] | 324 |
| 35 | 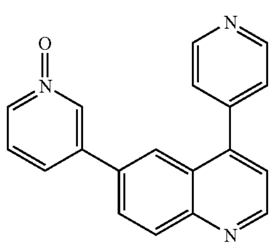 [SMILES: [O-][n+]1cccc(-c2ccc3nccc(-c4ccncc4)c3c2)c1] | 300 |
| 36 | 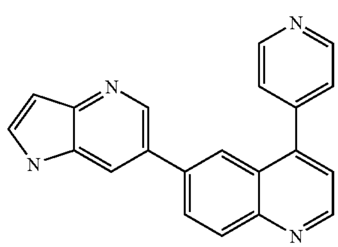 [SMILES: c1cc(-c2ccnc3ccc(-c4cnc5cc[nH]c5c4)cc23)ccn1] | 323 |
| 37 | 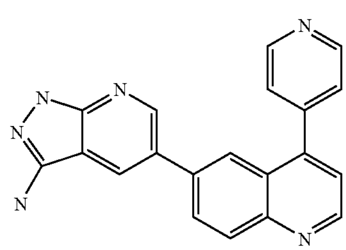 [SMILES: Nc1n[nH]c2ncc(-c3ccc4nccc(-c5ccncc5)c4c3)cc12] | 339 |

| Example | Structure | MS(ES) [M + H]⁺ |
|---|---|---|
| 38 | 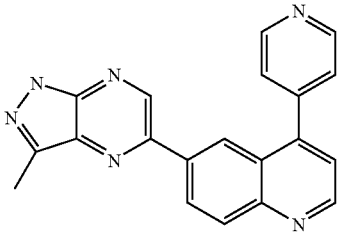 [SMILES: Cc1n[nH]c2ncc(-c3ccc4nccc(-c5ccncc5)c4c3)nc12] | 339 |
| 39 | 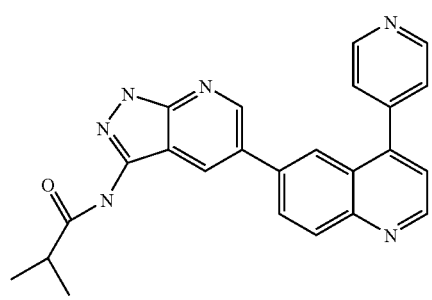 [SMILES: CC(C)C(=O)Nc1n[nH]c2ncc(-c3ccc4nccc(-c5ccncc5)c4c3)cc12] | 409 |
| 40 | 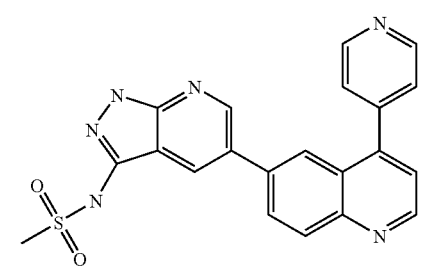 [SMILES: CS(=O)(=O)Nc1n[nH]c2ncc(-c3ccc4nccc(-c5ccncc5)c4c3)cc12] | 417 |
| 41 | 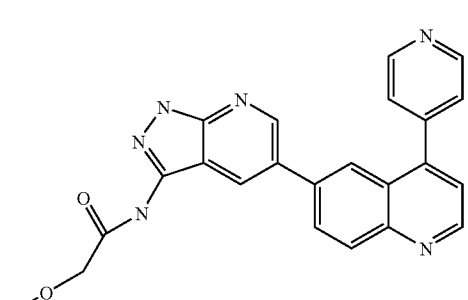 | 411 |
| 42 | 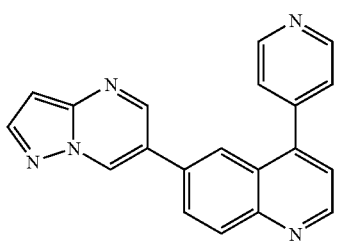 [SMILES: c1cc(-c2ccnc3ccc(-c4cnc5ccnn5c4)cc23)ccn1] | 324 |

-continued

| Example | Structure | MS(ES) [M + H]+ |
|---|---|---|
| 43 | 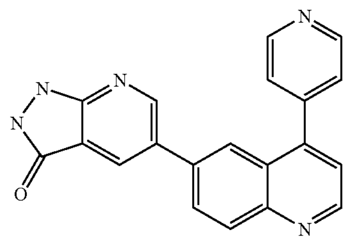 [SMILES: O=c1[nH][nH]c2ncc(-c3ccc4nccc(-c5ccncc5)c4c3)cc12] | 340 |
| 44 | 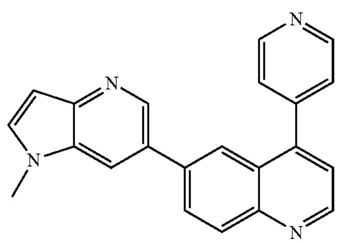 [SMILES: Cn1ccc2ncc(-c3ccc4nccc(-c5ccncc5)c4c3)cc21] | 337 |
| 45 | 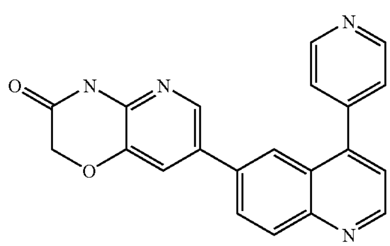 [SMILES: O=C1COc2cc(-c3ccc4nccc(-c5ccncc5)c4c3)cnc2N1] | 355 |
| 46 | 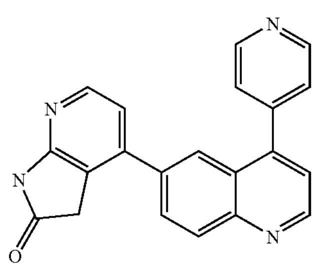 [SMILES: O=C1Cc2c(-c3ccc4nccc(-c5ccncc5)c4c3)ccnc2N1] | 339 |
| 47 | 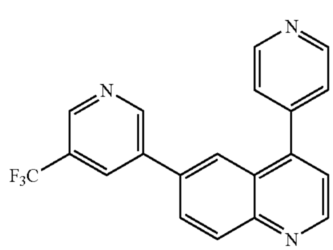 [SMILES: FC(F)(F)c1cncc(-c2ccc3nccc(-c4ccncc4)c3c2)c1] | 352 |
| 48 | 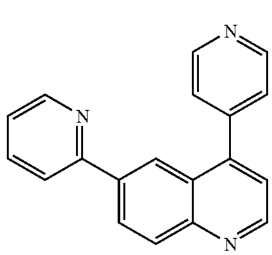 [SMILES: c1ccc(-c2ccc3nccc(-c4ccncc4)c3c2)nc1] | 284 |

-continued
| Example | Structure | MS(ES) [M + H]+ |
|---|---|---|
| 49 | 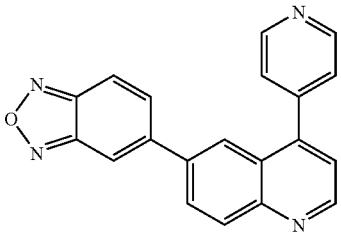 | 325 |
| 50 | 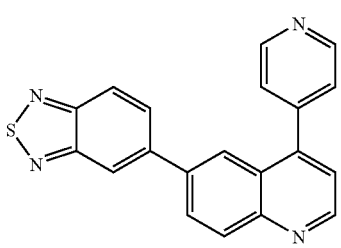 [SMILES: c1cc(-c2ccnc3ccc(-c4ccc5nsnc5c4)cc23)ccn1] | 341 |
| 51 | 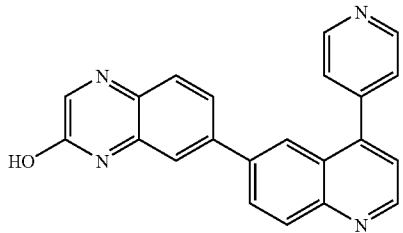 [SMILES: Oc1cnc2ccc(-c3ccc4nccc(-c5ccncc5)c4c3)cc2n1] | 351 |
| 52 | 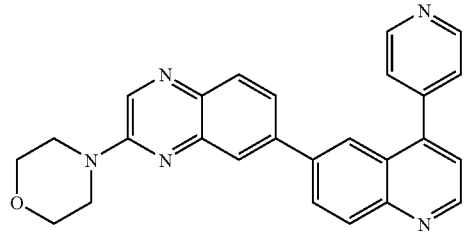 [SMILES: c1cc(-c2ccnc3ccc(-c4ccc5ncc(N6CCOCC6)nc5c4)cc23)ccn1] | 420 |
| 53 | 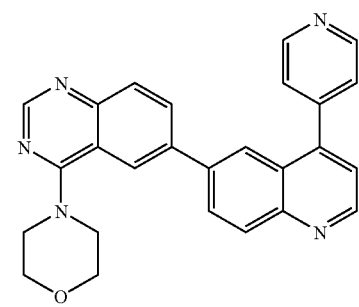 [SMILES: c1cc(-c2ccnc3ccc(-c4ccc5ncnc(N6CCOCC6)c5c4)cc23)ccn1] | 420 |

-continued

| Example | Structure | MS(ES) [M + H]⁺ |
|---|---|---|
| 59 | 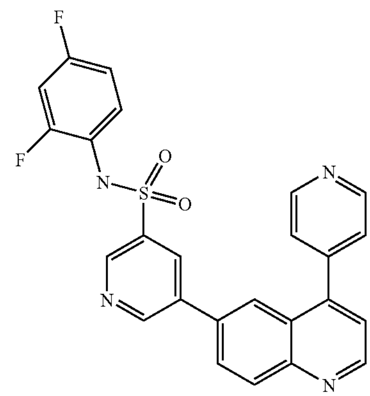 [SMILES: O=S(=O)(Nc1ccc(F)cc1F)c1cncc(-c2ccc3nccc(-c4ccncc4)c3c2)c1] | 475 |
| 60 | 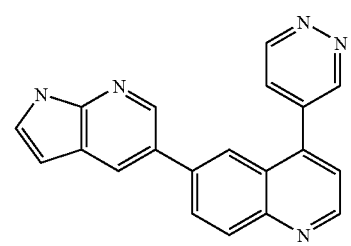 [SMILES: c1cc(-c2ccnc3ccc(-c4cnc5[nH]ccc5c4)cc23)cnn1] | 324 |
| 61 | 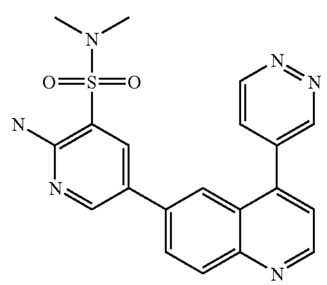 [SMILES: CN(C)S(=O)(=O)c1cc(-c2ccc3nccc(-c4ccnnc4)c3c2)cnc1N] | 407 |
| 62 | 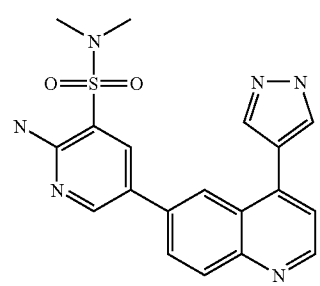 [SMILES: CN(C)S(=O)(=O)c1cc(-c2ccc3nccc(-c4cn[nH]c4)c3c2)cnc1N] | 395 |
| 63 | 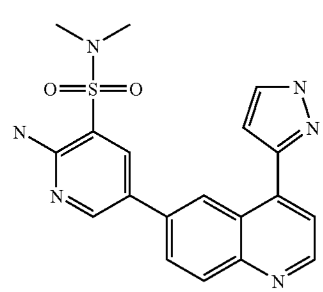 [SMILES: CN(C)S(=O)(=O)c1cc(-c2ccc3nccc(-c4cc[nH]n4)c3c2)cnc1N] | 395 |

-continued

| Example | Structure | MS(ES) [M + H]+ |
|---------|-----------|-----------------|
| 64 | 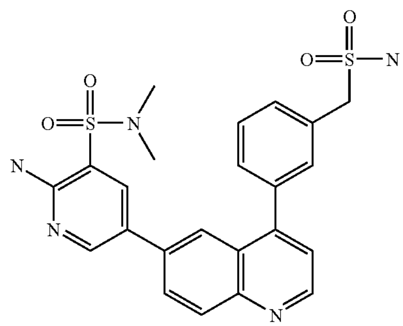 [SMILES: CN(C)S(=O)(=O)c1cc(-c2ccc3nccc(-c4cccc(CS(N)(=O)=O)c4)c3c2)cnc1N] | 498 |
| 65 | 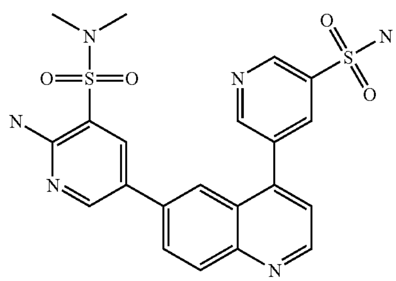 [SMILES: CN(C)S(=O)(=O)c1cc(-c2ccc3nccc(-c4cncc(S(N)(=O)=O)c4)c3c2)cnc1N] | 485 |
| 66 | 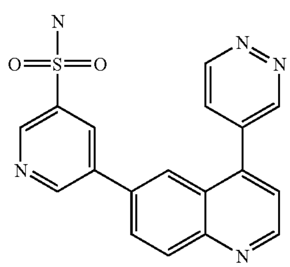 [SMILES: NS(=O)(=O)c1cncc(-c2ccc3nccc(-c4ccnnc4)c3c2)c1] | 364 |
| 67 | 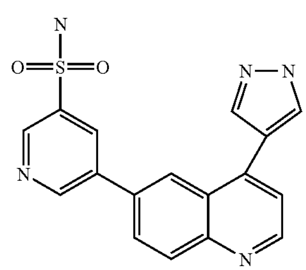 [SMILES: NS(=O)(=O)c1cncc(-c2ccc3nccc(-c4cn[nH]c4)c3c2)c1] | 352 |
| 68 | 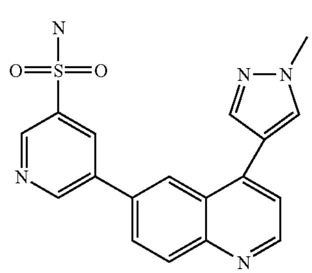 [SMILES: Cn1cc(-c2ccnc3ccc(-c4cncc(S(N)(=O)=O)c4)cc23)cn1] | 366 |

-continued
| Example | Structure | MS(ES) [M + H]+ |
|---|---|---|
| 69 | 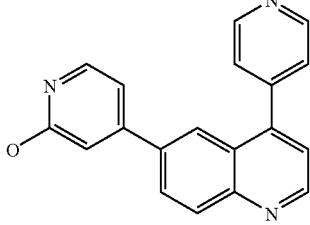 | 300 |
| 70 | 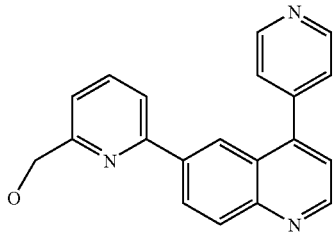 [SMILES: OCc1cccc(-c2ccc3nccc(-c4ccncc4)c3c2)n1] | 313 |
| 71 | 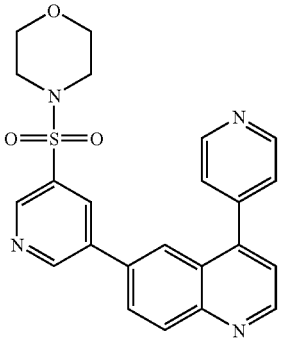 [SMILES: O=S(=O)(c1cncc(-c2ccc3nccc(-c4ccncc4)c3c2)c1)N1CCOCC1] | 433 |
| 72 | 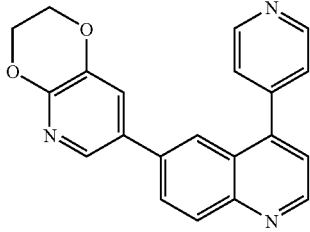 [SMILES: c1cc(-c2ccnc3ccc(-c4cnc5c(c4)OCCO5)cc23)ccn1] | 341 |
| 73 | 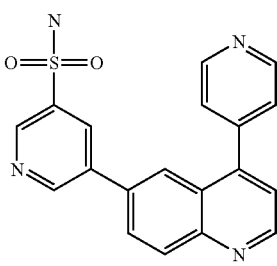 [SMILES: NS(=O)(=O)c1cncc(-c2ccc3nccc(-c4ccncc4)c3c2)c1] | 363 |

-continued

| Example | Structure | MS(ES) [M + H]+ |
|---|---|---|
| 74 | 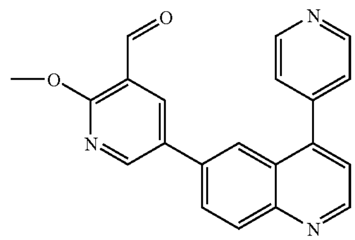 [SMILES: COc1ncc(-c2ccc3nccc(-c4ccncc4)c3c2)cc1C=O] | 341 |
| 75 | 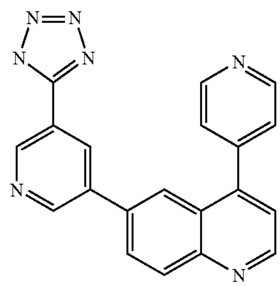 [SMILES: c1cc(-c2ccnc3ccc(-c4cncc(-c5nnn[nH]5)c4)cc23)ccn1] | 352 |
| 76 | 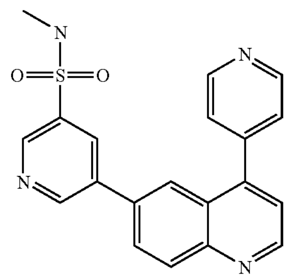 [SMILES: CNS(=O)(=O)c1cncc(-c2ccc3nccc(-c4ccncc4)c3c2)c1] | 377 |
| 77 | 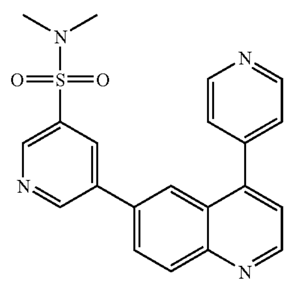 [SMILES: CN(C)S(=O)(=O)c1cncc(-c2ccc3nccc(-c4ccncc4)c3c2)c1] | 391 |
| 78 | 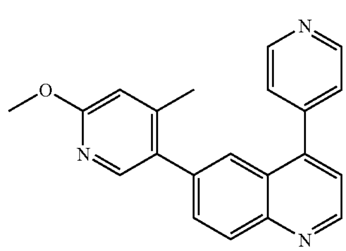 [SMILES: COc1cc(C)c(-c2ccc3nccc(-c4ccncc4)c3c2)cn1] | 328 |
| 79 | 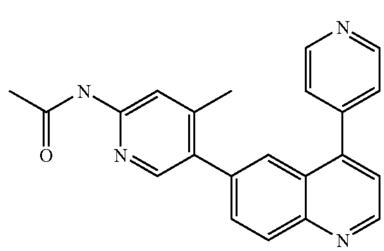 [SMILES: CC(=O)Nc1cc(C)c(-c2ccc3nccc(-c4ccncc4)c3c2)cn1] | 355 |

-continued

| Example | Structure | MS(ES) [M + H]+ |
|---|---|---|
| 80 | 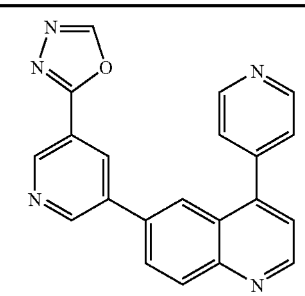 | 352 |
| 81 | 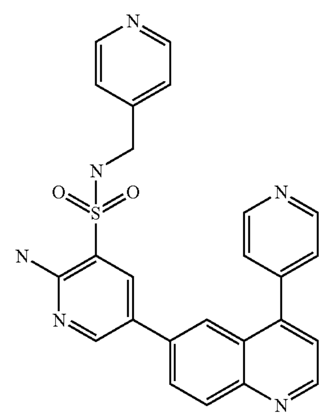 [SMILES: Nc1ncc(-c2ccc3nccc(-c4ccncc4)c3c2)cc1S(=O)(=O)NCc1ccncc1] | 469 |
| 82 | 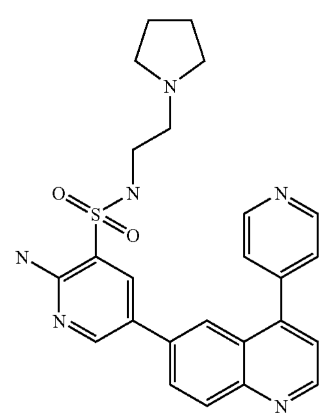 [SMILES: Nc1ncc(-c2ccc3nccc(-c4ccncc4)c3c2)cc1S(=O)(=O)NCCN1CCCC1] | 475 |
| 83 | 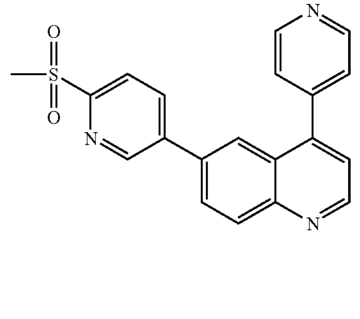 [SMILES: CS(=O)(=O)c1ccc(-c2ccc3nccc(-c4ccncc4)c3c2)cn1] | 362 |

-continued

| Example | Structure | MS(ES) [M + H]+ |
|---|---|---|
| 84 | 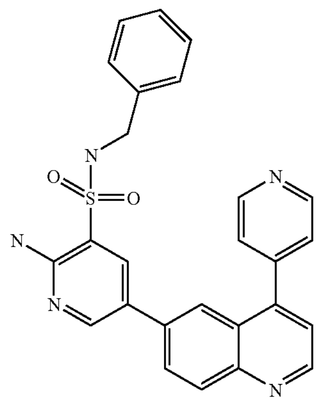 [SMILES: Nc1ncc(-c2ccc3nccc(-c4ccncc4)c3c2)cc1S(=O)(=O)NCc1ccccc1] | 468 |
| 85 | 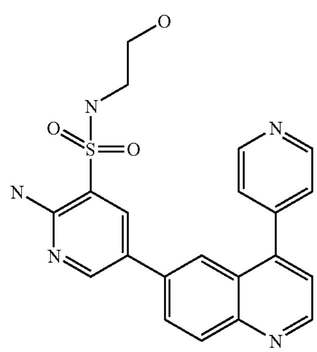 [SMILES: Nc1ncc(-c2ccc3nccc(-c4ccncc4)c3c2)cc1S(=O)(=O)NCCO] | 422 |
| 86 | 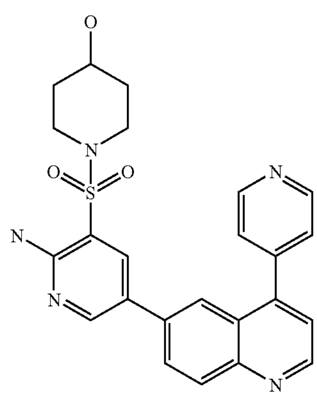 [SMILES: Nc1ncc(-c2ccc3nccc(-c4ccncc4)c3c2)cc1S(=O)(=O)N1CCC(O)CC1] | 462 |
| 87 | 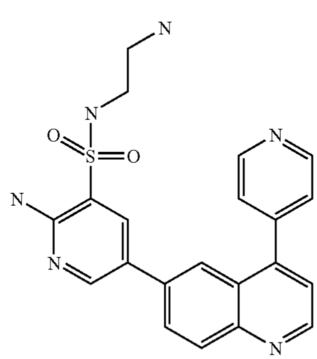 | 421 |

-continued

| Example | Structure | MS(ES) [M + H]+ |
|---|---|---|
| 88 | 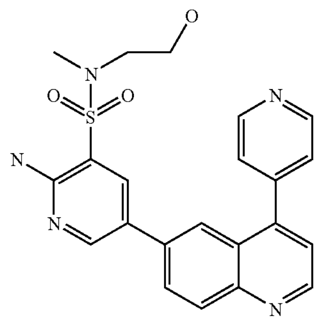 [SMILES: CN(CCO)S(=O)(=O)c1cc(-c2ccc3nccc(-c4ccncc4)c3c2)cnc1N] | 436 |
| 89 | 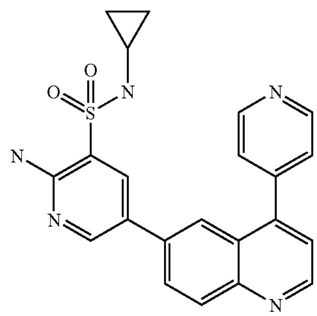 [SMILES: Nc1ncc(-c2ccc3nccc(-c4ccncc4)c3c2)cc1S(=O)(=O)NC1CC1] | 418 |
| 90 | 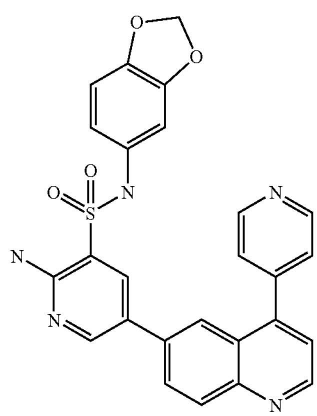 [SMILES: Nc1ncc(-c2ccc3nccc(-c4ccncc4)c3c2)cc1S(=O)(=O)Nc1ccc2c(c1)OCO2] | 498 |
| 91 | 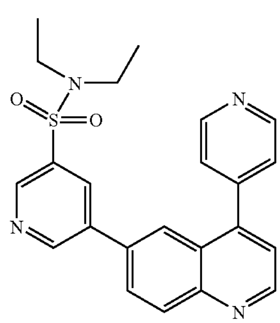 [SMILES: CCN(CC)S(=O)(=O)c1cncc(-c2ccc3nccc(-c4ccncc4)c3c2)c1] | 419 |

-continued

| Example | Structure | MS(ES) [M + H]+ |
|---------|-----------|-----------------|
| 92 | 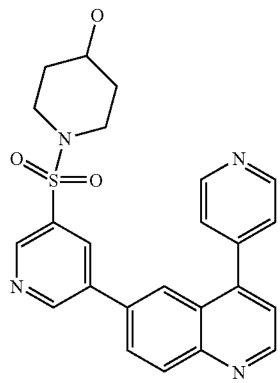 [SMILES: O=S(=O)(c1cncc(-c2ccc3nccc(-c4ccncc4)c3c2)c1)N1CCC(O)CC1] | 447 |
| 93 | 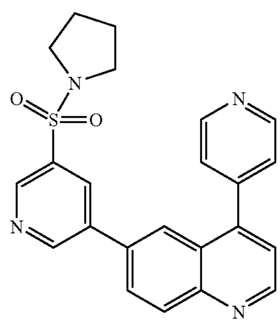 [SMILES: O=S(=O)(c1cncc(-c2ccc3nccc(-c4ccncc4)c3c2)c1)N1CCCC1] | 417 |
| 94 | 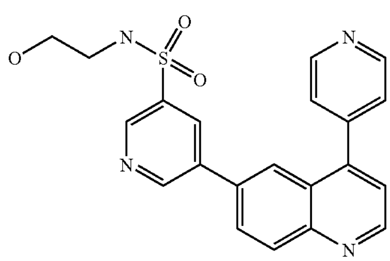 [SMILES: O=S(=O)(NCCO)c1cncc(-c2ccc3nccc(-c4ccncc4)c3c2)c1] | 407 |
| 95 | 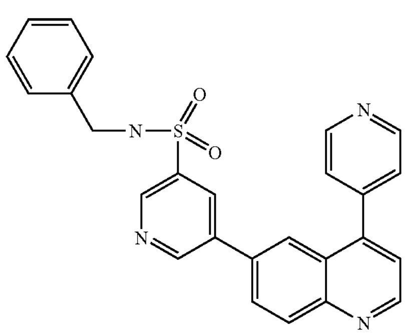 [SMILES: O=S(=O)(NCc1ccccc1)c1cncc(-c2ccc3nccc(-c4ccncc4)c3c2)c1] | 453 |
| 96 | 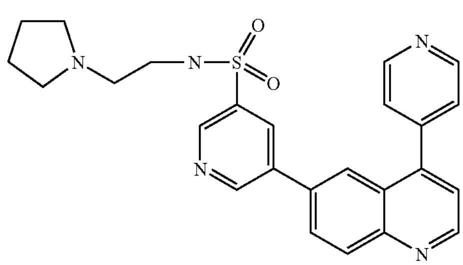 [SMILES: O=S(=O)(NCCN1CCCC1)c1cncc(-c2ccc3nccc(-c4ccncc4)c3c2)c1] | 460 |

-continued

| Example | Structure | MS(ES) [M + H]+ |
|---|---|---|
| 97 | 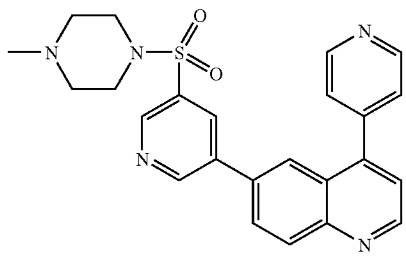 [SMILES: CN1CCN(S(=O)(=O)c2cncc(-c3ccc4nccc(-c5ccncc5)c4c3)c2)CC1] | 446 |
| 98 | 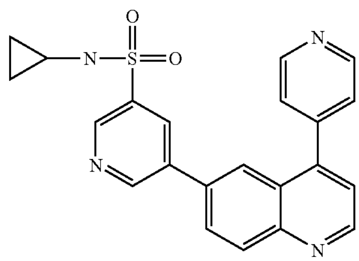 [SMILES: O=S(=O)(NC1CC1)c1cncc(-c2ccc3nccc(-c4ccncc4)c3c2)c1] | 403 |
| 99 | 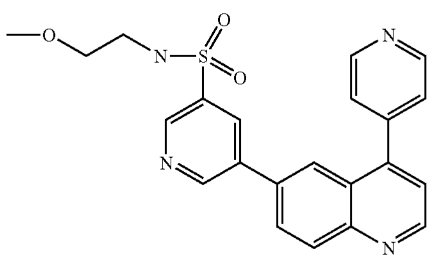 [SMILES: COCCNS(=O)(=O)c1cncc(-c2ccc3nccc(-c4ccncc4)c3c2)c1] | 421 |
| 100 | 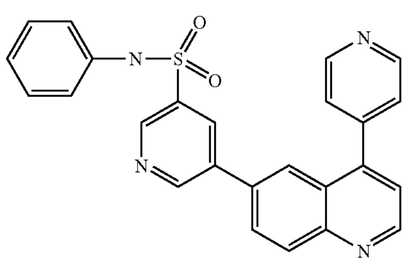 [SMILES: O=S(=O)(Nc1ccccc1)c1cncc(-c2ccc3nccc(-c4ccncc4)c3c2)c1] | 439 |
| 101 | 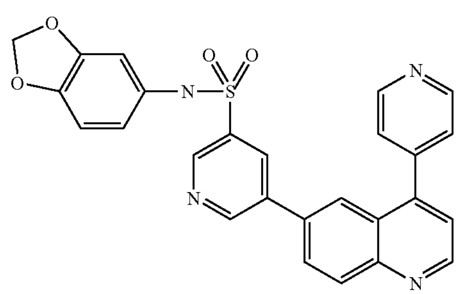 [SMILES: O=S(=O)(Nc1ccc2c(c1)OCO2)c1cncc(-c2ccc3nccc(-c4ccncc4)c3c2)c1] | 483 |

-continued

| Example | Structure | MS(ES) [M + H]+ |
|---------|-----------|-----------------|
| 102 | 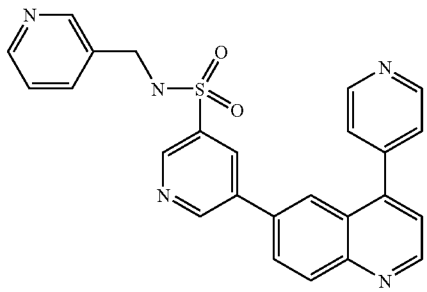 [SMILES: O=S(=O)(NCc1cccnc1)c1cncc(-c2ccc3nccc(-c4ccncc4)c3c2)c1] | 453 |
| 103 | 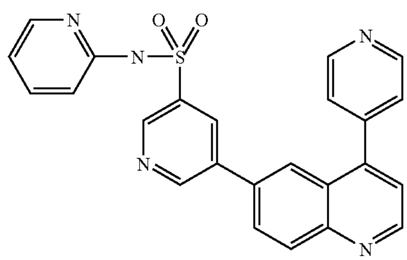 [SMILES: O=S(=O)(Nc1ccccn1)c1cncc(-c2ccc3nccc(-c4ccncc4)c3c2)c1] | 440 |
| 104 | 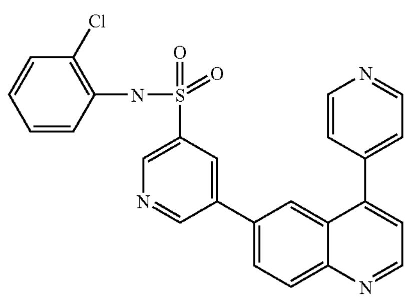 [SMILES: O=S(=O)(Nc1ccccc1Cl)c1cncc(-c2ccc3nccc(-c4ccncc4)c3c2)c1] | 473.2 |
| 105 | 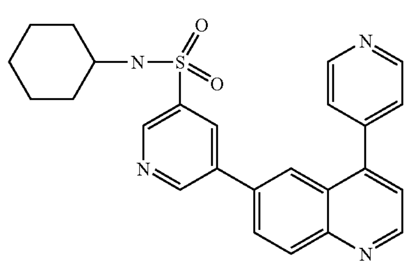 [SMILES: O=S(=O)(NC1CCCCC1)c1cncc(-c2ccc3nccc(-c4ccncc4)c3c2)c1] | 445.3 |
| 106 | 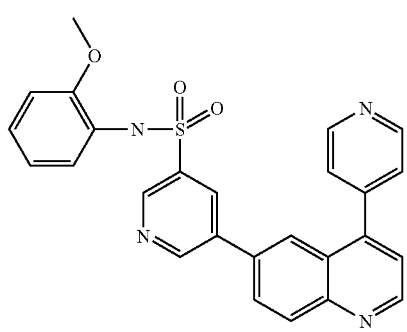 [SMILES: COc1ccccc1NS(=O)(=O)c1cncc(-c2ccc3nccc(-c4ccncc4)c3c2)c1] | 469.1 |

-continued

| Example | Structure | MS(ES) [M + H]+ |
|---|---|---|
| 249 | 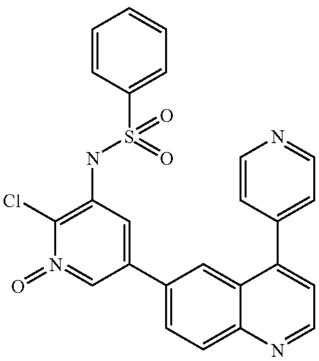 [SMILES: O=S(=O)(Nc1cc(-c2ccc3nccc(-c4ccncc4)c3c2)c[n+]([O-])c1Cl)c1ccccc1] | 489.1 |
| 250 | 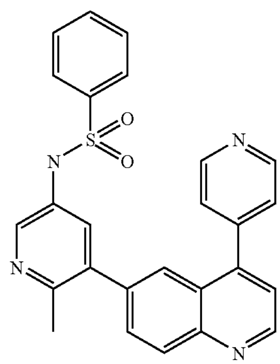 [SMILES: Cc1ncc(NS(=O)(=O)c2ccccc2)cc1-c1ccc2nccc(-c3ccncc3)c2c1] | 453.0 |
| 251 | 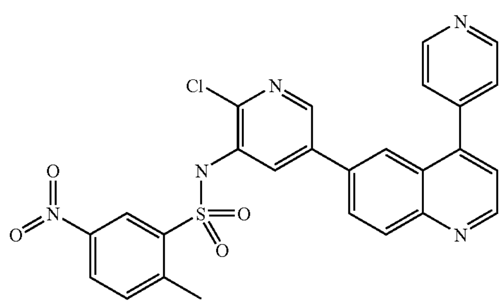 [SMILES: Cc1ccc([N+](=O)[O-])cc1S(=O)(=O)Nc1cc(-c2ccc3nccc(-c4ccncc4)c3c2)cnc1Cl] | 532 |
| 252 | 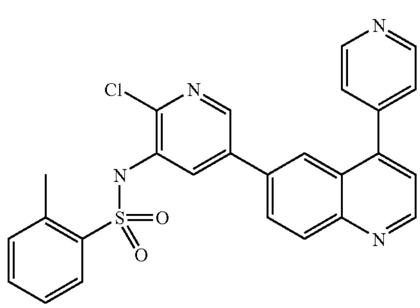 [SMILES: Cc1ccccc1S(=O)(=O)Nc1cc(-c2ccc3nccc(-c4ccncc4)c3c2)cnc1Cl] | 487.1 |

-continued

| Example | Structure | MS(ES) [M + H]+ |
|---|---|---|
| 253 | 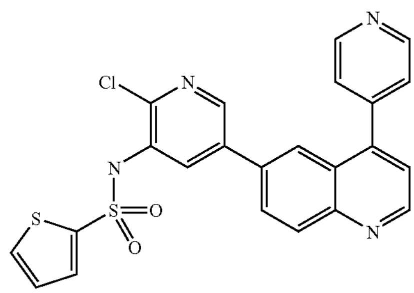 [SMILES: O=S(=O)(Nc1cc(-c2ccc3nccc(-c4ccncc4)c3c2)cnc1Cl)c1cccs1] | 478.9 |
| 254 | 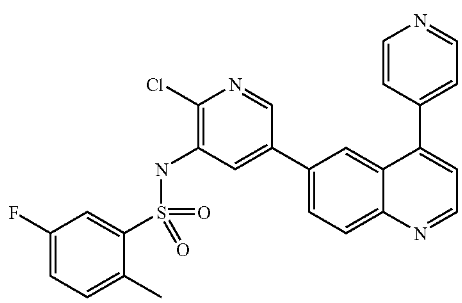 [SMILES: Cc1ccc(F)cc1S(=O)(=O)Nc1cc(-c2ccc3nccc(-c4ccncc4)c3c2)cnc1Cl] | 505.1 |
| 255 | 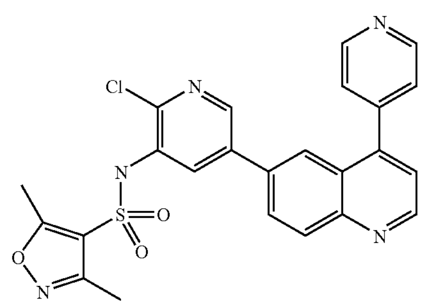 [SMILES: Cc1noc(C)c1S(=O)(=O)Nc1cc(-c2ccc3nccc(-c4ccncc4)c3c2)cnc1Cl] | 492.1 |
| 256 | 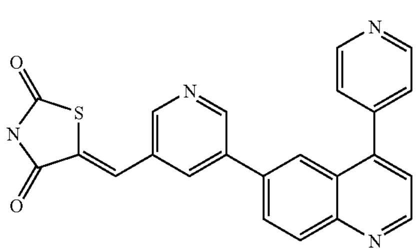 [SMILES: O=C1NC(=O)/C(=C/c2cncc(-c3ccc4nccc(-c5ccncc5)c4c3)c2)S1] | 411.1 |
| 257 | 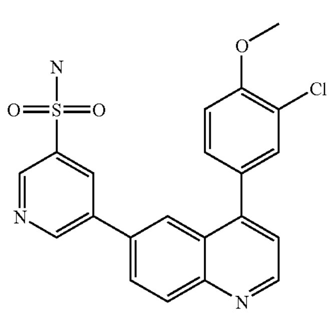 [SMILES: COc1ccc(-c2ccnc3ccc(-c4cncc(S(N)(=O)=O)c4)cc23)cc1Cl] | 426 |

-continued

| Example | Structure | MS(ES) [M + H]+ |
|---|---|---|
| 258 | 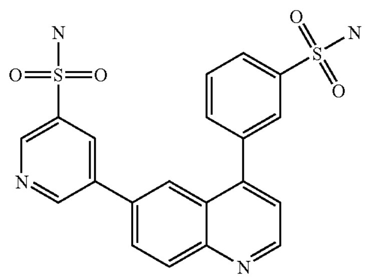 [SMILES: NS(=O)(=O)c1cncc(-c2ccc3nccc(-c4cccc(S(N)(=O)=O)c4)c3c2)c1] | 441 |
| 259 | 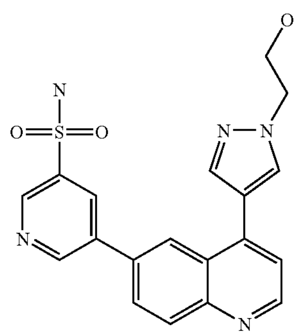 [SMILES: NS(=O)(=O)c1cncc(-c2ccc3nccc(-c4cnn(CCO)c4)c3c2)c1] | 396 |
| 260 | 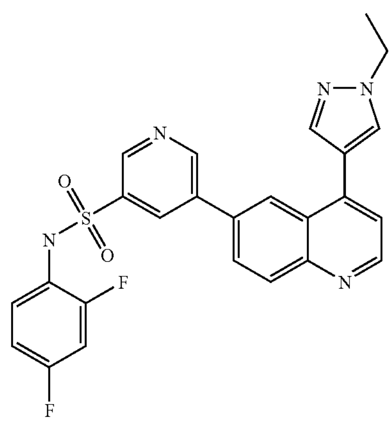 [SMILES: CCn1cc(-c2ccnc3ccc(-c4cncc(S(=O)(=O)Nc5ccc(F)cc5F)c4)cc23)cn1] | 492 |
| 261 | 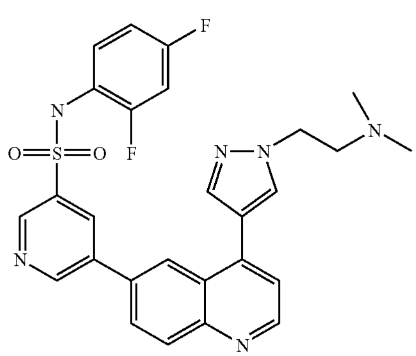 [SMILES: CN(C)CCn1cc(-c2ccnc3ccc(-c4cncc(S(=O)(=O)Nc5ccc(F)cc5F)c4)cc23)cn1] | 535 |

-continued
| Example | Structure | MS(ES) [M + H]+ |
|---|---|---|
| 262 | 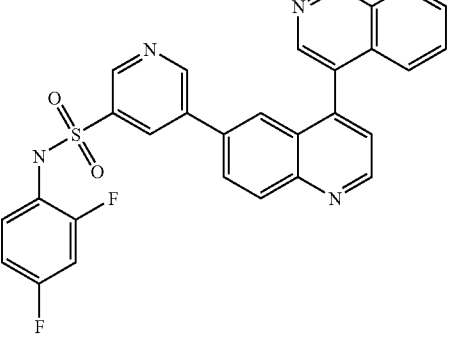 | 525 |
| 263 | 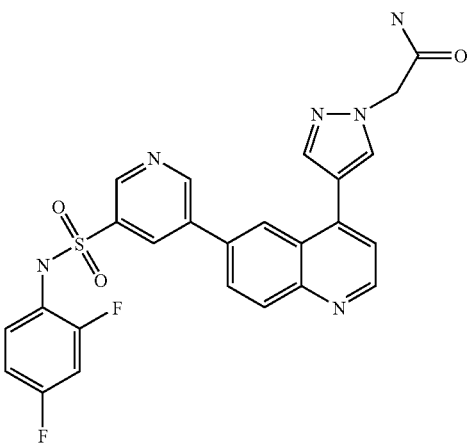 [SMILES: NC(=O)Cn1cc(-c2ccnc3ccc(-c4cncc(S(=O)(=O)Nc5ccc(F)cc5F)c4)cc23)cn1] | 521 |
| 264 | 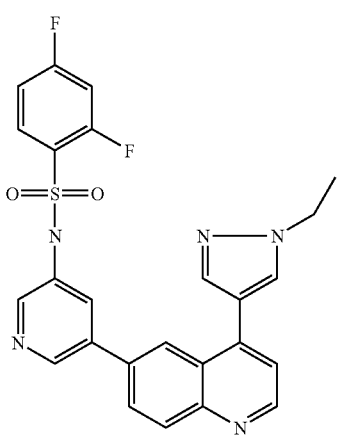 [SMILES: CCn1cc(-c2ccnc3ccc(-c4cncc(NS(=O)(=O)c5ccc(F)cc5F)c4)cc23)cn1] | 492 |
| 265 | 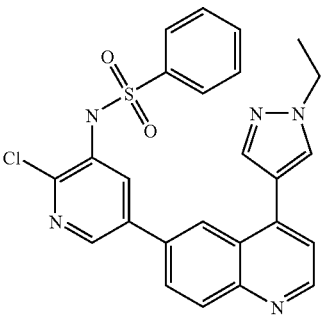 [SMILES: CCn1cc(-c2ccnc3ccc(-c4cnc(Cl)c(NS(=O)(=O)c5ccccc5)c4)cc23)cn1] | 490 |

| Example | Structure | MS(ES) [M + H]+ |
|---|---|---|
| 266 | 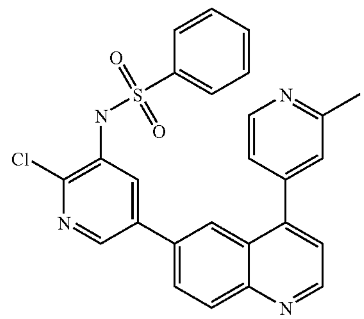 [SMILES: Cc1cc(-c2ccnc3ccc(-c4cnc(Cl)c(NS(=O)(=O)c5ccccc5)c4)cc23)ccn1] | 487 |
| 267 | 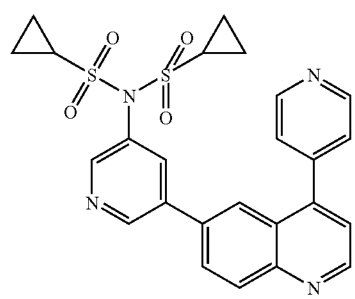 [SMILES: O=S(=O)(C1CC1)N(c1cncc(-c2ccc3nccc(-c4ccncc4)c3c2)c1)S(=O)(=O)C1CC1] | 507 |
| 268 | 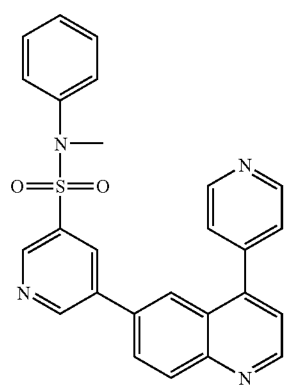 [SMILES: CN(c1ccccc1)S(=O)(=O)c1cncc(-c2ccc3nccc(-c4ccncc4)c3c2)c1] | 453 |
| 269 | 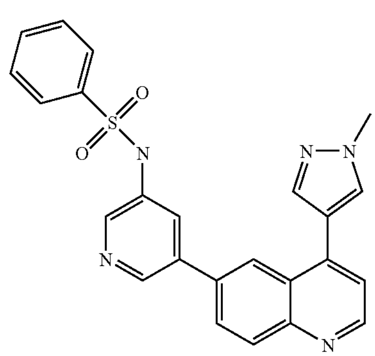 [SMILES: Cn1cc(-c2ccnc3ccc(-c4cncc(NS(=O)(=O)c5ccccc5)c4)cc23)cn1] | 442 |

-continued

| Example | Structure | MS(ES) [M + H]+ |
|---|---|---|
| 270 | 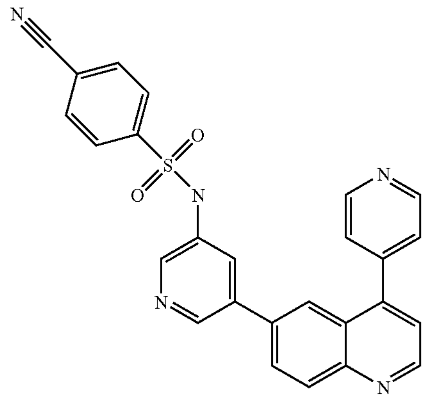 [SMILES: N#Cc1ccc(S(=O)(=O)Nc2cncc(-c3ccc4nccc(-c5ccncc5)c4c3)c2)cc1] | 464 |
| 271 | 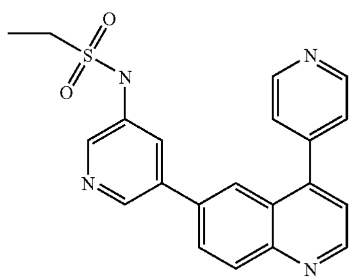 [SMILES: CCS(=O)(=O)Nc1cncc(-c2ccc3nccc(-c4ccncc4)c3c2)c1] | 391 |
| 272 | 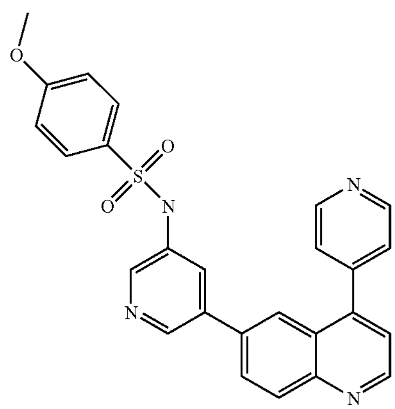 [SMILES: COc1ccc(S(=O)(=O)Nc2cncc(-c3ccc4nccc(-c5ccncc5)c4c3)c2)cc1] | 468 |
| 273 | 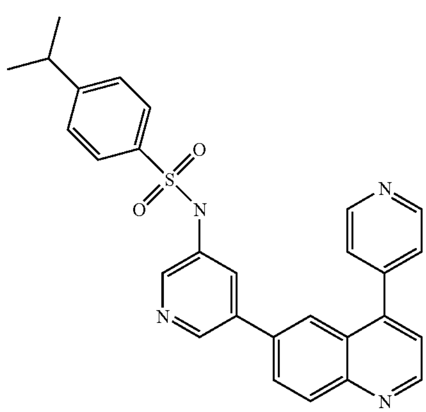 [SMILES: CC(C)c1ccc(S(=O)(=O)Nc2cncc(-c3ccc4nccc(-c5ccncc5)c4c3)c2)cc1] | 481 |

-continued
| Example | Structure | MS(ES) [M + H]+ |
|---|---|---|
| 274 | 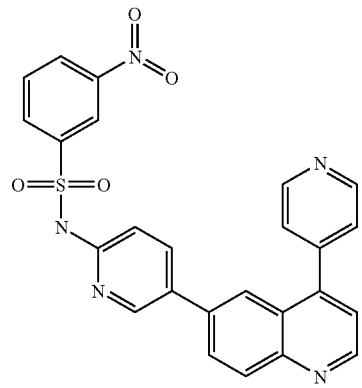 [SMILES: O=[N+]([O-])c1cccc(S(=O)(=O)Nc2ccc(-c3ccc4nccc(-c5ccncc5)c4c3)cn2)c1] | 484 |
| 275 | 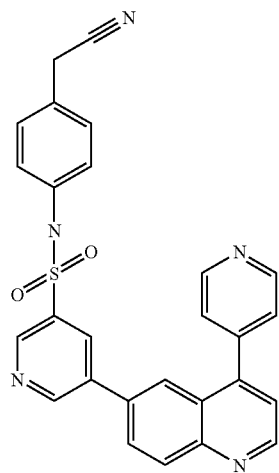 [SMILES: N#CCc1ccc(NS(=O)(=O)c2cncc(-c3ccc4nccc(-c5ccncc5)c4c3)c2)cc1] | 478 |
| 276 | 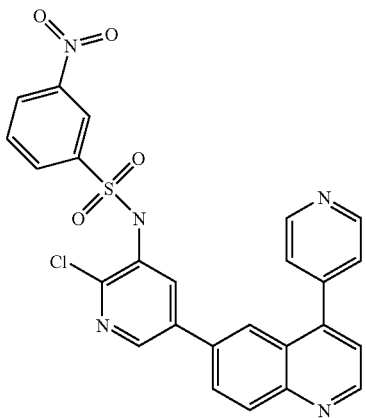 [SMILES: O=[N+]([O-])c1cccc(S(=O)(=O)Nc2cc(-c3ccc4nccc(-c5ccncc5)c4c3)cnc2Cl)c1] | 418 |

| Example | Structure | MS(ES) [M + H]+ |
|---|---|---|
| 277 | 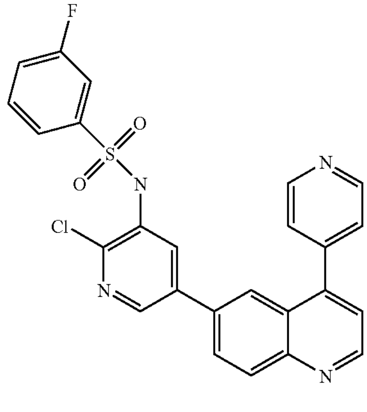 [SMILES: O=S(=O)(Nc1cc(-c2ccc3nccc(-c4ccncc4)c3c2)cnc1Cl)c1cccc(F)c1] | 491 |
| 278 | 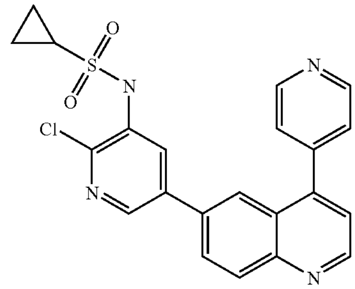 [SMILES: O=S(=O)(Nc1cc(-c2ccc3nccc(-c4ccncc4)c3c2)cnc1Cl)C1CC1] | 437 |

Scheme 2:

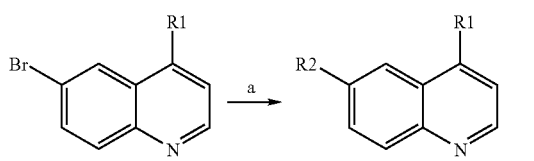

Conditions: a) heteroaryl (R2) boronic acid or heteroaryl (R2) boronate, palladium catalyst, 2 M potassium carbonate, heat; or heteroaryl (R2) stannane, palladium catalyst, dioxane, heat.

Example 107

6-[5-(methylsulfonyl)-3-pyridinyl]-4-(4-pyridinyl)quinoline

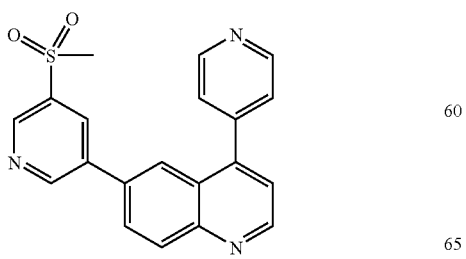

A mixture of (6-bromo-4-(4-pyridinyl)quinoline (250 mg, 0.88 mmol), 5-methylsulfonyl pyridine-3-boronic acid (201 mg, 1.0 mmol), tetrakistriphenylphosphine palladium(0) (104 mg, 0.09 mmol), and sat. aqueous NaHCO$_3$ (1.75 mL), in dioxane (5 mL) was heated at 110° C. for 1 h then cooled to room temperature. The rxn was filtered through Celite and Na$_2$SO$_4$ onto silica and the crude product was purified by column chromatography (5% EtOAc/Hex-10% Ethanol/EtOAc; 30 min gradient). Evaporation and precipitation from MeOH/water (2/98) provided the title compound as a yellow solid. (160 mg, 50%). ESMS [M+H]$^+$=362.1

The following compounds were or can be prepared following the general procedures used to prepare the compound of Example 107:

| Example | Structure | MS(ES) [M + H]+ |
|---------|-----------|-----------------|
| 108 | 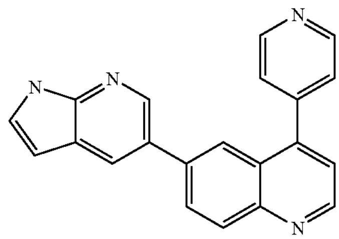 [SMILES: c1cc(-c2ccnc3ccc(-c4cnc5[nH]ccc5c4)cc23)ccn1] | 323 |
| 109 | 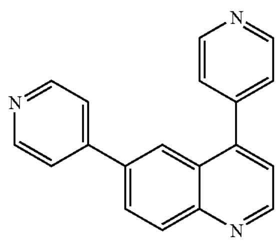 [SMILES: c1cc(-c2ccc3nccc(-c4ccncc4)c3c2)ccn1] | 284 |
| 110 | 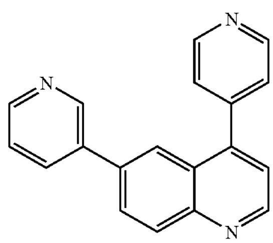 [SMILES: c1cncc(-c2ccc3nccc(-c4ccncc4)c3c2)c1] | 284 |
| 111 | 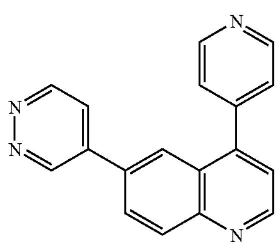 [SMILES: c1cc(-c2ccnc3ccc(-c4ccnnc4)cc23)ccn1] | 285 |
| 112 | 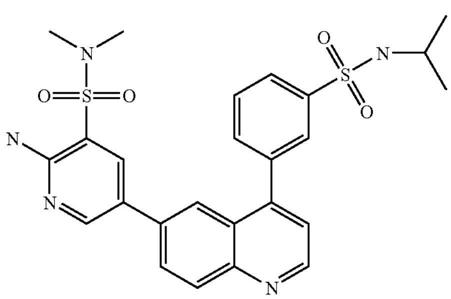 [SMILES: CC(C)NS(=O)(=O)c1cccc(-c2ccnc3ccc(-c4cnc(N)c(S(=O)(=O)N(C)C)c4)cc23)c1] | 527 |
| 113 | 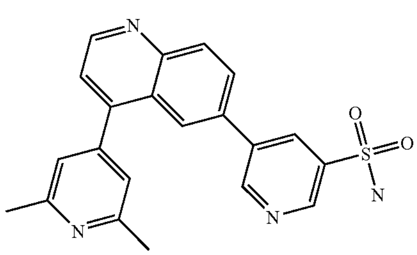 [SMILES: Cc1cc(-c2ccnc3ccc(-c4cncc(S(N)(=O)=O)c4)cc23)cc(C)n1] | 391 |

-continued

| Example | Structure | MS(ES) [M + H]+ |
|---|---|---|
| 114 | 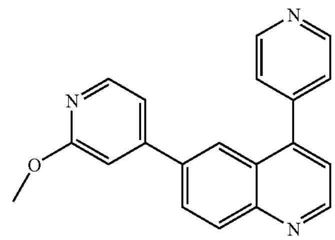 [SMILES: COc1cc(-c2ccc3nccc(-c4ccncc4)c3c2)ccn1] | 313 |
| 115 | 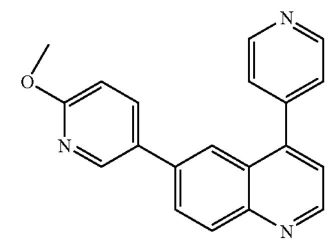 | 313 |
| 116 | 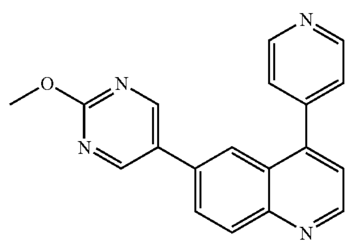 [SMILES: COc1ncc(-c2ccc3nccc(-c4ccncc4)c3c2)cn1] | 314 |
| 117 | 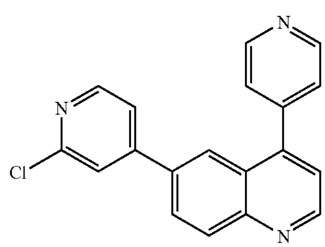 [SMILES: Clc1cc(-c2ccc3nccc(-c4ccncc4)c3c2)ccn1] | 317 |
| 118 | 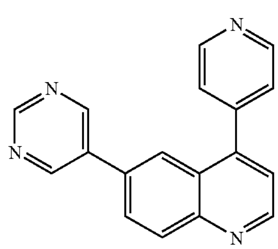 [SMILES: c1cc(-c2ccnc3ccc(-c4cncnc4)cc23)ccn1] | 285 |
| 119 | 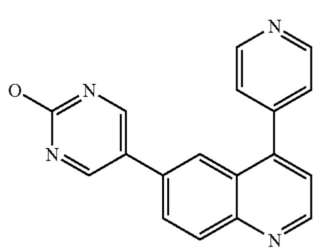 | 301 |

-continued

| Example | Structure | MS(ES) [M + H]+ |
|---|---|---|
| 120 | 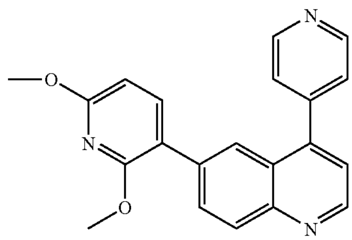 [SMILES: COc1ccc(-c2ccc3nccc(-c4ccncc4)c3c2)c(OC)n1] | 344 |
| 121 | 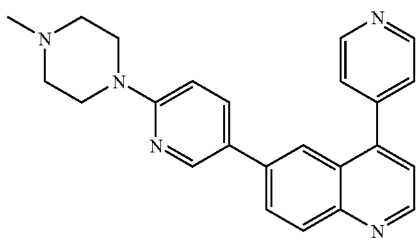 [SMILES: CN1CCN(c2ccc(-c3ccc4nccc(-c5ccncc5)c4c3)cn2)CC1] | 382 |
| 122 | 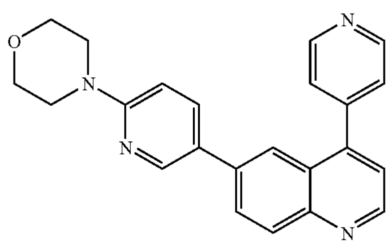 [SMILES: c1cc(-c2ccnc3ccc(-c4ccc(N5CCOCC5)nc4)cc23)ccn1] | 369 |
| 123 | 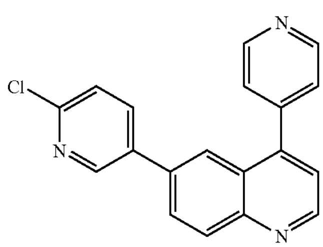 [SMILES: Clc1ccc(-c2ccc3nccc(-c4ccncc4)c3c2)cn1] | 318 |
| 124 | 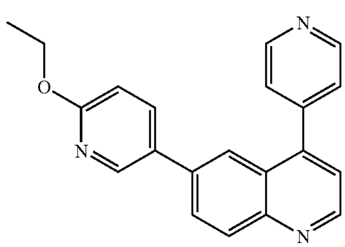 [SMILES: CCOc1ccc(-c2ccc3nccc(-c4ccncc4)c3c2)cn1] | 328 |
| 125 | 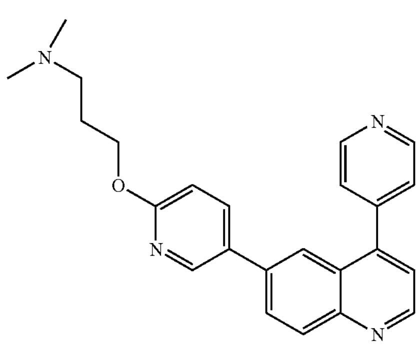 [SMILES: CN(C)CCCOc1ccc(-c2ccc3nccc(-c4ccncc4)c3c2)cn1] | 385 |

-continued

| Example | Structure | MS(ES) [M + H]+ |
|---------|-----------|-----------------|
| 126 | 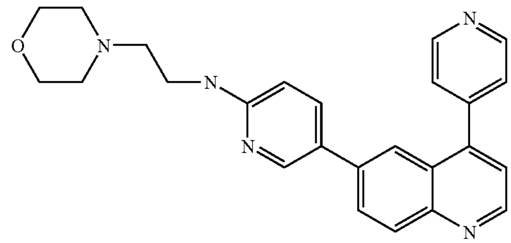 [SMILES: c1cc(-c2ccnc3ccc(-c4ccc(NCCN5CCOCC5)nc4)cc23)ccn1] | 412 |
| 127 | 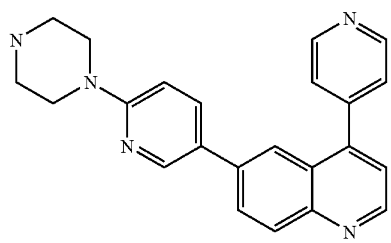 [SMILES: c1cc(-c2ccnc3ccc(-c4ccc(N5CCNCC5)nc4)cc23)ccn1] | 368 |
| 128 | 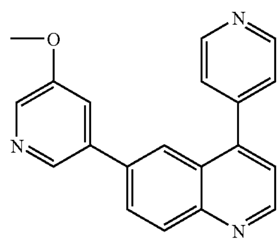 [SMILES: COc1cncc(-c2ccc3nccc(-c4ccncc4)c3c2)c1] | 313 |
| 129 | 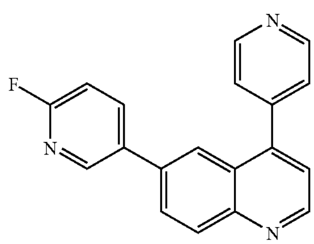 [SMILES: Fc1ccc(-c2ccc3nccc(-c4ccncc4)c3c2)cn1] | 302 |
| 130 | 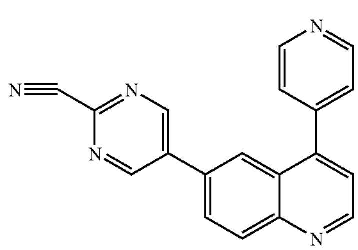 [SMILES: N#Cc1ncc(-c2ccc3nccc(-c4ccncc4)c3c2)cn1] | 310 |
| 131 | 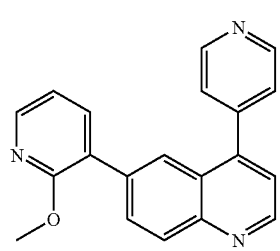 [SMILES: COc1ncccc1-c1ccc2nccc(-c3ccncc3)c2c1] | 313 |

-continued

| Example | Structure | MS(ES) [M + H]+ |
|---------|-----------|-----------------|
| 132 | 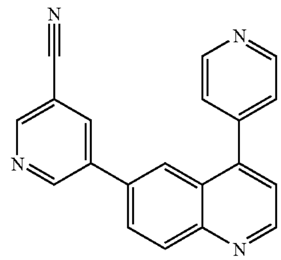 [SMILES: N#Cc1cncc(-c2ccc3nccc(-c4ccncc4)c3c2)c1] | 309 |
| 133 | 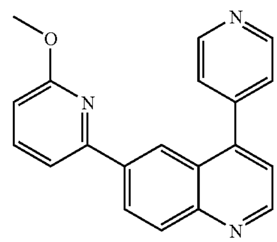 [SMILES: COc1cccc(-c2ccc3nccc(-c4ccncc4)c3c2)n1] | 313 |
| 134 | 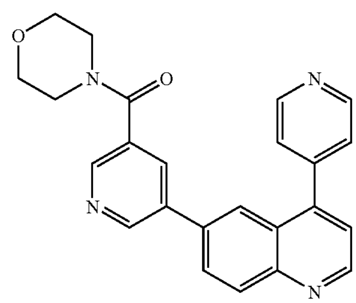 [SMILES: O=C(c1cncc(-c2ccc3nccc(-c4ccncc4)c3c2)c1)N1CCOCC1] | 397 |
| 135 | 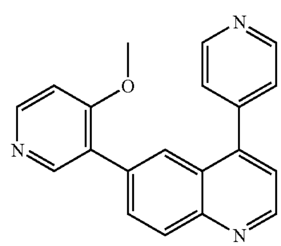 [SMILES: COc1ccncc1-c1ccc2nccc(-c3ccncc3)c2c1] | 3130 |
| 136 | 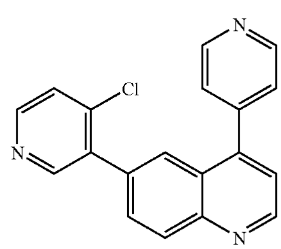 [SMILES: Clc1ccncc1-c1ccc2nccc(-c3ccncc3)c2c1] | 317 |
| 137 | 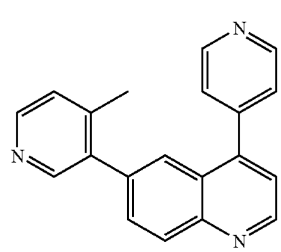 [SMILES: Cc1ccncc1-c1ccc2nccc(-c3ccncc3)c2c1] | 298 |

-continued

| Example | Structure | MS(ES) [M + H]+ |
|---|---|---|
| 138 | 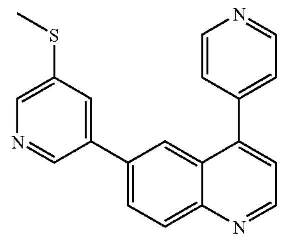 [SMILES: CSc1cncc(-c2ccc3nccc(-c4ccncc4)c3c2)c1] | 330 |
| 139 | 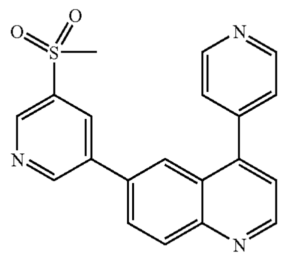 [SMILES: CS(=O)(=O)c1cncc(-c2ccc3nccc(-c4ccncc4)c3c2)c1] | 362 |
| 279 | 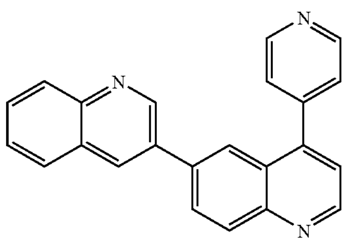 [SMILES: c1ccc2ncc(-c3ccc4nccc(-c5ccncc5)c4c3)cc2c1] | 334.1 |

Scheme 3:

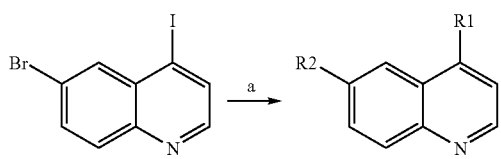

Conditions: a) aryl (R1) boronic acid or aryl (R1) boronate, palladium catalyst, 2 M potassium carbonate, dioxane, heat; or heteroaryl (R2) boronic acid or heteroaryl (R2) boronate, palladium catalyst, 2 M potassium carbonate, heat.

Example 139

2-amino-5-{4-[3-(aminosulfonyl)phenyl]-6-quinolinyl}-3-pyridinesulfonamide

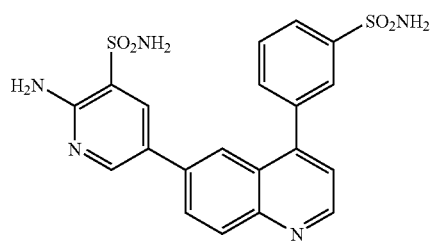 [SMILES: Nc1ncc(-c2ccc3nccc(-c4cccc(S(N)(=O)=O)c4)c3c2)cc1S(N)(=O)=O]

A mixture of 4-iodo-6-bromoquinoline (1.18 g, 3.53 mmol), 3-(4,4,5,5-tetramethyl-1,3,2-dioxaborolan-2-yl)benzenesulfonamide (1 g, 3.53 mmol), dichloro-[1,1'bis(diphenylphosphino)ferrocene]palladium(II)dichloromethane adduct (177 mg, 0.176 mmol), 2 M potassium carbonate (5 mL), in dioxane (15 mL) was heated at 100° C. for 1.5 h and cooled to room temperature. LCMS indicated the reaction was finished. To the finished reaction was added 2-amino-5-(4,4,5,5-tetramethyl-1,3,2-dioxaborolan-2-yl)-3-pyridinesulfonamide (1.2 g, 4 mmol), Dichloro-[1,1'bis(diphenylphosphino)ferrocene]Palladium(II)dichloromethane adduct (177 mg, 0.176 mmol), and 2 M potassium carbonate (5 mL). The reaction was heated at 100° C. for 3 h and cooled to room temperature. The dioxane and water were separated and the dioxane evaporated to get the crude product which was purified on silica gel eluting with ethyl acetate/methanol, 0-3% methanol. The product which crystallized from ethyl acetate contained ethyl acetate. The ethyl acetate was removed by dissolving the product in a excess of acetone and evaporation. Residual acetone was then removed by triturating with distilled water at 60 deg followed by filtration and drying under vacuum. A yield of the title compound (540 mg, 31%) was obtained. MS(ES)+m/e 484 [M+H]+.

The following compounds were or can be prepared following the general procedures used to prepare the compound of Example 139

| Example | Structure | MS(ES) [M + H]+ |
|---|---|---|
| 140 | 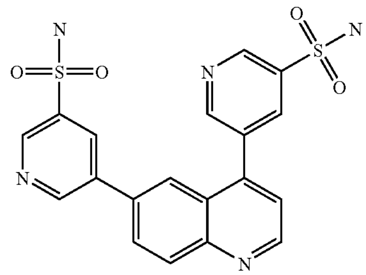 [SMILES: NS(=O)(=O)c1cncc(-c2ccc3nccc(-c4cncc(S(N)(=O)=O)c4)c3c2)c1] | 442 |
| 141 | 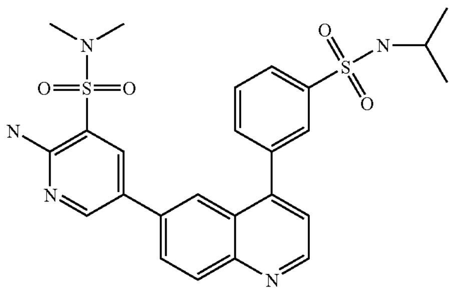 [SMILES: CC(C)NS(=O)(=O)c1cccc(-c2ccnc3ccc(-c4cnc(N)c(S(=O)(=O)N(C)C)c4)cc23)c1] | 527 |
| 142 | 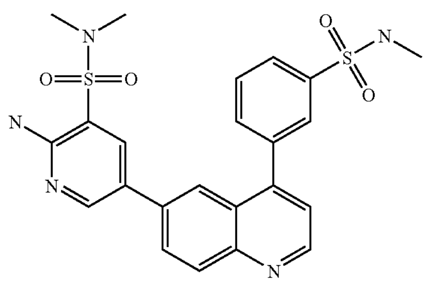 [SMILES: CNS(=O)(=O)c1cccc(-c2ccnc3ccc(-c4cnc(N)c(S(=O)(=O)N(C)C)c4)cc23)c1] | 498 |
| 143 | 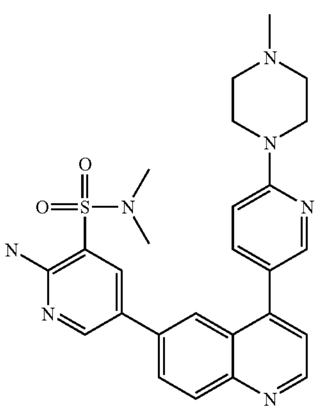 [SMILES: CN1CCN(c2ccc(-c3ccnc4ccc(-c5cnc(N)c(S(=O)(=O)N(C)C)c5)cc34)cn2)CC1] | 504 |
| 144 | 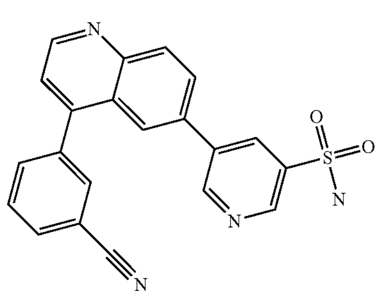 [SMILES: N#Cc1cccc(-c2ccnc3ccc(-c4cncc(S(N)(=O)=O)c4)cc23)c1] | 387 |

-continued

| Example | Structure | MS(ES) [M + H]+ |
|---|---|---|
| 145 | 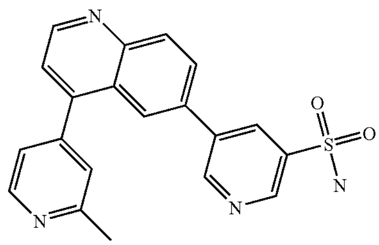 [SMILES: Cc1cc(-c2ccnc3ccc(-c4cncc(S(N)(=O)=O)c4)cc23)ccn1] | 377 |
| 146 | 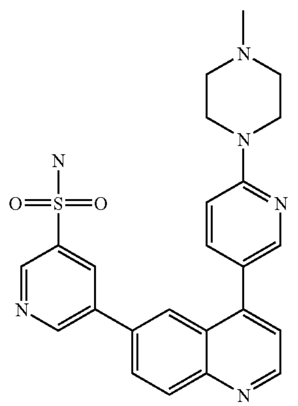 [SMILES: CN1CCN(c2ccc(-c3ccnc4ccc(-c5cncc(S(N)(=O)=O)c5)cc34)cn2)CC1] | 461 |
| 147 | 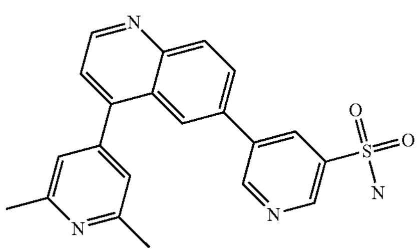 [SMILES: Cc1cc(-c2ccnc3ccc(-c4cncc(S(N)(=O)=O)c4)cc23)cc(C)n1] | 391 |
| 148 | 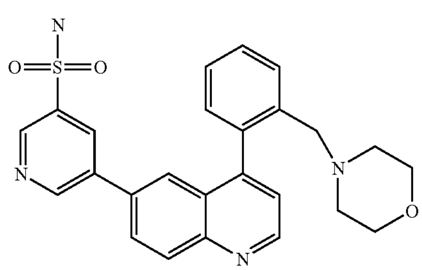 [SMILES: NS(=O)(=O)c1cncc(-c2ccc3nccc(-c4ccccc4CN4CCOCC4)c3c2)c1] | 461 |
| 149 | 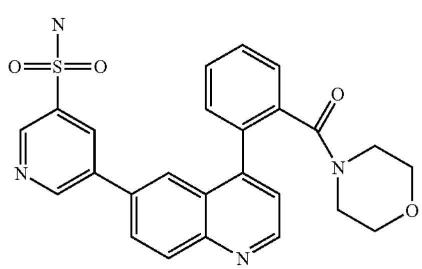 [SMILES: NS(=O)(=O)c1cncc(-c2ccc3nccc(-c4ccccc4C(=O)N4CCOCC4)c3c2)c1] | 475 |

| Example | Structure | MS(ES) [M + H]+ |
|---|---|---|
| 150 | 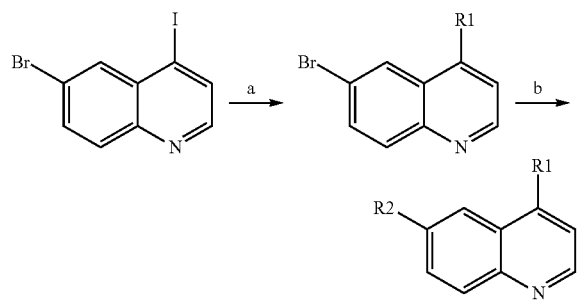 | 442 |
| 151 | 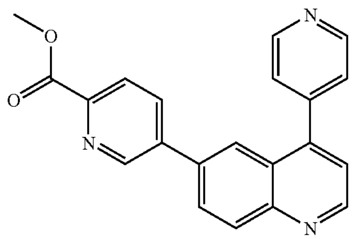 [SMILES: COC(=O)c1ccc(-c2ccc3nccc(-c4ccncc4)c3c2)cn1] | 341 |
| 152 | 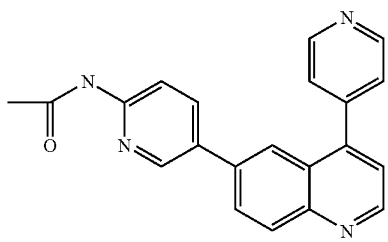 [SMILES: CC(=O)Nc1ccc(-c2ccc3nccc(-c4ccncc4)c3c2)cn1] | 341 |

Scheme 4:

Conditions: a) aryl (R1) boronic acid or aryl (R1) boronate, palladium catalyst, 2 M potassium carbonate, dioxane, heat; b) bis(pinacolato)diboron, potassium acetate, palladium catalyst, dioxane, heat; then heteroaryl (R2) bromide, palladium catalyst, 2 M potassium carbonate, heat.

Example 153

2-amino-5-[4-(1H-pyrazol-4-yl)-6-quinolinyl]-3-pyridinesulfonamide

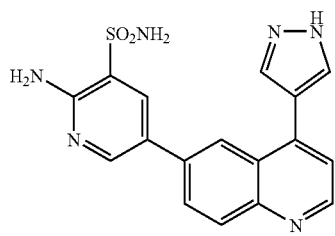 [SMILES: Nc1ncc(-c2ccc3nccc(-c4cn[nH]c4)c3c2)cc1S(N)(=O)=O]

a) 6-bromo-4-(1H-pyrazol-4-yl)quinoline

A mixture of 6-bromo-4-iodoquinoline (1.37 g, 4 mmol) and 4-(4,4,5,5-tetramethyl-1,3,2-dioxaborolan-2-yl)-1H-pyrazole (852 mg, 4 mmol), dichloro-[1,1'bis(diphenylphosphino)ferrocene]palladium(II)dichloromethane adduct (162 mg, 0 2 mmol), 2 M potassium carbonate (6 mL), in dioxane (25 mL) was heated at 100° C. for 1.5 h and cooled to room temperature. The dioxane and water were separated and the dioxane evaporated to get the crude product which was purified on silica gel eluting with ethyl acetate/methanol, 0-3% methanol. A yield of the title compound (340 mg, 34%) was obtained. MS(ES)+m/e 275 [M+H]+.

b) 2-amino-5-[4-(1H-pyrazol-4-yl)-6-quinolinyl]-3-pyridinesulfonamide 6-bromo-4-(1H-pyrazol-4-yl)quinoline(330 mg,1.2 mmol), 4,4,4',4',5,5,5', 5'-octamethyl-2,2'-bi-1,3,2-dioxaborolane (304 mg, 1.2 mmol), dichloro-[1,1'bis(diphenylphosphino)ferrocene]palladium(II)dichloromethane adduct (48 mg, 0.06 mmol), potassium acetate (352 mg, 3 6 mmol), in dioxane (5 mL) was heated at 100° C. for 1.5 h and cooled to room temperature. LCMS indicated the reaction was complete (formation of 4-(1H-pyrazol-4-yl)-6-(4,4,5,5-tetramethyl-1,3,2-dioxaborolan-2-yl)quinoline).

To this same reaction mixture was added dichloro-[1,1'bis (diphenylphosphino)ferrocene]palladium(II)dichloromethane adduct (48 mg, 0.06 mmol), 2-amino-5-bromo-3-pyridinesulfonamide (280 mg, 1 mmol) and 2 M potassium carbonate (1.5 mL). The reaction mixture was heated a second time to 115° C. for 18 h. The dioxane and water were separated and the dioxane evaporated. The crude product was triturated with methylene chloride (insoluble), then dissolved in DMF and filtered through a glass fiber filter. The DMF was evaporated and the product triturated with methanol, filtered and dried. A yield of the title compound (108 mg, 22%, two steps) was obtained. MS(ES)+ m/e 395 [M+H]+.

The following compounds were or can be prepared following the general procedures used to prepare the compound of Example 153

| Example | Structure | MS(ES) [M + H]+ |
|---------|-----------|-----------------|
| 154 | 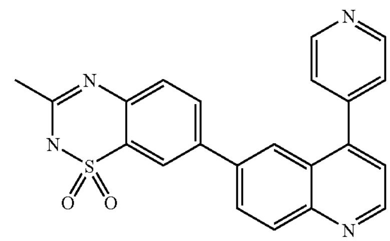 [SMILES: CC1=Nc2ccc(-c3ccc4nccc(-c5ccncc5)c4c3)cc2S(=O)(=O)N1] | 401 |
| 155 | 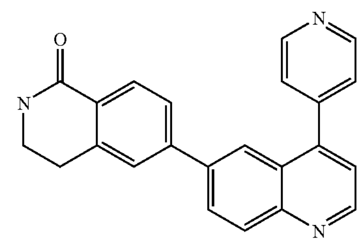 [SMILES: O=C1NCCc2cc(-c3ccc4nccc(-c5ccncc5)c4c3)ccc21] | 352 |
| 156 | 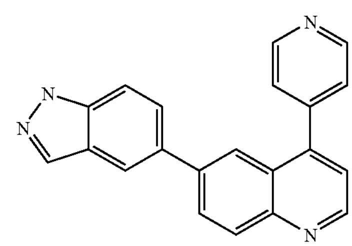 [SMILES: c1cc(-c2ccnc3ccc(-c4ccc5[nH]ncc5c4)cc23)ccn1] | 323 |
| 157 | 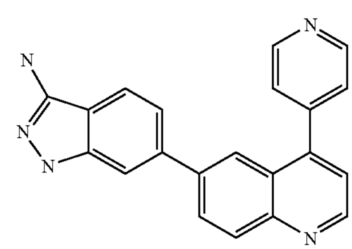 [SMILES: Nc1n[nH]c2cc(-c3ccc4nccc(-c5ccncc5)c4c3)ccc12] | 338 |
| 158 | 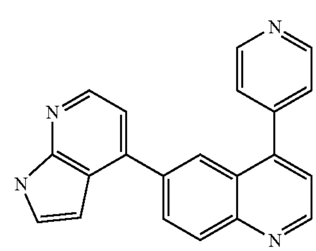 [SMILES: c1cc(-c2ccnc3ccc(-c4ccnc5[nH]ccc45)cc23)ccn1] | 323 |

-continued
| Example | Structure | MS(ES) [M + H]+ |
|---------|-----------|-----------------|
| 159 | 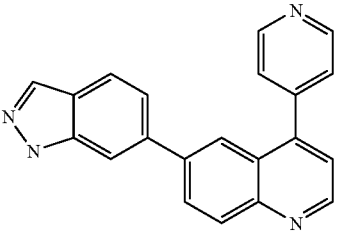 [SMILES: c1cc(-c2ccnc3ccc(-c4ccc5cn[nH]c5c4)cc23)ccn1] | 323 |
| 160 | 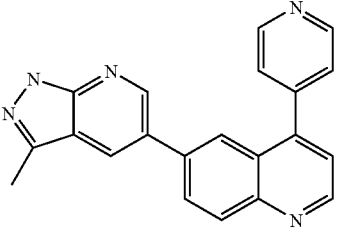 | 338 |
| 161 | 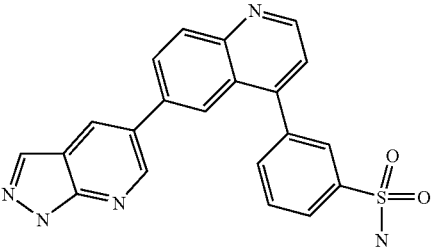 [SMILES: NS(=O)(=O)c1cccc(-c2ccnc3ccc(-c4cnc5[nH]ncc5c4)cc23)c1] | 402 |
| 162 | 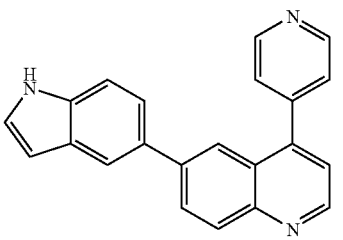 | 322 |
| 163 | 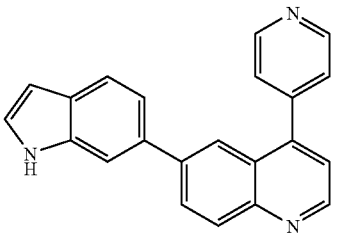 [SMILES: c1cc(-c2ccnc3ccc(-c4ccc5cc[nH]c5c4)cc23)ccn1] | 322 |
| 164 | 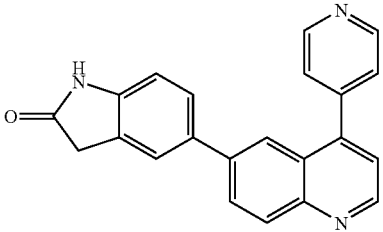 [SMILES: O=C1Cc2cc(-c3ccc4nccc(-c5ccncc5)c4c3)ccc2N1] | 338 |

-continued

| Example | Structure | MS(ES) [M + H]+ |
|---|---|---|
| 165 | 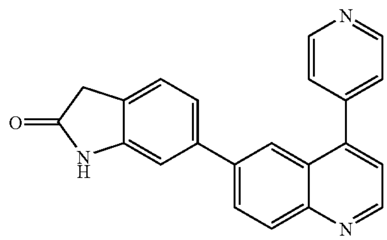 [SMILES: O=C1Cc2ccc(-c3ccc4nccc(-c5ccncc5)c4c3)cc2N1] | 338 |
| 166 | 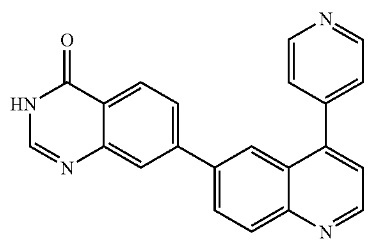 [SMILES: O=c1[nH]cnc2cc(-c3ccc4nccc(-c5ccncc5)c4c3)ccc12] | 351 |
| 167 | 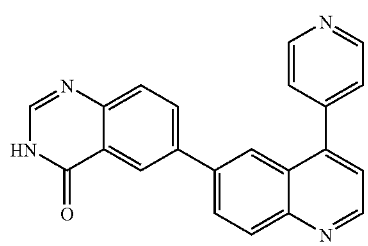 [SMILES: O=c1[nH]cnc2ccc(-c3ccc4nccc(-c5ccncc5)c4c3)cc12] | 351 |
| 168 | 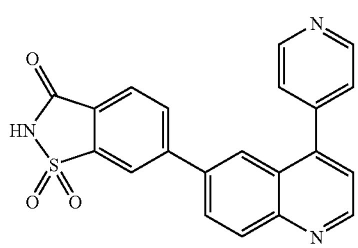 [SMILES: O=C1NS(=O)(=O)c2cc(-c3ccc4nccc(-c5ccncc5)c4c3)ccc21] | 388 |
| 169 | 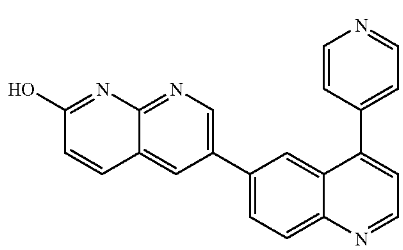 [SMILES: Oc1ccc2cc(-c3ccc4nccc(-c5ccncc5)c4c3)cnc2n1] | 351 |
| 170 | 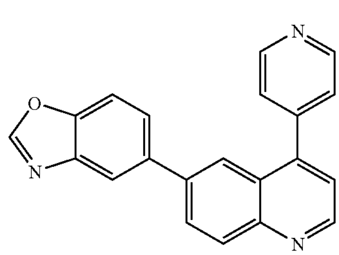 [SMILES: c1cc(-c2ccnc3ccc(-c4ccc5ocnc5c4)cc23)ccn1] | 324 |

-continued

| Example | Structure | MS(ES) [M + H]+ |
|---|---|---|
| 171 | 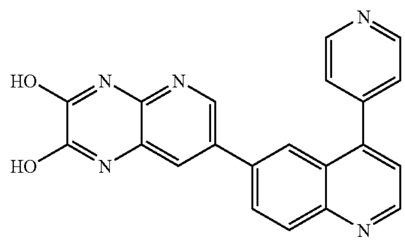 [SMILES: Oc1nc2cc(-c3ccc4nccc(-c5ccncc5)c4c3)cnc2nc1O] | 368 |
| 172 | 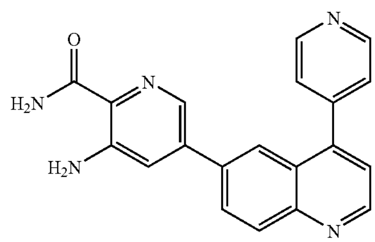 [SMILES: NC(=O)c1ncc(-c2ccc3nccc(-c4ccncc4)c3c2)cc1N] | 342 |
| 173 | 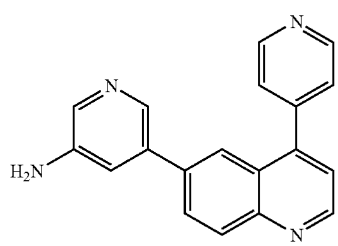 [SMILES: Nc1cncc(-c2ccc3nccc(-c4ccncc4)c3c2)c1] | 299 |
| 174 | 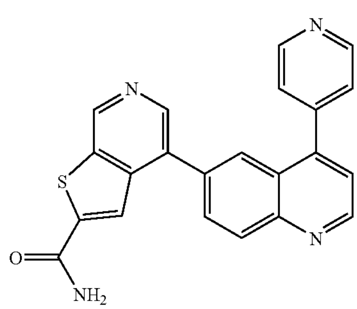 [SMILES: NC(=O)c1cc2c(-c3ccc4nccc(-c5ccncc5)c4c3)cncc2s1] | 383 |
| 175 | 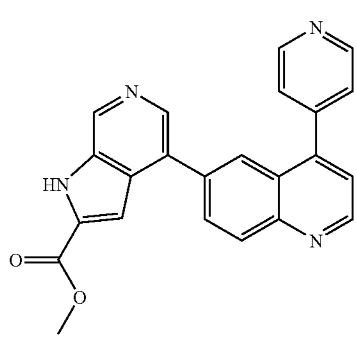 [SMILES: COC(=O)c1cc2c(-c3ccc4nccc(-c5ccncc5)c4c3)cncc2[nH]1] | 381 |

-continued

| Example | Structure | MS(ES) [M + H]+ |
|---|---|---|
| 176 | 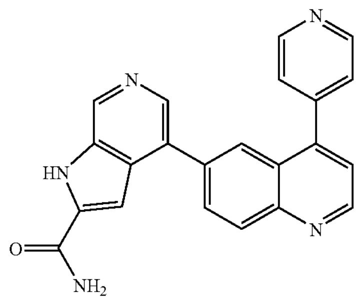 [SMILES: NC(=O)c1cc2c(-c3ccc4nccc(-c5ccncc5)c4c3)cncc2[nH]1] | 366 |
| 177 | 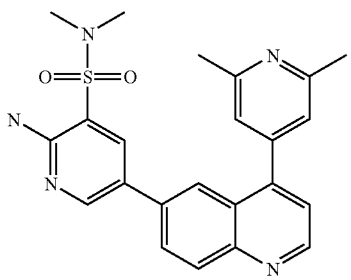 [SMILES: Cc1cc(-c2ccnc3ccc(-c4cnc(N)c(S(=O)(=O)N(C)C)c4)cc23)cc(C)n1] | 434 |
| 178 | 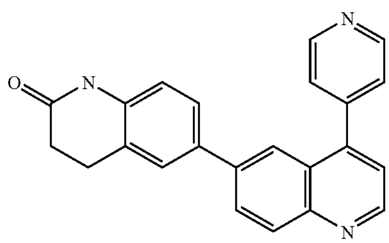 [SMILES: O=C1CCc2cc(-c3ccc4nccc(-c5ccncc5)c4c3)ccc2N1] | 352 |
| 179 | 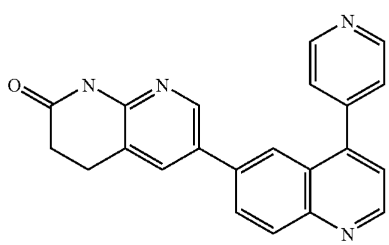 [SMILES: O=C1CCc2cc(-c3ccc4nccc(-c5ccncc5)c4c3)cnc2N1] | 353 |
| 180 | 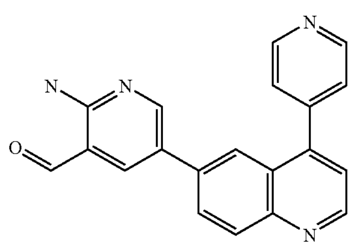 [SMILES: Nc1ncc(-c2ccc3nccc(-c4ccncc4)c3c2)cc1C=O] | 327 |
| 181 | 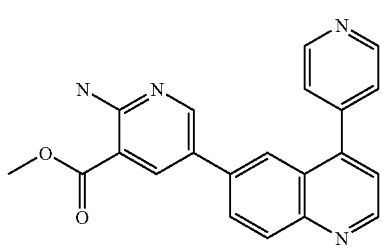 [SMILES: COC(=O)c1cc(-c2ccc3nccc(-c4ccncc4)c3c2)cnc1N] | 357 |

-continued

| Example | Structure | MS(ES) [M + H]+ |
|---------|-----------|-----------------|
| 182 | 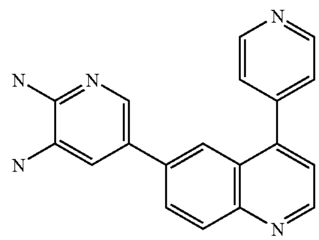 [SMILES: Nc1cc(-c2ccc3nccc(-c4ccncc4)c3c2)cnc1N] | 314 |
| 183 | 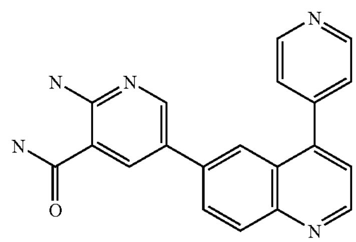 [SMILES: NC(=O)c1cc(-c2ccc3nccc(-c4ccncc4)c3c2)cnc1N] | 341 |
| 184 | 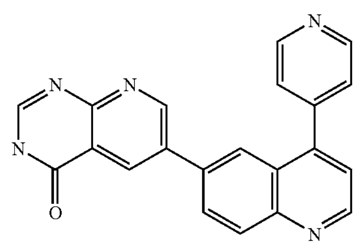 [SMILES: O=c1[nH]cnc2ncc(-c3ccc4nccc(-c5ccncc5)c4c3)cc12] | 352 |
| 185 | 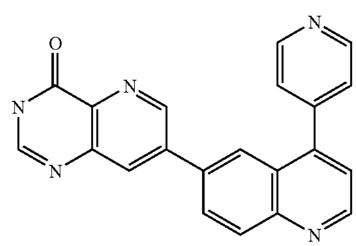 [SMILES: O=c1[nH]cnc2cc(-c3ccc4nccc(-c5ccncc5)c4c3)cnc12] | 352 |
| 186 | 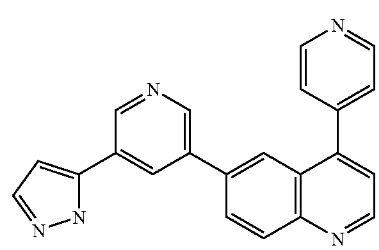 [SMILES: c1cc(-c2ccnc3ccc(-c4cncc(-c5ccn[nH]5)c4)cc23)ccn1] | 350 |
| 187 | 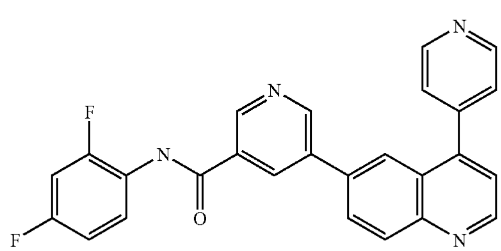 [SMILES: O=C(Nc1ccc(F)cc1F)c1cncc(-c2ccc3nccc(-c4ccncc4)c3c2)c1] | 439 |

-continued

| Example | Structure | MS(ES) [M + H]+ |
|---------|-----------|-----------------|
| 188 | 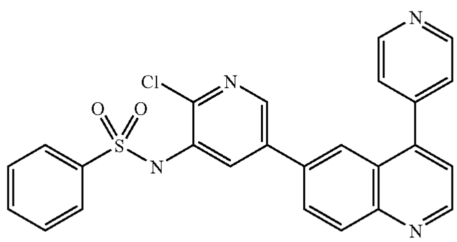 [SMILES: O=S(=O)(Nc1cc(-c2ccc3nccc(-c4ccncc4)c3c2)cnc1Cl)c1ccccc1] | 473 |
| 280 | 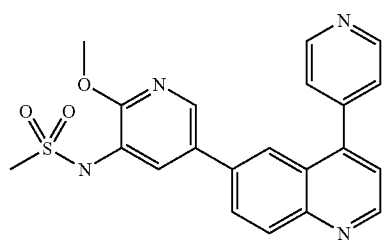 [SMILES: COc1ncc(-c2ccc3nccc(-c4ccncc4)c3c2)cc1NS(C)(=O)=O] | 411 |
| 281 | 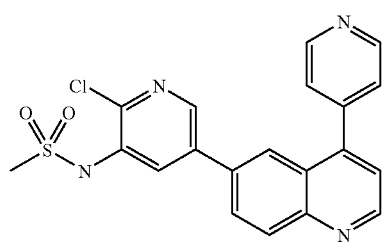 [SMILES: CS(=O)(=O)Nc1cc(-c2ccc3nccc(-c4ccncc4)c3c2)cnc1Cl] | 407.2 |
| 282 | 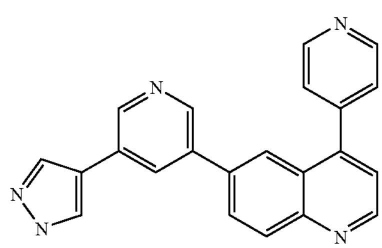 [SMILES: c1cc(-c2ccnc3ccc(-c4cncc(-c5cn[nH]c5)c4)cc23)ccn1] | 349.7 |
| 283 | 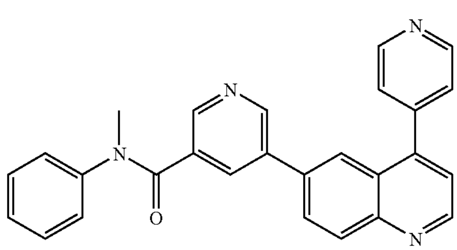 [SMILES: CN(C(=O)c1cncc(-c2ccc3nccc(-c4ccncc4)c3c2)c1)c1ccccc1] | 416.9 |
| 284 | 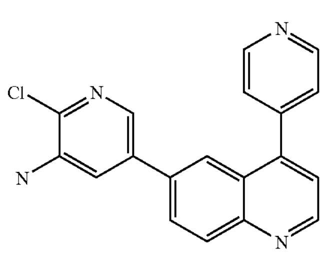 [SMILES: Nc1cc(-c2ccc3nccc(-c4ccncc4)c3c2)cnc1Cl] | 332.7 |

-continued

| Example | Structure | MS(ES) [M + H]+ |
|---------|-----------|-----------------|
| 285 | 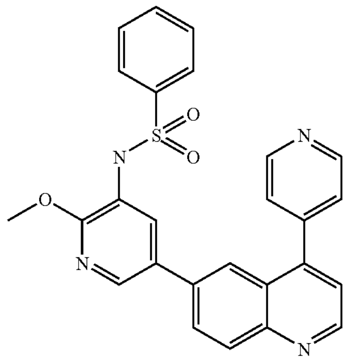 [SMILES: COc1ncc(-c2ccc3nccc(-c4ccncc4)c3c2)cc1NS(=O)(=O)c1ccccc1] | 469.1 |
| 286 | 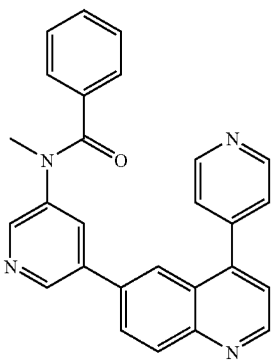 [SMILES: CN(C(=O)c1ccccc1)c1cncc(-c2ccc3nccc(-c4ccncc4)c3c2)c1] | 417.3 |
| 287 | 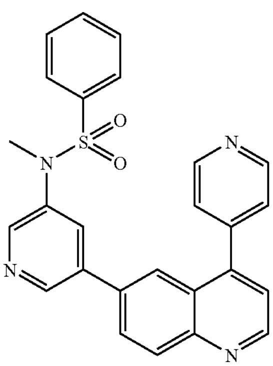 [SMILES: CN(c1cncc(-c2ccc3nccc(-c4ccncc4)c3c2)c1)S(=O)(=O)c1ccccc1] | 453.0 |
| 288 | 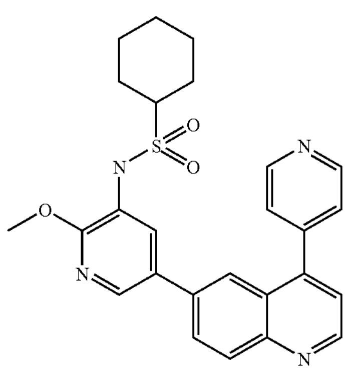 [SMILES: COc1ncc(-c2ccc3nccc(-c4ccncc4)c3c2)cc1NS(=O)(=O)C1CCCCC1] | 475.1 |

-continued

| Example | Structure | MS(ES) [M + H]+ |
|---------|-----------|-----------------|
| 289 | 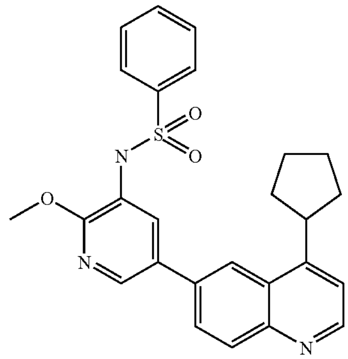 [SMILES: COc1ncc(-c2ccc3nccc(C4CCCC4)c3c2)cc1NS(=O)(=O)c1ccccc1] | 460.2 |
| 290 | 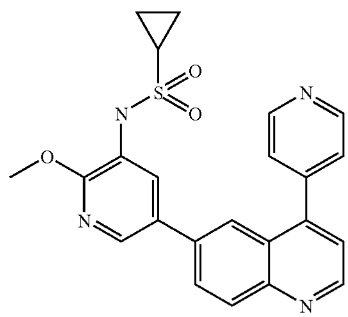 [SMILES: COc1ncc(-c2ccc3nccc(-c4ccncc4)c3c2)cc1NS(=O)(=O)C1CC1] | 432.2 |
| 291 | 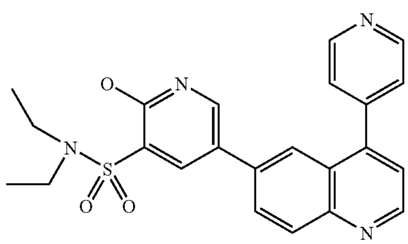 [SMILES: CCN(CC)S(=O)(=O)c1cc(-c2ccc3nccc(-c4ccncc4)c3c2)cnc1O] | 435.2 |
| 292 | 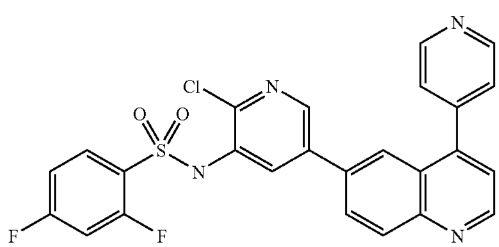 [SMILES: O=S(=O)(Nc1cc(-c2ccc3nccc(-c4ccncc4)c3c2)cnc1Cl)c1ccc(F)cc1F] | 509.1 |
| 293 | 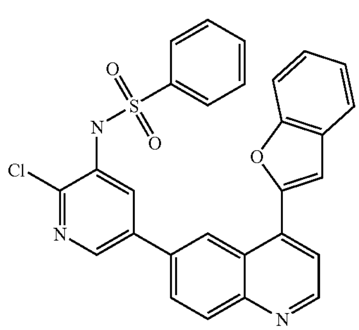 [SMILES: O=S(=O)(Nc1cc(-c2ccc3nccc(-c4cc5ccccc5o4)c3c2)cnc1Cl)c1ccccc1] | 513 |

Scheme 5:

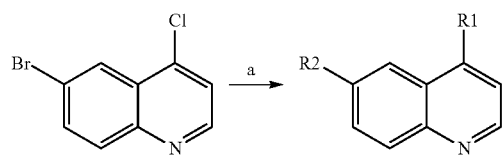

Conditions: a) bis(pinacolato)diboron, p palladium catalyst, potassium acetate, dioxane, heat; then heteroaryl (R2) bromide, palladium catalyst, 2 M potassium carbonate, heat; then aryl (R1) boronic acid or aryl (R1) boronate, palladium catalyst, 2 M potassium carbonate, heat.

Example 189

2-amino-5-{4-[3-(aminosulfonyl)phenyl]-6-quinolinyl}-3-pyridinesulfonamide

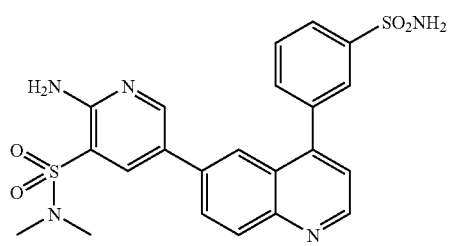 [SMILES: CN(C)S(=O)(=O)c1cc(-c2ccc3nccc(-c4cccc(S(N)(=O)=O)c4)c3c2)cnc1N]

This compound was prepared in one pot (three steps) with no workups between steps. A mixture of 6-bromo-4-chloroquinoline, (484 mg, 2 mmol), bis(pinacolato)diboron, (506 mg, 2 mmol), dichloro-[1,1'bis(diphenylphosphino)ferrocene]palladium(II)dichloromethane adduct (81.5 mg, 0.1 mmol), and potassium acetate (588 mg, 6 mmol) in dioxane (6 mL) was heated at 100° C. for 4 h. To this reaction was added 2-amino-5-bromo-3-pyridinesulfonamide, (560 mg 2 mmol) an equal amount of the palladium catalyst used above (0.1 mmol) and 2 M potassium carbonate (3 mL). The reaction was heated at 95 deg centigrade for one hour. To this reaction was added 3-(4,4,5,5-tetramethyl-1,3,2-dioxaborolan-2-yl)benzenesulfonamide, (566 mg 2 mmol), dichloro-[1,1'bis(diphenylphosphino)ferrocene]palladium(II)dichloromethane adduct (81.5 mg, 0.1 mmol) and 2 M potassium carbonate (3 mL). The reaction was heated at 95° C. for three hours. The solvent was evaporated and the crude material purified by silica gel chromatography, eluting with ethyl acetate. The product was purified further by crystallizing from hot ethyl acetate. Obtained 181 mg (18.7%) for three steps. MS(ES)+ m/e 484 [M+H]+.

The following compounds were or can be prepared following the general procedures used to prepare the compound of Example 189:

| Example | Structure | MS(ES) [M + H]+ |
|---|---|---|
| 190 | 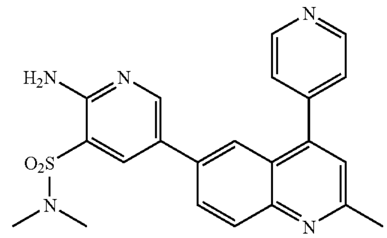 | 420 |
| 191 | 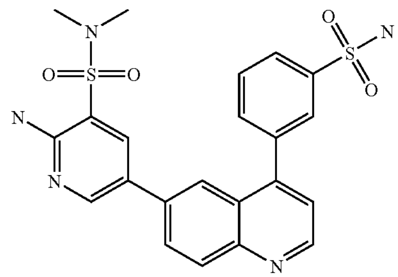 [SMILES: CN(C)S(=O)(=O)c1cc(-c2ccc3nccc(-c4cccc(S(N)(=O)=O)c4)c3c2)cnc1N] | 484 |
| 192 | 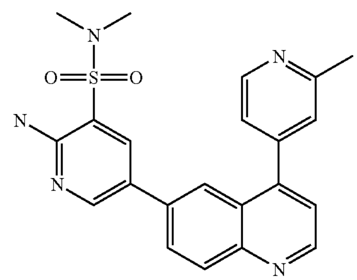 [SMILES: Cc1cc(-c2ccnc3ccc(-c4cnc(N)c(S(=O)(=O)N(C)C)c4)cc23)ccn1] | 420 |
| 193 | 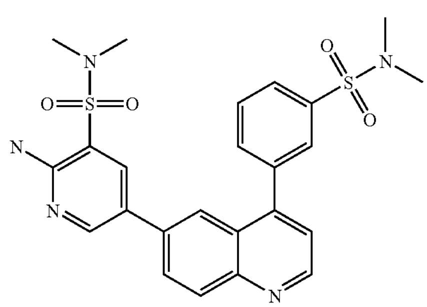 [SMILES: CN(C)S(=O)(=O)c1cccc(-c2ccnc3ccc(-c4cnc(N)c(S(=O)(=O)N(C)C)c4)cc23)c1] | 572 |
| 194 | 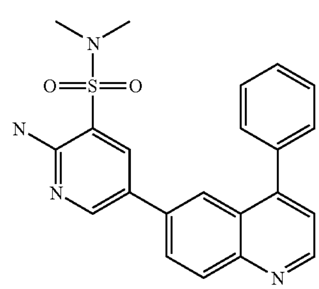 [SMILES: CN(C)S(=O)(=O)c1cc(-c2ccc3nccc(-c4ccccc4)c3c2)cnc1N] | 405 |

-continued

| Example | Structure | MS(ES) [M+H]+ |
|---|---|---|
| 195 | 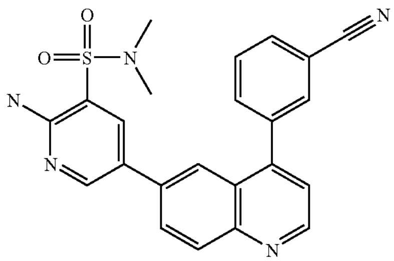 [SMILES: CN(C)S(=O)(=O)c1cc(-c2ccc3nccc(-c4cccc(C#N)c4)c3c2)cnc1N] | 420 |
| 196 | 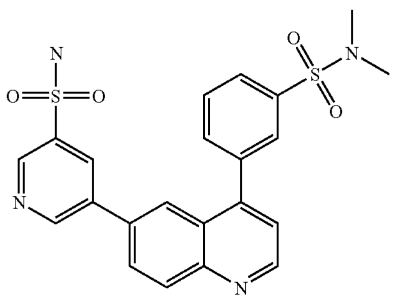 [SMILES: CN(C)S(=O)(=O)c1cccc(-c2ccnc3ccc(-c4cncc(S(N)(=O)=O)c4)cc23)c1] | 469 |
| 294 | 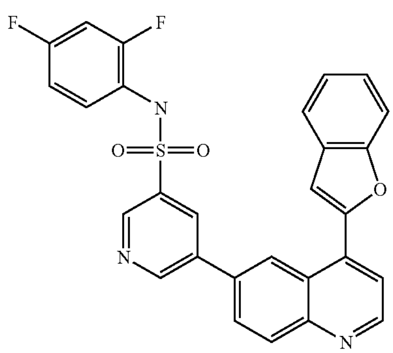 [SMILES: O=S(=O)(Nc1ccc(F)cc1F)c1cncc(-c2ccc3nccc(-c4cc5ccccc5o4)c3c2)c1] | 514 |
| 295 | 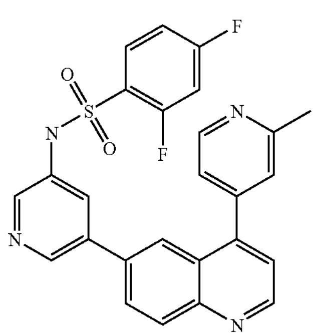 [SMILES: Cc1cc(-c2ccnc3ccc(-c4cncc(NS(=O)(=O)c5ccc(F)cc5F)c4)cc23)ccn1] | 489 |
| 296 | | 514 |
| 297 | | 492 |
| 298 | | 514 |

| Example | Structure | MS(ES) [M + H]+ |
|---|---|---|
| 299 | 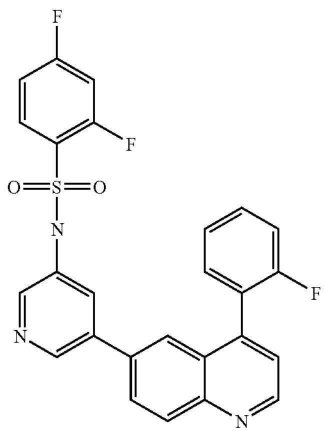 [SMILES: O=S(=O)(Nc1cncc(-c2ccc3nccc(-c4ccccc4F)c3c2)c1)c1ccc(F)cc1F] | 492 |
| 300 | 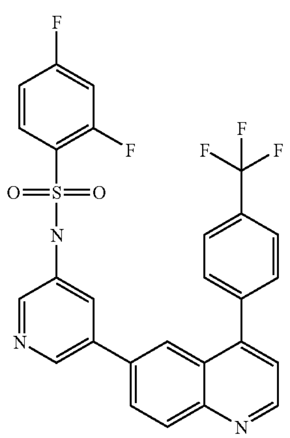 [SMILES: O=S(=O)(Nc1cncc(-c2ccc3nccc(-c4ccc(C(F)(F)F)cc4)c3c2)c1)c1ccc(F)cc1F] | 542 |
| 301 | 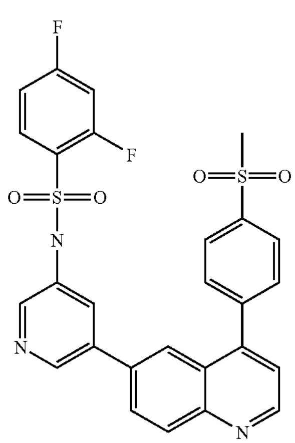 [SMILES: CS(=O)(=O)c1ccc(-c2ccnc3ccc(-c4cncc(NS(=O)(=O)c5ccc(F)cc5F)c4)cc23)cc1] | 552 |
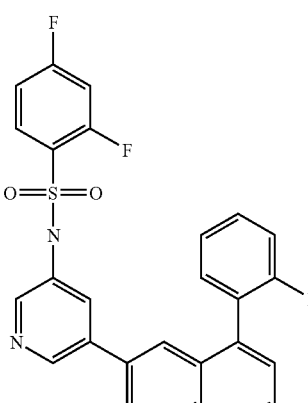
| Example | Structure | MS(ES) [M + H]+ |
|---|---|---|
| 302 | 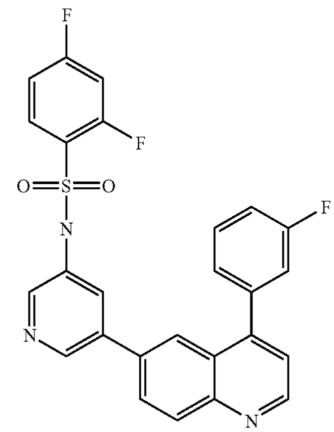 [SMILES: O=S(=O)(Nc1cncc(-c2ccc3nccc(-c4cccc(F)c4)c3c2)c1)c1ccc(F)cc1F] | 492 |
| 303 | 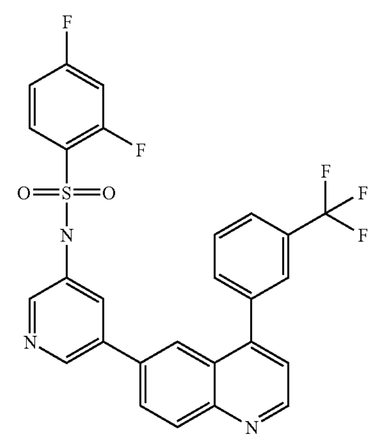 [SMILES: O=S(=O)(Nc1cncc(-c2ccc3nccc(-c4cccc(C(F)(F)F)c4)c3c2)c1)c1ccc(F)cc1F] | 542 |
| 304 | 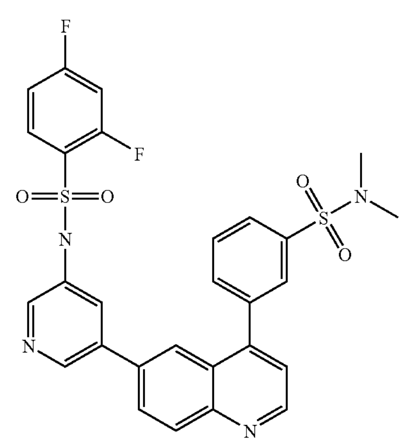 [SMILES: CN(C)S(=O)(=O)c1cccc(-c2ccnc3ccc(-c4cncc(NS(=O)(=O)c5ccc(F)cc5F)c4)cc23)c1] | 581 |
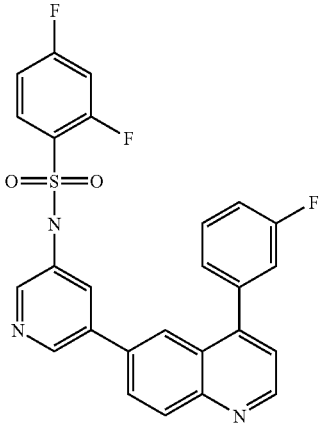

-continued

| Example | Structure | MS(ES) [M + H]+ |
|---|---|---|
| 305 | | 581 |
| 306 | | 517 |
| 307 | | 517 |
| 308 | 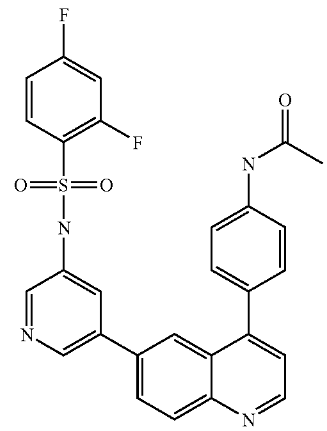 [SMILES: CC(=O)Nc1ccc(-c2ccnc3ccc(-c4cncc(NS(=O)(=O)c5ccc(F)cc5F)c4)cc23)cc1] | 531 |
| 309 | 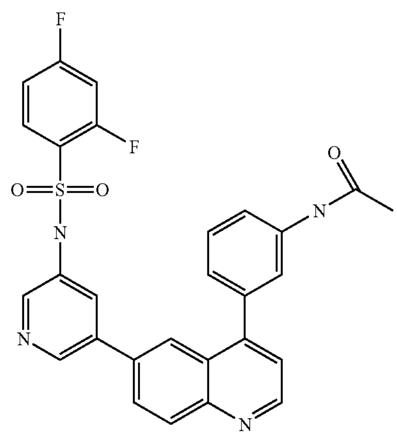 [SMILES: CC(=O)Nc1cccc(-c2ccnc3ccc(-c4cncc(NS(=O)(=O)c5ccc(F)cc5F)c4)cc23)c1] | 531 |
| 310 | 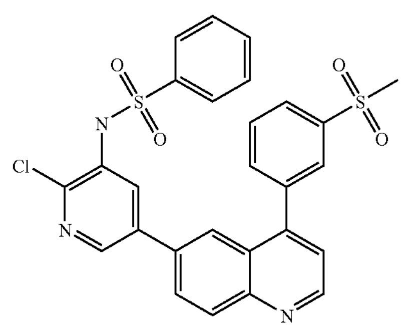 [SMILES: CS(=O)(=O)c1cccc(-c2ccnc3ccc(-c4cnc(Cl)c(NS(=O)(=O)c5ccccc5)c4)cc23)c1] | |
| 311 | 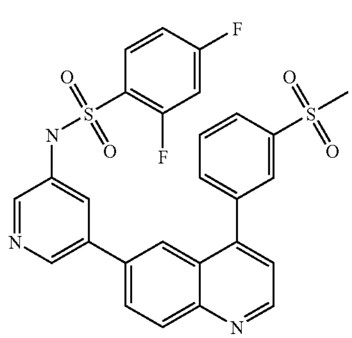 [SMILES: CS(=O)(=O)c1cccc(-c2ccnc3ccc(-c4cncc(NS(=O)(=O)c5ccc(F)cc5F)c4)cc23)c1] | |

Scheme 6:

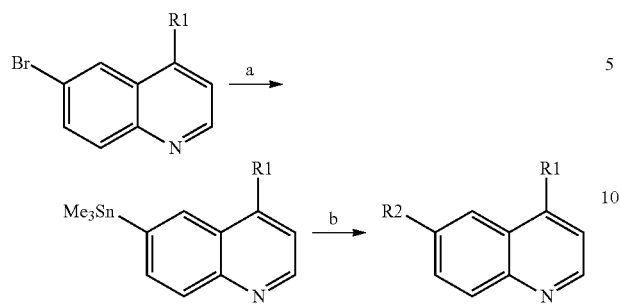

Conditions: a) hexamethylditin, tetrakis(thriphenylphosphine)palladium (0), lithium chloride, tetrahydrofuran, heat; b) heteroaryl (R2) bromide, palladium catalyst, dioxane, heat.

Example 197

4-(4-pyridinyl)-6-(1H-[1,2,3]triazolo[4,5-b]pyridin-6-yl)quinoline

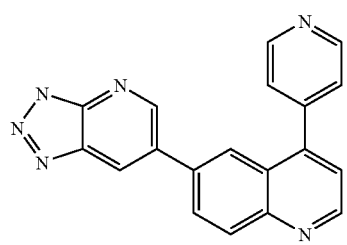 [SMILES: c1cc(-c2ccnc3ccc(-c4cnc5[nH]nnc5c4)cc23)ccn1]

a) 4-(4-pyridinyl)-6-(trimethylstannanyl)quinoline

A mixture of 4-(4-pyridinyl)-6-bromoquinoline (15 g, 53 mmol), hexamethylditin (19 g, 59 mmol), lithium chloride (16 g, 370 mmol), tetrakis(triphenyphosphine)-palladium(0) (3 g, 2.7 mmol), in tetrahydrofuran (400 mL) was heated at reflux for 16 hours, at which time the reaction was allowed to cool to room temperature and concentrated under reduced pressure. Methylene chloride (500 mL) was added to the residue and the mixture was stirred for 2 hours to help break up the solids. The mixture was then filtered and concentrated under reduced pressure. The resulting residue was purified by silica gel chromatography (gradient: $CH_2Cl_2$ to 2% MeOH/$CH_2Cl_2$) to give the title compound (11 g, 56%) as a beige solid. MS(ES)+ m/e 370 [M+H]+.

b) 4-(4-pyridinyl)-6-(1H-[1,2,3]triazolo[4,5-b]pyridin-6-yl)quinoline

A mixture of 6-bromo-1H-[1,2,3]triazolo[4,5-b]pyridine (100 mg, 0.5 mmol), 4-(4-pyridinyl)-6-(trimethylstannanyl)quinoline (204 mg, 0.55 mmol), and tetrakistriphenylphosphine palladium(0) (29 mg, 0.025 mmol) in 1,4-dioxane (3.0 mL) was heated at 100° C. for 18 h. The reaction was filtered to collect the precipitate. The solid was triturated in hot ethanol to give an off-white solid, which still contained some minor impurities. The off-white solid was triturated in hot ethanol to give the title product as a beige solid (22 mg, 14%). MS(ES)+ m/e 325.1 [M+H]+.

The following compounds were or can be prepared following the general procedures used to prepare the compound of Example 197:

| Example | Structure | MS(ES) [M + H]+ |
|---|---|---|
| 198 | 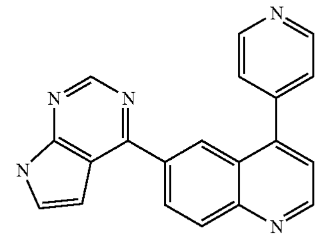 | 324 |
| 199 | 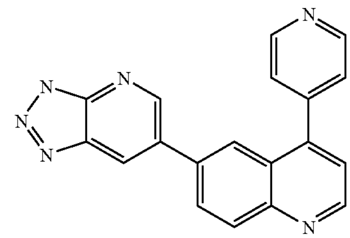 [SMILES: c1cc(-c2ccnc3ccc(-c4cnc5[nH]nnc5c4)cc23)ccn1] | 325 |
| 200 | 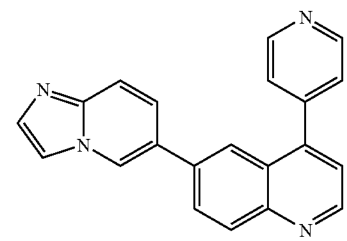 [SMILES: c1cc(-c2ccnc3ccc(-c4ccc5nccn5c4)cc23)ccn1] | 323 |
| 201 | 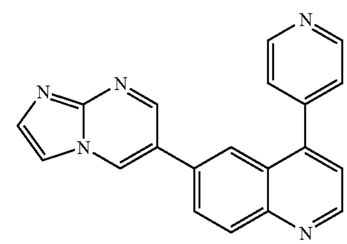 [SMILES: c1cc(-c2ccnc3ccc(-c4cnc5nccn5c4)cc23)ccn1] | 324 |
| 202 | 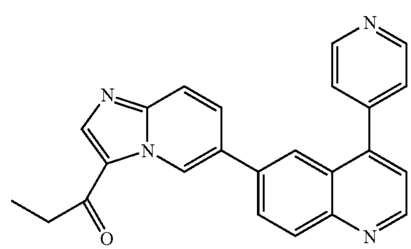 [SMILES: CCC(=O)c1cnc2ccc(-c3ccc4nccc(-c5ccncc5)c4c3)cn12] | 379 |
| 203 | 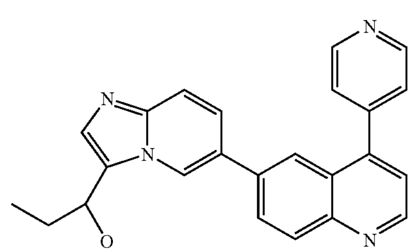 [SMILES: CCC(O)c1cnc2ccc(-c3ccc4nccc(-c5ccncc5)c4c3)cn12] | 381 |

Scheme 7:

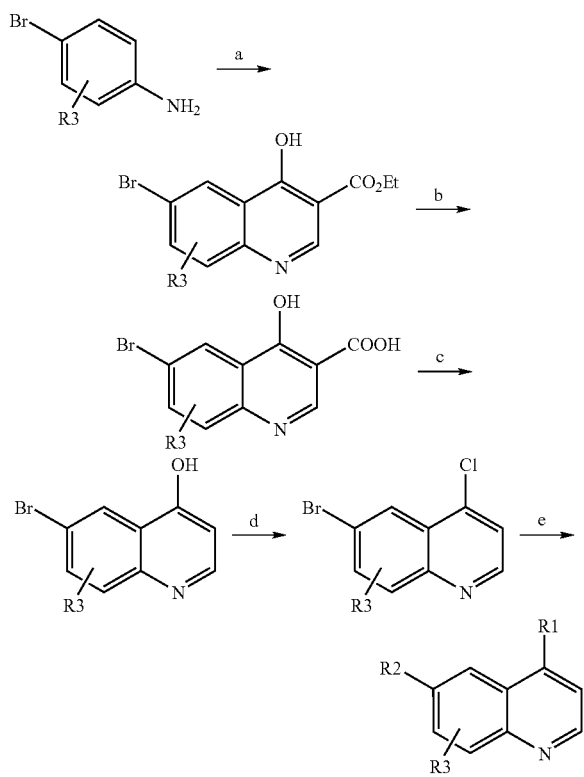

Conditions: a) diethylethoxymethylene malonate, 140° C., then Dowtherm A, 260° C.; b) 6 N sodium hydroxide, ethanol, reflux; c) Dowtherm A, 260° C.; d) phosphorus oxychloride, reflux; e) bis(pinacolato)diboron, palladium catalyst, potassium acetate, dioxane, heat; then heteroaryl (R2) bromide, palladium catalyst, 2 M aqueous potassium carbonate, heat; then aryl (R1) boronic acid/ester, palladium catalyst, 2 M aqueous potassium carbonate, dioxane, heat.

Example 204

2-amino-N,N-dimethyl-5-[8-methyl-4-(4-pyridinyl)-6-quinolinyl]-3-pyridinesulfonamide

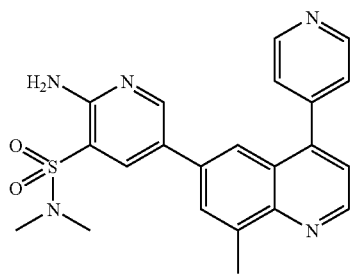 [SMILES: Cc1cc(-c2cnc(N)c(S(=O)(=O)N(C)C)c2)cc2c(-c3ccncc3)ccnc12]

a) ethyl 6-bromo-4-hydroxy-8-methyl-3-quinolinecarboxylate

A mixture of 4-bromo-2-methylaniline (1.50 g, 8.04 mmol) and diethylethoxymethylene malonate (1.74 g, 8.04 mmol) was heated at 140° C. with stirring in an oil bath for 5.0 h. The reaction was transferred to a heating mantle, diluted with Dowtherm A (4 mL), and heated at 260° C. for 1 h. The reaction was cooled, diluted with hexanes, and the suspension was stirred overnight at room temperature. The suspension was filtered and the filtered solid was washed with hexanes and dried in a Buchner funnel to give the title compound (1.90 g, 76%) as a tan solid. MS(ES)+ m/e 310 [M+H].

b) 6-bromo-4-hydroxy-8-methyl-3-quinolinecarboxylic acid

A mixture of ethyl 6-bromo-4-hydroxy-8-methyl-3-quinolinecarboxylate (1.89 g, 6.09 mmol) and 6 N NaOH (1.22 g, 30.45 mmol, 5.1 mL) in ethanol (30 mL) was heated at reflux for 2.0 h and concentrated in vacuo. The residue was diluted with water and acidified with 6 N HCl to pH 4. The resulting solid was filtered, washed with water and diethyl ether, and dried overnight in a Buchner funnel to give the title compound (1.72 g, 99%) as a tan solid. MS(ES)+ m/e 282 [M+H].

c) 6-bromo-8-methyl-4-quinolinol

A mixture of 6-bromo-4-hydroxy-8-methyl-3-quinolinecarboxylic acid (1.80 g, 6.36 mmol) and Dowtherm A (10 mL) was heated at 260° C. for 1.0 h. The reaction was cooled, triturated with hexanes, filtered and dried in a Buchner funnel to give the title compound (1.43 g, 95%) as a tan solid. MS(ES)+ m/e 238 [M+H].

d) 6-bromo-4-chloro-8-methylquinoline

A mixture of 6-bromo-8-methyl-4-quinolinol (1.42 g, 5.95 mmol) and phosphorous oxychloride (10.95 g, 71.40 mmol) was heated at reflux for 1 h, cooled, poured onto ice, and neutralized by addition of 30% ammonium hydroxide. The resulting solid was filtered and dried in a vacuum oven to give the title compound (1.45 g, 95%) as a tan solid. MS(ES)+ m/e 256 [M+H].

e) 2-amino-N,N-dimethyl-5-[8-methyl-4-(4-pyridinyl)-6-quinolinyl]-3-pyridinesulfonamide A mixture of 6-bromo-4-chloro-8-methylquinoline (0.300 g, 1.170 mmol), bis(pinacolato)diboron (0.297 g, 1.170 mmol), dichloro[1,1'-bis(diphenylphosphino)ferrocene]palladium(II)dichloromethane adduct (0.029 g, 0.035 mmol), and solid anhydrous potassium acetate (0.459 g, 4.676 mmol) in dry 1,4-dioxane (8 mL) was heated at reflux for 70 minutes. The oil bath was temporarily removed and to the reaction was added 2-amino-5-bromo-N,N-dimethyl-3-pyridinesulfonamide (0.327 g, 1.17 mmol), dichloro[1,1'-bis(diphenylphosphino)ferrocene]palladium(II)dichloromethane adduct (0.047 g, 0.058 mmol), and 2 M aqueous potassium carbonate (0.646 g, 4.676 mmol, 2.34 mL). The reaction was heated at reflux for 80 minutes. The oil bath was temporarily removed and to the reaction was added 4-(4,4,5,5-tetramethyl-1,3,2-dioxaborolan-2-yl)pyridine (0.240 g, 1.17 mmol), dichloro[1,1'-bis(diphenylphosphino)ferrocene]palladium (II) dichloromethane adduct (0.047 g, 0.058 mmol), 2 M aqueous potassium carbonate (0.485 g, 3.51 mmol, 1.76 mL), and 1,4-dioxane (6 mL). The reaction was heated at reflux for 17 h and concentrated in vacuo. The residue was triturated with 10% MeOH:EtOAc (45 mL), filtered through filter paper, and the filtrate was concentrated in vacuo. The residue was purified by flash chromatography on silica gel (7% MeOH:EtOAc) to give the title compound (0.135 g, 28%) as a yellow powder. MS(ES)+ m/e 420 [M+H].

The following compounds were or can be prepared following the general procedures used to prepare the compound of Example 204:

| Example | Structure | MS(ES) [M + H]+ |
|---|---|---|
| 205 | 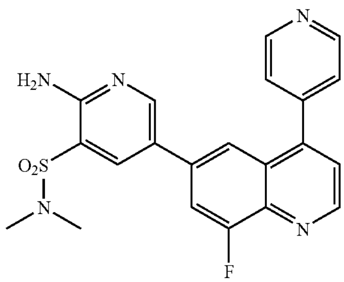 [SMILES: CN(C)S(=O)(=O)c1cc(-c2cc(F)c3nccc(-c4ccncc4)c3c2)cnc1N] | 424 |
| 206 | 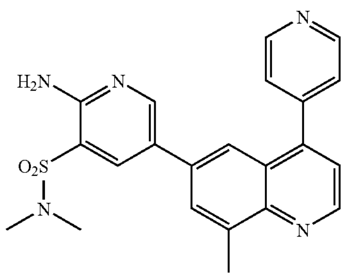 [SMILES: Cc1cc(-c2cnc(N)c(S(=O)(=O)N(C)C)c2)cc2c(-c3ccncc3)ccnc12] | 420 |
| 207 | 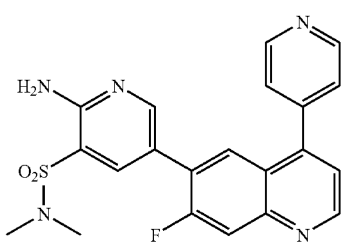 [SMILES: CN(C)S(=O)(=O)c1cc(-c2cc3c(-c4ccncc4)ccnc3cc2F)cnc1N] | 424 |
| 208 | 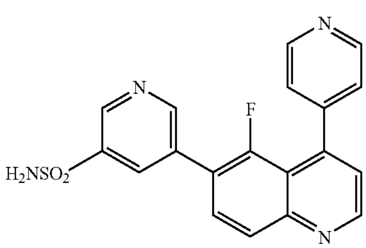 | 381 |
| 209 | 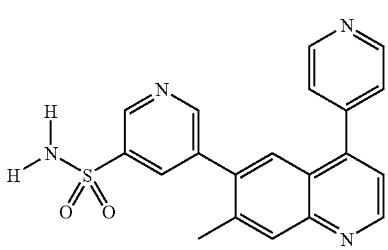 [SMILES: Cc1cc2nccc(-c3ccncc3)c2cc1-c1cncc(S(N)(=O)=O)c1] | 377 |
| 210 | 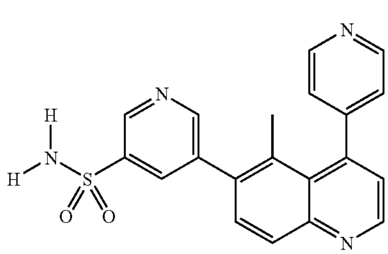 [SMILES: Cc1c(-c2cncc(S(N)(=O)=O)c2)ccc2nccc(-c3ccncc3)c12] | 377 |

Scheme 8:

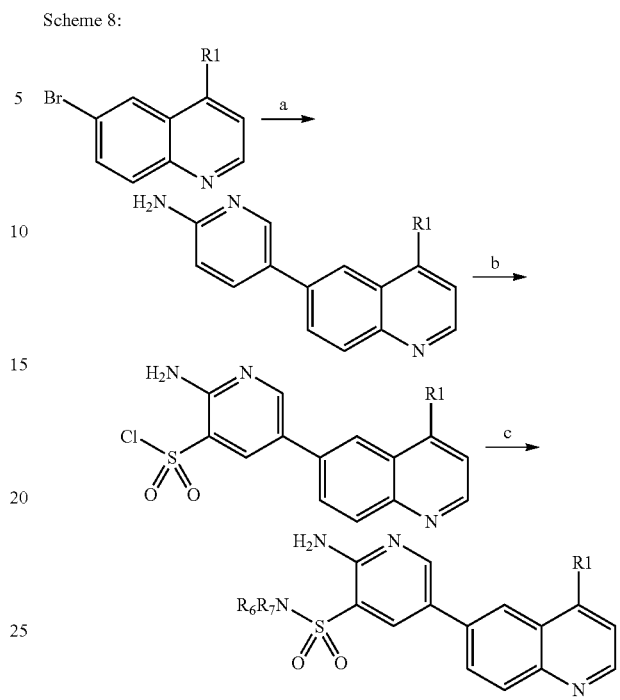

Conditions: a) bis(pinacolato)diboron, potassium acetate, palladium catalyst, dioxane, heat; then 5-bromo-2-pyridinamine, palladium catalyst, 2 M potassium carbonate, dioxane, heat; b) chlorosulfonic acid, 0° C.-reflux; c) $R_6R_7NH$, pyridine, dioxane, rt-50° C.

Example 211

3-(1-piperidinylsulfonyl)-5-[4-(4-pyridinyl)-6-quinolinyl]-2-pyridinamine

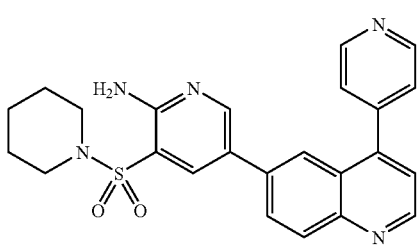 [SMILES: Nc1ncc(-c2ccc3nccc(-c4ccncc4)c3c2)cc1S(=O)(=O)N1CCCCC1]

a) 5-[4-(4-pyridinyl)-6-quinolinyl]-2-pyridinamine

To a 1 L pressure vessel was added 6-bromo-4-(4-pyridinyl)quinoline (12 g, 42.08 mmol), bis(pinacolato)diboron (12.8 g, 50.5 mmol), anhydrous potassium acetate (8.24 g, 84.16 mmol), [1,1'-bis(diphenylphosphino)-ferrocene]dichloropalladium(II)-complex with dichloromethane(1:1) (1.372 g, 1.68 mmol) and anhydrous dioxane (420 mL). The reaction vessel was purged with nitrogen, capped and heated at 100° C. for 15 hours. LCMS indicated 96% conversion to a mixture of the desired boronate ester MS(ES)+ m/e 333.2 $[M+H]^+$ and boronic acid MS(ES)+m/e 250.9 $[M+H]^+$.

To the reaction mixture above was added 5-bromo-2-pyridinamine (7.28 g, 42.08 mmol), [1,1'-bis(diphenylphosphino)-ferrocene]dichloropalladium(II)-complex with dichloromethane(1:1) (1.718 g, 2.1 mmol), 2 M aqueous K₂CO₃ (300 mL). The reaction was heated at 100° C. for 21 hours. After cooling to room temperature, the organic layer was separated and concentrated in vacuo. The residue was triturated with water, and dissolved in dichloromethane. This solution was filtered through a plug of silica, washing continuously with dicholormethane and ethanol. Concentration in vacuo provided the title compound as a yellow powder (8.767 g, 70% yield). MS(ES)+ m/e 299.0 [M+H].

b) 2-amino-5-[4-(4-pyridinyl)-6-quinolinyl]-3-pyridinesulfonyl chloride

To cold (0° C.) chlorosulfonic acid (15 mL) under vigorous stirring was added 5-[4-(4-pyridinyl)-6-quinolinyl]-2-pyridinamine (4.348 g, 14.57 mmol) portionwise. The reaction mixture was then heated at reflux for 16 hrs. Upon cooling to room temperature, LCMS indicated 47% of the title compound MS(ES)+m/e 396.9 [M+]⁺ and 37% of sulfonic acid by-product MS(ES)+ m/e 379.1 [M+]⁺. A 2 mL aliquot of this 0.456M solution of the title compound was used in the next reaction without further workup.

c) 3-(1-piperidinylsulfonyl)-5-[4-(4-pyridinyl)-6-quinolinyl]-2-pyridinamine To a cold (5° C.) solution of the 0.456 M solution of 2-amino-5-[4-(4-pyridinyl)-6-quinolinyl]-3-pyridinesulfonyl chloride (2 mL, 0.912 mmol) in chlorosulfonic acid from above was added anhydrous dioxane (1 mL) and piperidine (1.8 mL, 18.24 mmol). After 30 minutes of stirring, pyridine (1 mL, 12.3 mmol) was added and the reaction mixture stirred for an additional hour at room temperature. The reaction mixture was concentrated in vacuo, the residue dissolved in CH₂Cl₂ and the pH adjusted to 14 using 6 N NaOH (aq). The solution was extracted with CH₂Cl₂ (×4) and the combined organic layers dried (Na₂SO₄), filtered and concentrated in vacuo. The resulting residue was purified twice by silica gel chromatography (0-5% MeOH in EtOAC) to give the title compound as a pale yellow solid (269 mg, 66% yield). MS(ES)+ m/e 446.3 [M+H]⁺.

The following compounds were or can be prepared following the general procedures used to prepare the compound of Example 211:

| Example | Structure | MS(ES) [M + H]⁺ |
|---|---|---|
| 212 | 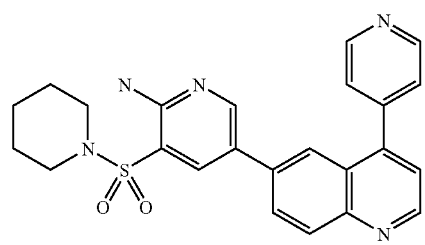 [SMILES: Nc1ncc(-c2ccc3nccc(-c4ccncc4)c3c2)cc1S(=O)(=O)N1CCCCC1] | 446 |
| 213 | 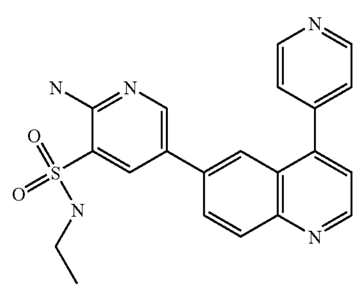 [SMILES: CCNS(=O)(=O)c1cc(-c2ccc3nccc(-c4ccncc4)c3c2)cnc1N] | 406 |
| 214 | 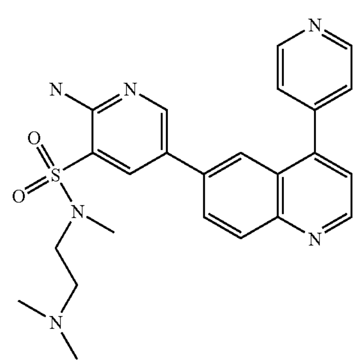 [SMILES: CN(C)CCN(C)S(=O)(=O)c1cc(-c2ccc3nccc(-c4ccncc4)c3c2)cnc1N] | 463 |

-continued

| Example | Structure | MS(ES) [M + H]+ |
|---|---|---|
| 215 | 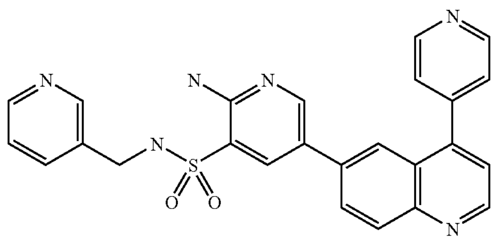 [SMILES: Nc1ncc(-c2ccc3nccc(-c4ccncc4)c3c2)cc1S(=O)(=O)NCc1cccnc1] | 469 |
| 216 | 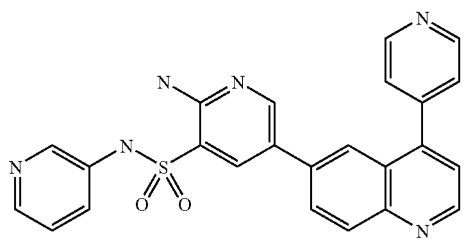 [SMILES: Nc1ncc(-c2ccc3nccc(-c4ccncc4)c3c2)cc1S(=O)(=O)Nc1cccnc1] | 454 |
| 217 | 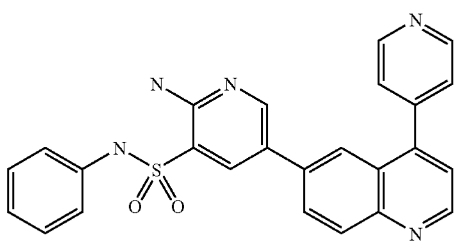 [SMILES: Nc1ncc(-c2ccc3nccc(-c4ccncc4)c3c2)cc1S(=O)(=O)Nc1ccccc1] | 453 |
| 218 | 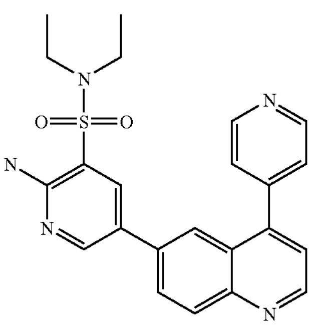 [SMILES: CCN(CC)S(=O)(=O)c1cc(-c2ccc3nccc(-c4ccncc4)c3c2)cnc1N] | 434 |
| 219 | 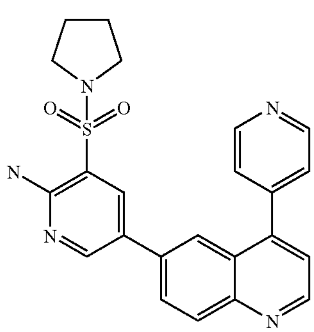 [SMILES: Nc1ncc(-c2ccc3nccc(-c4ccncc4)c3c2)cc1S(=O)(=O)N1CCCC1] | 432 |

Scheme 9:

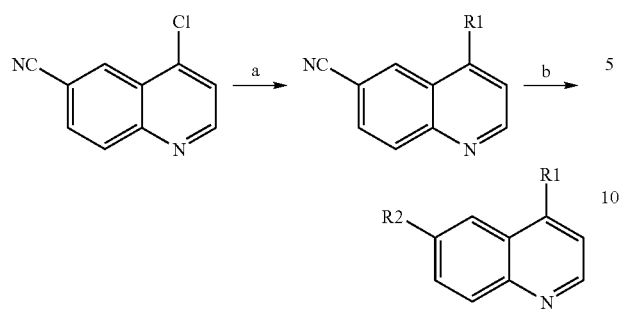

Conditions: a) aryl (R1) boronic acid or aryl (R1) boronate, palladium catalyst, 2 M potassium carbonate, dioxane, heat; b) bis(pinacolato)diboron, potassium acetate, palladium catalyst, dioxane, heat; then heteroaryl (R2) bromide, palladium catalyst, 2 M potassium carbonate, heat.

Example 220

Preparation of 6-(1H-benzimidazol-2-yl)-4-(4-pyridinyl)quinoline

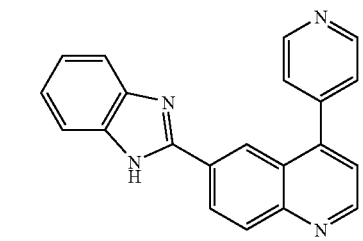 [SMILES: c1ccc2[nH]c(-c3ccc4nccc(-c5ccncc5)c4c3)nc2c1]

a) 4-(4-pyridinyl)-6-quinolinecarbonitrile

A mixture of 4-chloro-6-quinolinecarbonitrile (8.7 g, 46.2 mmol), 4-pyridineboronic acid (8.52 g, 69.3 mmol), tetrakis(triphenylphosphine)palladium(0) (2.67 g, 2.31 mmol) and 2 M potassium carbonate (69.3 mL, 3 eq) in 1,4-dioxane (380 mL) is heated at reflux for 3.5 hours. The dioxane is evaporated and the crude product purified by silica gel chromatography eluting with methylene chloride/methanol 0-4%. A yield of 10.23 g (95%) of the title compounds was obtained.

b) 1H-benzimidazol-2-yl)-4-(4-pyridinyl)quinoline

A mixture of 4-(4-pyridinyl)-6-quinolinecarbonitrile, (231 mg, 1 mmol) 1,2-diaminobenzene (108 mg, 1 mmol) and polyphosphoric acid (1.4 g) was heated in the microwave at 250° C. for 1.5 hours. The reaction was poured onto water which was neutralized with bicarbonate. The product was filtered, washed with water, and dried. The product was further purified by dissolving in hot methanol, filtering and cooling to obtain crystals. The yield was 47.7 mg, 30%. MS(ES)+ m/e 323 [M+H]+.

The following compounds were or can be prepared following the general procedures used to prepare the compound of Example 220:

| Example | Structure | MS(ES) [M + H]+ |
|---|---|---|
| 221 | 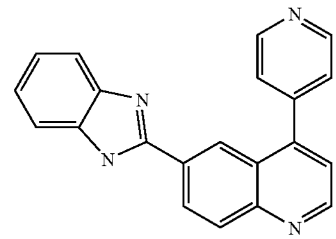 | 323 |
| 222 | 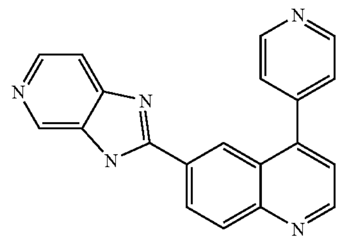 [SMILES: c1cc(-c2ccnc3ccc(-c4nc5ccncc5[nH]4)cc23)ccn1] | 324 |
| 223 | 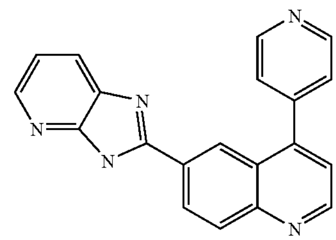 [SMILES: c1cnc2[nH]c(-c3ccc4nccc(-c5ccncc5)c4c3)nc2c1] | 324 |
| 224 | 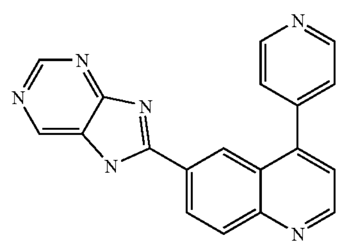 [SMILES: c1cc(-c2ccnc3ccc(-c4nc5ncncc5[nH]4)cc23)ccn1] | 325 |

Scheme 10:

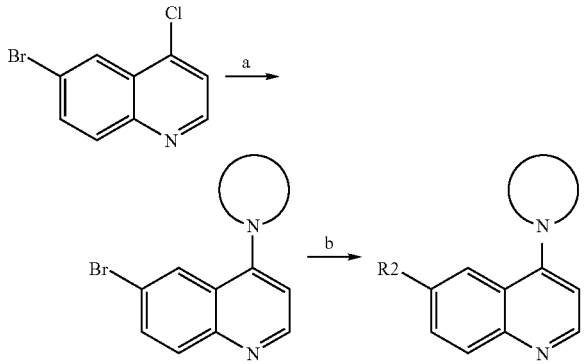

Conditions: a) cyclic secondary amine, dimethylformamide, heat; b) bis(pinacolato)diboron, potassium acetate, palladium catalyst, dioxane, heat; then heteroaryl (R2) bromide, palladium catalyst, 2 M potassium carbonate, heat.

Example 225

4-(1-piperidinyl)-6-(4,4,5,5-tetramethyl-1,3,2-dioxaborolan-2-yl)quinoline

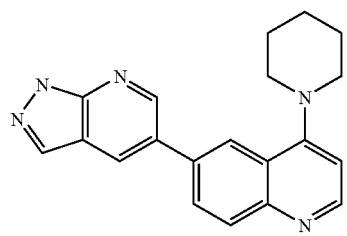 [SMILES: c1cc(N2CCCCC2)c2cc(-c3cnc4[nH]ncc4c3)ccc2n1]

a) 6-bromo-4-(1-piperidinyl)quinoline

To a solution of 4-chloro-6-bromoquinoline (726 mg, 3 mmol) in 3 mL of 1-methyl-2-pyrrolidinone was added piperidine (510 mg, 6 mmol). The reaction was heated to 150° C. for 5 h. The solvents were removed in vacuo at 100° C. and the residue dissolved in methylene chloride and washed with water. The methylene chloride was dried with sodium sulfate and concentrated. The residue was triturated with hexane and the solid filtered off to give 6-bromo-4-(1-piperidinyl)quinoline (877 mg, 73%).

b) 6-(7,7a-dihydro-1H-pyrazolo[3,4-b]pyridin-5-yl)-4-(1-piperidinyl)quinoline To a solution of 6-bromo-4-(1-piperidinyl)quinoline (429 mg, 1.47 mmol) in dioxane (4 mL) was added 4,4,4',4',5,5,5',5'-octamethyl-2,2'-bi-1,3,2-dioxaborolane (373 mg, 1.76 mmol), potassium acetate (441 mg, 4.5 mmol), and PdCl2(dppf)2 (36 mg, 0.045 mmol). The reaction was heated to 150° C. for 30 minutes to give crude 4-(1-piperidinyl)-6-(4,4,5,5-tetramethyl-1,3,2-dioxaborolan-2-yl)quinoline. The reaction was then cooled and 5-bromo-7,7a-dihydro-1H-pyrazolo[3,4-b]pyridine (348 mg, 1.76 mmol) was added, followed by PdCl2(dppf)2 (36 mg, 0.045 mmol) and 2 M potassium carbonate (2.25 mL). The reaction was heated at 150° C. for 30 min, at which time the dioxane was evaporated and the crude product triturated water and collected by filtration. The crude product was partially purified by HPLC chromatography acetonitrile/water/0.1% TFA. At this point the product was 85% pure. It was free based with sodium carbonate and further purified by silica gel chromatography eluting with methylene chloride/0-2% (methanol/concentrated ammonium hydroxide solution 9/1) to obtain the title compound (29 mg, 0 6%). MS(ES)+ m/e 330 [M+H]+.

The following compounds were or can be prepared following the general procedures used to prepare the compound of Example 225:

| Example | Structure | MS(ES) [M + H]+ |
|---|---|---|
| 226 | 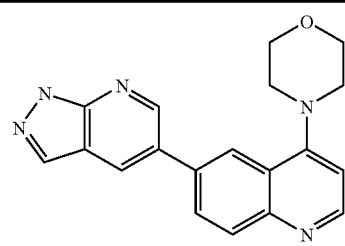 | 332 |
| 227 | 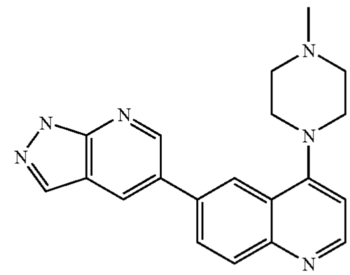 [SMILES: CN1CCN(c2ccnc3ccc(-c4cnc5[nH]ncc5c4)cc23)CC1] | 345 |
| 228 | 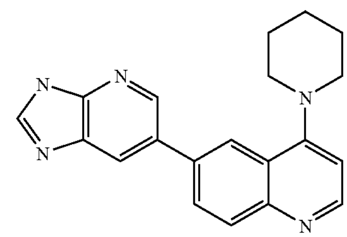 [SMILES: c1cc(N2CCCCC2)c2cc(-c3cnc4[nH]cnc4c3)ccc2n1] | 330 |
| 229 | 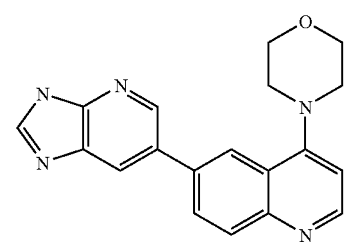 [SMILES: c1cc(N2CCOCC2)c2cc(-c3cnc4[nH]cnc4c3)ccc2n1] | 332 |

Scheme 11:

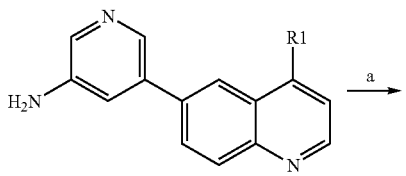

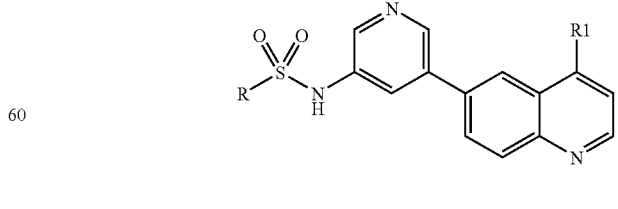

Conditions: a) R-sulfonyl chloride, pyridine, methylene chloride.

Example 230

2,4-difluoro-N-{5-[4-(4-pyridinyl)-6-quinolinyl]-3-pyridinyl}benzenesulfonamide

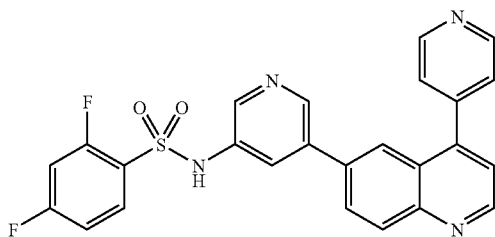 [SMILES: O=S(=O)(Nc1cncc(-c2ccc3nccc(-c4ccncc4)c3c2)c1)c1ccc(F)cc1F]

a) 2,4-difluoro-N-{5-[4-(4-pyridinyl)-6-quinolinyl]-3-pyridinyl}benzenesulfonamide A solution of 5-[4-(4-pyridinyl)-6-quinolinyl]-3-pyridinamine (82 mg, 0.27 mmol) in anhydrous pyridine (2.0 ml) was treated with neat 2,4-difluorobenzenesulfonyl chloride in one portion. The reaction was stirred at room temperature for 30 minutes then was purified directly by prep-HPLC. The combined, desired fractions were evaporated under reduced pressure to remove organic solvents then diluted with small portions of brine and saturated aqueous sodium bicarbonate. The basic solution was extracted with ethyl acetate then the extracts were dried over anhydrous sodium sulfate and evaporated under reduced pressure. The resulting colorless film was crystallized from methylene chloride and diethyl ether. The solids were collected by filtration, rinsed with diethyl ether then vacuum dried to afford the title compound (219 mg, 48%) as a white solid. MS(ES)+m/e 475 [M+H]$^+$.

The following compounds were or can be prepared following the general procedures used to prepare the compound of Example 230:

| Example | Structure | MS(ES) [M + H]$^+$ |
|---|---|---|
| 231 | 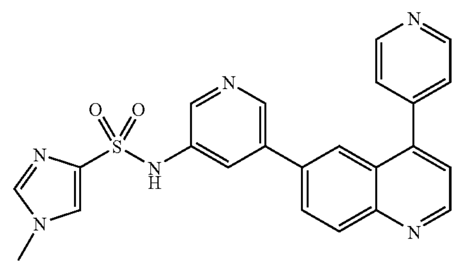 [SMILES: Cn1cnc(S(=O)(=O)Nc2cncc(-c3ccc4nccc(-c5ccncc5)c4c3)c2)c1] | 443 |
| 232 | 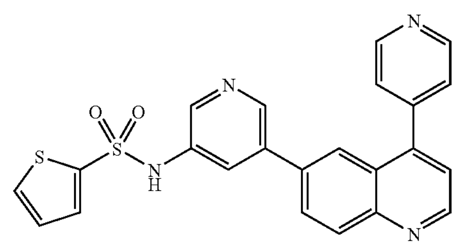 [SMILES: O=S(=O)(Nc1cncc(-c2ccc3nccc(-c4ccncc4)c3c2)c1)c1cccs1] | 445 |
| 233 | 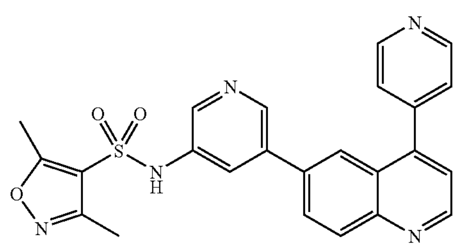 [SMILES: Cc1noc(C)c1S(=O)(=O)Nc1cncc(-c2ccc3nccc(-c4ccncc4)c3c2)c1] | 458 |
| 234 | 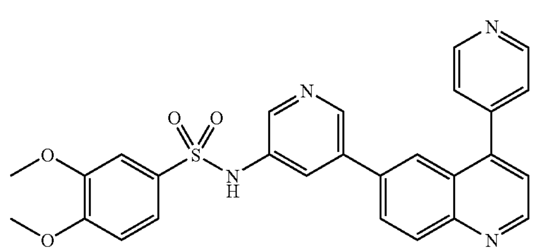 [SMILES: COc1ccc(S(=O)(=O)Nc2cncc(-c3ccc4nccc(-c5ccncc5)c4c3)c2)cc1OC] | 499 |

-continued
| Example | Structure | MS(ES) [M + H]+ |
|---|---|---|
| 235 | 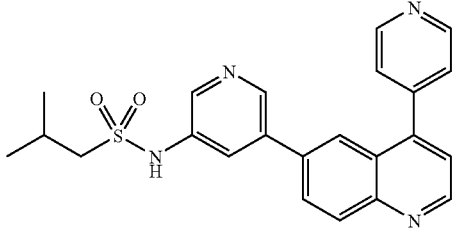 [SMILES: CC(C)CS(=O)(=O)Nc1cncc(-c2ccc3nccc(-c4ccncc4)c3c2)c1] | 419 |
| 236 | 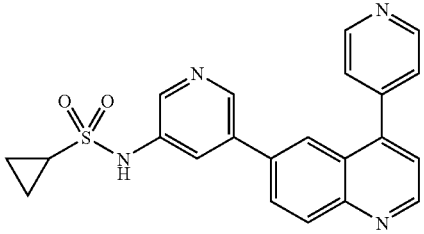 [SMILES: O=S(=O)(Nc1cncc(-c2ccc3nccc(-c4ccncc4)c3c2)c1)C1CC1] | 403 |
| 237 | 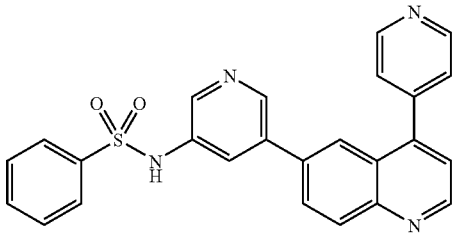 [SMILES: O=S(=O)(Nc1cncc(-c2ccc3nccc(-c4ccncc4)c3c2)c1)c1ccccc1] | 439 |
| 238 | 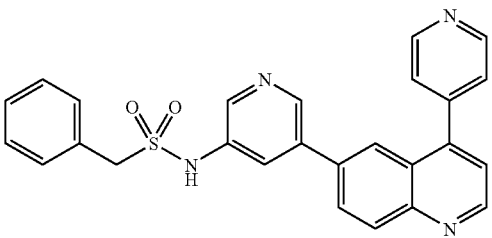 [SMILES: O=S(=O)(Cc1ccccc1)Nc1cncc(-c2ccc3nccc(-c4ccncc4)c3c2)c1] | 453 |
| 312 | 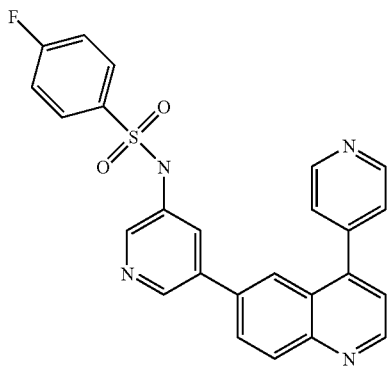 [SMILES: O=S(=O)(Nc1cncc(-c2ccc3nccc(-c4ccncc4)c3c2)c1)c1ccc(F)cc1] | 457 |

-continued

| Example | Structure | MS(ES) [M + H]+ |
|---|---|---|
| 313 | 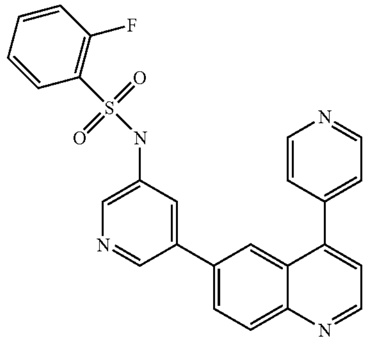 [SMILES: O=S(=O)(Nc1cncc(-c2ccc3nccc(-c4ccncc4)c3c2)c1)c1ccccc1F] | 457 |
| 314 | 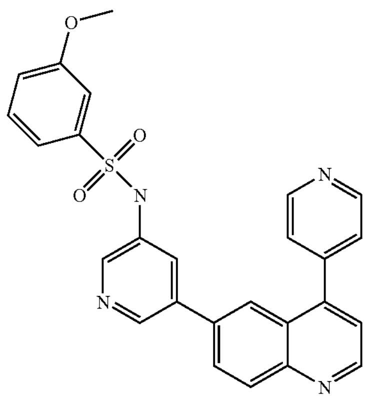 [SMILES: COc1cccc(S(=O)(=O)Nc2cncc(-c3ccc4nccc(-c5ccncc5)c4c3)c2)c1] | 469 |
| 315 | 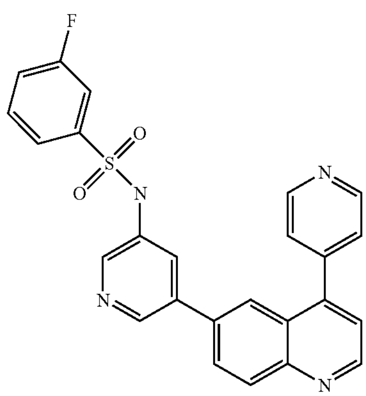 [SMILES: O=S(=O)(Nc1cncc(-c2ccc3nccc(-c4ccncc4)c3c2)c1)c1cccc(F)c1] | 457 |
| 316 | 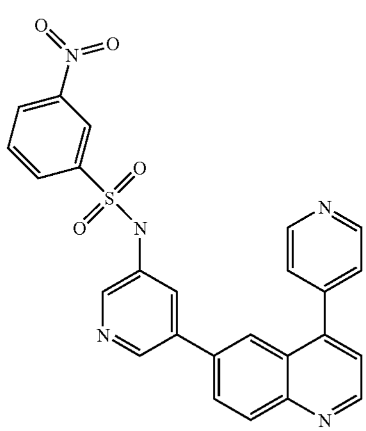 [SMILES: O=[N+]([O-])c1cccc(S(=O)(=O)Nc2cncc(-c3ccc4nccc(-c5ccncc5)c4c3)c2)c1] | 484 |

| Example | Structure | MS(ES) [M + H]+ |
|---|---|---|
| 317 | 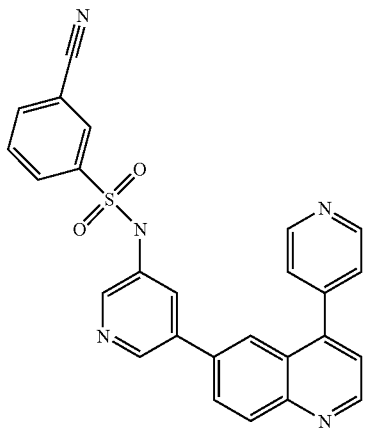 [SMILES: N#Cc1cccc(S(=O)(=O)Nc2cncc(-c3ccc4nccc(-c5ccncc5)c4c3)c2)c1] | 464 |
| 318 | 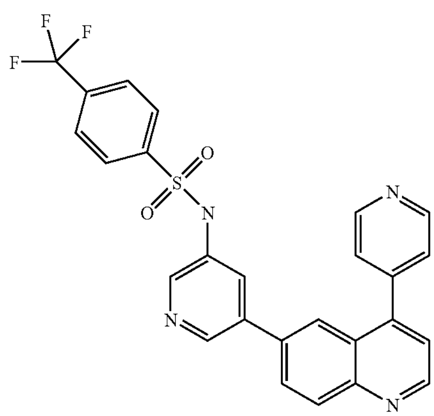 [SMILES: O=S(=O)(Nc1cncc(-c2ccc3nccc(-c4ccncc4)c3c2)c1)c1ccc(C(F)(F)F)cc1] | 507 |
| 319 | 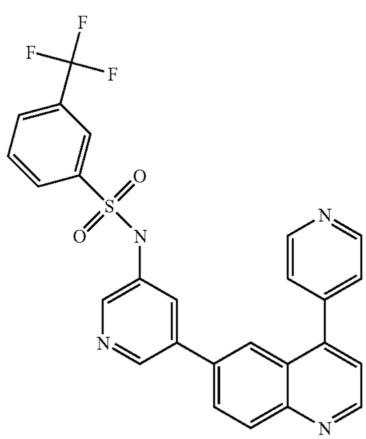 [SMILES: O=S(=O)(Nc1cncc(-c2ccc3nccc(-c4ccncc4)c3c2)c1)c1cccc(C(F)(F)F)c1] | 507 |
| 320 | 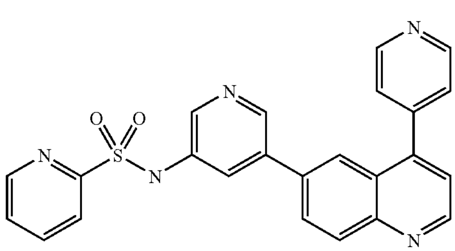 [SMILES: O=S(=O)(Nc1cncc(-c2ccc3nccc(-c4ccncc4)c3c2)c1)c1ccccn1] | 440.1 |

-continued

| Example | Structure | MS(ES) [M + H]+ |
|---|---|---|
| 321 | 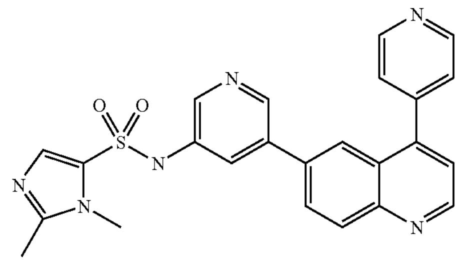 [SMILES: Cc1ncc(S(=O)(=O)Nc2cncc(-c3ccc4nccc(-c5ccncc5)c4c3)c2)n1C] | 457.1 |
| 322 | 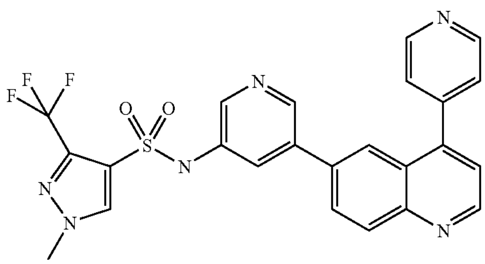 [SMILES: Cn1cc(S(=O)(=O)Nc2cncc(-c3ccc4nccc(-c5ccncc5)c4c3)c2)c(C(F)(F)F)n1] | 511.1 |
| 323 | 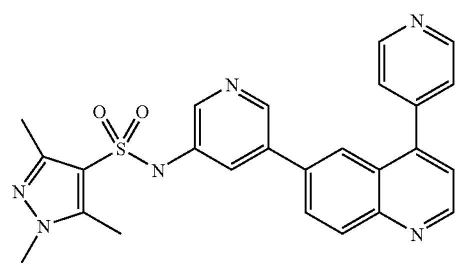 [SMILES: Cc1nn(C)c(C)c1S(=O)(=O)Nc1cncc(-c2ccc3nccc(-c4ccncc4)c3c2)c1] | 471.2 |
| 324 | 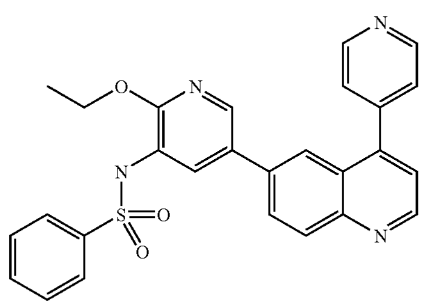 [SMILES: CCOc1ncc(-c2ccc3nccc(-c4ccncc4)c3c2)cc1NS(=O)(=O)c1ccccc1] | 483.1 |
| 325 | 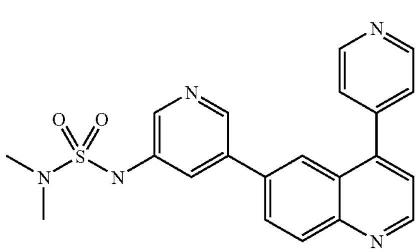 [SMILES: CN(C)S(=O)(=O)Nc1cncc(-c2ccc3nccc(-c4ccncc4)c3c2)c1] | 406.3 |
| 326 | 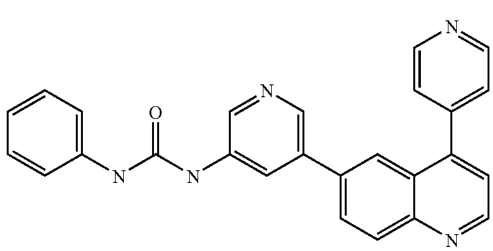 [SMILES: O=C(Nc1ccccc1)Nc1cncc(-c2ccc3nccc(-c4ccncc4)c3c2)c1] | 418.3 |

-continued

| Example | Structure | MS(ES) [M + H]+ |
|---|---|---|
| 327 | 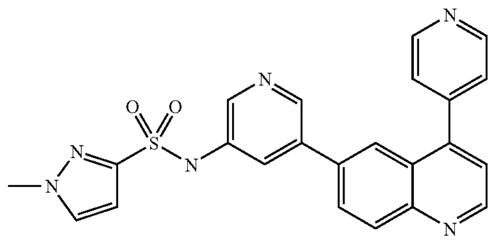 [SMILES: Cn1ccc(S(=O)(=O)Nc2cncc(-c3ccc4nccc(-c5ccncc5)c4c3)c2)n1] | 443.2 |
| 328 | 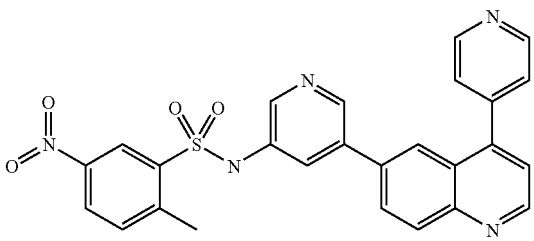 [SMILES: Cc1ccc([N+](=O)[O-])cc1S(=O)(=O)Nc1cncc(-c2ccc3nccc(-c4ccncc4)c3c2)c1] | 498.2 |
| 329 | 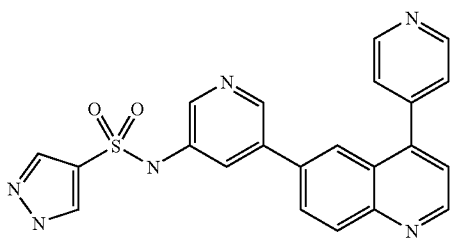 [SMILES: O=S(=O)(Nc1cncc(-c2ccc3nccc(-c4ccncc4)c3c2)c1)c1cn[nH]c1] | 429 |
| 330 | 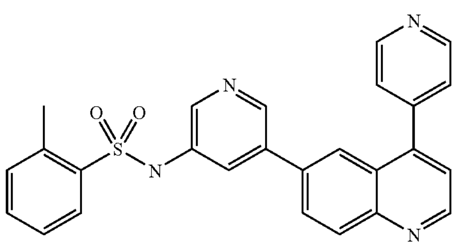 [SMILES: Cc1ccccc1S(=O)(=O)Nc1cncc(-c2ccc3nccc(-c4ccncc4)c3c2)c1] | 453 |
| 331 | 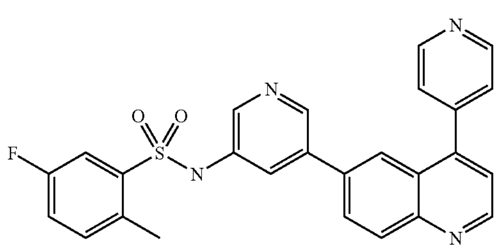 [SMILES: Cc1ccc(F)cc1S(=O)(=O)Nc1cncc(-c2ccc3nccc(-c4ccncc4)c3c2)c1] | 471.2 |
| 332 | 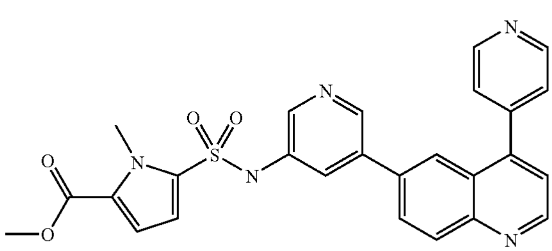 [SMILES: COC(=O)c1ccc(S(=O)(=O)Nc2cncc(-c3ccc4nccc(-c5ccncc5)c4c3)c2)n1C] | 500.3 |

-continued

| Example | Structure | MS(ES) [M + H]+ |
|---|---|---|
| 333 | 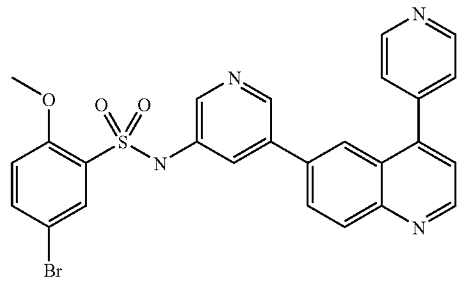 [SMILES: COc1ccc(Br)cc1S(=O)(=O)Nc1cncc(-c2ccc3nccc(-c4ccncc4)c3c2)c1] | 547.0, 549.1 |
| 334 | 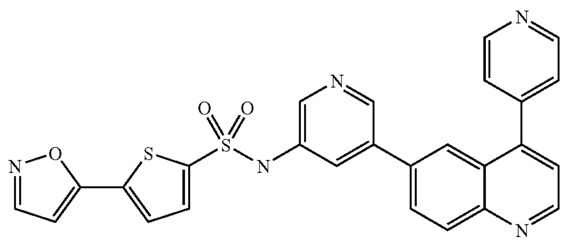 [SMILES: O=S(=O)(Nc1cncc(-c2ccc3nccc(-c4ccncc4)c3c2)c1)c1ccc(-c2ccno2)s1] | 512.2 |
| 335 | 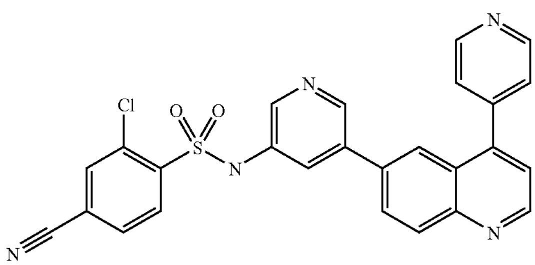 [SMILES: N#Cc1ccc(S(=O)(=O)Nc2cncc(-c3ccc4nccc(-c5ccncc5)c4c3)c2)c(Cl)c1] | 498.2 |
| 336 | 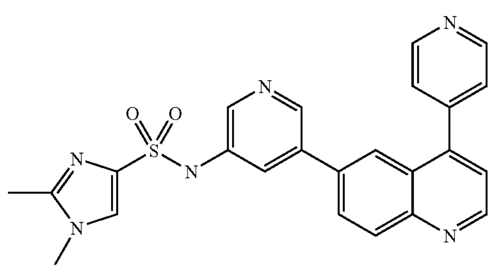 [SMILES: Cc1nc(S(=O)(=O)Nc2cncc(-c3ccc4nccc(-c5ccncc5)c4c3)c2)cn1C] | 457.1 |
| 337 | 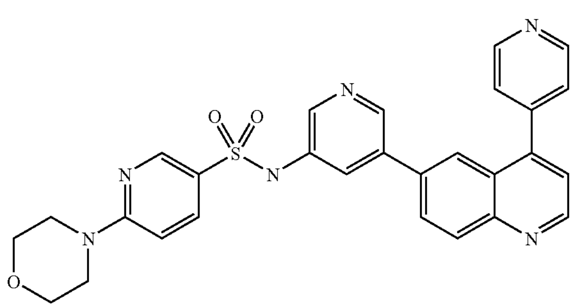 [SMILES: O=S(=O)(Nc1cncc(-c2ccc3nccc(-c4ccncc4)c3c2)c1)c1ccc(N2CCOCC2)nc1] | 525.4 |

-continued

| Example | Structure | MS(ES) [M + H]+ |
|---|---|---|
| 338 | 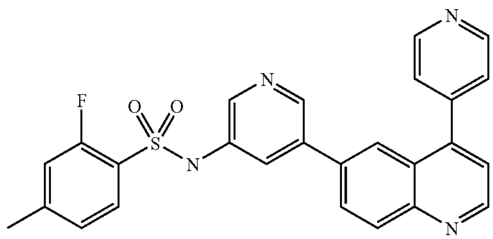 [SMILES: Cc1ccc(S(=O)(=O)Nc2cncc(-c3ccc4nccc(-c5ccncc5)c4c3)c2)c(F)c1] | 471.2 |
| 339 | 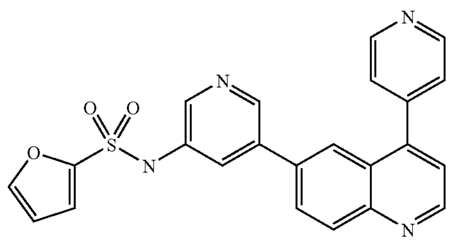 [SMILES: O=S(=O)(Nc1cncc(-c2ccc3nccc(-c4ccncc4)c3c2)c1)c1ccco1] | 429.1 |
| 340 | 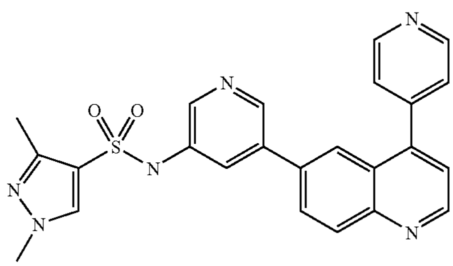 [SMILES: Cc1nn(C)cc1S(=O)(=O)Nc1cncc(-c2ccc3nccc(-c4ccncc4)c3c2)c1] | 457.1 |
| 341 | 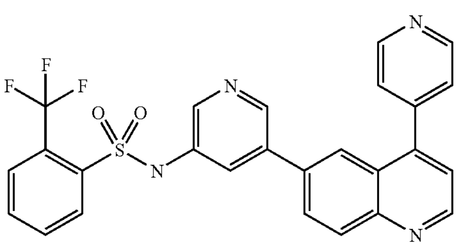 [SMILES: O=S(=O)(Nc1cncc(-c2ccc3nccc(-c4ccncc4)c3c2)c1)c1ccccc1C(F)(F)F] | 507 |
| 342 | 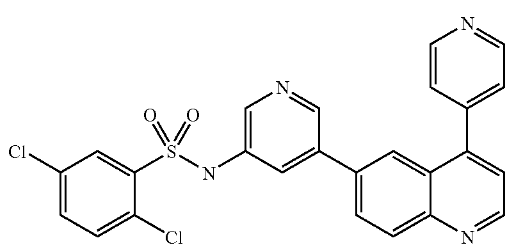 [SMILES: O=S(=O)(Nc1cncc(-c2ccc3nccc(-c4ccncc4)c3c2)c1)c1cc(Cl)ccc1Cl] | 507 |
| 343 | 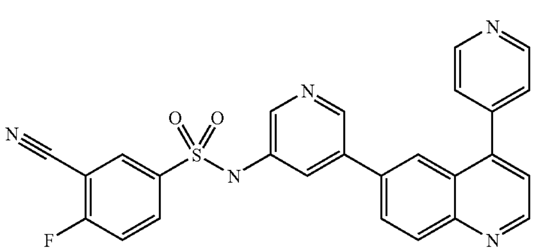 [SMILES: N#Cc1cc(S(=O)(=O)Nc2cncc(-c3ccc4nccc(-c5ccncc5)c4c3)c2)ccc1F] | 481.9 |

| Example | Structure | MS(ES) [M + H]+ |
|---|---|---|
| 344 | 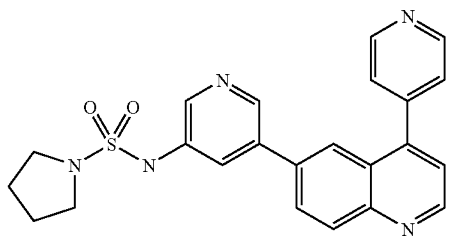 [SMILES: O=S(=O)(Nc1cncc(-c2ccc3nccc(-c4ccncc4)c3c2)c1)N1CCCC1] | 432.2 |

Some non-commercially available heteroaryl (R1) bromides were prepared and coupled to the corresponding boronic ester or boronic acid as noted above.

Scheme 12:

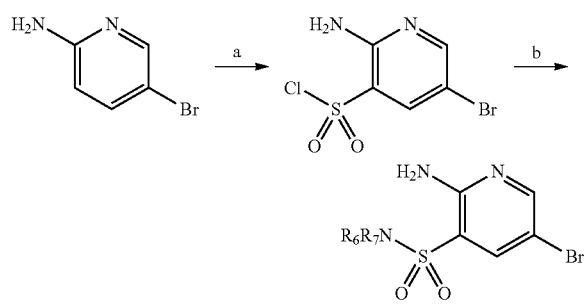

Conditions: a) Chlorosulfonic acid, 0° C.-reflux; b) Morpholine, pyridine, dioxane, 5° C.-rt-50° C.

Example 239

3-(4-morpholinylsulfonyl)-5-[4-(4-pyridinyl)-6-quinolinyl]-2-pyridinamine

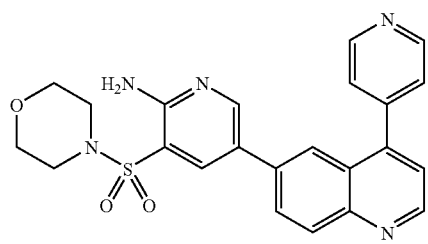 [SMILES: Nc1ncc(-c2ccc3nccc(-c4ccncc4)c3c2)cc1S(=O)(=O)N1CCOCC1]

a) 2-amino-5-bromo-3-pyridinesulfonyl chloride

To a cooled (0° C.) solution of chlorosulfonic acid (58 mL) under vigorous stirring was added 5-bromo-2-pyridinamine (15 g, 86.7 mmol) portionwise. The reaction mixture was then heated at reflux for 3 hrs. Upon cooling to room temperature, the reaction mixture was poured over ice (~100 g) with vigorous stirring. The resulting yellow precipitate was collected by suction filtration, washing with cold water and petroleum ether to provide the title compound as an orange-yellow solid (18.1 g, 77% yield). MS(ES)+ m/e 272.8 [M+H]+.

b) 5-bromo-3-(4-morpholinylsulfonyl)-2-pyridinamine

To a solution of 2-amino-5-bromo-3-pyridinesulfonyl chloride (0.50 g, 1.84 mmol) in anhydrous dioxane (2 mL) cooled to 5° C. was added (0.16 mL, 1.84 mmol) of morpholine followed by (0.174 mL, 2.15 mmol) of pyridine. The reaction mixture was stirred at room temperature for 2 hrs and then heated at 50° C. for 1 hour. After cooling to room temperature, a white precipitate formed which was collected by suction filtration, washing with water and petroleum ether to give the title compound as an off-white solid. (0.539 g, 91% yield). MS(ES)+ m/e 323.9 [M+H]+.

c) 3-(4-morpholinylsulfonyl)-5-[4-(4-pyridinyl)-6-quinolinyl]-2-pyridinamine

A mixture of 5-bromo-3-(4-morpholinylsulfonyl)-2-pyridinamine (0.296 g, 0.92 mmol), 4-(4-pyridinyl)-6-(4,4,5,5-tetramethyl-1,3,2-dioxaborolan-2-yl)quinoline (0.306 mg, 0.92 mmol), [1,1'-bis(diphenylphosphino)-ferrocene]dichloropalladium(II)-complex with dichloromethane(1:1) (37.6 mg, 0.046 mmol), 2 M aqueous $K_2CO_3$ (5 mL) and dioxane (5 mL) was heated at 100° C. for 18 h. After cooling to room temperature, the organic layer was separated and the aqueous portion extracted three times with EtOAc. The combined organic layers were dried ($Na_2SO_4$), filtered and concentrated in vacuo. The residue was purified twice by silica gel chromatography (eluent: i) 1-5% MeOH in $CH_2Cl_2$ and ii) 0-20% MeOH in $CH_2Cl_2$) to provide the title compound as a white solid (150 mg, 37% yield). MS(ES)+ m/e 448.0 [M+H]+.

Scheme 13:

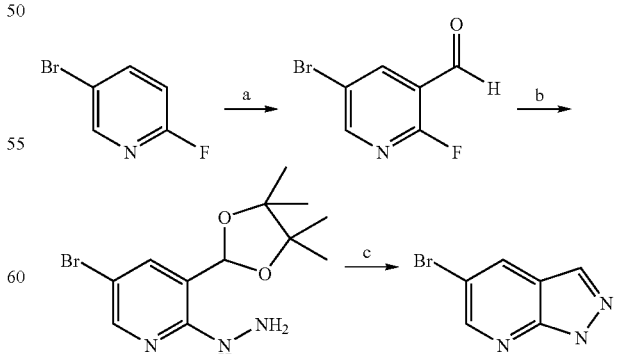

Conditions: a) i) LDA, THF, -78° C.; ii) N-formylpiperidine, -78° C.; b) i) pinacol, p-TsOH, benzene, reflux; ii) anhydrous hydrazine, DIPEA, EtOH, reflux; c) conc aq HCl (36.5%-38%), EtOH, $H_2O$, 60° C. to rt.

Example 240

5-bromo-1H-pyrazolo[3,4-b]pyridine

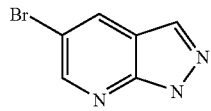

a) 5-bromo-2-fluoro-3-pyridinecarbaldehyde

Following the procedure described in WO2006015124 and trituration of the crude product in hexanes instead of crystallization from cyclohexane afforded the title compound as an off-white solid (68%). MS(ES)+ m/e 203.8, 205.7 [M+H]$^+$.

b) 5-bromo-3-(4,4,5,5-tetramethyl-1,3-dioxolan-2-yl)-2(1H)-pyridinone hydrazone Following the procedure described in WO2006015124 without the addition of hydrogen chloride provided the title compound as a yellow solid. MS(ES)+ m/e 317.9 [M+H]$^+$. This crude material was used directly in the next step.

c) 5-bromo-1H-pyrazolo[3,4-b]pyridine

Following the procedure described in WO2006015124 provided the title compound as a yellow solid (94%, 2 steps). MS(ES)+ m/e 197.7, 199.7 [M+H]$^+$.

Scheme 14:

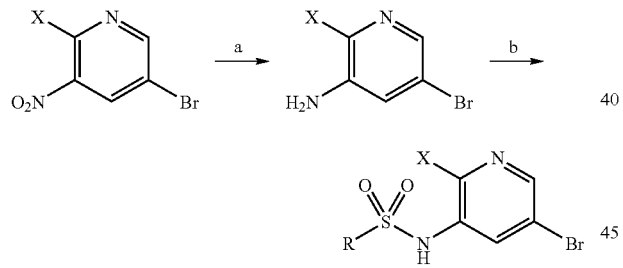

Conditions: a) tin(II)chloride, concentrated HCl, room temperature; b) R-sulfonyl chloride, pyridine, methylene chloride.

Example 241

N-(5-bromo-2-chloro-3-pyridinyl)benzenesulfonamide

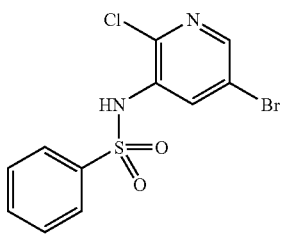 [SMILES: O=S(=O)(Nc1cc(Br)cnc1Cl)c1ccccc1]

a) 3-amino-5-bromo-2-chloropyridine

To a stirred suspension of 5-bromo-2-chloro-3-nitropyridine (20.0 g, 84.2 mMol) in conc. HCl (90 mL) was added SnCl$_2$.2H$_2$O (60.0 g, 266 mMol) portionwise over 2 h. (The reaction got very warm to the touch.) The reaction was stirred at RT for 18 h, poured onto ice, and basified with aq. 6 N NaOH (300 mL). The resultant slurry was filtered, washed with H$_2$O, and dried under vacuum to give the title compound (15.53 g, 89%) as an off-white solid: $^1$H NMR (400 MHz, DMSO-d$_6$) δ ppm 7.66 (d, J=2.3 Hz, 1H), 7.30 (d, J=2.3 Hz, 1H), 5.90 (br.s., 2 H); MS (ES) m/e 206.7 (M+H)$^+$.

b) N-(5-bromo-2-chloro-3-pyridinyl)benzenesulfonamide

To a stirred solution of 3-amino-5-bromo-2-chloropyridine (5.0 g, 24 mMol) in CH$_2$Cl$_2$ (50 mL) was added pyridine (3.0 mL, 37 mMol) followed by benzenesulfonyl chloride (4.5 mL, 35 mMol) drop wise over 5 minutes. The reaction was stirred at RT for 18 h and evaporated to dryness under vacuum. Purified by flash chromatography on silica gel (15% hexanes in CH$_2$Cl$_2$ then 0 to 5% EtOAc in 15% hexanes in CH$_2$Cl$_2$). During evaporation of the solvents the product crashed out. The resultant slurry was diluted with hexane, filtered and dried under vacuum to give the title compound (2.89 g, 34%) as a white solid. [An overlap fraction which contained 30% starting amine (2.60 g) was also obtained.]: $^1$H NMR (400 MHz, DMSO-d$_6$) δ ppm 10.61 (br. s., 1H), 8.41 (d, J=2.27 Hz, 1H), 7.91 (d, J=2.27 Hz, 1H), 7.73-7.77 (m, 2H), 7.67-7.72 (m, 1H), 7.56-7.64 (m, 2H); MS (ES) m/e 346.7 (M+H)$^+$.

Other non-commercially available heteroaryl (R1) bromides were prepared according to the following literature procedures and coupled to the corresponding boronic ester as noted above:

WO2005110410 was used to prepare intermediates A-C.

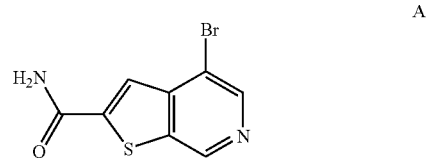
A

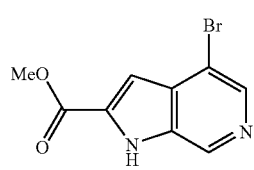
B

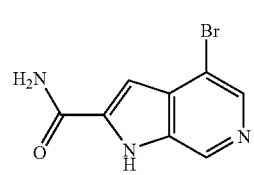
C

Scheme 15:

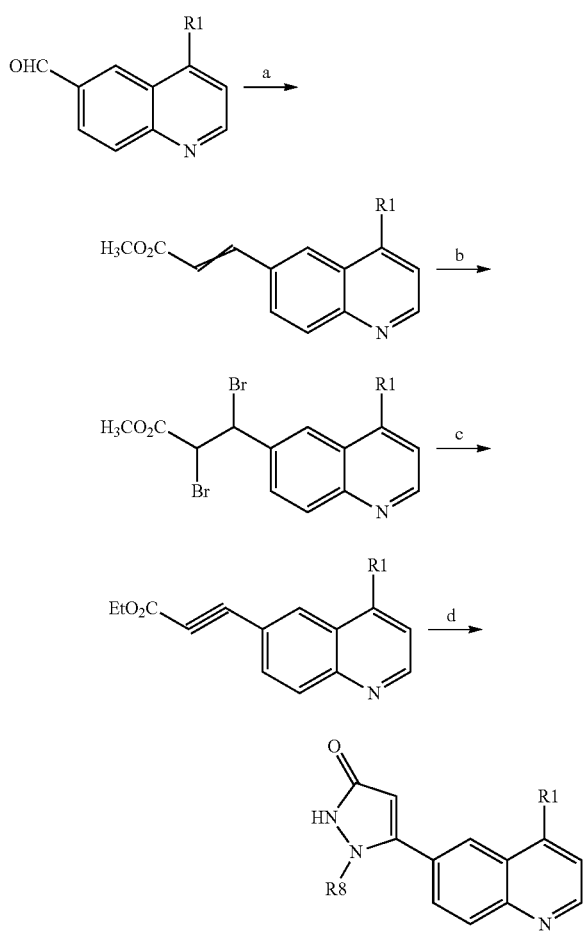

Conditions: a) methyl (triphenylphosphoranylidene)acetate, methanol, rt; b) bromine, methylene chloride, rt; c) i] potassium hydroxide, ethanol, 95° C.; ii] sulfuric acid, ethanol, 95° C.; d) potassium tert-butoxide, (R8)-hydrazine, tetrahydrofuran, rt-65° C.

Example 242

1-phenyl-5-[4-(4-pyridinyl)-6-quinolinyl]-1,2-dihydro-3H-pyrazol-3-one

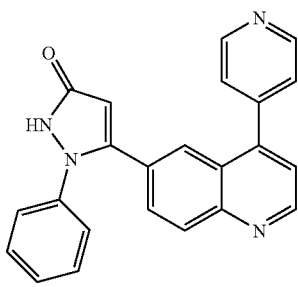 [SMILES: O=c1cc(-c2ccc3nccc(-c4ccncc4)c3c2)n(-c2ccccc2)[nH]1]

a) methyl 3-[4-(4-pyridinyl)-6-quinolinyl]-2-propenoate

A mixture of 4-(4-pyridinyl)-6-quinolinecarbaldehyde (2.29 g, 9.78 mmol), methyl (triphenylphosphoranylidene) acetate (3.30 g, 9.78 mmol) in MeOH (75 mL) was stirred at room temperature for 1 hour. The reaction was evaporated under reduced pressure and the resulting residue was purified by silica gel chromatography (1% MeOH in EtOAc) to give the title compound (2.71 g, 95%) as a white solid. MS(ES)+ m/e 291 [M+H]+.

b) methyl 2,3-dibromo-3-[4-(4-pyridinyl)-6-quinolinyl]propanoate

A solution of methyl 3-[4-(4-pyridinyl)-6-quinolinyl]-2-propenoate (2.71 g, 9.33 mmol) in dichloromethane (90 ml) was treated with neat bromine (4.80 ml, 9.33 mmol) then stirred at room temperature for 4 hours. Evaporation under reduced pressure gave the title compound (4.20 g, 100%) as a yellow solid. MS(ES)+ m/e 451 [M+H]+.

c) ethyl 3-[4-(4-pyridinyl)-6-quinolinyl]-2-propynoate

A slurry of methyl 2,3-dibromo-3-[4-(4-pyridinyl)-6-quinolinyl]propanoate (4.20 g, 9.33 mmol) in ethanol (120 ml) was treated with solid potassium hydroxide pellets in one portion then heated at 95° C. for 2 hours. The reaction was cooled to room temperature then evaporated under reduced pressure. The resulting residue was diluted with ethanol (90 ml) and concentrated $H_2SO_4$ (3 ml) then heated at 95° C. for 3.5 hours. Cooled to room temperature then concentrated under reduced pressure. The resulting wet residue was taken into a minimum of water then made neutral with the addition of saturated aqueous $NaHCO_3$ solution. This solution was extracted with EtOAc and the extracts were dried over anhydrous sodium sulfate, filtered and evaporated under reduced pressure. The resulting residue was purified by silica gel chromatography (EtOAc) to give the title compound (1.68 g, 60%) as a pale yellow solid. MS(ES)+ m/e 303 [M+H]+.

d) 1-phenyl-5-[4-(4-pyridinyl)-6-quinolinyl]-1,2-dihydro-3H-pyrazol-3-one

A solution of phenylhydrazine (0.093 ml, 0.95 mmol) in anhydrous THF (4.0 ml) was treated with a 1M solution of potassium tert-butoxide in THF (1.89 ml, 1.89 mmol). The resulting solution was added to a solution of ethyl 3-[4-(4-pyridinyl)-6-quinolinyl]-2-propynoate (0.268 g, 0.95 mmol) in THF (10 ml). The resulting brown solution was stirred at room temperature for 1 hour then at 65° C. for 1 hour. The resulting orange slurry was cooled to room temperature then concentrated under reduced pressure. The resulting residue was taken into saturated aqueous $NaHCO_3$ then extracted into methylene chloride and the extracts were dried over sodium sulfate then evaporated under reduced pressure. The resulting oil was purified by HPLC (acetonitrile/water, 5-80% gradient). The product was concentrated to a residue then recrystallized from ethanol to give the title compound (0.020 g, 6%) as a white solid. MS(ES)+ m/e 365 [M+H]+.

The following compounds were or can be prepared following the general procedures used to prepare the compound of Example 242:

| Example | Structure | MS(ES) [M + H]+ |
|---|---|---|
| 243 | 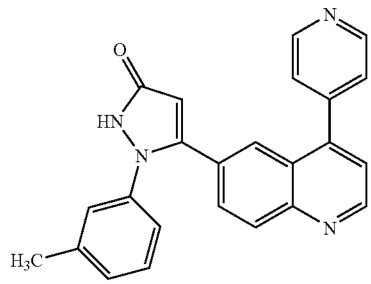 [SMILES: Cc1cccc(-n2[nH]c(=O)cc2-c2ccc3nccc(-c4ccncc4)c3c2)c1] | 379 |
| 244 | 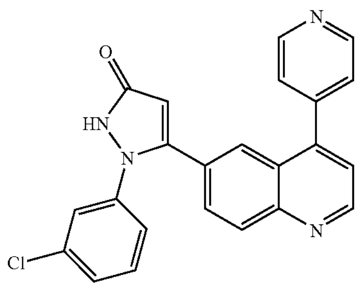 [SMILES: O=c1cc(-c2ccc3nccc(-c4ccncc4)c3c2)n(-c2cccc(Cl)c2)[nH]1] | 399 |
| 245 | 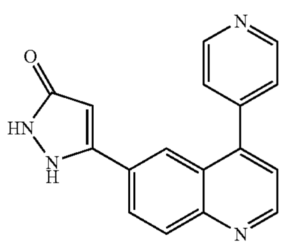 [SMILES: O=c1cc(-c2ccc3nccc(-c4ccncc4)c3c2)[nH][nH]1] | 289 |
| 246 | 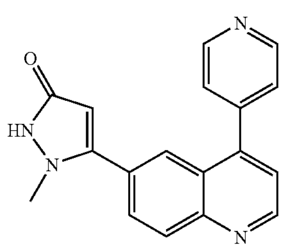 [SMILES: Cn1[nH]c(=O)cc1-c1ccc2nccc(-c3ccncc3)c2c1] | 303 |

Following the procedure used to prepare Example 242, 2-ethyl-6-[4-(4-pyridinyl)-6-quinolinyl]-4(1H)-pyrimidinone was or can be prepared by substituting ethylamidine hydrochloride for hydrazine. MS(ES)+ m/e 329 [M+H]+.

| Example | Structure | MS(ES) [M + H]+ |
|---|---|---|
| 247 | 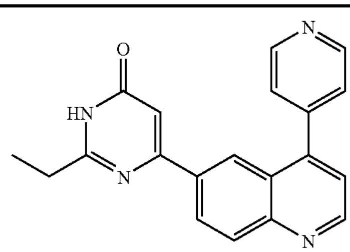 | 329 |

Following the procedure used to prepare Example 242, 2-phenyl-5-[4-(4-pyridinyl)-6-quinolinyl]-1,2-dihydro-3H-pyrazol-3-one was or can be prepared by substituting an alkynyl methyl ester for the alkynyl ethyl ester. MS(ES)+ m/e 365 [M+H]+.

| Example | Structure | MS(ES) [M + H]+ |
|---|---|---|
| 248 | 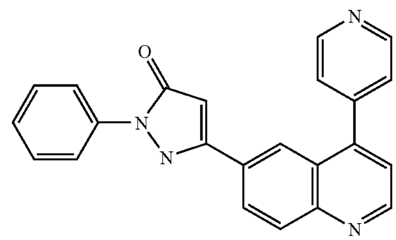 [SMILES: O=c1cc(-c2ccc3nccc(-c4ccncc4)c3c2)[nH]n1-c1ccccc1] | 365 |

Scheme 16:

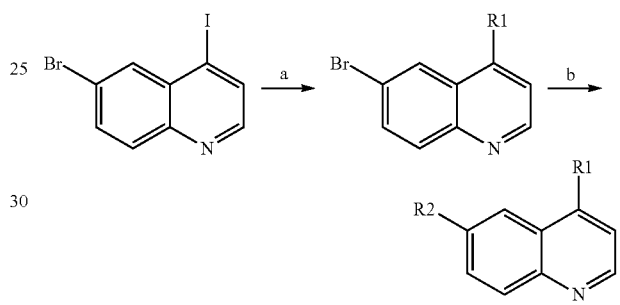

Conditions: a) aryl (R1) stannane, palladium catalyst, dioxane, heat; b) bis(pinacolato)diburon, potassium acetate, palladium catalyst, dioxane, heat; then heteroaryl (R2) bromide, palladium catalyst, saturated aqueous Na2CO3, dioxane, heat.

Example 345

2,4-difluoro-N-{2-(methyloxy)-5-[4-(4-pyridazinyl)-6-quinolinyl]-3-pyridinyl}benzenesulfonamide

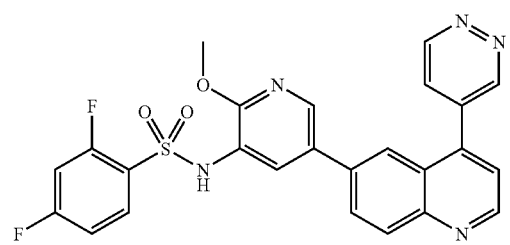 [SMILES: COc1ncc(-c2ccc3nccc(-c4ccnnc4)c3c2)cc1NS(=O)(=O)c1ccc(F)cc1F]

a) 6-bromo-4-(4-pyridazinyl)quinoline

Dissolved 6-bromo-4-iodoquinoline (17.43 g, 52.2 mmol), 4-(tributylstannanyl)pyridazine (19.27 g, 52.2 mmol), and PdCl2(dppf)—CH2Cl2 (2.132 g, 2.61 mmol) in 1,4-dioxane (200 mL) and heated to 105° C. After 3 h, added more palladium catalyst and heated for 6 h. Concentrated and dissolved in methylene chloride/methanol. Purified by column chromatography (combiflash) with 2% MeOH/EtOAc to 5% MeOH/EtOAc to give the crude title compound. Trituration with EtOAc furnished 6-bromo-4-(4-pyridazinyl)quinoline (5.8 g, 20.27 mmol, 38.8% yield). MS(ES)+ m/e 285.9, 287.9 [M+H]$^+$.

b) 2,4-difluoro-N-{2-(methyloxy)-5-[4-(4-pyridazinyl)-6-quinolinyl]-3-pyridinyl}benzenesulfonamide A slurry of 6-bromo-4-(4-pyridazinyl)quinoline (4.8 g, 16.78 mmol), bis(pinacolato)diboron (4.69 g, 18.45 mmol), PdCl2(dppf)-CH2Cl2 (530 mg, 0.649 mmol) and potassium acetate (3.29 g, 33.6 mmol) in anhydrous 1,4-dioxane (120 ml) was heated at 100° C. for 3 h. The complete disappearance of the starting bromide was observed by LCMS. The reaction was then treated with N-[5-bromo-2-(methyloxy)-3-pyridinyl]-2,4-difluorobenzenesulfonamide (6.68 g, 17.61 mmol) and another portion of PdCl2(dppf)-CH2Cl2 (550 mg, 0.673 mmol), then heated at 110° C. for 16 h. The reaction was allowed to cool to room temperature, filtered, and concentrated. Purification of the residue by chromatography (Analogix; 5% MeOH/5% CH2Cl2/90% EtOAC) gave 6.5 g (76%) desired product. MS(ES)+ m/e 505.9 [M+H]$^+$.

The following examples were or can be prepared following the general procedure used in Example 345

| Example | Structure | MS(ES) [M + H]$^+$ |
|---|---|---|
| 346 | 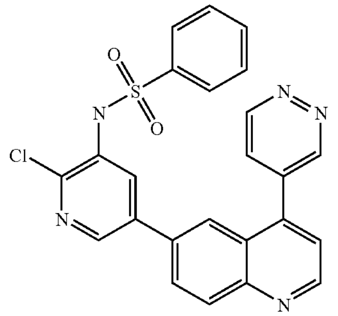 [SMILES: O=S(=O)(Nc1cc(-c2ccc3nccc(-c4ccnnc4)c3c2)cnc1Cl)c1ccccc1] | 474 |
| 347 | 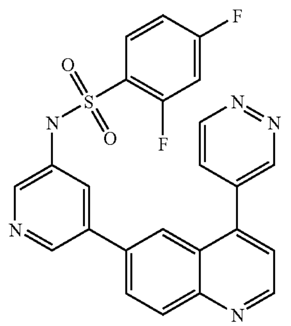 [SMILES: O=S(=O)(Nc1cncc(-c2ccc3nccc(-c4ccnnc4)c3c2)c1)c1ccc(F)cc1F] | 476 |
| 348 | 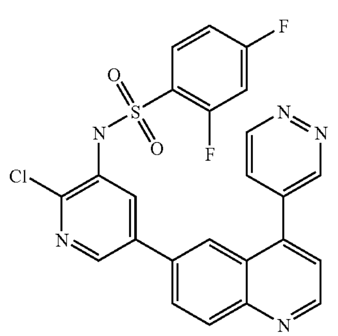 [SMILES: O=S(=O)(Nc1cc(-c2ccc3nccc(-c4ccnnc4)c3c2)cnc1Cl)c1ccc(F)cc1F] | 510 |

Intermediates

Intermediate 1

Scheme A:

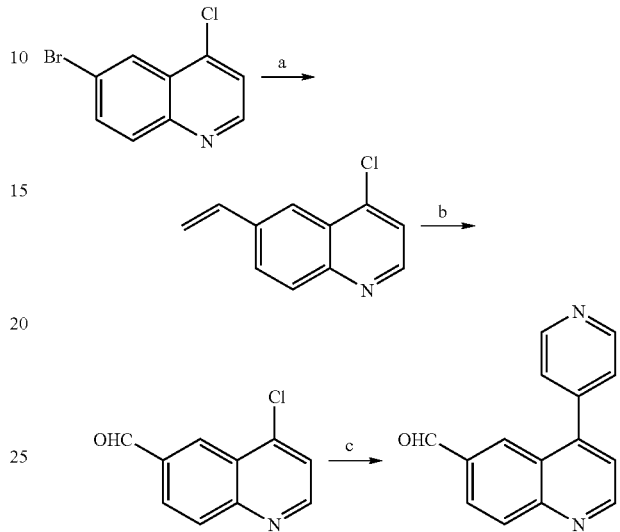

Conditions: a) Tributyl(vinyl)tin, Pd(PPh$_3$)$_4$, dioxane, reflux; b) OsO$_4$, NaIO$_4$, 2,6-lutidine, t-BuOH, dioxane, H$_2$O, rt; c) (4-pyridyl)boronic acid, Pd(PPh$_3$)$_4$, 2 M K$_2$CO$_3$, DMF, 100 C.

4-(4-pyridinyl)-6-quinolinecarbaldehyde

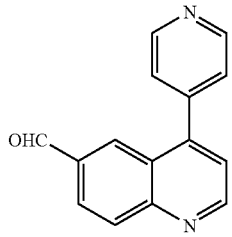 [SMILES: O=Cc1ccc2nccc(-c3ccncc3)c2c1]

a) 4-chloro-6-ethenylquinoline

A mixture of 6-bromo-4-chloroquinoline (6.52 g, 26.88 mmol; see *J. Med. Chem.*, 21, 268 (1978)), tributyl(vinyl)tin (8.95 g, 28.22 mmol), and tetrakistriphenylphosphine palladium(0) (0.62 g, 0.54 mmol) in 1,4-dioxane (150 mL) was refluxed for 2.0 h, cooled to room temperature, and concentrated in vacuo. The residue was purified by flash chromatography on silica gel (0-4% MeOH:CH$_2$Cl$_2$) to give the title compound (5.1 g) as a pale yellow solid. MS (ES)+ m/e 190 [M+H]$^+$. This material was used directly in the next step.

b) 4-chloro-6-quinolinecarbaldehyde

A mixture of 4-chloro-6-ethenylquinoline (5.1 g, 26.88 mmol), 2,6-lutidine (5.76 g, 53.75 mmol), sodium (meta) periodate (22.99 g, 107.51 mmol), and osmium tetroxide (5.48 g of a 2.5% solution in tert-butanol, 0.538 mmol) in 1,4-dioxane:H$_2$O (350 mL of 3:1 mixture) was stirred for 3.5 h at room temperature and concentrated in vacuo. The residue was purified by flash chromatography on silica gel (CH$_2$Cl$_2$) to give the title compound (4.26 g, 83% for 2 steps) as a pale yellow solid. MS (ES)+ m/e 192 [M+H]$^+$.

c) 4-(4-pyridinyl)-6-quinolinecarbaldehyde

A mixture of 4-chloro-6-quinolinecarbaldehyde (3.24 g, 16.92 mmol), 4-pyridylboronic acid (3.12 g, 25.38 mmol), tetrakistriphenylphosphine palladium(0) (0.978 g, 0.846 mmol), and 2M aqueous K$_2$CO$_3$ (7.02 g, 50.76 mmol, 25.4 mls of 2M solution) in DMF (100 mL) was heated at 100° C. for 3.0 h and cooled to room temperature. The mixture was filtered through Celite and the Celite was washed with EtOAc. The filtrate was transferred to a separatory funnel, washed with water and saturated NaCl, dried (Na$_2$SO$_4$), filtered and concentrated in vacuo. The residue was purified by flash chromatography on silica gel (5% MeOH:CH$_2$Cl$_2$) to give the title compound (2.03 g, 51%) as a tan solid. MS (ES)+ m/e 235 [M+H]$^+$.

Intermediate 2

Preparation of 2-amino-5-bromo-N,N-dimethyl-3-pyridinesulfonamide

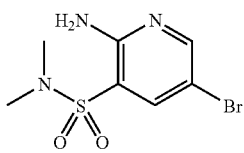

a) 2-amino-5-bromo-3-pyridinesulfonyl chloride

To a cooled (0° C.) solution of chlorosulfonic acid (58 mL) under vigorous stirring was added 5-bromo-2-pyridinamine (86.7 mmol) portionwise. The reaction mixture was then heated at reflux for 3 hrs. Upon cooling to room temperature, the reaction mixture was poured over ice (~100 g) with vigorous stirring. The resulting yellow precipitate was collected by suction filtration, washing with cold water and petroleum ether to provide the title compound as an orange-yellow solid (18.1 g, 77% yield). MS(ES)+ m/e 272.8 [M+H]$^+$.

* Other sulfonyl chlorides can be prepared using this procedure by varying the choice of substituted aryl or heteroaryl.

b) 2-amino-5-bromo-N,N-dimethyl-3-pyridinesulfonamide

To a cold (0° C.) suspension of 2-amino-5-bromo-3-pyridinesulfonyl chloride (92.1 mmol) in dry 1,4-dioxane (92 mL) was added pyridine (101.3 mmol) followed by a 2M solution of dimethylamine in THF (101.3 mmol). The reaction was allowed to warm to rt for 2 h, heated to 50 □C for 1 h, then cooled to rt. After standing for 2 h, the precipitate was collected by filtration and rinsed with a minimal amount of cold water. Drying the precipitate to constant weight under high vacuum provided 14.1 g (55%) of the title compound as a white solid. MS(ES)+ m/e 279.8, 282.0 [M+H]$^+$.

*Other sulfonamides were or can be prepared using this procedure by varying the choice of sulfonyl chloride and amine.

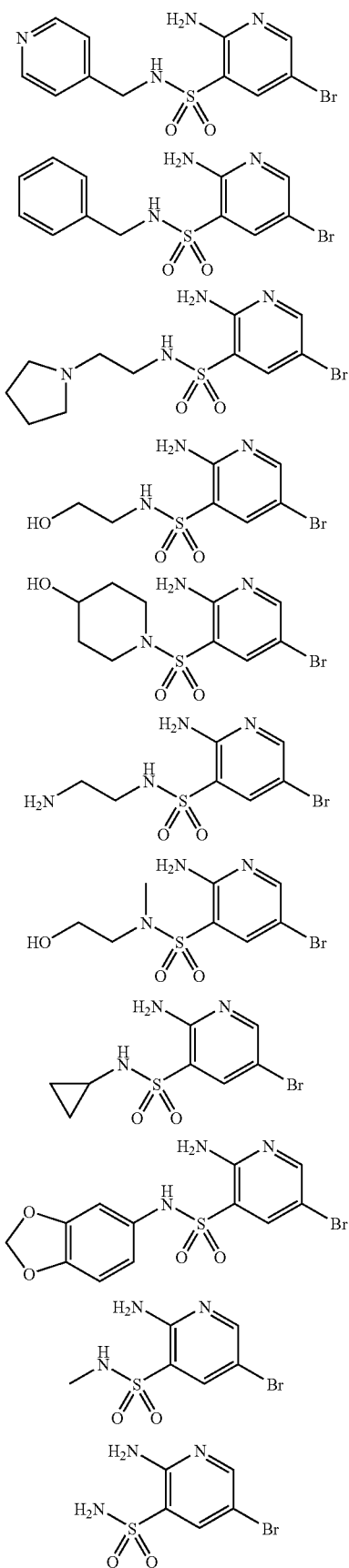

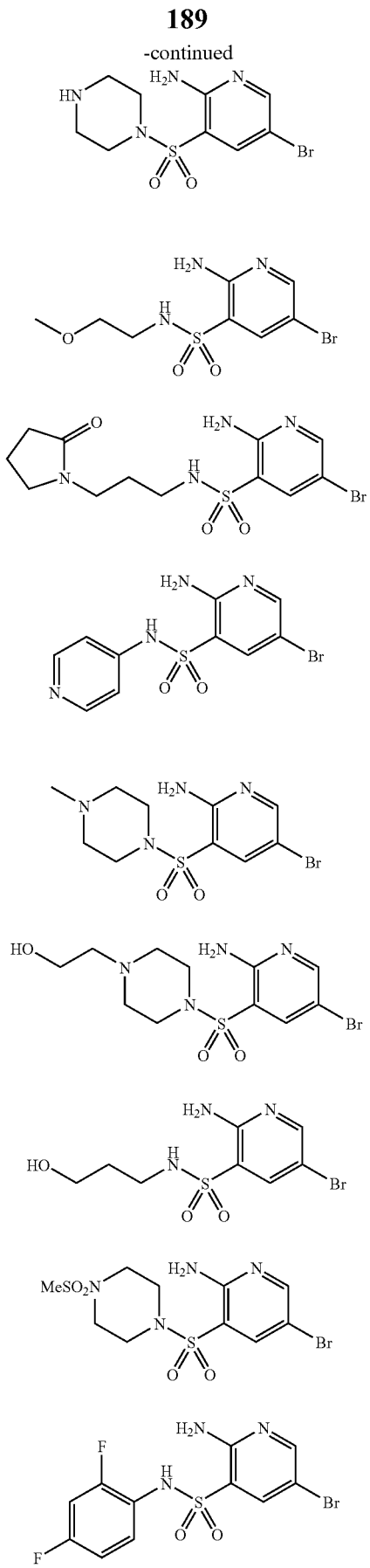

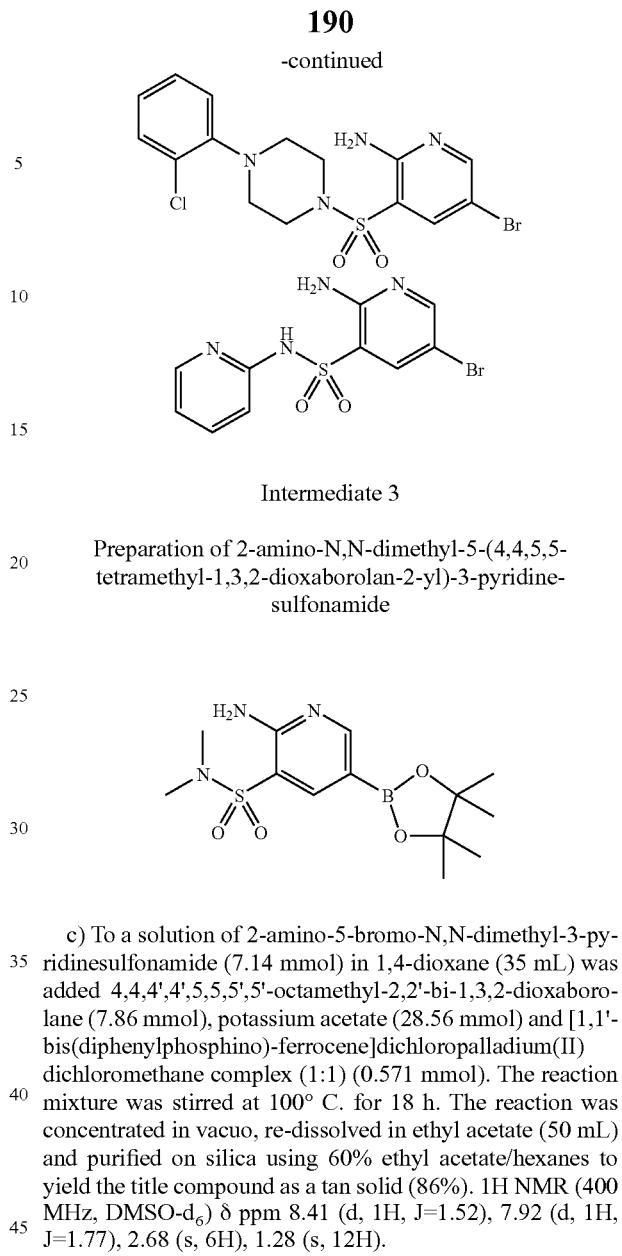

Intermediate 3

Preparation of 2-amino-N,N-dimethyl-5-(4,4,5,5-tetramethyl-1,3,2-dioxaborolan-2-yl)-3-pyridine-sulfonamide c) To a solution of 2-amino-5-bromo-N,N-dimethyl-3-pyridinesulfonamide (7.14 mmol) in 1,4-dioxane (35 mL) was added 4,4,4',4',5,5,5',5'-octamethyl-2,2'-bi-1,3,2-dioxaborolane (7.86 mmol), potassium acetate (28.56 mmol) and [1,1'-bis(diphenylphosphino)-ferrocene]dichloropalladium(II) dichloromethane complex (1:1) (0.571 mmol). The reaction mixture was stirred at 100° C. for 18 h. The reaction was concentrated in vacuo, re-dissolved in ethyl acetate (50 mL) and purified on silica using 60% ethyl acetate/hexanes to yield the title compound as a tan solid (86%). 1H NMR (400 MHz, DMSO-d$_6$) δ ppm 8.41 (d, 1H, J=1.52), 7.92 (d, 1H, J=1.77), 2.68 (s, 6H), 1.28 (s, 12H).

\* Other boronate or boronic acids can be prepared using this procedure by varying the choice of aryl or heteroaryl bromide.

Scheme 17:

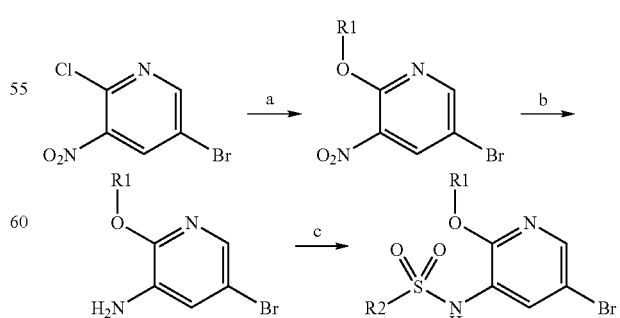

Conditions: a) NaO(R1), (R1)OH, 0° C. to room temperature; b) SnCl$_2$·2H$_2$O, ethyl acetate, reflux; c) (R2)SO$_2$Cl, pyridine, 0° C. to room temperature.

Intermediate 4

Preparation of N-[5-bromo-2-(methyloxy)-3-pyridinyl]-2,4-difluorobenzenesulfonamide

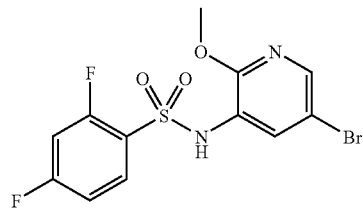 [SMILES: COc1ncc(Br)cc1NS(=O)(=O)c1ccc(F)cc1F]

a) 5-bromo-2-(methyloxy)-3-nitropyridine

To a cooled (0° C.) solution of 5-bromo-2-chloro-3-nitropyridine (50 g, 211 mmol) in methanol (200 mL) was added dropwise over 10 minutes 20% sodium methoxide (50 mL, 211 mmol) solution. The reaction, which quickly became heterogeneous, was allowed to warm to ambient temperature and stirred for 16 h. The reaction was filtered and the precipitate diluted with water (200 mL) and stirred for 1 h. The solids were filtered, washed with water (3×100 mL) and dried in a vac oven (40° C.) to give 5-bromo-2-(methyloxy)-3-nitropyridine (36 g, 154 mmol, 73.4% yield) as a pale yellow powder. The original filtrate was concentrated in vacuo and diluted with water (150 mL). Saturated ammonium chloride (25 mL) was added and the mixture stirred for 1 h. The solids were filtered, washed with water, and dried in a vac oven (40° C.) to give a second crop of 5-bromo-2-(methyloxy)-3-nitropyridine (9 g, 38.6 mmol, 18.34% yield). Total yield=90%. MS(ES)+ m/e 232.8, 234.7 [M+H]+.

b) 5-bromo-2-(methyloxy)-3-pyridinamine

To a solution of 5-bromo-2-(methyloxy)-3-nitropyridine (45 g, 193 mmol) in ethyl acetate (1 L) was added tin(II) chloride dihydrate (174 g, 772 mmol). The reaction mixture was heated at reflux for 4 h. LC/MS indicated some starting material remained, so added 20 mol % tin(II)chloride dihydrate and continued to heat at reflux. After 2 h, the reaction was allowed to cool to ambient temperature and concentrated in vacuo. The residue was treated with 2 N sodium hydroxide and the mixture stirred for 1 h. The mixture was then with methylene chloride (1 L), filtered through Celite, and washed with methylene chloride (500 mL). The layers were separated and the organics dried over magnesium sulfate and concentrated to give 5-bromo-2-(methyloxy)-3-pyridinamine (23 g, 113 mmol, 58.7% yield). The product was used crude in subsequent reactions. MS(ES)+ m/e 201.9, 203.9 [M+H]+.

c) N-[5-bromo-2-(methyloxy)-3-pyridinyl]-2,4-difluorobenzenesulfonamide

To a cooled (0° C.) solution of 5-bromo-2-(methyloxy)-3-pyridinamine (20.3 g, 100 mmol) in pyridine (200 mL) was added slowly 2,4-difluorobenzenesulfonyl chloride (21.3 g, 100 mmol) over 15 min (reaction became heterogeneous). The ice bath was removed and the reaction was stirred at ambient temperature for 16 h, at which time the reaction was diluted with water (500 mL) and the solids filtered off and washed with copious amounts of water. The precipitate was dried in a vacuum oven at 50° C. to give N-[5-bromo-2-(methyloxy)-3-pyridinyl]-2,4-difluorobenzenesulfonamide (12 g, 31.6 mmol, 31.7% yield) MS(ES)+ m/e 379.0, 380.9 [M+H]+.

*Other N-[5-bromo-2-(alkoxy)-3-pyridinyl]sulfonamides were or can be prepared using this procedure by varying the choice of sulfonyl chloride and alkoxide.

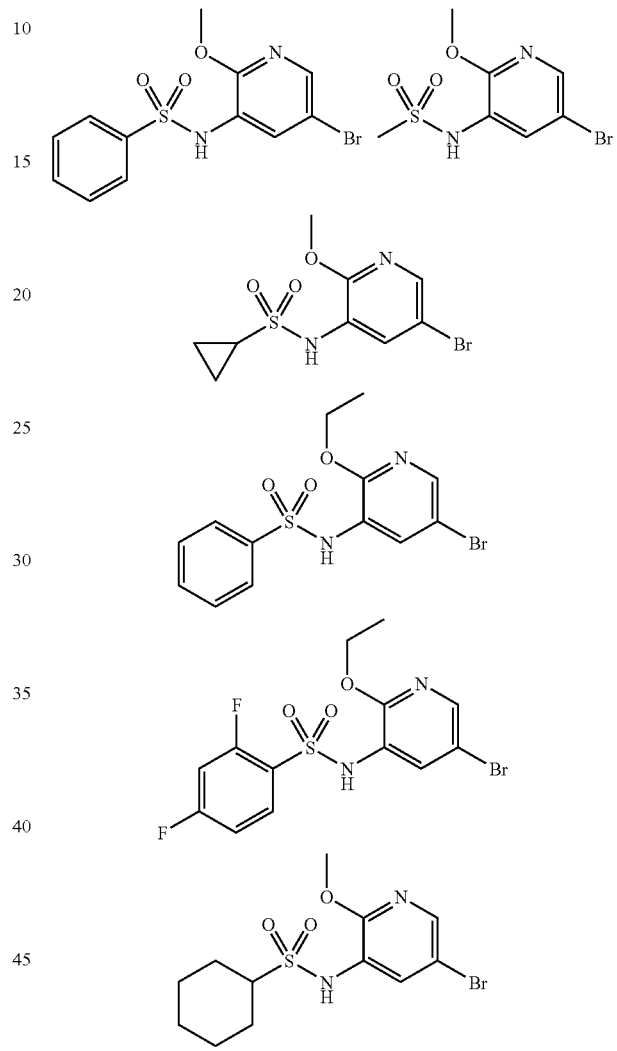

Exemplary Capsule Composition

An oral dosage form for administering the present invention is produced by filing a standard two piece hard gelatin capsule with the ingredients in the proportions shown in Table I, below.

TABLE I

| INGREDIENTS | AMOUNTS |
|---|---|
| compound of example 1 | 25 mg |
| Lactose | 55 mg |
| Talc | 16 mg |
| Magnesium Stearate | 4 mg |

Exemplary Injectable Parenteral Composition

An injectable form for administering the present invention is produced by stifling 1.5% by weight of compound of example 1 in 10% by volume propylene glycol in water.

Exemplary Tablet Composition

The sucrose, calcium sulfate dihydrate and an PI3K inhibitor as shown in Table II below, are mixed and granulated in the proportions shown with a 10% gelatin solution. The wet granules are screened, dried, mixed with the starch, talc and stearic acid;, screened and compressed into a tablet.

TABLE II

| INGREDIENTS | AMOUNTS |
| --- | --- |
| compound of example 1 | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of Formula (I):

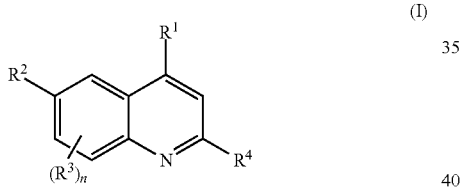

(I)

in which
$R^2$ is a pyridinyl or substituted pyridinyl group,
$R^1$ is selected from a group consisting of: heterocycloalkyl, substituted heterocycloalkyl, aryl, substituted aryl, heteroaryl and substituted heteroaryl;
each $R^3$ is independently selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, nitro, acyloxy, and aryloxy;
$R^4$ is selected from: hydrogen, halogen, acyl, amino, substituted amino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, nitro, acyloxy, and aryloxy; and
n is 1 or 2;
or a pharmaceutically acceptable salt thereof.

2. A compound of formula (I)(G):

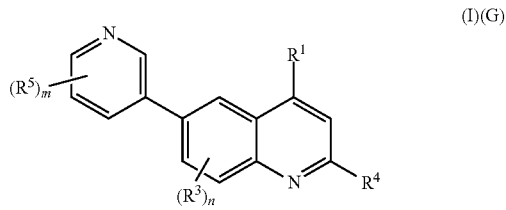

(I)(G)

in which
$R^1$ is selected from a group consisting of: heterocycloalkyl, substituted heterocycloalkyl, aryl, substituted aryl, heteroaryl and substituted heteroaryl;
each $R^3$ and $R^5$ is independently selected from: hydrogen, halogen, acyl, amino, substituted amino, arylamino, acylamino, heterocycloalkylamino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, substituted aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, acyloxy, and aryloxy;
or $R^5$ is $R^6$, wherein $R^6$ is —$SO_2NHR^{80}$ or —$NHSO_2R^{80}$, in which $R^{80}$ is selected from a group consisting of: $C_1$-$C_6$alkyl, $C_3$-$C_6$cycloalkyl, $C_3$-$C_6$heterocycloalkyl, substituted $C_3$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo and —$(CH_2)_pCOOH$, and heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, —$(CH_2)_pCOOH$, wherein p is 0, 1, or 2;
n is 1 or 2, m is 0, 1, 2, or 3; and
$R^4$ is selected from: hydrogen, halogen, acyl, amino, substituted amino, arylamino, acylamino, heterocycloalkylamino, $C_1$-$C_6$alkyl, substituted $C_1$-$C_6$alkyl, $C_3$-$C_7$cycloalkyl, substituted $C_3$-$C_7$cycloalkyl, $C_3$-$C_7$heterocycloalkyl, substituted $C_3$-$C_7$heterocycloalkyl, alkylcarboxy, aminoalkyl, aryl, heteroaryl, substituted heteroaryl, arylalkyl, substituted arylalkyl, arylcycloalkyl, substituted arylcycloalkyl, heteroarylalkyl, substituted heteroarylalkyl, cyano, hydroxyl, alkoxy, acyloxy, and aryloxy;
or a pharmaceutically acceptable salt thereof.

3. The compound according to claim 2, wherein the compound is a compound of formula (I)(K):

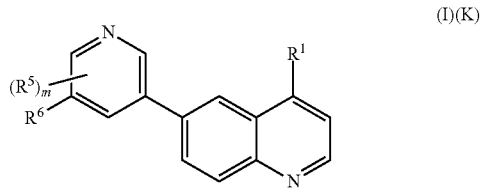

(I)(K)

in which
$R^1$ is selected from a group consisting of: heteroaryl, substituted heteroaryl, heterocycloalkyl, and substituted heterocycloalkyl;

$R^5$ is selected from: hydrogen, halogen, acyl, amino, substituted amino, $C_1$-$C_6$alkyl, substituted $C_1$-$C_6$alkyl, cyano, hydroxyl, and alkoxy;

m is 0 or 1; and $R^6$ is —$SO_2NHR^{80}$ or —$NHSO_2R^{80}$, in which $R^{80}$ is selected from a group consisting of: $C_1$-$C_6$alkyl, $C_3$-$C_6$cycloalkyl, $C_3$-$C_6$heterocycloalkyl, substituted $C_1$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo and —$(CH_2)_pCOOH$, and heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, and —$(CH_2)_pCOOH$, wherein p is 0, 1, or 2;

or a pharmaceutically acceptable salt thereof.

4. The compound according to claim 2, wherein the compound is a compound of formula (I)(M):

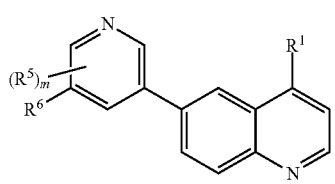

(I)(M)

in which $R^1$ is selected from a group consisting of: heteroaryl, substituted heteroaryl, heterocycloalkyl, and substituted heterocycloalkyl; $R^5$ is selected from: hydrogen, halogen, acyl, amino, substituted amino, $C_1$-$C_6$alkyl, substituted $C_1$-$C_6$alkyl, cyano, hydroxyl, and alkoxy;

m is 0 or 1; and $R^6$ is —$NHSO_2R^{80}$, wherein $R^{80}$ is selected from a group consisting of: $C_1$-$C_6$alkyl, $C_3$-$C_6$cycloalkyl, $C_3$-$C_6$heterocycloalkyl, substituted $C_3$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo and —$(CH_2)_pCOOH$, and heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo and —$(CH_2)_pCOOH$, wherein p is 0, 1, or 2;

or a pharmaceutically acceptable salt thereof.

5. The compound according to claim 2, wherein the compound is a compound of formula (I)(N):

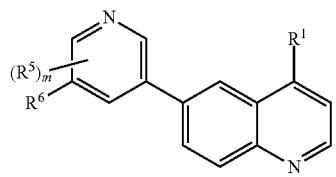

(I)(N)

in which $R^1$ is selected from a group consisting of: heteroaryl, substituted heteroaryl, heterocycloalkyl, and substituted heterocycloalkyl;

$R^5$ is selected from: hydrogen, halogen, acyl, amino, substituted amino, $C_1$-$C_6$alkyl, substituted $C_1$-$C_6$alkyl, cyano, hydroxyl, and alkoxy;

m is 0 or 1; and $R^6$ is —$SO_2NHR^{80}$, wherein $R^{80}$ is selected from a group consisting of: $C_1$-$C_6$alkyl, $C_3$-$C_6$cycloalkyl, $C_3$-$C_6$heterocycloalkyl, substituted $C_3$-$C_6$alkyl, substituted $C_3$-$C_6$cycloalkyl, substituted $C_3$-$C_6$heterocycloalkyl, aryl optionally fused with a five-membered ring or substituted with one to five groups selected from a group consisting of: $C_1$-$C_6$alkyl, $C_3$-$C_6$cycloalkyl, halogen, amino, substituted amino, trifluoromethyl, cyano, hydroxyl, alkoxy, oxo and —$(CH_2)_pCOOH$, and heteroaryl optionally fused with a five-membered ring or substituted with one to five groups selected from a group consisting of: $C_1$-$C_6$alkyl, $C_3$-$C_6$cycloalkyl, halogen, amino, trifluoromethyl, cyano, hydroxyl, alkoxy, oxo, and —$(CH_2)_pCOOH$, wherein p is 0, 1, or 2;

or a pharmaceutically acceptable salt thereof.

6. The compound of claim 4.

7. The compound of claim 5.

8. The compound of claim 1, which is selected from the group consisting of:

5-[4-(4-pyridinyl)-6-quinolinyl]-1H-indazol-3-amine;
4,4'-di-4-pyridinyl-6,6'-biquinoline;
3-(4-morpholinylsulfonyl)-5-[4-(4-pyridinyl)-6-quinolinyl]-2-pyridinamine;
2-amino-N-methyl-5-[4-(4-pyridinyl)-6-quinolinyl]-3-pyridinesulfonamide;
2-amino-N,N-dimethyl-5-[4-(4-pyridinyl)-6-quinolinyl]-3-pyridinesulfonamide;
2-amino-5-[4-(4-pyridinyl)-6-quinolinyl]-3-pyridinesulfonamide;
5-[4-(4-pyridinyl)-6-quinolinyl]-3-(1H-tetrazol-5-yl)-2-pyridinamine;
6-(3-methyl-3H-imidazo[4,5-b]pyridin-6-yl)-4-(4-pyridinyl)quinoline;
6-(1-methyl-1H-imidazo[4,5-b]pyridin-6-yl)-4-(4-pyridinyl)quinoline;
3-(1-piperidinylsulfonyl)-5-[4-(4-pyridinyl)-6-quinolinyl]-2-pyridinamine;
2-amino-N-ethyl-5-[4-(4-pyridinyl)-6-quinolinyl]-3-pyridinesulfonamide;
2-amino-N-[2-(dimethylamino)ethyl]-N-methyl-5-[4-(4-pyridinyl)-6-quinolinyl]-3-pyridinesulfonamide;
2-amino-N-(3-pyridinylmethyl)-5-[4-(4-pyridinyl)-6-quinolinyl]-3-pyridinesulfonamide;
2-amino-N-3-pyridinyl-5-[4-(4-pyridinyl)-6-quinolinyl]-3-pyridinesulfonamide;
2-amino-N-phenyl-5-[4-(4-pyridinyl)-6-quinolinyl]-3-pyridine sulfonamide;
2-amino-N-(3-hydroxypropyl)-5-[4-(4-pyridinyl)-6-quinolinyl]-3-pyridinesulfonamide;
3-(1-piperazinylsulfonyl)-5-[4-(4-pyridinyl)-6-quinolinyl]-2-pyridinamine;
3-{[4-(methylsulfonyl)-1-piperazinyl]sulfonyl}-5-[4-(4-pyridinyl)-6-quinolinyl]-2-pyridinamine;
2-amino-5-[4-(4-pyridinyl)-6-quinolinyl]-N-[3-(1-pyrrolidinyl)propyl]-3-pyridinesulfonamide;
3-[(3-amino-1H-pyrazol-1-yl)sulfonyl]-5-[4-(4-pyridinyl)-6-quinolinyl]-2-pyridinamine;
3-[(4-methyl-1-piperazinyl)sulfonyl]-5-[4-(4-pyridinyl)-6-quinolinyl]-2-pyridinamine;
2-[4-({2-amino-5-[4-(4-pyridinyl)-6-quinolinyl]-3-pyridinyl}sulfonyl)-1-piperazinyl]ethanol;

2-amino-N-(2,4-difluorophenyl)-5-[4-(4-pyridinyl)-6-quinolinyl]-3-pyridinesulfonamide;
2-amino-N-[3-(2-oxo-1-pyrrolidinyl)propyl]-5-[4-(4-pyridinyl)-6-quinolinyl]-3-pyridinesulfonamide;
2-amino-N-2-pyridinyl-5-[4-(4-pyridinyl)-6-quinolinyl]-3-pyridinesulfonamide;
2-amino-N-4-pyridinyl-5-[4-(4-pyridinyl)-6-quinolinyl]-3-pyridinesulfonamide;
3-{[4-(2-chlorophenyl)-1-piperazinyl]sulfonyl}-5-[4-(4-pyridinyl)-6-quinolinyl]-2-pyridinamine;
2-amino-N-[2-(methyloxy)ethyl]-5-[4-(4-pyridinyl)-6-quinolinyl]-3-pyridinesulfonamide;
N,N-dimethyl-3-(4-morpholinylsulfonyl)-5-[4-(4-pyridinyl)-6-quinolinyl]-2-pyridinamine;
N-methyl-3-(4-morpholinylsulfonyl)-5-[4-(4-pyridinyl)-6-quinolinyl]-2-pyridinamine;
N-ethyl-3-(4-morpholinylsulfonyl)-5-[4-(4-pyridinyl)-6-quinolinyl]-2-pyridinamine;
N,N-diethyl-3-(4-morpholinylsulfonyl)-5-[4-(4-pyridinyl)-6-quinolinyl]-2-pyridinamine;
6-[6-(ethyloxy)-5-(4-morpholinylsulfonyl)-3-pyridinyl]-4-(4-pyridinyl)quinoline;
6-[6-(methyloxy)-5-(4-morpholinylsulfonyl)-3-pyridinyl]-4-(4-pyridinyl)quinoline;
3-methyl-7-[4-(4-pyridinyl)-6-quinolinyl]-2H-1,2,4-benzothiadiazine 1,1-dioxide;
6-[4-(4-pyridinyl)-6-quinolinyl]-3,4-dihydro-1(2H)-isoquinolinone;
4-(4-pyridinyl)-6-(1H-pyrrolo[2,3-b]pyridin-5-yl)quinoline;
6-(1H-indazol-5-yl)-4-(4-pyridinyl)quinoline;
6-[4-(4-pyridinyl)-6-quinolinyl]-1H-indazol-3-amine;
4-(4-pyridinyl)-6-(1H-pyrrolo[2,3-b]pyridin-4-yl)quinoline;
6-(1H-indazol-6-yl)-4-(4-pyridinyl)quinoline;
{3-oxo-6-[4-(4-pyridinyl)-6-quinolinyl]-2,3-dihydro-1H-isoindol-1-yl}acetic acid;
4-(4-pyridinyl)-6-(7H-pyrrolo[2,3-d]pyrimidin-4-yl)quinoline;
6-[4-(4-pyridinyl)-6-quinolinyl]-1,3-dihydro-2H-imidazo[4,5-b]pyridin-2-one;
6-[4-(4-pyridinyl)-6-quinolinyl][1,3]oxazolo[4,5-b]pyridin-2(3H)-one;
6-(1H-pyrazolo[3,4-b]pyridin-5-yl)-4-(4-pyridinyl)quinoline;
4-(4-pyridinyl)-6-(1H-[1,2,3]triazolo[4,5-b]pyridin-6-yl)quinoline;
6-(1H-imidazo[4,5-b]pyridin-6-yl)-4-(4-pyridinyl)quinoline;
6-(1-oxido-3-pyridinyl)-4-(4-pyridinyl)quinoline;
4-(4-pyridinyl)-6-(1H-pyrrolo[3,2-b]pyridin-6-yl)quinoline;
5-[4-(4-pyridinyl)-6-quinolinyl]-1H-pyrazolo[3,4-b]pyridin-3-amine;
6-(3-methyl-1H-pyrazolo[3,4-b]pyrazin-5-yl)-4-(4-pyridinyl)quinoline;
2-methyl-N-{5-[4-(4-pyridinyl)-6-quinolinyl]-1H-pyrazolo[3,4-b]pyridin-3-yl}propanamide;
N-{5-[4-(4-pyridinyl)-6-quinolinyl]-1H-pyrazolo[3,4-b]pyridin-3-yl}acetamide;
N-{5-[4-(4-pyridinyl)-6-quinolinyl]-1H-pyrazolo[3,4-b]pyridin-3-yl}methanesulfonamide;
2-(methyloxy)-N-{5-[4-(4-pyridinyl)-6-quinolinyl]-1H-pyrazolo[3,4-b]pyridin-3-yl}acetamide;
6-pyrazolo[1,5-a]pyrimidin-6-yl-4-(4-pyridinyl)quinoline;
5-[4-(4-pyridinyl)-6-quinolinyl]-1,2-dihydro-3H-pyrazolo[3,4-b]pyridin-3-one;
6-(1-methyl-1H-pyrrolo[3,2-b]pyridin-6-yl)-4-(4-pyridinyl)quinoline;
6-(3-methyl-1H-pyrazolo[3,4-b]pyridin-5-yl)-4-(4-pyridinyl)quinoline;
3-[6-(1H-pyrazolo[3,4-b]pyridin-5-yl)-4-quinolinyl]benzenesulfonamide;
7-[4-(4-pyridinyl)-6-quinolinyl]-2H-pyrido[3,2-b][1,4]oxazin-3(4H)-one;
4-[4-(4-pyridinyl)-6-quinolinyl]-1,3-dihydro-2H-pyrrolo[2,3-b]pyridin-2-one;
2-amino-N,N-dimethyl-5-[2-methyl-4-(4-pyridinyl)-6-quinolinyl]-3-pyridinesulfonamide;
2-amino-5-[8-fluoro-4-(4-pyridinyl)-6-quinolinyl]-N,N-dimethyl-3-pyridinesulfonamide;
2-amino-N,N-dimethyl-5-[8-methyl-4-(4-pyridinyl)-6-quinolinyl]-3-pyridinesulfonamide;
2-amino-5-[7-fluoro-4-(4-pyridinyl)-6-quinolinyl]-N,N-dimethyl-3-pyridinesulfonamide;
5-[5-fluoro-4-(4-pyridinyl)-6-quinolinyl]-3-pyridinesulfonamide;
5-[7-methyl-4-(4-pyridinyl)-6-quinolinyl]-3-pyridinesulfonamide;
5-[5-methyl-4-(4-pyridinyl)-6-quinolinyl]-3-pyridinesulfonamide;
4-(4-pyridinyl)-6-[5-(trifluoromethyl)-3-pyridinyl]quinoline;
(4,6-di-4-pyridinylquinoline;
6-(3-pyridinyl)-4-(4-pyridinyl)quinoline;
6-(2-pyridinyl)-4-(4-pyridinyl)quinoline;
6-(2,1,3-benzoxadiazol-5-yl)-4-(4-pyridinyl)quinoline;
6-(2,1,3-benzothiadiazol-5-yl)-4-(4-pyridinyl)quinoline;
5-[4-(4-pyridinyl)-6-quinolinyl]-1,2-dihydro-3H-pyrazol-3-one;
2-ethyl-6-[4-(4-pyridinyl)-6-quinolinyl]-4(1H)-pyrimidinone;
7-[4-(4-pyridinyl)-6-quinolinyl]-2-quinoxalinol;
2-(4-morpholinyl)-7-[4-(4-pyridinyl)-6-quinolinyl]quinoxaline;
4-(4-morpholinyl)-6-[4-(4-pyridinyl)-6-quinolinyl]quinazoline;
1-phenyl-5-[4-(4-pyridinyl)-6-quinolinyl]-1,2-dihydro-3H-pyrazol-3-one;
1-(3-methylphenyl)-5-[4-(4-pyridinyl)-6-quinolinyl]-1,2-dihydro-3H-pyrazol-3-one;
1-(3-chlorophenyl)-5-[4-(4-pyridinyl)-6-quinolinyl]-1,2-dihydro-3H-pyrazol-3-one;
1-methyl-5-[4-(4-pyridinyl)-6-quinolinyl]-1,2-dihydro-3H-pyrazol-3-one;
N-(2,4-difluorophenyl)-5-[4-(4-pyridinyl)-6-quinolinyl]-3-pyridinesulfonamide;
6-(1H-indol-5-yl)-4-(4-pyridinyl)quinoline;
6-(1H-indol-6-yl)-4-(4-pyridinyl)quinoline;
5-[4-(4-pyridinyl)-6-quinolinyl]-1,3-dihydro-2H-indol-2-one;
6-[4-(4-pyridinyl)-6-quinolinyl]-1,3-dihydro-2H-indol-2-one;
7-[4-(4-pyridinyl)-6-quinolinyl]-4(1H)-quinazolinone;
6-[4-(4-pyridinyl)-6-quinolinyl]-4(1H)-quinazolinone;
6-[4-(4-pyridinyl)-6-quinolinyl]-1,2-benzisothiazol-3(2H)one 1,1-dioxide;
6-[4-(4-pyridinyl)-6-quinolinyl]-1,8-naphthyridin-2(1H)one;
6-(1,3-benzoxazol-5-yl)-4-(4-pyridinyl)quinoline;
7-[4-(4-pyridinyl)-6-quinolinyl]-1,4-dihydropyrido[2,3-b]pyrazine-2,3-dione;

3-amino-5-[4-(4-pyridinyl)-6-quinolinyl]-2-pyridinecarboxamide;
5-[4-(4-pyridinyl)-6-quinolinyl]-3-pyridinamine;
4-[4-(4-pyridinyl)-6-quinolinyl]thieno[2,3-c]pyridine-2-carboxamide;
methyl 4-[4-(4-pyridinyl)-6-quinolinyl]-1H-pyrrolo[2,3-c]pyridine-2-carboxylate;
4-[4-(4-pyridinyl)-6-quinolinyl]-1H-pyrrolo[2,3-c]pyridine-2-carboxamide;
6-(1H-benzimidazol-2-yl)-4-(4-pyridinyl)quinoline;
6-(1H-imidazo[4,5-c]pyridin-2-yl)-4-(4-pyridinyl)quinoline;
6-(1H-imidazo[4,5-b]pyridin-2-yl)-4-(4-pyridinyl)quinoline;
6-(1H-purin-8-yl)-4-(4-pyridinyl)quinoline;
6-imidazo[1,2-a]pyridin-6-yl-4-(4-pyridinyl)quinoline;
6-imidazo[1,2-a]pyrimidin-6-yl-4-(4-pyridinyl)quinoline;
1-{6-[4-(4-pyridinyl)-6-quinolinyl]imidazo[1,2-a]pyridin-3-yl}-1-propanone;
6-(4-pyridazinyl)-4-(4-pyridinyl)quinoline;
1-{6-[4-(4-pyridinyl)-6-quinolinyl]imidazo[1,2-a]pyridin-3-yl}-1-propanol;
4-(1-piperidinyl)-6-(1H-pyrazolo[3,4-b]pyridin-5-yl)quinoline;
4-(4-morpholinyl)-6-(1H-pyrazolo[3,4-b]pyridin-5-yl)quinoline;
4-(4-methyl-1-piperazinyl)-6-(1H-pyrazolo[3,4-b]pyridin-5-yl)quinoline;
4-(4-pyridazinyl)-6-(1H-pyrrolo[2,3-b]pyridin-5-yl)quinoline;
6-(1H-imidazo[4,5-b]pyridin-6-yl)-4-(1-piperidinyl)quinoline;
6-(1H-imidazo[4,5-b]pyridin-6-yl)-4-(4-morpholinyl)quinoline;
2-amino-5-{4-[3-(aminosulfonyl)phenyl]-6-quinolinyl}-N,N-dimethyl-3-pyridinesulfonamide;
2-amino-N,N-dimethyl-5-[4-(2-methyl-4-pyridinyl)-6-quinolinyl]-3-pyridinesulfonamide;
2-amino-5-(4-{3-[(dimethylamino)sulfonyl]phenyl}-6-quinolinyl)-N,N-dimethyl-3-pyridinesulfonamide;
2-amino-N,N-dimethyl-5-[4-(4-pyridazinyl)-6-quinolinyl]-3-pyridinesulfonamide;
2-amino-N,N-dimethyl-5-[4-(1H-pyrazol-4-yl)-6-quinolinyl]-3-pyridinesulfonamide;
2-amino-N,N-dimethyl-5-(4-phenyl-6-quinolinyl)-3-pyridinesulfonamide;
2-amino-N,N-dimethyl-5-[4-(1H-pyrazol-3-yl)-6-quinolinyl]-3-pyridinesulfonamide;
2-amino-5-[4-(2,6-dimethyl-4-pyridinyl)-6-quinolinyl]-N,N-dimethyl-3-pyridinesulfonamide;
2-amino-5-(4-{3-[(aminosulfonyl)methyl]phenyl}-6-quinolinyl)-N,N-dimethyl-3-pyridinesulfonamide;
2-amino-5-[4-(3-cyanophenyl)-6-quinolinyl]-N,N-dimethyl-3-pyridine sulfonamide;
2-amino-5-{4-[5-(aminosulfonyl)-3-pyridinyl]-6-quinolinyl}-N,N-dimethyl-3-pyridinesulfonamide;
5,5'-(4,6-quinolinediyl)di(3-pyridinesulfonamide);
2-amino-N,N-dimethyl-5-[4-(3-{[(1-methylethyl)amino]sulfonyl}phenyl)-6-quinolinyl]-3-pyridinesulfonamide;
2-amino-N,N-dimethyl-5-(4-{3-[(methylamino)sulfonyl]phenyl}-6-quinolinyl)-3-pyridinesulfonamide;
2-amino-N,N-dimethyl-5-{4-[6-(4-methyl-1-piperazinyl)-3-pyridinyl]-6-quinolinyl}-3-pyridinesulfonamide;
5-[4-(3-cyanophenyl)-6-quinolinyl]-3-pyridinesulfonamide;
5-[4-(2-methyl-4-pyridinyl)-6-quinolinyl]-3-pyridinesulfonamide;
5-[4-(4-pyridazinyl)-6-quinolinyl]-3-pyridinesulfonamide;
5-{4-[6-(4-methyl-1-piperazinyl)-3-pyridinyl]-6-quinolinyl}-3-pyridinesulfonamide;
5-[4-(2,6-dimethyl-4-pyridinyl)-6-quinolinyl]-3-pyridinesulfonamide;
5-[4-(1H-pyrazol-4-yl)-6-quinolinyl]-3-pyridinesulfonamide;
5-(4-{3-[(dimethylamino)sulfonyl]phenyl}-6-quinolinyl)-3-pyridinesulfonamide;
5-[4-(1-methyl-1H-pyrazol-4-yl)-6-quinolinyl]-3-pyridinesulfonamide;
5-{4-[2-(4-morpholinylmethyl)phenyl]-6-quinolinyl}-3-pyridinesulfonamide;
5-{4-[2-(4-morpholinylcarbonyl)phenyl]-6-quinolinyl}-3-pyridinesulfonamide;
5-{4-[2-(4-morpholinyl)phenyl]-6-quinolinyl}-3-pyridinesulfonamide;
4'-(4-pyridinyl)-3,4-dihydro-6,6'-biquinolin-2(1H)-one;
6-[4-(4-pyridinyl)-6-quinolinyl]-3,4-dihydro-1,8-naphthyridin-2(1H)-one;
2-amino-5-[4-(4-pyridinyl)-6-quinolinyl]-3-pyridinecarbaldehyde;
{2-amino-5-[4-(4-pyridinyl)-6-quinolinyl]-3-pyridinyl} methyl acetate;
5-[4-(4-pyridinyl)-6-quinolinyl]-2,3-pyridinediamine;
2-amino-5-[4-(4-pyridinyl)-6-quinolinyl]-3-pyridinecarboxamide;
6-[4-(4-pyridinyl)-6-quinolinyl]pyrido[2,3-c/]pyrimidin-4(1H)-one;
5-{5-[4-(4-pyridinyl)-6-quinolinyl]-3-pyridinyl}-1,2-dihydro-3H-pyrazol-3-one;
7-[4-(4-pyridinyl)-6-quinolinyl]pyrido[3,2-c/]pyrimidin-4(1H)-one;
6-[5-(1H-pyrazol-5-yl)-3-pyridinyl]-4-(4-pyridinyl)quinoline;
N-(2,4-difluorophenyl)-5-[4-(4-pyridinyl)-6-quinolinyl]-3-pyridinecarboxamide;
6-[2-(methyloxy)-4-pyridinyl]-4-(4-pyridinyl)quinoline;
6-[6-(methyloxy)-3-pyridinyl]-4-(4-pyridinyl)quinoline;
4-[4-(4-pyridinyl)-6-quinolinyl]-2-pyridinol;
6-[2-(methyloxy)-5-pyrimidinyl]-4-(4-pyridinyl)quinoline;
{6-[4-(4-pyridinyl)-6-quinolinyl]-2-pyridinyl}methanol;
6-(2-chloro-4-pyridinyl)-4-(4-pyridinyl)quinoline;
4-(4-pyridinyl)-6-(5-pyrimidinyl)quinoline;
5-[4-(4-pyridinyl)-6-quinolinyl]-2(1H)-pyrimidinone;
6-[2,6-bis(methyloxy)-3-pyridinyl]-4-(4-pyridinyl)quinoline;
6-[6-(4-methyl-1-piperazinyl)-3-pyridinyl]-4-(4-pyridinyl)quinoline;
6-[6-(4-morpholinyl)-3-pyridinyl]-4-(4-pyridinyl)quinoline;
6-(6-chloro-3-pyridinyl)-4-(4-pyridinyl)quinoline;
6-[6-(ethyloxy)-3-pyridinyl]-4-(4-pyridinyl)quinoline;
N,N-dimethyl-3-({5-[4-(4-pyridinyl)-6-quinolinyl]-2-pyridinyl}oxy)-1-propanamine;
5-[4-(4-pyridinyl)-6-quinolinyl]-3-pyridinecarboxamide;
methyl 5-[4-(4-pyridinyl)-6-quinolinyl]-2-pyridinecarboxylate;
N-{5-[4-(4-pyridinyl)-6-quinolinyl]-2-pyridinyl}acetamide;
N-[2-(4-morpholinyl)ethyl]-5-[4-(4-pyridinyl)-6-quinolinyl]-2-pyridinamine;

6-[6-(1-piperazinyl)-3-pyridinyl]-4-(4-pyridinyl)quinoline;
6-[5-(methyloxy)-3-pyridinyl]-4-(4-pyridinyl)quinoline;
6-(6-fluoro-3-pyridinyl)-4-(4-pyridinyl)quinoline;
5-[4-(4-pyridinyl)-6-quinolinyl]-2-pyrimidinecarbonitrile;
6-[2-(methyloxy)-3-pyridinyl]-4-(4-pyridinyl)quinoline;
5-[4-(4-pyridinyl)-6-quinolinyl]-3-pyridinecarbonitrile;
6-[6-(methyloxy)-2-pyridinyl]-4-(4-pyridinyl)quinoline;
6-[5-(4-morpholinylcarbonyl)-3-pyridinyl]-4-(4-pyridinyl)quinoline;
6-[4-(methyloxy)-3-pyridinyl]-4-(4-pyridinyl)quinoline;
6-[5-(4-morpholinylsulfonyl)-3-pyridinyl]-4-(4-pyridinyl)quinoline;
7-[4-(4-pyridinyl)-6-quinolinyl]-2,3-dihydro[1,4]dioxino[2,3-b]pyridine;
5-[4-(4-pyridinyl)-6-quinolinyl]-3-pyridinesulfonamide;
2-(methyloxy)-5-[4-(4-pyridinyl)-6-quinolinyl]-3-pyridinecarbaldehyde;
6-(4-chloro-3-pyridinyl)-4-(4-pyridinyl)quinoline;
4-(4-pyridinyl)-6-[5-(1H-tetrazol-5-yl)-3-pyridinyl]quinoline;
N-methyl-5-[4-(4-pyridinyl)-6-quinolinyl]-3-pyridinesulfonamide;
N,N-dimethyl-5-[4-(4-pyridinyl)-6-quinolinyl]-3-pyridinesulfonamide;
6-[4-methyl-6-(methyloxy)-3-pyridinyl]-4-(4-pyridinyl)quinoline;
N-{4-methyl-5-[4-(4-pyridinyl)-6-quinolinyl]-2-pyridinyl}acetamide;
6-(4-methyl-3-pyridinyl)-4-(4-pyridinyl)quinoline;
6-[5-(1,3,4-oxadiazol-2-yl)-3-pyridinyl]-4-(4-pyridinyl)quinoline;
2-amino-N-(4-pyridinylmethyl)-5-[4-(4-pyridinyl)-6-quinolinyl]-3-pyridinesulfonamide;
2-amino-N,N-diethyl-5-[4-(4-pyridinyl)-6-quinolinyl]-3-pyridinesulfonamide;
5-[4-(4-pyridinyl)-6-quinolinyl]-3-(1-pyrrolidinylsulfonyl)-2-pyridinamine;
2-amino-5-[4-(4-pyridinyl)-6-quinolinyl]-N-[2-(1-pyrrolidinyl)ethyl]-3-pyridinesulfonamide;
6-[6-(methylsulfonyl)-3-pyridinyl]-4-(4-pyridinyl)quinoline;
2-amino-N-(phenylmethyl)-5-[4-(4-pyridinyl)-6-quinolinyl]-3-pyridinesulfonamide;
2-amino-N-(2-hydroxyethyl)-5-[4-(4-pyridinyl)-6-quinolinyl]-3-pyridinesulfonamide;
1-({2-amino-5-[4-(4-pyridinyl)-6-quinolinyl]-3-pyridinyl}sulfonyl)-4-piperidinol;
2-amino-N-(2-aminoethyl)-5-[4-(4-pyridinyl)-6-quinolinyl]-3-pyridinesulfonamide;
6-[5-(methylthio)-3-pyridinyl]-4-(4-pyridinyl)quinoline;
6-[5-(methylsulfonyl)-3-pyridinyl]-4-(4-pyridinyl)quinoline;
2-amino-N-(2-hydroxyethyl)-N-methyl-5-[4-(4-pyridinyl)-6-quinolinyl]-3-pyridinesulfonamide;
2-amino-N-cyclopropyl-5-[4-(4-pyridinyl)-6-quinolinyl]-3-pyridinesulfonamide;
2-amino-N-1,3-benzodioxol-5-yl-5-[4-(4-pyridinyl)-6-quinolinyl]-3-pyridinesulfonamide;
N,N-diethyl-5-[4-(4-pyridinyl)-6-quinolinyl]-3-pyridinesulfonamide;
1-({5-[4-(4-pyridinyl)-6-quinolinyl]-3-pyridinyl}sulfonyl)-4-piperidinol;
4-(4-pyridinyl)-6-[5-(1-pyrrolidinylsulfonyl)-3-pyridinyl]quinoline;
N-(2-hydroxyethyl)-5-[4-(4-pyridinyl)-6-quinolinyl]-3-pyridinesulfonamide;
N-(phenylmethyl)-5-[4-(4-pyridinyl)-6-quinolinyl]-3-pyridinesulfonamide;
5-[4-(4-pyridinyl)-6-quinolinyl]-N-[2-(1-pyrrolidinyl)ethyl]-3-pyridinesulfonamide;
6-{5-[(4-methyl-1-piperazinyl)sulfonyl]-3-pyridinyl}-4-(4-pyridinyl)quinoline;
N-cyclopropyl-5-[4-(4-pyridinyl)-6-quinolinyl]-3-pyridinesulfonamide;
N-[2-(methyloxy)ethyl]-5-[4-(4-pyridinyl)-6-quinolinyl]-3-pyridinesulfonamide;
N-phenyl-5-[4-(4-pyridinyl)-6-quinolinyl]-3-pyridinesulfonamide;
N-1,3-benzodioxol-5-yl-5-[4-(4-pyridinyl)-6-quinolinyl]-3-pyridinesulfonamide;
N-(3-pyridinylmethyl)-5-[4-(4-pyridinyl)-6-quinolinyl]-3-pyridinesulfonamide;
N-2-pyridinyl-5-[4-(4-pyridinyl)-6-quinolinyl]-3-pyridinesulfonamide;
N-(2-chlorophenyl)-5-[4-(4-pyridinyl)-6-quinolinyl]-3-pyridinesulfonamide;
N-cyclohexyl-5-[4-(4-pyridinyl)-6-quinolinyl]-3-pyridinesulfonamide;
N-[2-(methyloxy)phenyl]-5-[4-(4-pyridinyl)-6-quinolinyl]-3-pyridinesulfonamide;
2,4-difluoro-N-{5-[4-(4-pyridinyl)-6-quinolinyl]-3-pyridinyl}benzenesulfonamide;
1-methyl-N-{5-[4-(4-pyridinyl)-6-quinolinyl]-3-pyridinyl}-1H-imidazole-4-sulfonamide;
N-{5-[4-(4-pyridinyl)-6-quinolinyl]-3-pyridinyl}-2-thiophenesulfonamide;
3,5-dimethyl-N-{5-[4-(4-pyridinyl)-6-quinolinyl]-3-pyridinyl}-4-isoxazolesulfonamide;
3,4-bis(methyloxy)-N-{5-[4-(4-pyridinyl)-6-quinolinyl]-3-pyridinyl}benzenesulfonamide;
2-methyl-N-{5-[4-(4-pyridinyl)-6-quinolinyl]-3-pyridinyl}-1-propanesulfonamide;
N-{5-[4-(4-pyridinyl)-6-quinolinyl]-3-pyridinyl}cyclopropanesulfonamide;
N-{5-[4-(4-pyridinyl)-6-quinolinyl]-3-pyridinyl}benzenesulfonamide;
N-{2-chloro-5-[4-(4-pyridinyl)-6-quinolinyl]-3-pyridinyl}benzenesulfonamide; and
1-phenyl-N-{5-[4-(4-pyridinyl)-6-quinolinyl]-3-pyridinyl}methanesulfonamide;
5-{4-[3-chloro-4-(methyloxy)phenyl]-6-quinolinyl}-3-pyridinesulfonamide;
5-{4-[3-(aminosulfonyl)phenyl]-6-quinolinyl}-3-pyridinesulfonamide;
5-{4-[1-(2-hydroxyethyl)-1H-pyrazol-4-yl]-6-quinolinyl}-3-pyridinesulfonamide;
N-(cyclopropylsulfonyl)-N-{5-[4-(4-pyridinyl)-6-quinolinyl]-3-pyridinyl}cyclopropanesulfonamide;
N-(2,4-difluorophenyl)-5-[4-(1-ethyl-1H-pyrazol-4-yl)-6-quinolinyl]-3-pyridinesulfonamide;
N-methyl-N-phenyl-5-[4-(4-pyridinyl)-6-quinolinyl]-3-pyridinesulfonamide;
N-(2,4-difluorophenyl)-5-(4-{1-[2-(dimethylamino)ethyl]-1H-pyrazol-4-yl}-6-quinolinyl)-3-pyridinesulfonamide;
N-(2,4-difluorophenyl)-5-[4-(4-isoquinolinyl)-6-quinolinyl]-3-pyridinesulfonamide;
N-phenyl-N'-{5-[4-(4-pyridinyl)-6-quinolinyl]-3-pyridinyl}urea;
2-{4-[6-(5-{[(2,4-difluorophenyl)amino]sulfonyl}-3-pyridinyl)-4-quinolinyl]-1H-pyrazol-1-yl}acetamide;

N-{5-[4-(1-methyl-1H-pyrazol-4-yl)-6-quinolinyl]-3-pyridinyl}benzenesulfonamide;
4'-(4-pyridinyl)-3,6'-biquinoline;
N-{5-[4-(4-pyridinyl)-6-quinolinyl]-3-pyridinyl}benzamide;
5-[4-(1-benzofuran-2-yl)-6-quinolinyl]-N-(2,4-difluorophenyl)-3-pyridinesulfonamide;
6-[5-(1H-pyrazol-4-yl)-3-pyridinyl]-4-(4-pyridinyl)quinoline;
N,N-diethyl-2-oxo-5-[4-(4-pyridinyl)-6-quinolinyl]-1,2-dihydro-3-pyridinesulfonamide;
4-cyano-N-{5-[4-(4-pyridinyl)-6-quinolinyl]-3-pyridinyl}benzenesulfonamide;
N-methyl-N-phenyl-5-[4-(4-pyridinyl)-6-quinolinyl]-3-pyridinecarboxamide;
N-{5-[4-(4-pyridinyl)-6-quinolinyl]-3-pyridinyl}ethanesulfonamide;
4-(methyloxy)-N-{5-[4-(4-pyridinyl)-6-quinolinyl]-3-pyridinyl}benzenesulfonamide;
4-(1-methylethyl)-N-{5-[4-(4-pyridinyl)-6-quinolinyl]-3-pyridinyl}benzenesulfonamide;
2-chloro-5-[4-(4-pyridinyl)-6-quinolinyl]-3-pyridinamine;
4-fluoro-N-{5-[4-(4-pyridinyl)-6-quinolinyl]-3-pyridinyl} benzenesulfonamide;
N-{5-[4-(1-ethyl-1H-pyrazol-4-yl)-6-quinolinyl]-3-pyridinyl}-2,4-difluorobenzenesulfonamide;
1-methyl-N-{5-[4-(4-pyridinyl)-6-quinolinyl]-3-pyridinyl}-1H-pyrazole-3-sulfonamide;
2-fluoro-N-{5-[4-(4-pyridinyl)-6-quinolinyl]-3-pyridinyl}benzenesulfonamide;
N-{2-amino-5-[4-(4-pyridinyl)-6-quinolinyl]-3-pyridinyl}benzenesulfonamide;
N-{2-methyl-5-[4-(4-pyridinyl)-6-quinolinyl]-3-pyridinyl}benzenesulfonamide;
N-{2-cyano-5-[4-(4-pyridinyl)-6-quinolinyl]-3-pyridinyl}benzenesulfonamide;
2-methyl-5-nitro-N-{5-[4-(4-pyridinyl)-6-quinolinyl]-3-pyridinyl}benzenesulfonamide;
N-{5-[4-(4-pyridinyl)-6-quinolinyl]-3-pyridinyl}-1H-pyrazole-4-sulfonamide;
N-{2-chloro-5-[4-(4-pyridinyl)-6-quinolinyl]-3-pyridinyl}-2-methyl-5-nitrobenzenesulfonamide;
N-{2-chloro-5-[4-(1-ethyl-1H-pyrazol-4-yl)-6-quinolinyl]-3-pyridinyl}benzenesulfonamide;
N-{2-chloro-5-[4-(4-pyridazinyl)-6-quinolinyl]-3-pyridinyl}benzenesulfonamide;
3-nitro-N-{5-[4-(4-pyridinyl)-6-quinolinyl]-2-pyridinyl}benzenesulfonamide;
2-methyl-N-{5-[4-(4-pyridinyl)-6-quinolinyl]-3-pyridinyl}benzenesulfonamide;
2,4-difluoro-N-{5-[4-(4-pyridazinyl)-6-quinolinyl]-3-pyridinyl}benzenesulfonamide;
5-fluoro-2-methyl-N-{5-[4-(4-pyridinyl)-6-quinolinyl]-3-pyridinyl}benzenesulfonamide;
N-{2-chloro-5-[4-(4-pyridinyl)-6-quinolinyl]-3-pyridinyl}-3-nitrobenzenesulfonamide;
N-{2-chloro-5-[4-(2-methyl-4-pyridinyl)-6-quinolinyl]-3-pyridinyl}benzenesulfonamide;
N-{2-chloro-5-[4-(4-pyridinyl)-6-quinolinyl]-3-pyridinyl}-2-methylbenzenesulfonamide;
N-{2-chloro-5-[4-(4-pyridinyl)-6-quinolinyl]-3-pyridinyl}-3-fluorobenzenesulfonamide;
N-{2-chloro-5-[4-(4-pyridinyl)-6-quinolinyl]-3-pyridinyl}-2-thiophenesulfonamide;
N-{2-chloro-5-[4-(4-pyridinyl)-6-quinolinyl]-3-pyridinyl}cyclopropanesulfonamide;
N-{2-chloro-5-[4-(4-pyridinyl)-6-quinolinyl]-3-pyridinyl}-5-fluoro-2-methylbenzenesulfonamide;
N-(2-chloro-5-{4-[3-(methylsulfonyl)phenyl]-6-quinolinyl}-3-pyridinyl)benzenesulfonamide;
N-{2-chloro-5-[4-(4-pyridinyl)-6-quinolinyl]-3-pyridinyl}-3,5-dimethyl-4-isoxazolesulfonamide;
2,4-difluoro-N-(5-{4-[3-(methylsulfonyl)phenyl]-6-quinolinyl}-3-pyridinyl)benzenesulfonamide;
2,4-difluoro-N-{5-[4-(2-methyl-4-pyridinyl)-6-quinolinyl]-3-pyridinyl}benzenesulfonamide;
3-(methyloxy)-N-{5-[4-(4-pyridinyl)-6-quinolinyl]-3-pyridinyl}benzenesulfonamide;
N-[4-(cyanomethyl)phenyl]-5-[4-(4-pyridinyl)-6-quinolinyl]-3-pyridinesulfonamide;
3-fluoro-N-{5-[4-(4-pyridinyl)-6-quinolinyl]-3-pyridinyl}benzenesulfonamide;
N-{2-(methyloxy)-5-[4-(4-pyridinyl)-6-quinolinyl]-3-pyridinyl}benzenesulfonamide;
N-{2-chloro-5-[4-(4-pyridinyl)-6-quinolinyl]-3-pyridinyl}-2,4-difluorobenzenesulfonamide;
3-nitro-N-{5-[4-(4-pyridinyl)-6-quinolinyl]-3-pyridinyl}benzenesulfonamide;
N-{5-[4-(1-benzofuran-2-yl)-6-quinolinyl]-3-pyridinyl}-2,4-difluorobenzenesulfonamide;
3-cyano-N-{5-[4-(4-pyridinyl)-6-quinolinyl]-3-pyridinyl}benzenesulfonamide;
N-{5-[4-(4-pyridinyl)-6-quinolinyl]-3-pyridinyl}-4-(trifluoromethyl)benzenesulfonamide;
N-{2-hydroxy-5-[4-(4-pyridinyl)-6-quinolinyl]-3-pyridinyl}benzenesulfonamide;
N-{5-[4-(4-pyridinyl)-6-quinolinyl]-3-pyridinyl}-3-(trifluoromethyl)benzenesulfonamide;
N-{5-[4-(1-benzofuran-2-yl)-6-quinolinyl]-2-chloro-3-pyridinyl}benzenesulfonamide;
N-methyl-N-{5-[4-(4-pyridinyl)-6-quinolinyl]-3-pyridinyl}benzamide;
2,4-difluoro-N-{5-[4-(4-fluorophenyl)-6-quinolinyl]-3-pyridinyl}benzenesulfonamide;
N-methyl-N-{5-[4-(4-pyridinyl)-6-quinolinyl]-3-pyridinyl}benzenesulfonamide;
2,4-difluoro-N-[5-(4-pyrazolo[1,5-a]pyridin-3-yl-6-quinolinyl)-3-pyridinyl]benzenesulfonamide;
2,4-difluoro-N-{5-[4-(2-fluorophenyl)-6-quinolinyl]-3-pyridinyl}benzenesulfonamide;
2,4-difluoro-N-(5-{4-[4-(trifluoromethyl)phenyl]-6-quinolinyl}-3-pyridinyl)benzenesulfonamide;
2,4-difluoro-N-(5-{4-[4-(methylsulfonyl)phenyl]-6-quinolinyl}-3-pyridinyl)benzenesulfonamide;
methyl 1-methyl-5-[({5-[4-(4-pyridinyl)-6-quinolinyl]-3-pyridinyl}amino)sulfonyl]-1H-pyrrole-2-carboxylate;
5-bromo-2-(methyloxy)-N-{5-[4-(4-pyridinyl)-6-quinolinyl]-3-pyridinyl}benzenesulfonamide;
545-isoxazolyl)-N-{5-[4-(4-pyridinyl)-6-quinolinyl]-3-pyridinyl}-2-thiophenesulfonamide;
2,4-difluoro-N-{5-[4-(3-fluorophenyl)-6-quinolinyl]-3-pyridinyl}benzenesulfonamide;
2,4-difluoro-N-(5-{4-[3-(trifluoromethyl)phenyl]-6-quinolinyl}-3-pyridinyl)benzenesulfonamide;
2-chloro-4-cyano-N-{5-[4-(4-pyridinyl)-6-quinolinyl]-3-pyridinyl}benzenesulfonamide;
N-[5-(4-{3-[(dimethylamino)sulfonyl]phenyl}-6-quinolinyl)-3-pyridinyl]-2,4-difluorobenzenesulfonamide;
N-[5-(4-{4-[(dimethylamino)sulfonyl]phenyl}-6-quinolinyl)-3-pyridinyl]-2,4-difluorobenzenesulfonamide;
1,2-dimethyl-N-{5-[4-(4-pyridinyl)-6-quinolinyl]-3-pyridinyl}-1H-imidazole-4-sulfonamide;

3-[6-(5-{[(2,4-difluorophenyl)sulfonyl]amino}-3-pyridinyl)-4-quinolinyl]benzamide;
4-[6-(5-{[(2,4-difluorophenyl)sulfonyl]amino}-3-pyridinyl)-4-quinolinyl]benzamide;
N-{4-[6-(5-{[(2,4-difluorophenyl)sulfonyl]amino}-3-pyridinyl)-4-quinolinyl]phenyl}acetamide;
N-{3-[6-(5-{[(2,4-difluorophenyl)sulfonyl]amino}-3-pyridinyl)-4-quinolinyl]phenyl}acetamide;
6-(4-morpholinyl)-N-{5-[4-(4-pyridinyl)-6-quinolinyl]-3-pyridinyl}-3-pyridinesulfonamide;
2-fluoro-4-methyl-N-{5-[4-(4-pyridinyl)-6-quinolinyl]-3-pyridinyl}benzenesulfonamide;
N-{5-[4-(4-pyridinyl)-6-quinolinyl]-3-pyridinyl}-2-furansulfonamide;
1,3-dimethyl-N-{5-[4-(4-pyridinyl)-6-quinolinyl]-3-pyridinyl}-1H-pyrazole-4-sulfonamide;
N-{5-[4-(4-pyridinyl)-6-quinolinyl]-3-pyridinyl}-2-(trifluoromethyl)benzenesulfonamide;
N-{2-(methyloxy)-5-[4-(4-pyridinyl)-6-quinolinyl]-3-pyridinyl}cyclohexanesulfonamide;
N-[5-(4-cyclopentyl-6-quinolinyl)-2-(methyloxy)-3-pyridinyl]benzenesulfonamide;
2,5-dichloro-N-{5-[4-(4-pyridinyl)-6-quinolinyl]-3-pyridinyl}benzenesulfonamide;
3-cyano-4-fluoro-N-{5-[4-(4-pyridinyl)-6-quinolinyl]-3-pyridinyl}benzenesulfonamide;
N-{5-[4-(4-pyridinyl)-6-quinolinyl]-3-pyridinyl}-1-pyrrolidinesulfonamide;
(5Z)-5-({5-[4-(4-pyridinyl)-6-quinolinyl]-3-pyridinyl}methylidene)-1,3-thiazolidine-2,4-dione;
N-{2-(methyloxy)-5-[4-(4-pyridinyl)-6-quinolinyl]-3-pyridinyl}cyclopropanesulfonamide;
N-{5-[4-(4-pyridinyl)-6-quinolinyl]-3-pyridinyl}-2-pyridinesulfonamide;
1,2-dimethyl-N-{5-[4-(4-pyridinyl)-6-quinolinyl]-3-pyridinyl}-1H-imidazole-5-sulfonamide;
1-methyl-N-{5-[4-(4-pyridinyl)-6-quinolinyl]-3-pyridinyl}-3-(trifluoromethyl)-1H-pyrazole-4-sulfonamide;
1,3,5-trimethyl-N-{5-[4-(4-pyridinyl)-6-quinolinyl]-3-pyridinyl}-1H-pyrazole-4-sulfonamide;
N-{2-(ethyloxy)-5-[4-(4-pyridinyl)-6-quinolinyl]-3-pyridinyl}benzenesulfonamide;
N,N-dimethyl-N-{5-[4-(4-pyridinyl)-6-quinolinyl]-3-pyridinyl}sulfamide;
N-{2-chloro-1-oxido-5-[4-(4-pyridinyl)-6-quinolinyl]-3-pyridinyl}benzenesulfonamide;
N-{6-methyl-5-[4-(4-pyridinyl)-6-quinolinyl]-3-pyridinyl}benzenesulfonamide;
N-{2-(methyloxy)-5-[4-(4-pyridinyl)-6-quinolinyl]-3-pyridinyl}methanesulfonamide; and
N-{2-chloro-5-[4-(4-pyridinyl)-6-quinolinyl]-3-pyridinyl}methanesulfonamide;
or a pharmaceutically acceptable salt thereof.

9. A pharmaceutical composition comprising the compound according to claim 1 or a pharmaceutically acceptable salt thereof, and a pharmaceutically acceptable carrier.

* * * * *